United States Patent
Li et al.

(10) Patent No.: US 12,091,398 B2
(45) Date of Patent: Sep. 17, 2024

(54) PD-L1 ANTAGONIST COMPOUND

(71) Applicant: ADLAI NORTYE BIOPHARMA CO., LTD., Zhejiang (CN)

(72) Inventors: Pan Li, Zhejiang (CN); Beidi Xu, Zhejiang (CN); Qiaodong Wen, Zhejiang (CN); Enguang Feng, Zhejiang (CN); Ji Wang, Zhejiang (CN); Yang Lu, Zhejiang (CN); Yu Zhou, Zhejiang (CN); Zhiyong Yu, Zhejiang (CN); Zhiying Huang, Zhejiang (CN)

(73) Assignee: ADLAI NORTYE BIOPHARMA CO., LTD., Zhejiang (CN)

( * ) Notice: Subject to any disclaimer, the term of this patent is extended or adjusted under 35 U.S.C. 154(b) by 656 days.

(21) Appl. No.: 17/281,251

(22) PCT Filed: Feb. 20, 2020

(86) PCT No.: PCT/CN2020/075938
§ 371 (c)(1),
(2) Date: Mar. 30, 2021

(87) PCT Pub. No.: WO2020/169058
PCT Pub. Date: Aug. 27, 2020

(65) Prior Publication Data
US 2022/0227733 A1    Jul. 21, 2022

(30) Foreign Application Priority Data

Feb. 21, 2019 (CN) .......................... 201910130313.1
Jul. 30, 2019 (CN) .......................... 201910695768.8

(51) Int. Cl.
| | | |
|---|---|---|
| C07D 401/14 | (2006.01) |
| C07D 401/12 | (2006.01) |
| C07D 403/06 | (2006.01) |
| C07D 403/12 | (2006.01) |
| C07D 405/14 | (2006.01) |
| C07D 471/04 | (2006.01) |
| C07D 471/10 | (2006.01) |

(52) U.S. Cl.
CPC ......... *C07D 401/14* (2013.01); *C07D 401/12* (2013.01); *C07D 403/06* (2013.01); *C07D 403/12* (2013.01); *C07D 405/14* (2013.01); *C07D 471/04* (2013.01); *C07D 471/10* (2013.01)

(58) Field of Classification Search
CPC .. C07D 401/14; C07D 401/12; C07D 403/06; C07D 403/12; C07D 405/14; C07D 471/04; C07D 471/10; C07D 401/06; A61K 9/145; A61K 9/19; A61P 37/02
See application file for complete search history.

(56) References Cited

U.S. PATENT DOCUMENTS

| | | |
|---|---|---|
| 2015/0291549 A1 | 10/2015 | Chupak et al. |
| 2016/0194307 A1 | 7/2016 | Chupak et al. |
| 2018/0177784 A1 | 6/2018 | Wu et al. |

FOREIGN PATENT DOCUMENTS

| | | | |
|---|---|---|---|
| CN | 105705489 A | 6/2016 | |
| CN | 106536515 A | 3/2017 | |
| CN | 109665968 A | 4/2019 | |
| WO | 2018009505 A1 | 1/2018 | |
| WO | WO-2018009505 A1 * | 1/2018 | ......... A61K 31/4427 |
| WO | 2018119263 A1 | 6/2018 | |
| WO | 2018195321 A1 | 10/2018 | |

OTHER PUBLICATIONS

Patani et al. Bioisosterism: A rational Approach in Drug Design, Chem. Rev., 96, 3147-3176. (Year: 1996).*
Sheridan, The Most Common Chemical Replacements in Drug-Like Compounds, J. Chem. Inf. Comput. Sci, 42, 103-108. (Year: 2002).*
the Japanese 1st Office Action issued on Mar. 24, 2022 for JP2021-517249.
International Search Report for PCT/CN2020/075938 mailed May 20, 2020, ISA/CN.

* cited by examiner

*Primary Examiner* — Matthew P Coughlin
*Assistant Examiner* — Meghan C Heasley
(74) *Attorney, Agent, or Firm* — Yue (Robert) Xu; Apex Attorneys at Law, LLP

(57) ABSTRACT

Provided is a compound represented by formula (I) and a pharmaceutical composition thereof, as well as a method for using a compound represented by formula (I) to prevent and/or treat immune-related disorders.

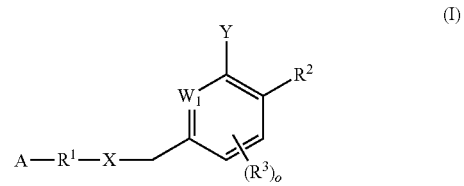

(I)

29 Claims, No Drawings

PD-L1 ANTAGONIST COMPOUND

This application is the national phase of International Application No. PCT/CN2020/075938, titled "PD-L1 ANTAGONIST COMPOUND", filed on Feb. 20, 2020, which claims the priority to Chinese Patent Application No. 201910130313.1 filed with the China National Intellectual Property Administration on Feb. 21, 2019 and titled "PD-L1 ANTAGONIST COMPOUND", and to Chinese Patent Application No. 201910695768.8 filed with the China National Intellectual Property Administration on Jul. 30, 2019 and titled "PD-L1 ANTAGONIST COMPOUND", the content of which are incorporated herein by reference in their entirety.

TECHNICAL FIELD

The present invention relates to a PD-L1 antagonist compound and a method for treating/preventing immune-related conditions.

BACKGROUND

Because of its excellent efficacy and innovation, cancer immunotherapy was named the most important scientific breakthrough of the year by Science magazine in 2013. Cancer immunotherapy is expected to become an innovation in the field of tumor therapy after surgery, chemotherapy, radiotherapy and targeted therapy. According to cancer immunotherapy, the immunogenicity of tumor cells and the sensitivity to effector cell killing are improved, and the body's anti-tumor immune response is stimulated and enhanced through the application of immunological principles and methods; and tumors are killed and tumor growth is inhibited by using immune cells and effector molecules to infuse the host in vivo, and cooperating with the body's immune system. Cancer immunotherapy has attracted much attention recently and is the focus of tumor therapy. In recent years, the good news of cancer immunotherapy has continued. At present, it has shown strong anti-tumor activity in the treatment of some tumor types such as melanoma and non-small cell lung cancer, and cancer immunotherapy drugs have been approved by the U.S. FDA (Food and Drug Administration, FDA) for clinical use.

PD-1 (programmed death 1) is a member of the CD28 superfamily. Immunomodulation targeting PD-1 is of great significance in anti-tumor, anti-infection, anti-autoimmune diseases and survival of organ transplant. Its ligand PD-L1 can also serve as a target and the corresponding antibody can also play the same role. PD-L1 (programmed cell death-Ligand 1) is a first type transmembrane protein of 40 kDa in size. Under normal circumstances, the immune system will respond to foreign antigens that accumulate in the lymph nodes or spleen, and promote the proliferation of antigen-specific T cells. The binding of PD-1 to PD-L1 can transmit inhibitory signals and reduce the proliferation of T cells. One way for tumor cells to evade destruction by T cells is to produce PD-L1 on the surface of T cells. When PD-1 on the surface of immune T cells recognizes PD-L1, inhibitory signals can be transmitted, and T cells is not able to detect tumor cells and send out attack signals to the tumor cells. PD-1 is a novel immunotherapy that evades the immune system the depletion of tumor cells. The mechanism of PD-1 immunotherapy is to design specific protein antibodies against PD-1 or PD-L1, prevent the recognition process of PD-1 and PD-L1, and partially restore T cell function, so that T cells can kill tumor cells.

PD-1 is expressed in activated T cells, B cells and myeloid cells with two ligands, PD-L1 and PD-L2. PD-L1/L2 is expressed in antigen presenting cells, and PD-L1 is also expressed in various tissues. The binding of PD-1 to PD-L1 mediates co-inhibitory signaling of T cell activation, regulates T cell activation and proliferation, and plays a negative regulatory role similar to CTLA-4. Chinese scientist Chen Lieping's laboratory first discovered that PD-L1 is highly expressed in tumor tissues and regulates the function of tumor infiltrating CD8 T cells. Therefore, the immunoregulation targeting PD-1/PD-L1 is of great significance against tumors.

A number of therapeutic monoclonal antibodies (mAbs) targeting the PD-1/PD-L1 interaction have been approved by the U.S. FDA for marketing. In addition to the development of related monoclonal antibodies, the search for oral small molecule compounds that are convenient for cancer patients to target inhibition of immune checkpoints is also a frontier domain of cancer immunotherapy. Small molecule compounds can pass through the cell membrane and act on intracellular targets, so they have a wide range of applications. Secondly, small molecules often have good bioavailability and compliance after chemical modification, effectively avoiding the decomposition and inactivation of enzymes in the digestive intestine. Finally, the research on small molecules is also quite mature in many aspects such as production process, dosage form design and administration mode.

Most monoclonal antibodies (mAbs) are administered by high-dose intravenous injection. Small molecule drugs, which are more suitable for oral administration, can reduce serious immune-related adverse events. Compared with monoclonal antibodies, small molecule drug inhibitors have many other benefits, such as more economical and stable manufacturing costs, and better permeability to organs and tumors. Given the numerous advantages of small molecule pharmacokinetic properties, it will exhibit dose flexibility in monotherapy or other combination schemes. The small molecule compounds of the present invention may provide an attractive treatment option for patients and physicians.

SUMMARY

The present invention provides a compound of Formula (I),

Formula (I)

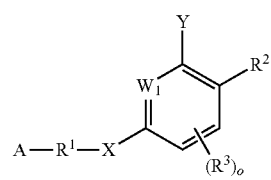

where,
$R^1$ is selected from the following groups:

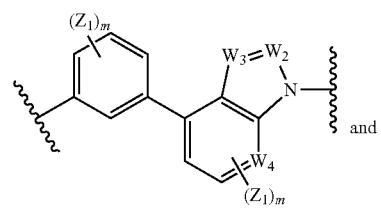

-continued

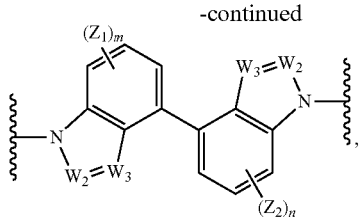

where $W_1$, $W_2$, $W_3$, and $W_4$ each independently represent $CR^c$ or N; $Z_1$ and $Z_2$ each independently represent hydrogen, ($C_1$-$C_6$) alkyl, ($C_3$-$C_6$) cycloalkyl, halo ($C_1$-$C_6$) alkyl, halo, —$OR^a$, —$C(O)OR^a$, ($C_1$-$C_6$) alkoxy, —$NR^aR^b$, —$SO_2R^a$, cyano, or nitro;

$R^2$ represents —($C_0$-$C_6$ alkylene) $NR^AR^B$ or —O ($C_0$-$C_6$ alkylene) $NR^AR^B$;

$R^3$ represents hydrogen, ($C_1$-$C_6$) alkyl, ($C_3$-$C_6$) cycloalkyl, ($C_1$-$C_6$) haloalkyl, halogen, —$OR^a$, —$C(O)OR^a$, ($C_1$-$C_6$) alkoxy, —$NR^aR^b$, —$SO_2R^a$, cyano, or nitro;

X represents —($C_0$-$C_6$ alkylene)-, —($C_0$-$C_6$ alkylene)O—, or —O ($C_0$-$C_6$ alkylene)-;

Y represents —($C_0$-$C_6$ alkylene)($C_6$-$C_{10}$ aryl), —($C_0$-$C_6$ alkylene)(5- to 10-membered heteroaryl), —O($C_1$-$C_6$) alkyl, —O($C_0$-$C_6$ alkylene)($C_6$-$C_{10}$ aryl), —O($C_0$-$C_6$ alkylene)(5- to 10-membered heteroaryl), —($C_0$-$C_6$ alkylene)O($C_6$-$C_{10}$ aryl), —($C_0$-$C_6$ alkylene)O(5- to 10-membered heteroaryl), —O($C_0$-$C_6$ alkylene)($C_3$-$C_6$ cycloalkyl), or —O($C_0$-$C_6$ alkylene)(3- to 6-membered heterocycloalkyl);

for alkylene, alkyl, cycloalkyl, heterocycloalkyl, aryl, heteroaryl in the above-mentioned definition of Y, they are optionally substituted by 0, 1, 2 or 3 substituents selected from the group consisting of: —$OR^a$, cyano, oxo(=O), halogen, $C_1$-$C_6$ alkyl, —($C_1$-$C_6$ alkylene)$OR^a$, $C_1$-$C_6$ cyanoalkyl, $C_1$-$C_6$ haloalkyl, $C_3$-$C_8$ cycloalkyl, —$C(O)R^a$, —($C_1$-$C_6$ alkylene)$C(O)R^a$, —$C(O)OR^a$, —($C_1$-$C_6$ alkyl)$C(O)OR^a$, —$NR^aR^b$, —($C_1$-$C_6$ alkylene)$NR^aR^b$, —$C(O)NR^aR^b$, $SO_2R^a$, —$C(O)NR^aSO_2R^a$, or —$NR^aC(O)R^b$;

or Y represents —O($C_0$-$C_6$ alkylene)$CONR^AR^B$;

A represents —($C_0$-$C_6$ alkylene)$NR^AR^B$, —O($C_0$-$C_6$ alkylene)$NR^AR^B$, —$C(O)$($C_0$-$C_6$ alkylene)$NR^AR^B$, —($C_0$-$C_6$ alkylene)($C_3$-$C_6$ cycloalkyl)$NR^AR^B$, or -(3- to 6-membered heterocycloalkyl)$CHR^AR^B$;

or A represents

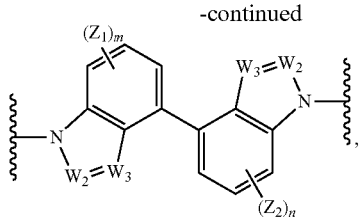

wherein Q represents —($C_0$-$C_6$ alkylene)-, —($C_0$-$C_6$ alkylene)O—, or —O($C_0$-$C_6$ alkylene)-;

$W_5$ represents CH or N;

$R^4$ represents —($C_0$-$C_6$ alkylene)$NR^AR^B$, —O($C_0$-$C_6$ alkylene)$NR^AR^B$, or —$C(O)NR^AR^B$;

$R^5$ represents hydrogen, ($C_1$-$C_6$) alkyl, ($C_3$-$C_6$) cycloalkyl, ($C_1$-$C_6$) haloalkyl, halogen, —$OR^a$, —$C(O)OR^a$, ($C_1$-$C_6$) alkoxy, —$NR^aR^b$, —$SO_2R^a$, cyano, or nitro;

$R^6$ represents hydrogen, —($C_0$-$C_6$ alkylene)($C_6$-$C_{10}$ aryl), —($C_0$-$C_6$ alkylene)(5- to 10-membered heteroaryl), —O($C_1$-$C_6$)alkyl, —O($C_0$-$C_6$ alkylene)$CONR^AR^B$, —O($C_0$-$C_6$ alkylene)($C_6$-$C_{10}$ aryl), —O($C_0$-$C_6$ alkylene)(5- to 10-membered heteroaryl), —($C_0$-$C_6$ alkylene)O($C_6$-$C_{10}$ aryl), —($C_0$-$C_6$ alkylene)O(5- to 10-membered heteroaryl), —O($C_0$-$C_6$ alkylene)($C_3$-$C_6$ cycloalkyl), or —O($C_0$-$C_6$ alkylene)(3- to 6-membered heterocycloalkyl);

for alkylene, alkyl, cycloalkyl, heterocycloalkyl, aryl, and heteroaryl in the above-mentioned definition of $R^6$, they are optionally substituted by 0, 1, 2 or 3 substituents selected from the group consisting of: —$OR^a$, cyano, halogen, $C_1$-$C_6$ alkyl, —($C_1$-$C_6$ alkylene)$OR^a$, $C_1$-$C_6$ cyanoalkyl, $C_1$-$C_6$ haloalkyl, $C_3$-$C_8$ cycloalkyl, —$C(O)R^a$, —($C_1$-$C_6$ alkylene) $C(O)R^a$, —$C(O)OR^a$, —($C_1$-$C_6$ alkyl)$C(O)OR^a$, —$NR^aR^b$, —($C_1$-$C_6$ alkylene)$NR^aR^b$, —$C(O)NR^aR^b$, —$SO_2R^a$, —$C(O)NR^aSO_2R$ e, and —$NR^aC(O)R^b$;

∿∿∿ represents an arbitrary connection position;

m, n, o, and p are selected from 0, 1, 2, and 3;

$R^A$ and $R^B$ each independently represent hydrogen, $C_1$-$C_6$ alkyl, $C_2$-$C_6$ alkenyl, $C_2$-$C_6$ alkynyl, —($C_0$-$C_6$ alkylene)($C_3$-$C_6$ cycloalkyl), —($C_0$-$C_6$ alkylene)3- to 6-membered heterocycloalkyl), —($C_0$-$C_6$ alkylene)($C_6$-$C_{10}$ aryl), —($C_0$-$C_6$ alkylene)(5- to 10-membered heteroaryl), —($C_0$-$C_6$ aryl)$C(O)OR^a$, —$SO_2R^a$, —$SO_2NR^aR^b$, or —$C(O)NR^aSO_2R^b$;

for alkylene, alkyl, alkenyl, alkynyl, cycloalkyl, heterocycloalkyl, aryl, and heteroaryl in the above-mentioned definition of R and $R^B$, they are optionally substituted with 0, 1, 2 or 3 substituents selected from the group consisting of: —$OR^a$, cyano, oxo, halogen, $C_1$-$C_6$ alkyl, —($C_1$-$C_6$ alkylene)$OR^a$, $C_1$-$C_6$ cyanoalkyl, $C_1$-$C_6$ haloalkyl, $C_3$-$C_8$ cycloalkyl, —$C(O)R^a$, —($C_1$-$C_6$ alkylene)$C(O)R^a$, —$C(O)OR^a$, —($C_1$-$C_6$ alkyl)$C(O)OR^a$, —$NR^aR^b$, —($C_1$-$C_6$ alkylene)$NR^aR^b$, —$C(O)NR^aR^b$, —$SO_2R^a$, —$C(O)NR^aSO_2R^b$, and —$NR^aC(O)R^b$;

or $R^A$ and $R^B$ together with atoms bound thereto are optionally cyclized to each other into a 5- to 7-membered ring, and the ring also optionally has 0, 1, 2 or 3 heteroatoms selected from O, N, S, further the ring is optionally substituted by 0, 1, 2 or 3 substituents selected from the group consisting of: oxo, cyano, $C_1$-$C_6$ alkyl, $C_3$-$C_6$ cycloalkyl, $C_2$-$C_6$ alkenyl, $C_2$-$C_6$ alkynyl, —$OR^a$, —$C(O)OR^a$, —($C_1$-$C_6$) cyanoalkyl, ($C_1$-$C_6$) haloalkyl, —($C_1$-$C_6$ alkylene)$OR^a$, —$C(O)R^a$, —$NR^aR^b$, —($C_1$-$C_6$ alkylene)$NR^aR^b$, —$C(O)NR^aR^b$, —($C_1$-$C_6$ alkylene)$C(O)NR^aR^b$, —$SO_2R^a$, —($C_1$-$C_6$ alkylene)$SO_2R^a$, —$SO_2NR^aR^b$, and —($C_1$-$C_6$ alkylene)$SO_2NR^aR^b$;

where $R^a$ and $R^b$ each independently represent hydrogen, $C_1$-$C_6$ alkyl, —($C_0$-$C_6$ alkylene) ($C_3$-$C_6$ cycloalkyl), —($C_0$-$C_6$ alkylene)($C_3$-$C_6$ heterocycloalkyl), —($C_0$-$C_6$ alkylene)($C_6$-$C_{10}$ aryl), or —($C_0$-$C_6$ alkylene)(5- to 10-membered heteroaryl);

or $R^a$ and $R^b$ together with atoms bound thereto are optionally cyclized to each other into a 5- to 7-membered ring, and the ring also optionally has 0, 1, 2 or 3 heteroatoms selected from O, N, S, further the ring is optionally substituted by 0, 1, 2 or 3 substituents selected from the group consisting of: oxo, cyano, $C_1$-$C_6$ alkyl, $C_3$-$C_6$ cycloalkyl, $C_2$-$C_6$ alkenyl, $C_2$-$C_6$ alkynyl, —$OR^d$, —$C(O)OR^d$, —($C_1$-$C_6$) cyanoalkyl, ($C_1$-$C_6$) haloalkyl, —($C_1$-$C_6$ alkylene)$OR^d$, —$C(O)R^d$, —$NR^dR^e$, —($C_1$-$C_6$ alkylene)$NR^dR^e$, —$C(O)NR^dR^e$, —($C_1$-$C_6$ alkylene)$C(O)NR^dR^e$, —$SO_2R^d$, —($C_1$-$C_6$ alkylene)$SO_2R^d$, —$SO_2NR^dR^e$, and —($C_1$-$C_6$ alkylene)$SO_2NR^dR^e$;

where $R^c$, $R^d$, and $R^e$ each independently represent hydrogen, $C_1$-$C_6$ alkyl, or $C_3$-$C_6$ cycloalkyl.

In addition, the present invention also provides a compound having a structure of Formula (II),

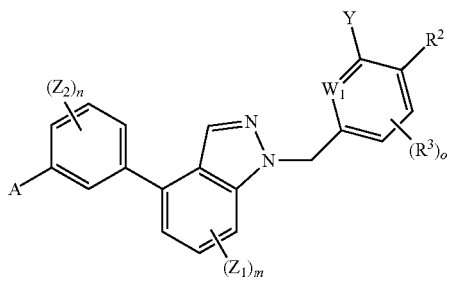

Formula (II)

where $R^2$, $R^3$, A, $W_1$, $Z_1$, $Z_2$, Y, m, n, and o are as defined in Formula (I).

In addition, the present invention also provides a compound having a structure of Formula (III),

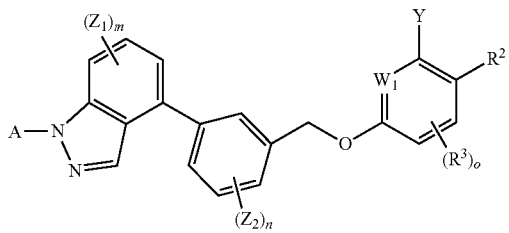

Formula (III)

where $R^2$, $R^3$, A, $Z_1$, $Z_2$, $W_1$, Y, m, n, and o are as defined in Formula (I).

In addition, the present invention also provides a compound having a structure of Formula (IV),

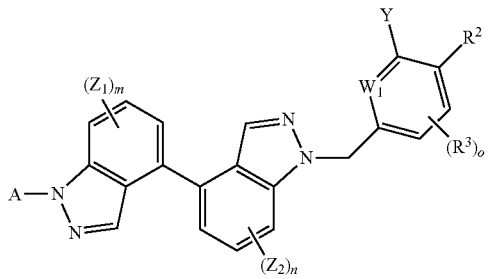

Formula (IV)

where $R^2$, $R^3$, A, $Z_1$, $Z_2$, $W_1$, Y, m, n, and o are as defined in Formula (I).

In the compounds of the present invention, $R^2$ is preferably selected from —($C_0$-$C_6$ alkylene)$NR^A R^B$ where $R^A$ and $R^B$ each independently represent hydrogen or $C_1$-$C_6$ alkyl substituted by —$OR^a$, —$C(O)R^a$, or —$C(O)OR^a$, where $R^a$ and $R^b$ each independently represent hydrogen or $C_1$-$C_6$ alkyl.

In the compounds of the present invention, Y is preferably selected from the group consisting of —$O(C_1$-$C_6)$alkyl, —$O(C_0$-$C_6$ alkylene)($C_6$-$C_{10}$ aryl), —$O(C_0$-$C_6$ alkylene)(5- to 10-membered heteroaryl), —$O(C_1$-$C_6)$alkyl, —($C_0$-$C_6$ alkylene)$O(C_6$-$C_{10}$ aryl), or —($C_0$-$C_6$ alkylene)$O$(5- to 10-membered heteroaryl) substituted by —$OR^a$, cyano, halogen, $C_1$-$C_6$ alkyl, —($C_1$-$C_6$ alkylene)$OR^a$, $C_1$-$C_6$ cyanoalkyl, —$C(O)OR^a$, —$NR^a R^b$, —$C(O)NR^a R^b$, $SO_2 R^a$, —$C(O)NR^a SO_2 R^b$, or —$NR^a C(O)R^b$, where $R^a$ and $R^b$ each independently represent hydrogen or $C_1$-$C_6$ alkyl.

In the compounds of the present invention, Y is preferably selected from —O—($C_1$-$C_6$ alkyl), where the $C_1$-$C_6$ alkyl is optionally substituted by 0, 1, or 2 cyano, halogen, hydroxy, —$C(O)NH_2$, amino, sulfo, or carboxyl, preferably Y is selected from the group consisting of

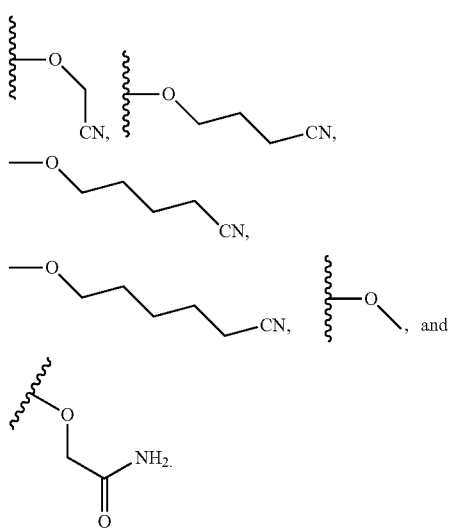

In the compounds of the present invention, Y is preferably selected from —$O(C_0$-$C_6$ alkylene)(3- to 6-membered heterocycloalkyl), where the 3- to 6-membered heterocycloalkyl is optionally substituted by oxo, $C_1$-$C_6$ alkyl, or hydroxy, preferably Y is selected from the group consisting of

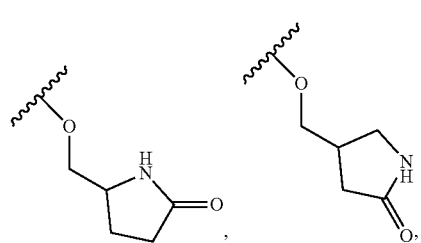

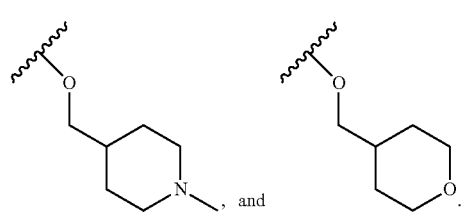

In the compounds of the present invention, Y is preferably selected from the group consisting of

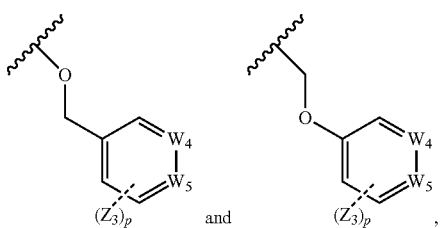

where $W_4$ and $W_5$ each independently represent CH or N; p represents 0, 1, 2 or 3; $Z_3$ represents hydrogen, $(C_1\text{-}C_6)$ alkyl, $(C_3\text{-}C_6)$ cycloalkyl, halo $(C_1\text{-}C_6)$ alkyl, halogen, —$OR^a$, —$C(O)OR^a$, $(C_1\text{-}C_6)$ alkoxy, —$NR^aR^b$, —$SO_2R^a$, cyano, or nitro; $R^a$ and $R^b$ represent hydrogen or $C_1\text{-}C_6$ alkyl; preferably Y is selected from the group consisting of

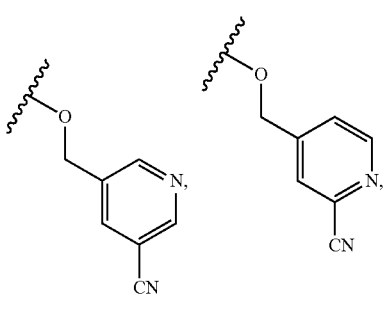

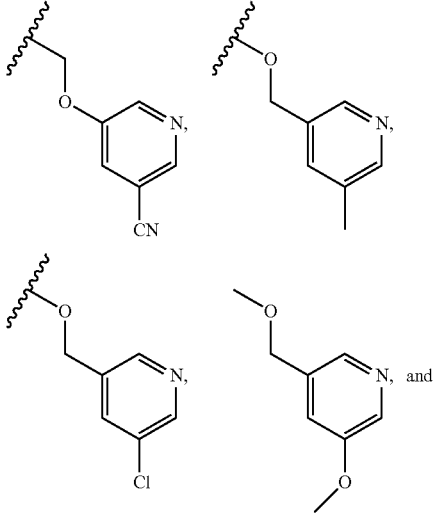

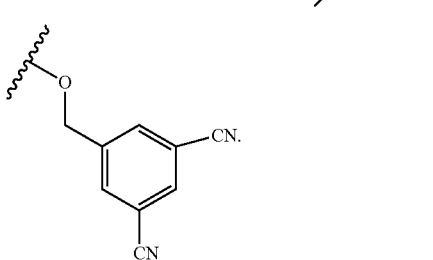

In the compounds of the present invention, Y is preferably selected from

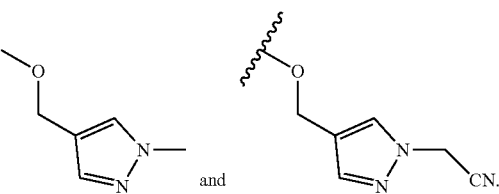

where $Z_4$ represents hydrogen, $C_1\text{-}C_6$ alkyl, cyano, cyanomethyl or $C_3\text{-}C_6$ cycloalkyl, preferably Y is selected from the group consisting of

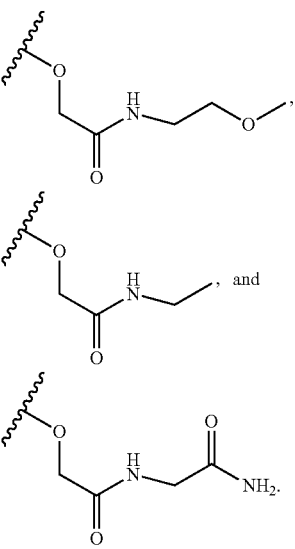

In the compounds of the present invention, Y is preferably selected from —$O(C_0\text{-}C_6$ alkylene$)CONR^AR^B$, where $R^A$ and $R^B$ each independently represent hydrogen or $C_1\text{-}C_6$ alkyl optionally substituted by —$OR^a$, —$NR^aR^b$, or —$C(O)NR^aR^b$, where $R^a$ and $R^b$ each independently represent hydrogen or $C_1\text{-}C_6$ alkyl; preferably, Y is selected from the group consisting of In the compounds of the present invention, Y is preferably selected from —$O(C_0\text{-}C_6$ alkylene$)CONR^AR^B$, where $R^A$ and $R^B$ together with nitrogen atom bound thereto are optionally cyclized to each other into a 5- to 7-membered ring, and the ring also optionally has 0, 1, 2 or 3 heteroatoms selected from O, N, S, further the ring is also optionally substituted by 0, 1, 2 or 3 substituents selected from the group consisting of: cyano, $C_1\text{-}C_6$ alkyl, $C_3\text{-}C_6$ cycloalkyl, $C_2\text{-}C_6$ alkenyl, $C_2\text{-}C_6$ alkynyl, —$OR^a$, —$C(O)OR^a$, —$(C_1\text{-}C_6)$ cyanoalkyl, $(C_1\text{-}C_6)$ haloalkyl, —$(C_1\text{-}C_6$ alkylene$)OR^a$, —$C(O)R^a$, and —$NR^aR^b$, where $R^a$ and $R^b$ each independently represent hydrogen or $C_1\text{-}C_6$ alkyl; preferably, Y is selected from

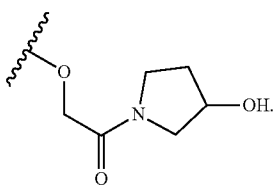 [SMILES: *OCC(=O)N1CCC(O)C1]

In the compounds of the present invention, A is preferably selected from —($C_0$-$C_6$ alkylene)$NR^A R^B$ wherein $R^A$ and $R^B$ together with atoms bound thereto are optionally cyclized to each other into a 5- to 7-membered ring, and the ring also optionally has 0, 1, 2 or 3 heteroatoms selected from O, N, S, further the ring may also be optionally substituted by 0, 1, 2 or 3 substituents selected from the group consisting of: oxo, cyano, $C_1$-$C_6$ alkyl, $C_3$-$C_6$ cycloalkyl, $C_2$-$C_6$ alkenyl, $C_2$-$C_6$ alkynyl, —$OR^a$, —$C(O)OR^a$, —($C_1$-$C_6$)cyanoalkyl, ($C_1$-$C_6$)haloalkyl, —($C_1$-$C_6$ alkylene)$OR^a$, —$C(O)R^a$, —$NR^a R^b$, —($C_1$-$C_6$ alkylene)$NR^a R^b$, —$C(O)NR^a R^b$, —($C_1$-$C_6$ alkylene)$C(O)NR^a R^b$, —$SO_2 R^a$, —($C_1$-$C_6$ alkylene)$SO_2 R^a$, —$SO_2 NR^a R^b$, or —($C_1$-$C_6$ alkylene)$SO_2 NR^a R^b$, wherein $R^a$ and $R^b$ each independently represents hydrogen or $C_1$-$C_6$ alkyl.

In the compounds of the present invention, A is preferably selected from the group consisting of:

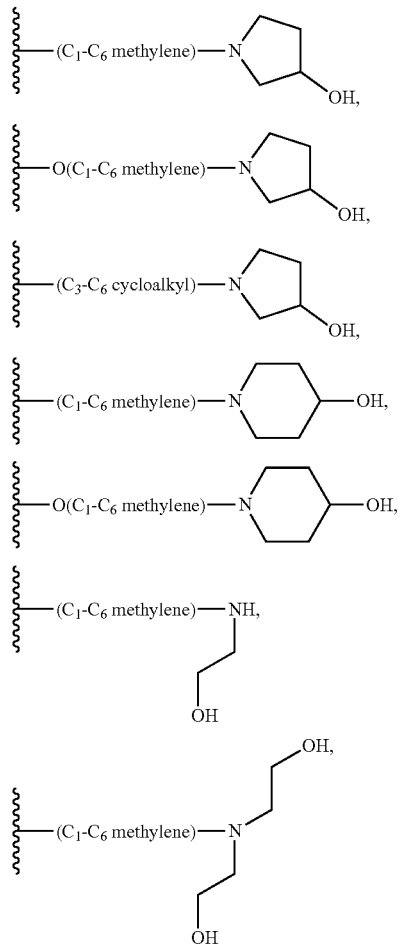

more preferably selected from the group consisting of

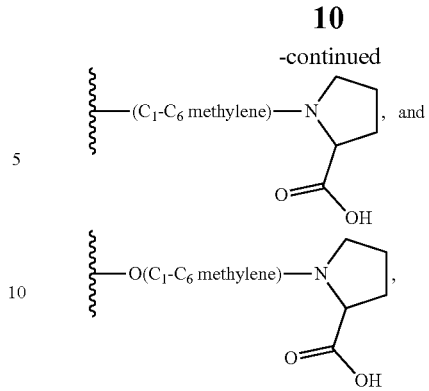

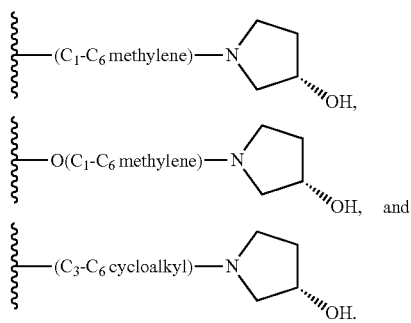

In the compounds of the present invention, A may also represent

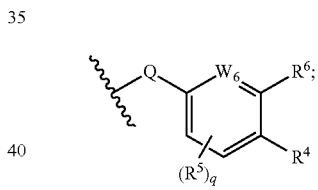

where Q represents —($C_0$-$C_6$ alkylene)-, —($C_0$-$C_6$ alkylene)O—, or —O($C_0$-$C_6$ alkylene)-;

$W_6$ represents CH or N;

$R^4$ represents —($C_0$-$C_6$ alkylene)$NR^A R^B$, where $R^A$ and $R^B$ each independently represent hydrogen or $C_1$-$C_6$ alkyl substituted by —$OR^a$, —$C(O)R^a$, —$C(O)OR^a$, —$C(O)NR^a R^b$, —$SO_2 R^a$, —$C(O)NR^a SO_2 R^b$, or —$NR^a C(O)R^b$;

$R^5$ represents hydrogen, ($C_1$-$C_6$) alkyl, ($C_3$-$C_6$) cycloalkyl, ($C_1$-$C_6$) haloalkyl, halogen, —$OR^a$, —$C(O)OR^a$, ($C_1$-$C_6$) alkoxy, —$NR^a R^b$, —$SO_2 R^a$, cyano, or nitro;

$R^6$ represents hydrogen or —O($C_1$-$C_6$) alkyl, —O($C_0$-$C_6$ alkylene)($C_6$-$C_{10}$ aryl), or —O($C_0$-$C_6$ alkylene)(5- to 10-membered heteroaryl) substituted by the group consisting of: —$OR^a$, cyano, halogen, $C_1$-$C_6$ alkyl, —($C_1$-$C_6$ alkylene)$OR^a$, $C_1$-$C_6$ cyanoalkyl, —$C(O)OR^a$, —$NR^a R^b$, —$C(O)NR^a R^b$, $SO_2 R^a$, —$C(O)NR^a SO_2 R^b$, or —$NR^a C(O)R^b$; where $R^a$ and R each independently represent hydrogen or $C_1$-$C_6$ alkyl;

q represents 0, 1, 2 or 3;

In the compounds of the present invention, $R^2$ is preferably selected from the group consisting of

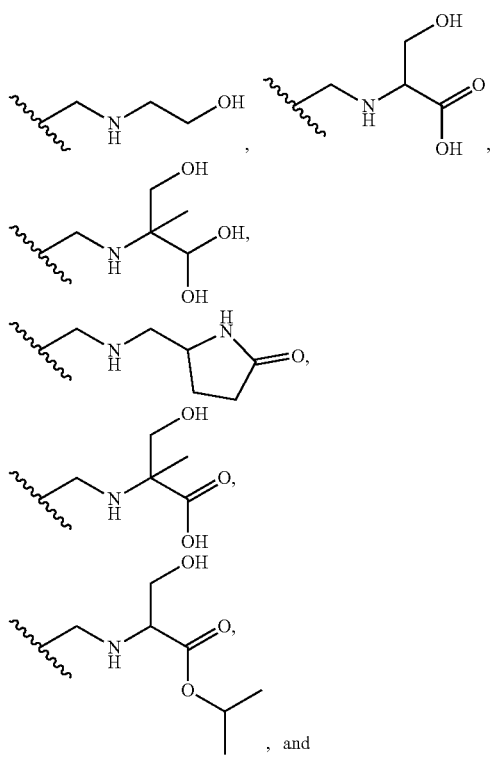

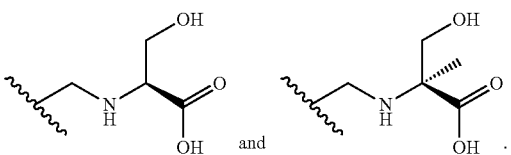

more preferably selected from the group consisting of

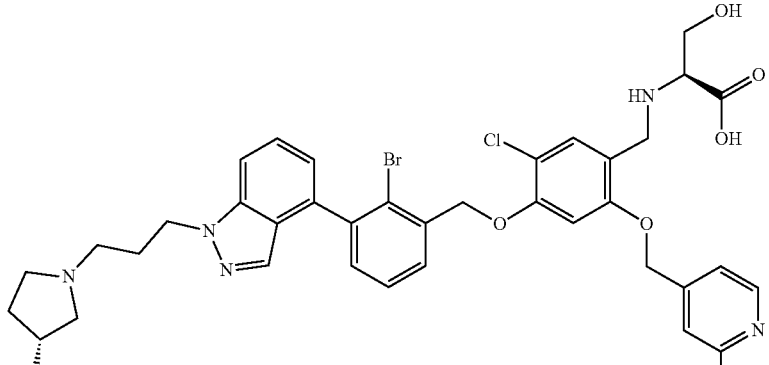

In the compounds of the present invention, $W_5$ is preferably CH.

In the compounds of the present invention, $Z_1$ or $Z_2$ represents hydrogen, halogen, cyano, or $C_1$-$C_6$ alkyl; where the halogen is preferably chlorine or bromine.

Specifically, the present invention provides a compound having the following structures:

| No. | Structure |
|---|---|
| 1 | 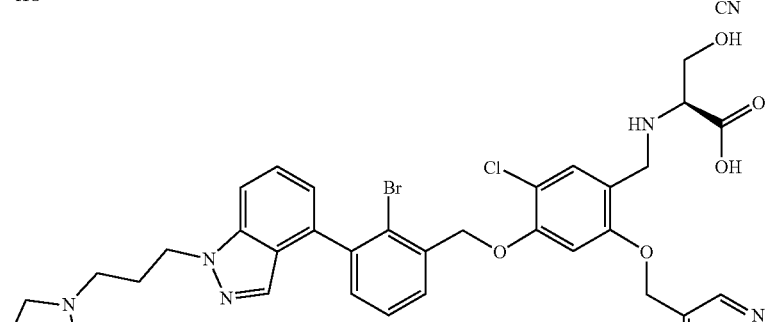 |
| 2 | 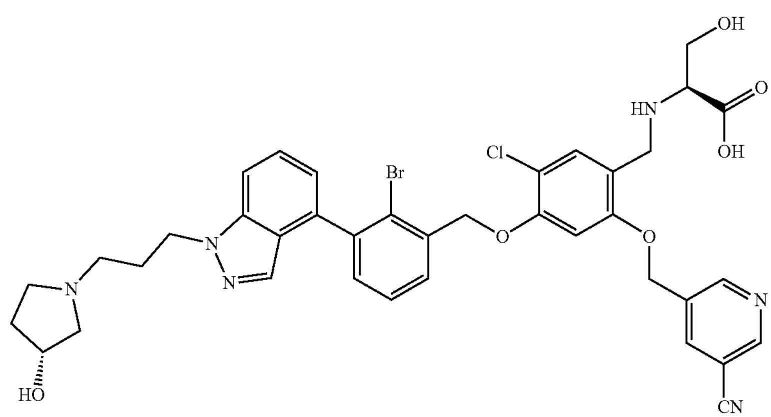 [SMILES: N#Cc1cncc(COc2cc(OCc3cccc(-c4cccc5c4cnn5CCCN4CC[C@@H](O)C4)c3Br)c(Cl)cc2CN[C@@H](CO)C(=O)O)c1] |

-continued

| No. | Structure |
|---|---|
| 3 | 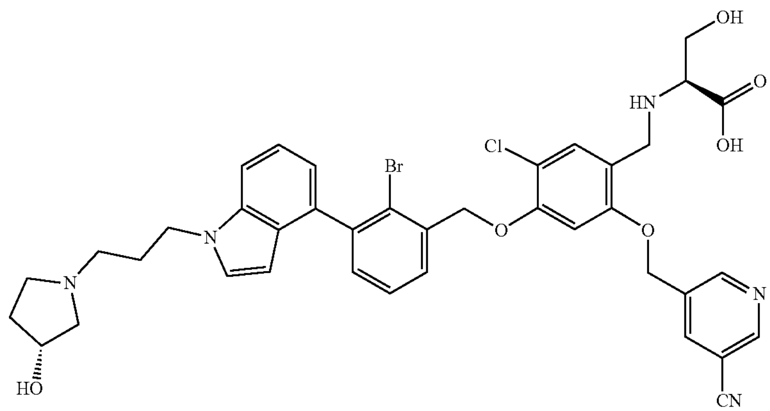 [SMILES: N#Cc1cncc(COc2cc(OCc3cccc(-c4cccc5c4ccn5CCCN4CC[C@@H](O)C4)c3Br)c(Cl)cc2CN[C@@H](CO)C(=O)O)c1] |
| 4 | 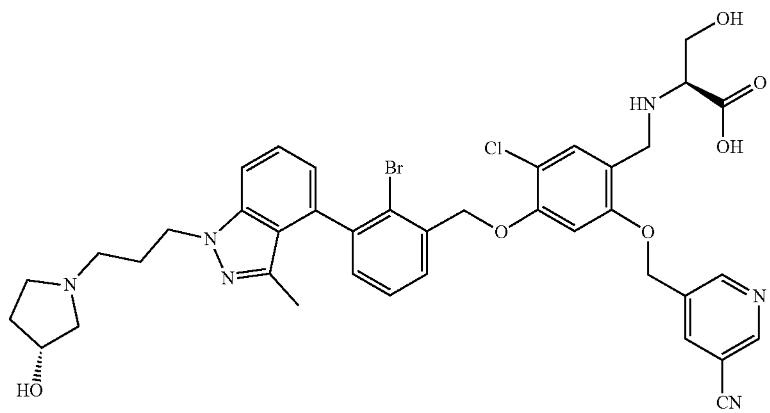 [SMILES: Cc1nn(CCCN2CC[C@@H](O)C2)c2cccc(-c3cccc(COc4cc(OCc5cncc(C#N)c5)c(CN[C@@H](CO)C(=O)O)cc4Cl)c3Br)c12] |
| 5 | 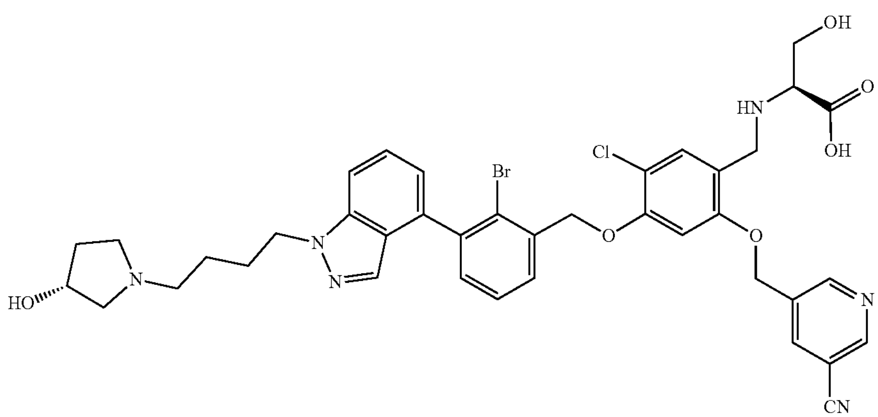 [SMILES: N#Cc1cncc(COc2cc(OCc3cccc(-c4cccc5c4cnn5CCCCN4CC[C@@H](O)C4)c3Br)c(Cl)cc2CN[C@@H](CO)C(=O)O)c1] |
| 6 | 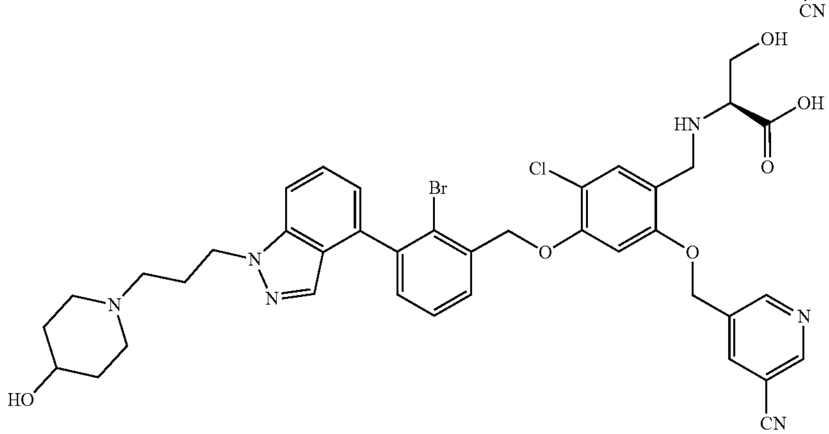 |

| No. | Structure |
|---|---|
| 7 | 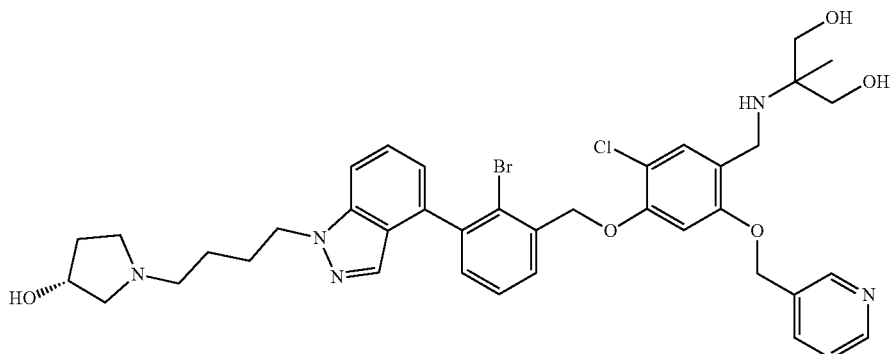 |
| 8 | 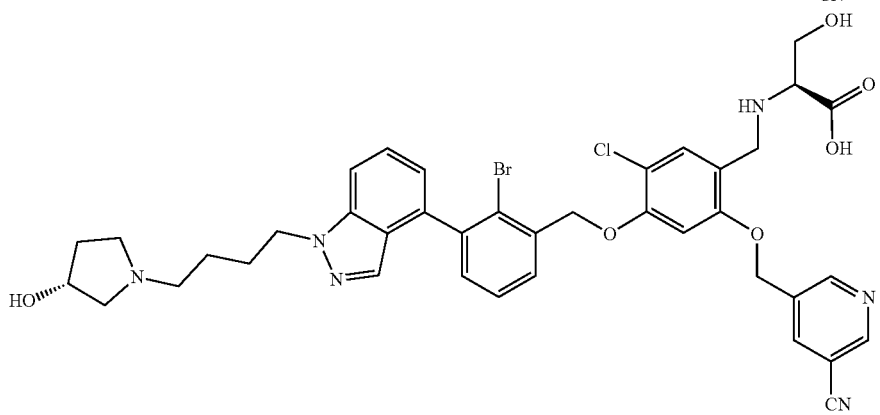 |
| 9 | 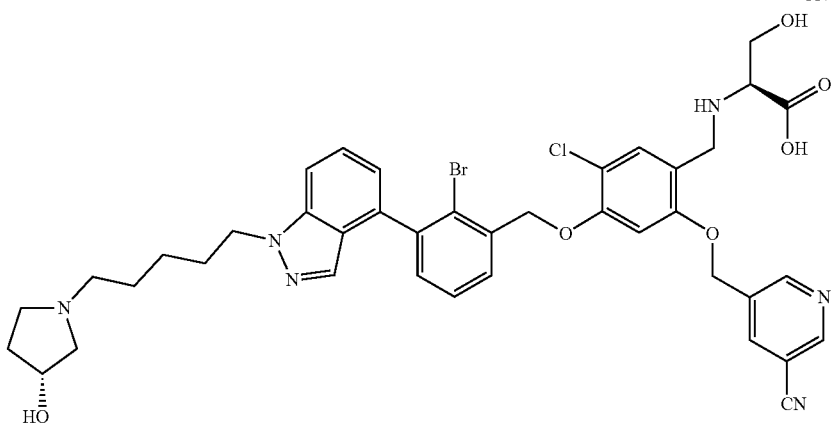 |
| 10 | 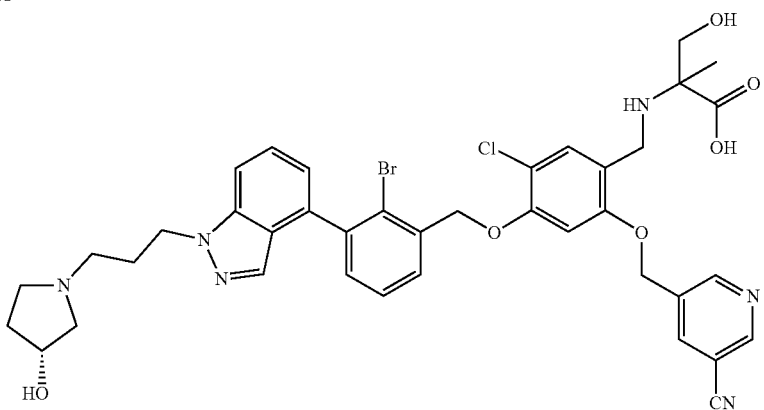 |

| No. | Structure |
|---|---|
| 11 | 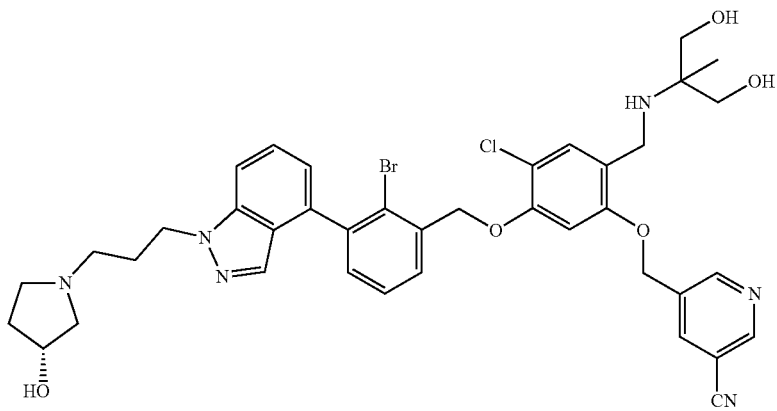 [SMILES: CC(CO)(CO)NCc1cc(Cl)c(OCc2cccc(-c3cccc4c3cnn4CCCN3CC[C@@H](O)C3)c2Br)cc1OCc1cncc(C#N)c1] |
| 12 | 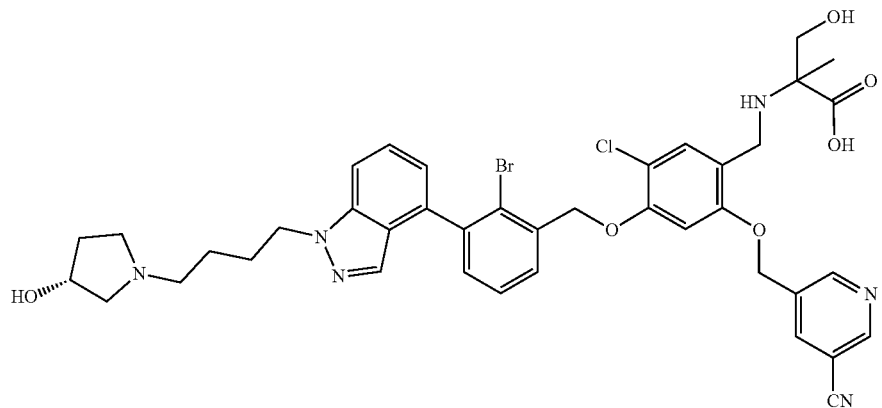 [SMILES: CC(CO)(NCc1cc(Cl)c(OCc2cccc(-c3cccc4c3cnn4CCCCN3CC[C@@H](O)C3)c2Br)cc1OCc1cncc(C#N)c1)C(=O)O] |
| 13 | 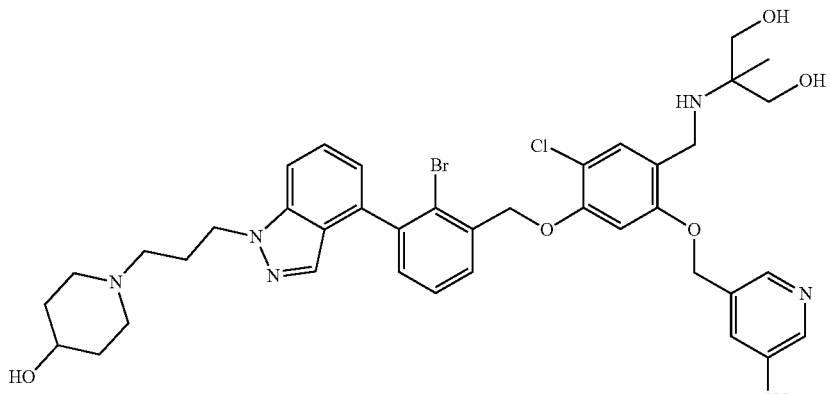 |
| 14 | 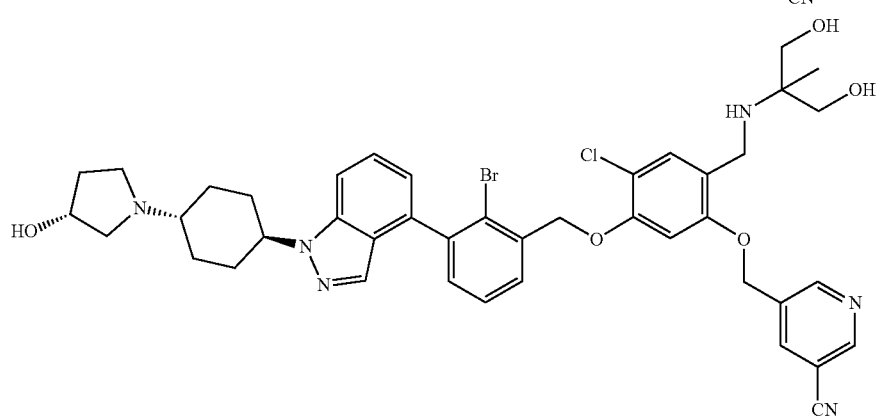 |

-continued
| No. | Structure |
|---|---|
| 15 | 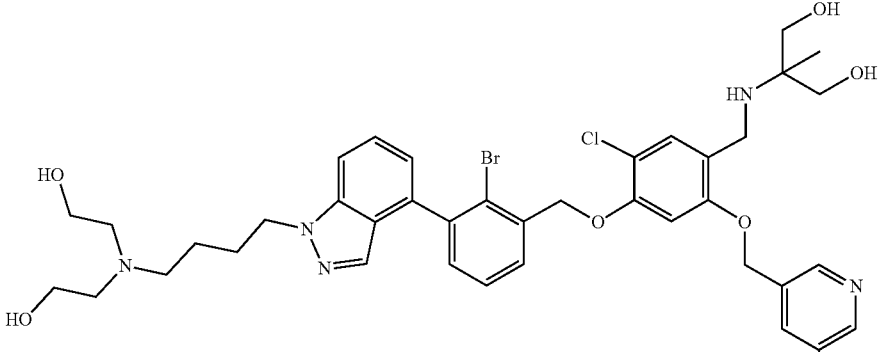 |
| 16 | 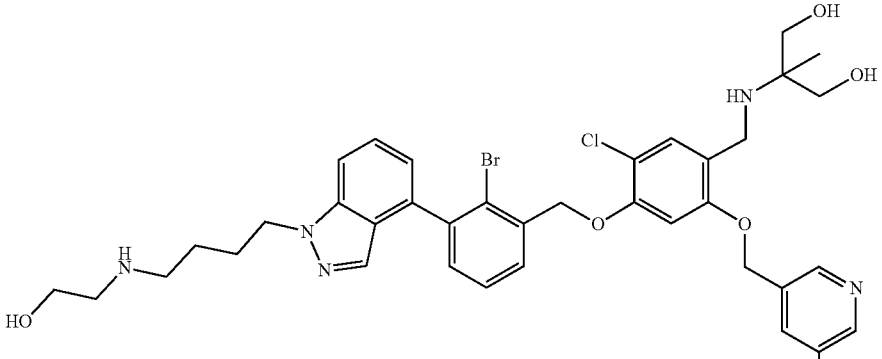 |
| 17 | 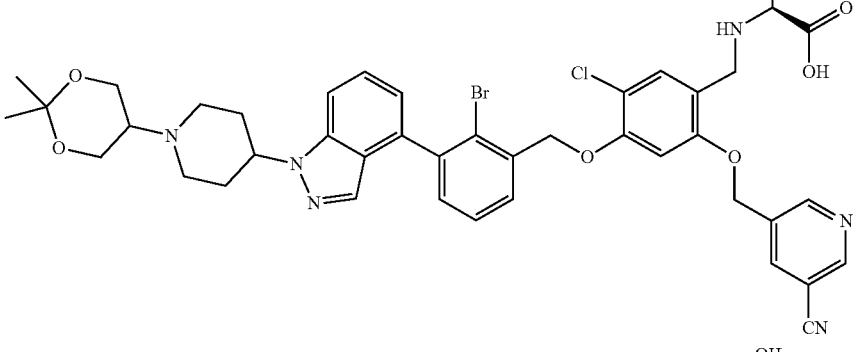 |
| 18 | 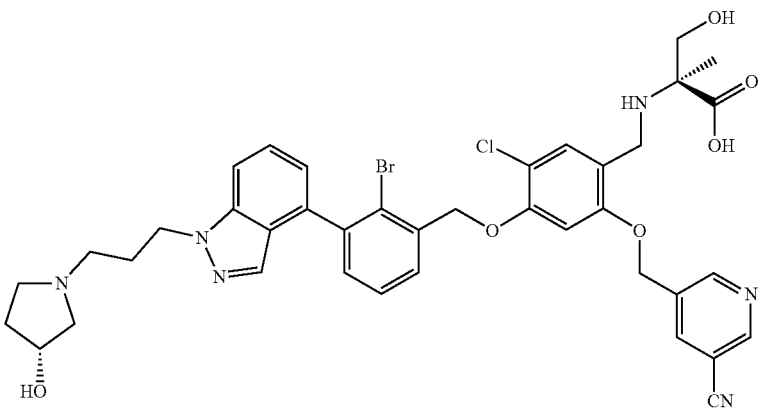 [SMILES: C[C@@](CO)(NCc1cc(Cl)c(OCc2cccc(-c3cccc4c3cnn4CCCN3CC[C@@H](O)C3)c2Br)cc1OCc1cncc(C#N)c1)C(=O)O] |

| No. | Structure |
|---|---|
| 19 | 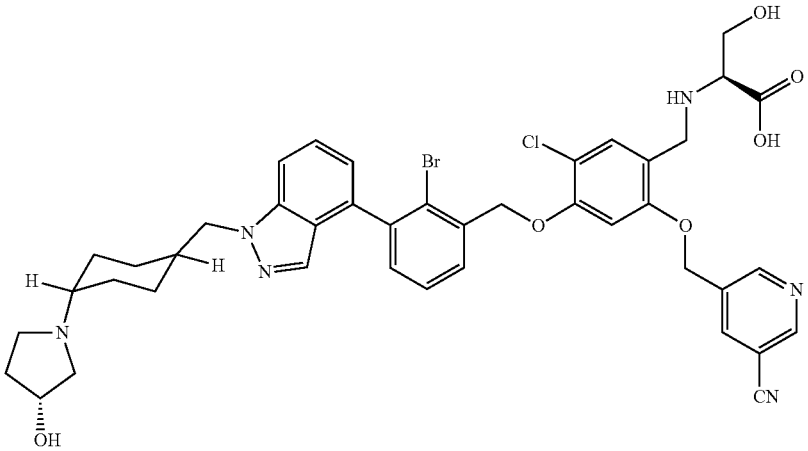 [SMILES: N#Cc1cncc(COc2cc(OCc3cccc(-c4cccc5c4cnn5CC4CCC(N5CC[C@@H](O)C5)CC4)c3Br)c(Cl)cc2CN[C@@H](CO)C(=O)O)c1] |
| 20 | 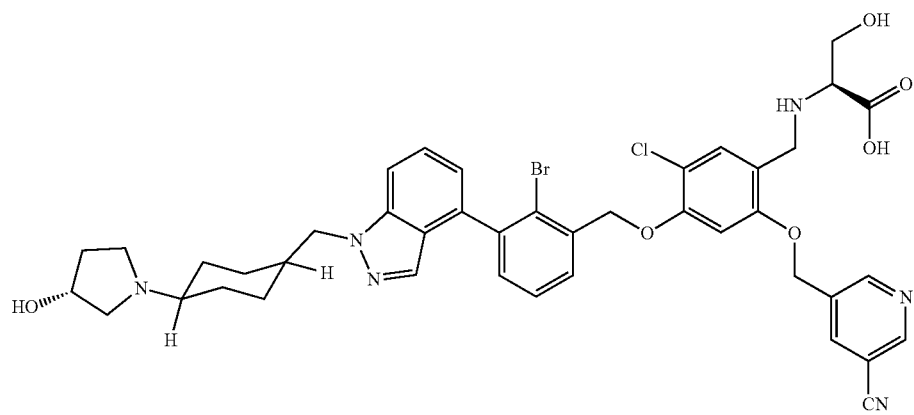 [SMILES: N#Cc1cncc(COc2cc(OCc3cccc(-c4cccc5c4cnn5CC4CCC(N5CC[C@@H](O)C5)CC4)c3Br)c(Cl)cc2CN[C@@H](CO)C(=O)O)c1] |
| 21 | 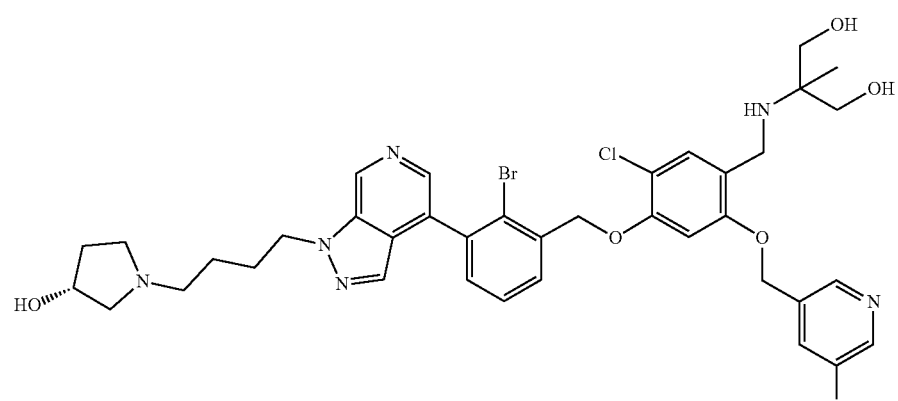 |

-continued
| No. | Structure |
|---|---|
| 22 | 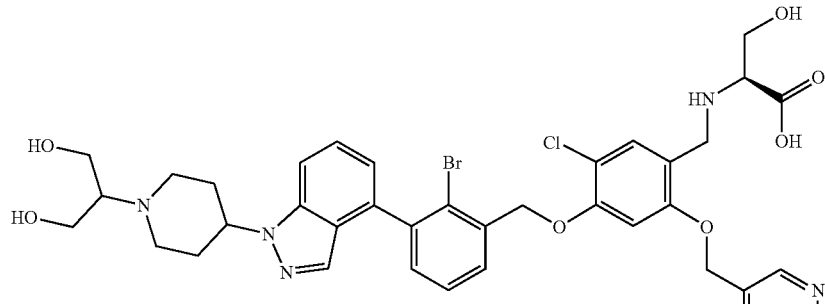 |
| 23 | 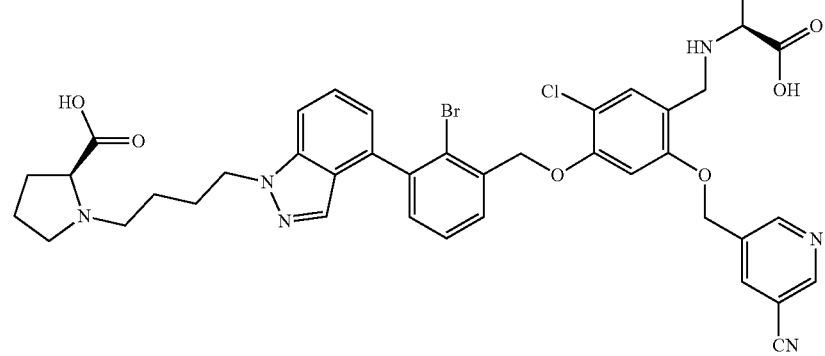 |
| 24 | 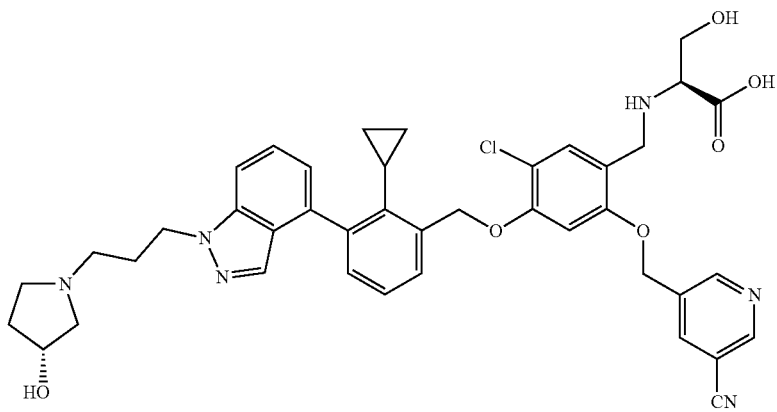 [SMILES: N#Cc1cncc(COc2cc(OCc3cccc(-c4cccc5c4cnn5CCCN4CC[C@@H](O)C4)c3C3CC3)c(Cl)cc2CN[C@@H](CO)C(=O)O)c1] |
| 25 | 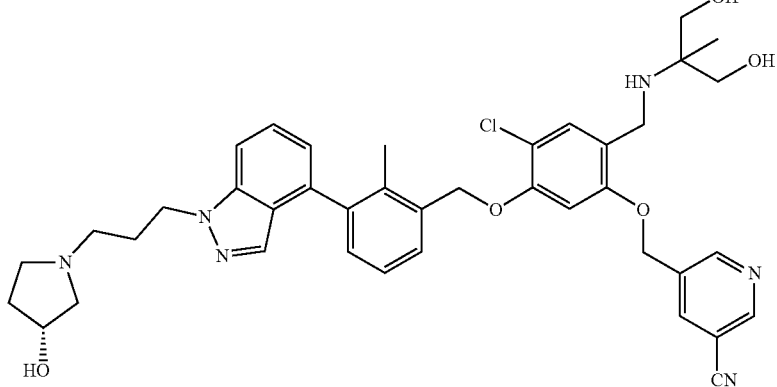 |

| No. | Structure |
|---|---|
| 26 | 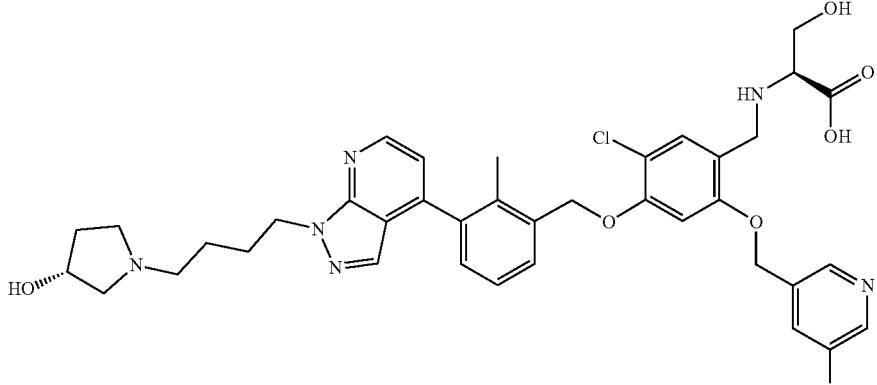 |
| 27 | 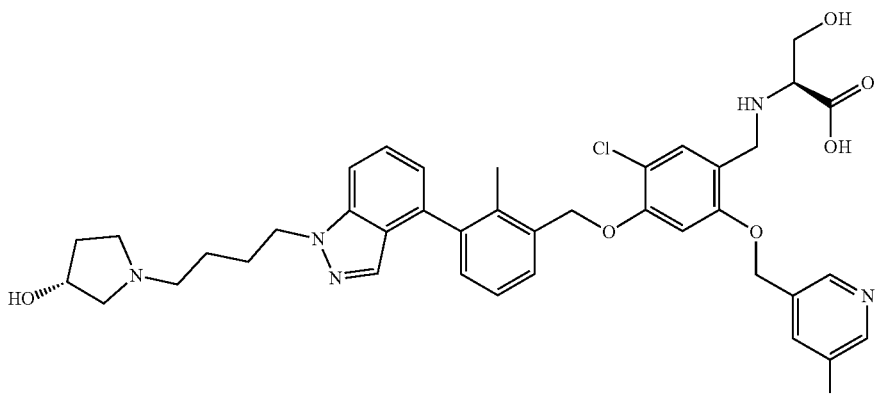 |
| 28 | 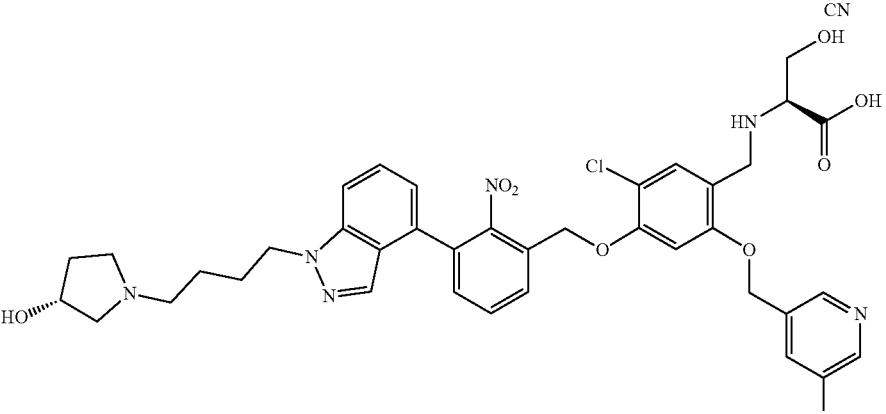 |
| 29 | 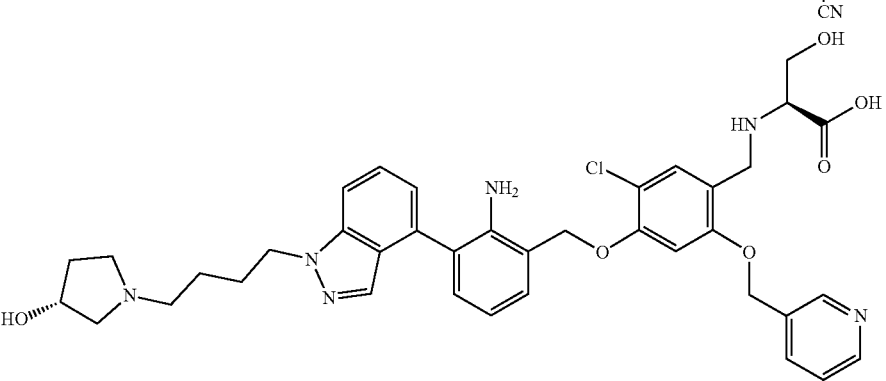 |

| No. | Structure |
|---|---|
| 30 | 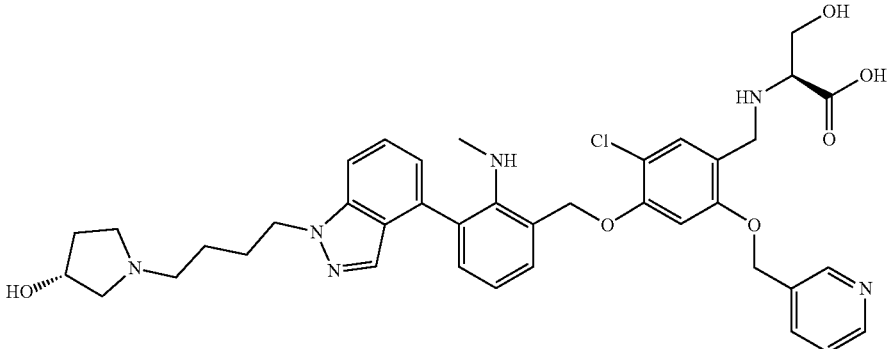 |
| 31 | 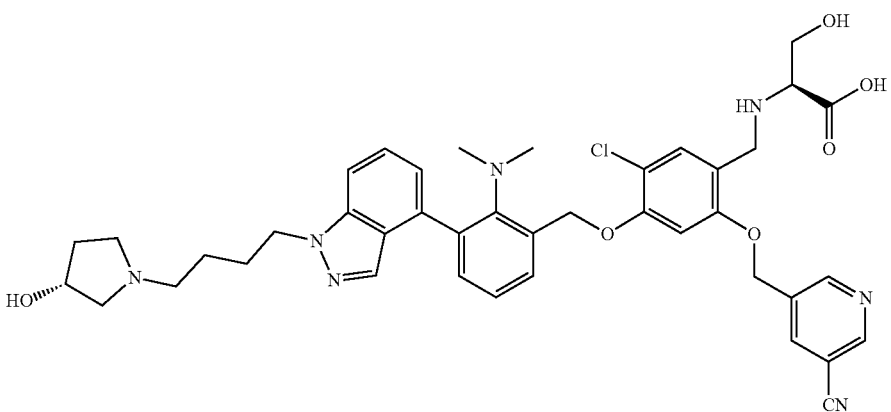 [SMILES: CN(C)c1c(COc2cc(OCc3cncc(C#N)c3)c(CN[C@@H](CO)C(=O)O)cc2Cl)cccc1-c1cccc2c1cnn2CCCCN1CC[C@@H](O)C1] |
| 32 | 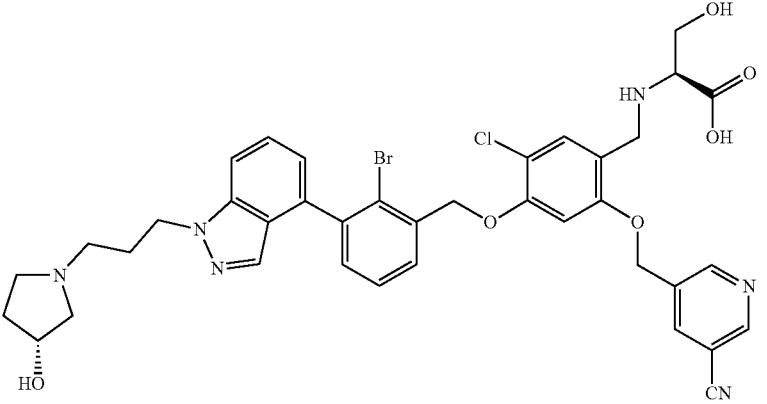 [SMILES: N#Cc1cncc(COc2cc(OCc3cccc(-c4cccc5c4cnn5CCCN4CC[C@@H](O)C4)c3Br)c(Cl)cc2CN[C@@H](CO)C(=O)O)c1] |
| 33 | 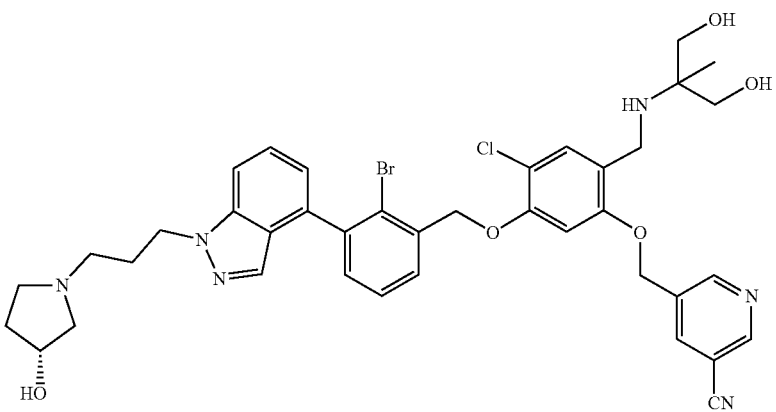 [SMILES: CC(CO)(CO)NCc1cc(Cl)c(OCc2cccc(-c3cccc4c3cnn4CCCN3CC[C@@H](O)C3)c2Br)cc1OCc1cncc(C#N)c1] |

-continued
| No. | Structure |
|---|---|
| 34 | 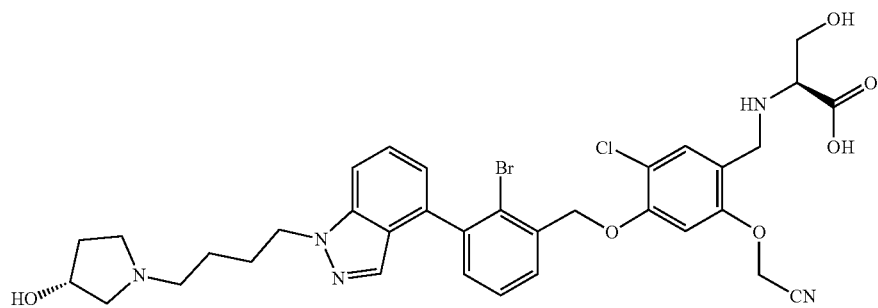 [SMILES: N#CCOc1cc(OCc2cccc(-c3cccc4c3cnn4CCCCN3CC[C@@H](O)C3)c2Br)c(Cl)cc1CN[C@@H](CO)C(=O)O] |
| 35 | 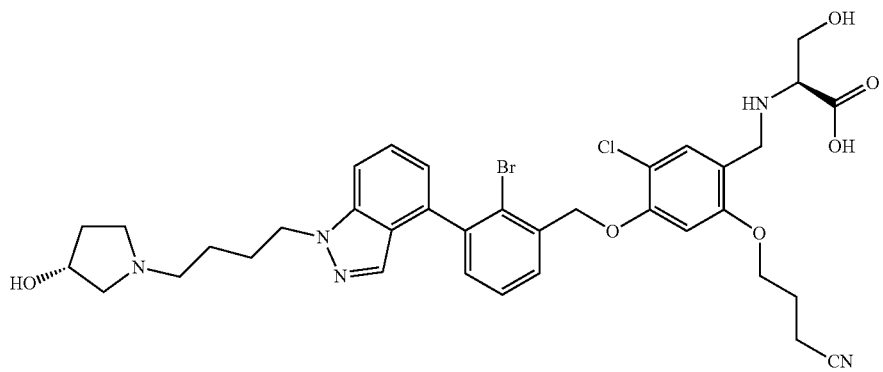 [SMILES: N#CCCCOc1cc(OCc2cccc(-c3cccc4c3cnn4CCCCN3CC[C@@H](O)C3)c2Br)c(Cl)cc1CN[C@@H](CO)C(=O)O] |
| 36 | 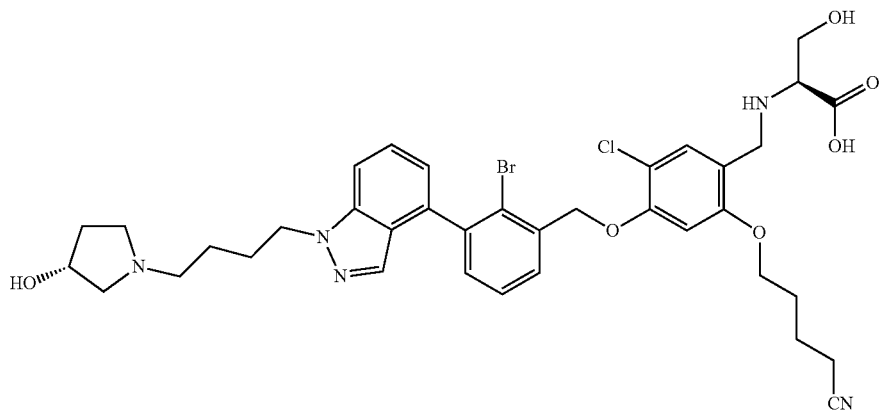 [SMILES: N#CCCCCOc1cc(OCc2cccc(-c3cccc4c3cnn4CCCCN3CC[C@@H](O)C3)c2Br)c(Cl)cc1CN[C@@H](CO)C(=O)O] |
| 37 | 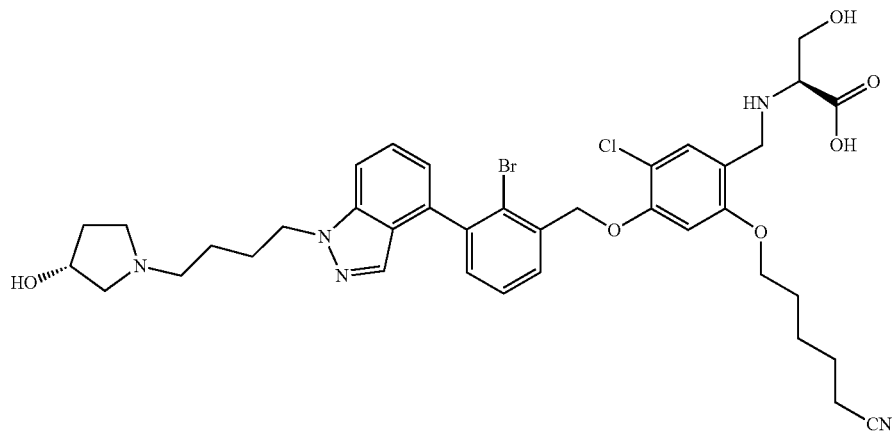 [SMILES: N#CCCCCCOc1cc(OCc2cccc(-c3cccc4c3cnn4CCCCN3CC[C@@H](O)C3)c2Br)c(Cl)cc1CN[C@@H](CO)C(=O)O] |

| No. | Structure |
|---|---|
| 38 | 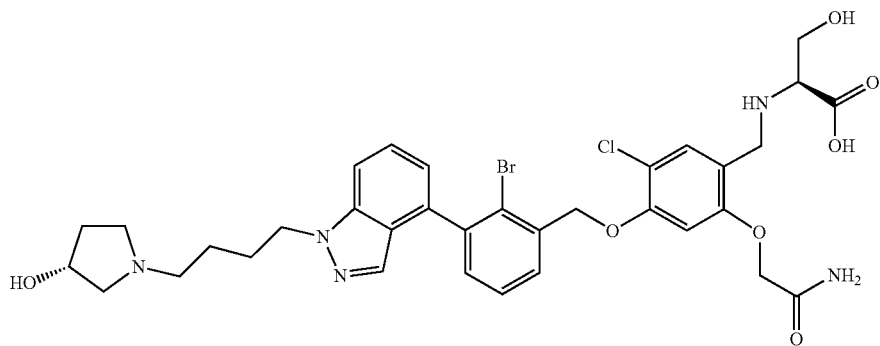 [SMILES: NC(=O)COc1cc(OCc2cccc(-c3cccc4c3cnn4CCCCN3CC[C@@H](O)C3)c2Br)c(Cl)cc1CN[C@@H](CO)C(=O)O] |
| 39 | 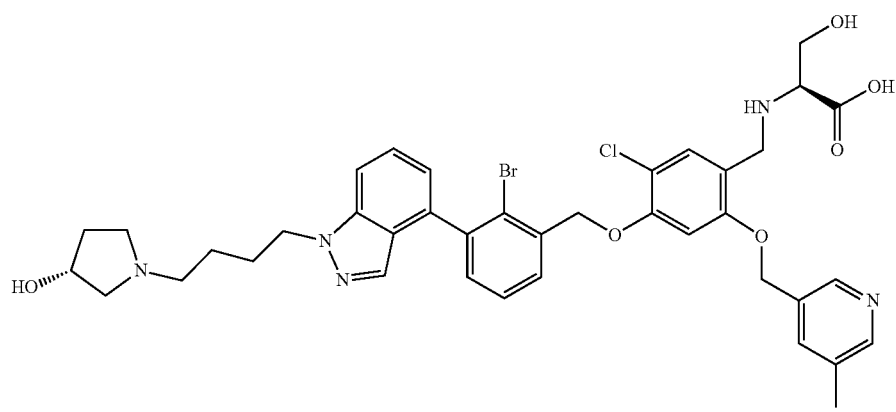 [SMILES: Cc1cncc(COc2cc(OCc3cccc(-c4cccc5c4cnn5CCCCN4CC[C@@H](O)C4)c3Br)c(Cl)cc2CN[C@@H](CO)C(=O)O)c1] |
| 40 | 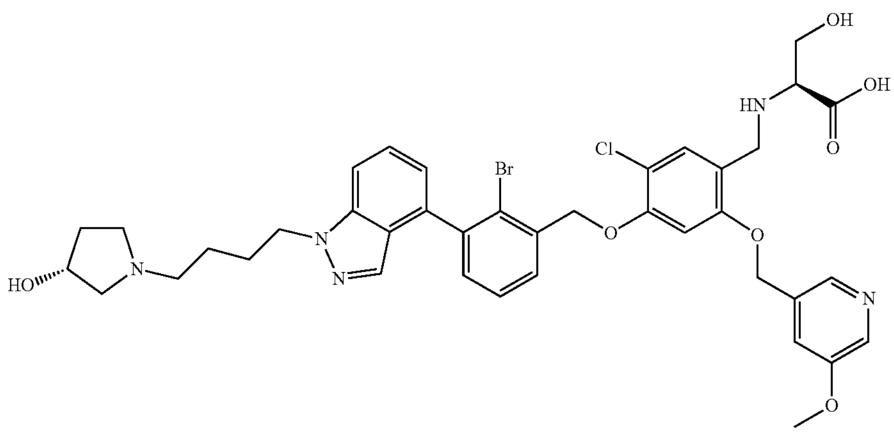 [SMILES: COc1cncc(COc2cc(OCc3cccc(-c4cccc5c4cnn5CCCCN4CC[C@@H](O)C4)c3Br)c(Cl)cc2CN[C@@H](CO)C(=O)O)c1] |
| 41 | 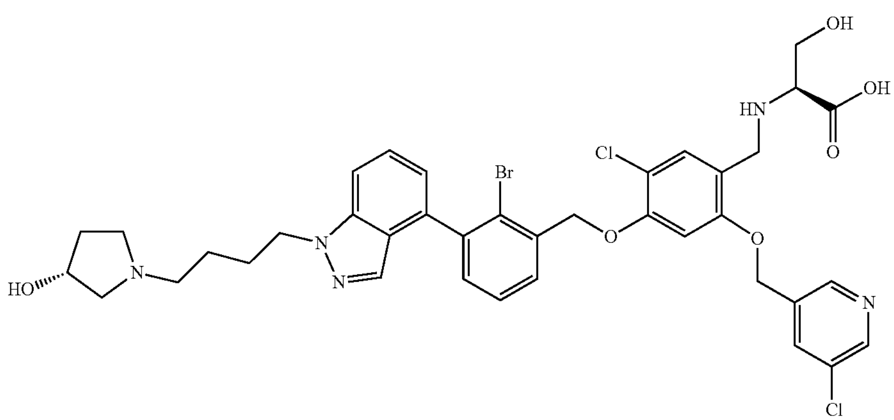 [SMILES: O=C(O)[C@H](CO)NCc1cc(Cl)c(OCc2cccc(-c3cccc4c3cnn4CCCCN3CC[C@@H](O)C3)c2Br)cc1OCc1cncc(Cl)c1] |

| No. | Structure |
|-----|-----------|
| 42 | 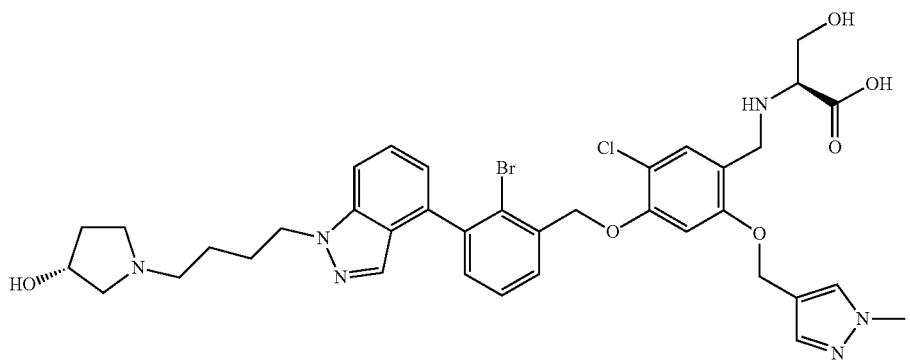 [SMILES: Cn1cc(COc2cc(OCc3cccc(-c4cccc5c4cnn5CCCCN4CC[C@@H](O)C4)c3Br)c(Cl)cc2CN[C@@H](CO)C(=O)O)cn1] |
| 43 | 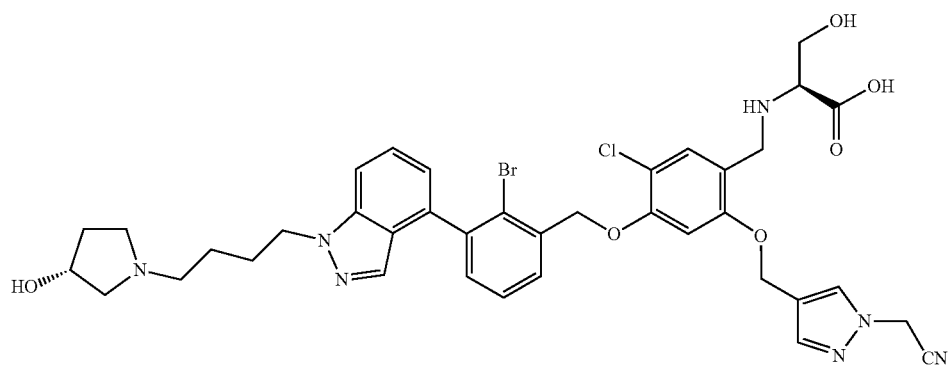 [SMILES: N#CCn1cc(COc2cc(OCc3cccc(-c4cccc5c4cnn5CCCCN4CC[C@@H](O)C4)c3Br)c(Cl)cc2CN[C@@H](CO)C(=O)O)cn1] |
| 44 | 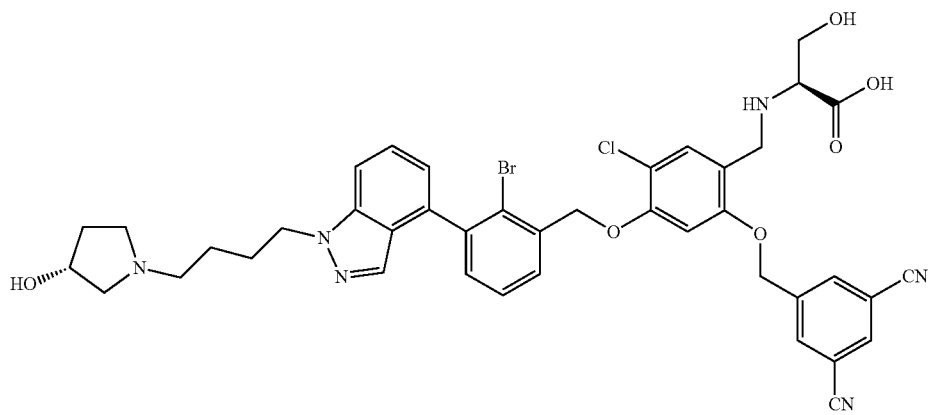 [SMILES: N#Cc1cc(C#N)cc(COc2cc(OCc3cccc(-c4cccc5c4cnn5CCCCN4CC[C@@H](O)C4)c3Br)c(Cl)cc2CN[C@@H](CO)C(=O)O)c1] |
| 45 | 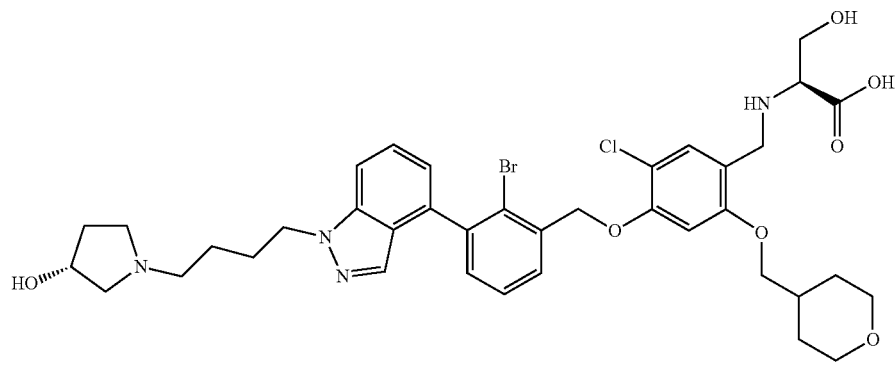 [SMILES: O=C(O)[C@H](CO)NCc1cc(Cl)c(OCc2cccc(-c3cccc4c3cnn4CCCCN3CC[C@@H](O)C3)c2Br)cc1OCC1CCOCC1] |

-continued
| No. | Structure |
|---|---|
| 46 | 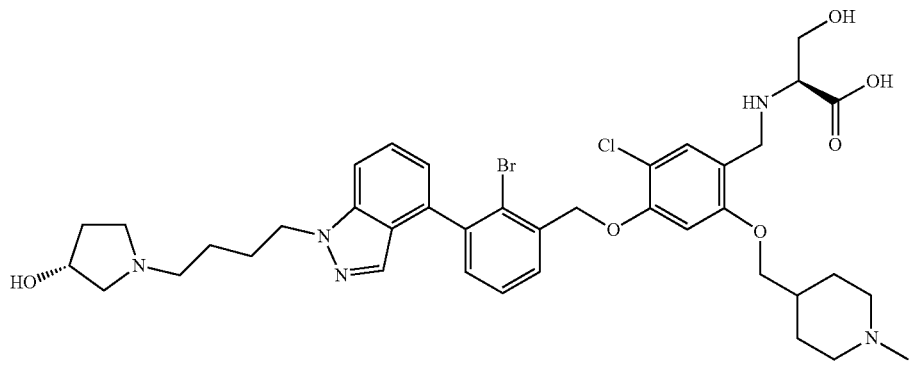 [SMILES: CN1CCC(COc2cc(OCc3cccc(-c4cccc5c4cnn5CCCCN4CC[C@@H](O)C4)c3Br)c(Cl)cc2CN[C@@H](CO)C(=O)O)CC1] |
| 47 | 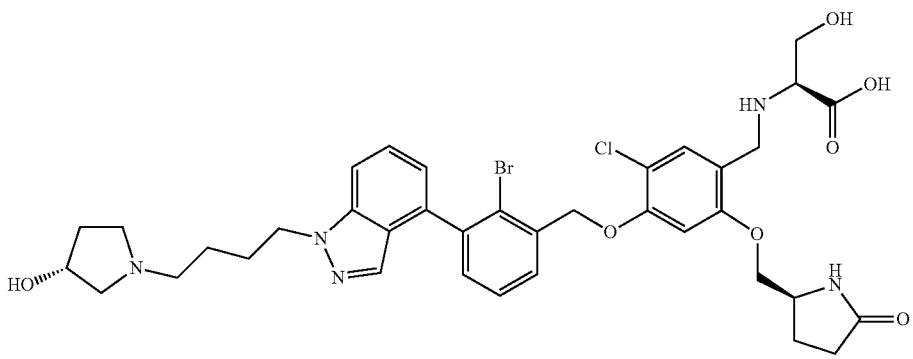 [SMILES: O=C1CC[C@@H](COc2cc(OCc3cccc(-c4cccc5c4cnn5CCCCN4CC[C@@H](O)C4)c3Br)c(Cl)cc2CN[C@@H](CO)C(=O)O)N1] |
| 48 | 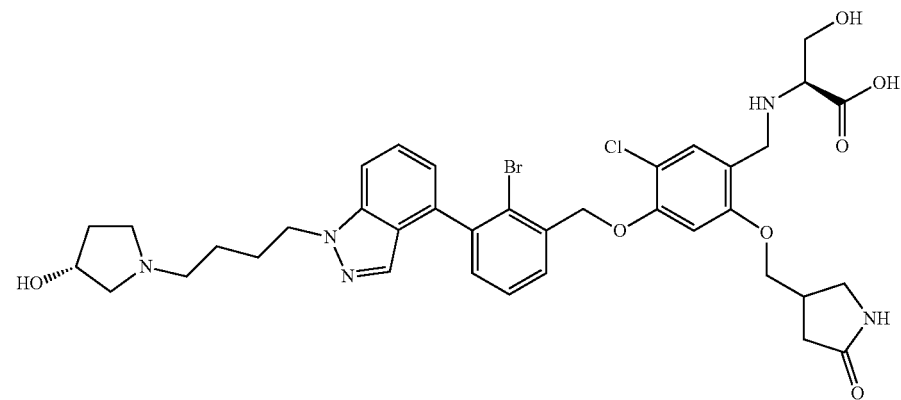 [SMILES: O=C1CC(COc2cc(OCc3cccc(-c4cccc5c4cnn5CCCCN4CC[C@@H](O)C4)c3Br)c(Cl)cc2CN[C@@H](CO)C(=O)O)CN1] |
| 49 | 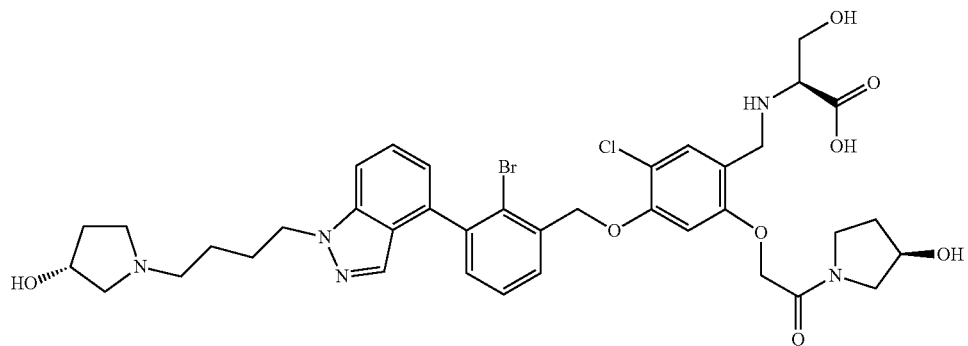 [SMILES: O=C(O)[C@H](CO)NCc1cc(Cl)c(OCc2cccc(-c3cccc4c3cnn4CCCCN3CC[C@@H](O)C3)c2Br)cc1OCC(=O)N1CC[C@@H](O)C1] |

| No. | Structure |
|---|---|
| 50 | 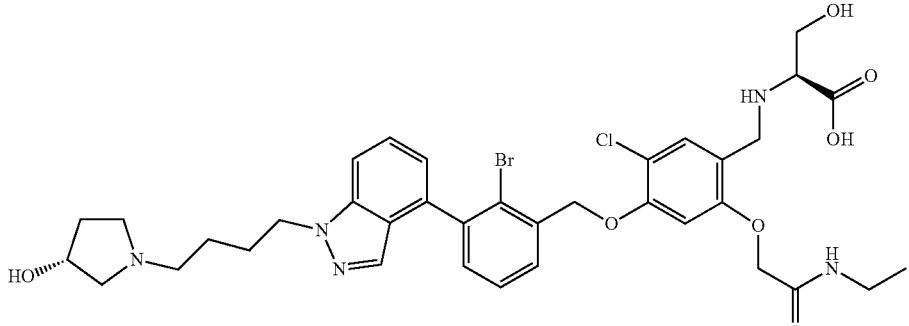 |
| 51 | 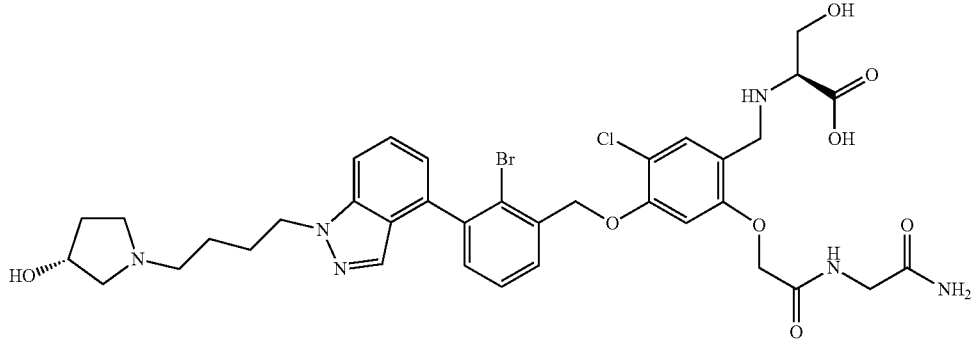 [SMILES: NC(=O)CNC(=O)COc1cc(OCc2cccc(-c3cccc4c3cnn4CCCCN3CC[C@@H](O)C3)c2Br)c(Cl)cc1CN[C@@H](CO)C(=O)O] |
| 52 | 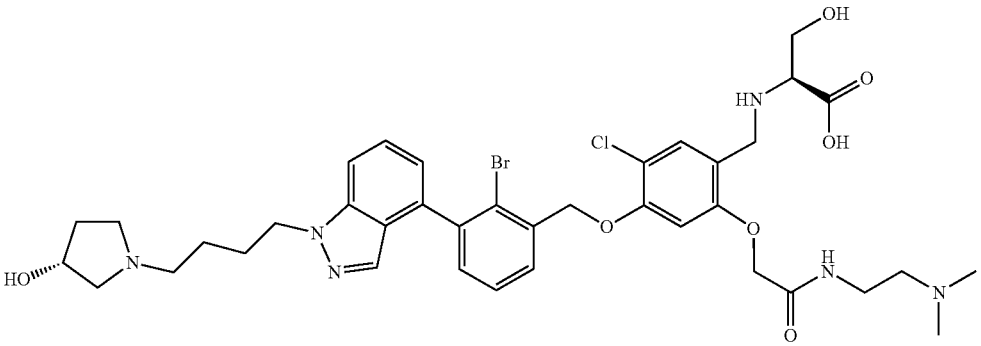 [SMILES: CN(C)CCNC(=O)COc1cc(OCc2cccc(-c3cccc4c3cnn4CCCCN3CC[C@@H](O)C3)c2Br)c(Cl)cc1CN[C@@H](CO)C(=O)O] |
| 53 | 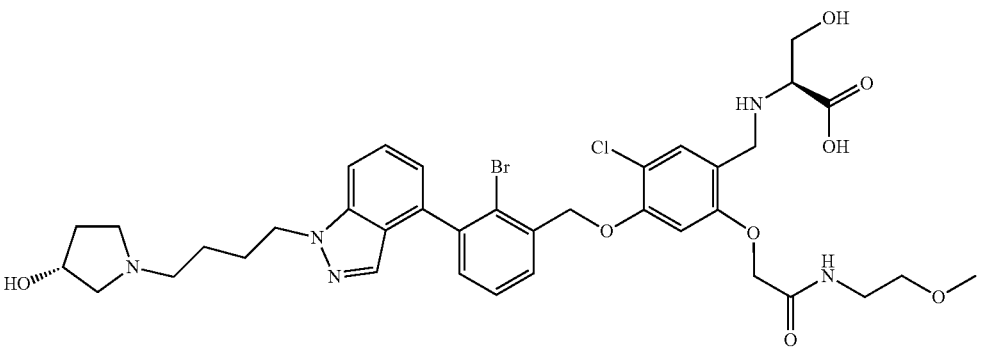 [SMILES: COCCNC(=O)COc1cc(OCc2cccc(-c3cccc4c3cnn4CCCCN3CC[C@@H](O)C3)c2Br)c(Cl)cc1CN[C@@H](CO)C(=O)O] |

-continued
| No. | Structure |
|---|---|
| 54 | 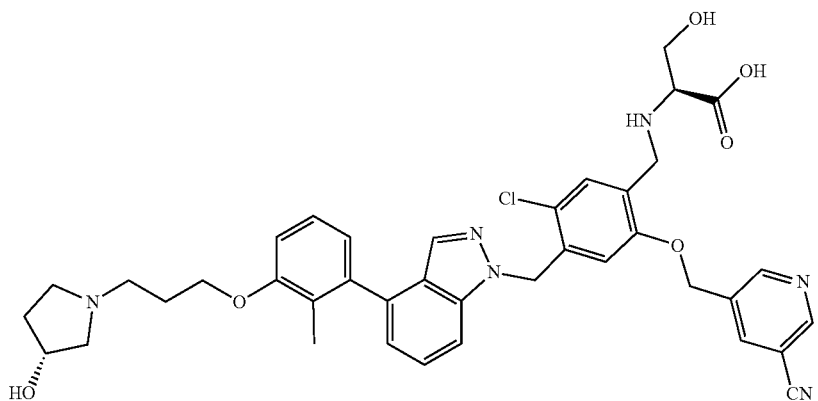 [SMILES: Cc1c(OCCCN2CC[C@@H](O)C2)cccc1-c1cccc2c1cnn2Cc1cc(OCc2cncc(C#N)c2)c(CN[C@@H](CO)C(=O)O)cc1Cl] |
| 55 | 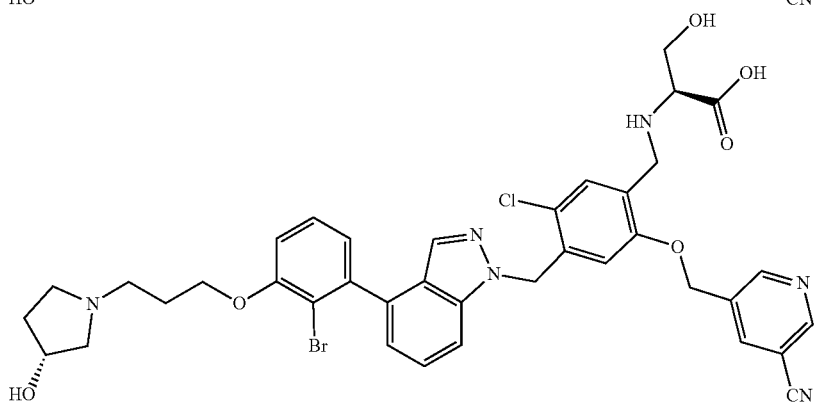 |
| 56 | 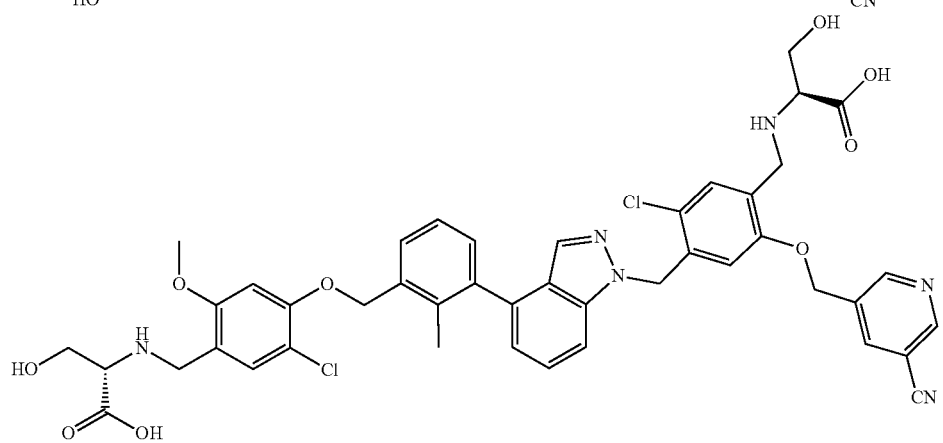 |
| 57 | 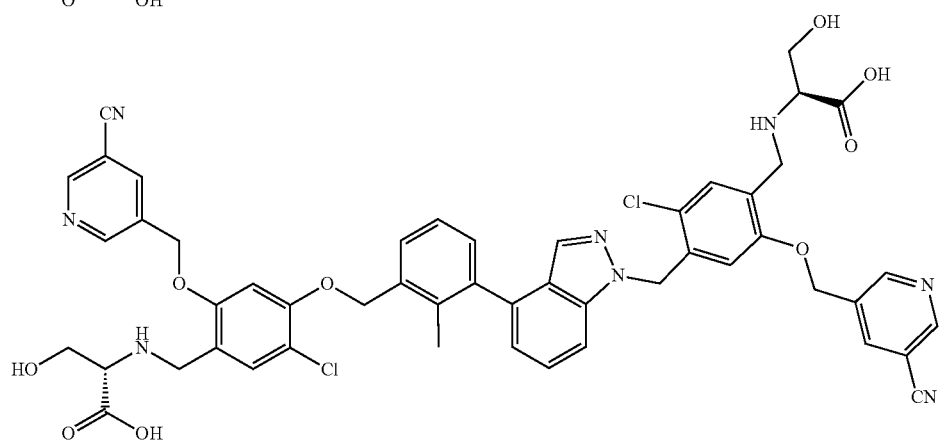 |

| No. | Structure |
|---|---|
| 58 | 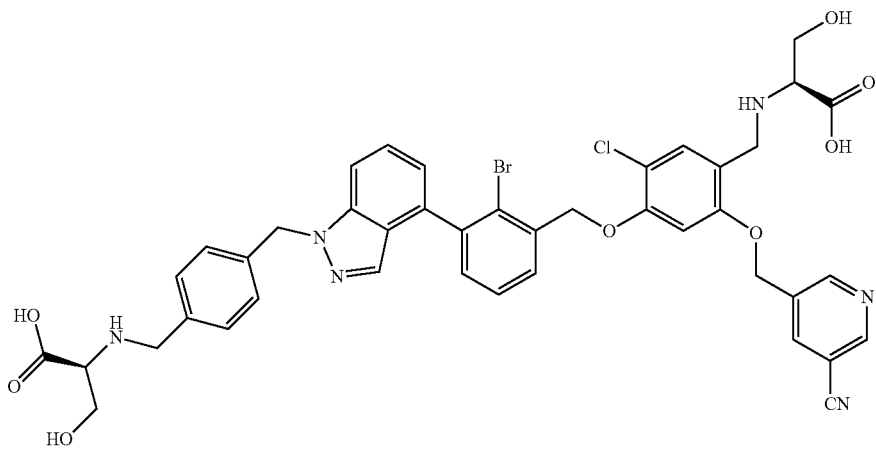 [SMILES: N#Cc1cncc(COc2cc(OCc3cccc(-c4cccc5c4cnn5Cc4ccc(CN[C@@H](CO)C(=O)O)cc4)c3Br)c(Cl)cc2CN[C@@H](CO)C(=O)O)c1] |
| 59 | 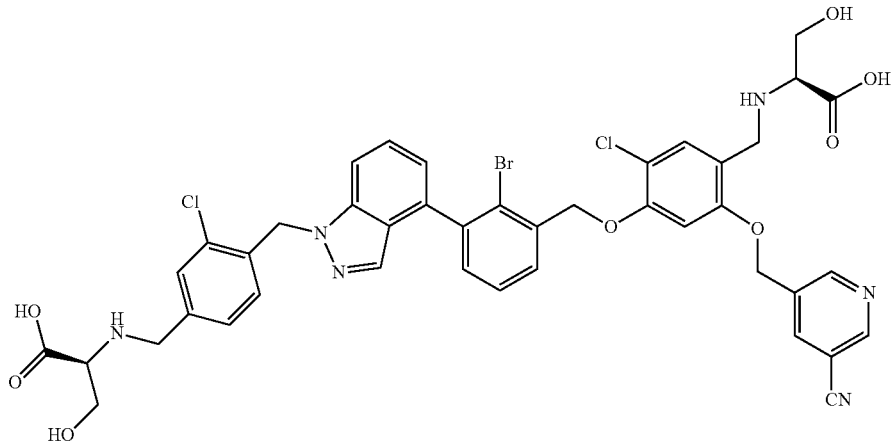 [SMILES: N#Cc1cncc(COc2cc(OCc3cccc(-c4cccc5c4cnn5Cc4ccc(CN[C@@H](CO)C(=O)O)cc4Cl)c3Br)c(Cl)cc2CN[C@@H](CO)C(=O)O)c1] |
| 60 | 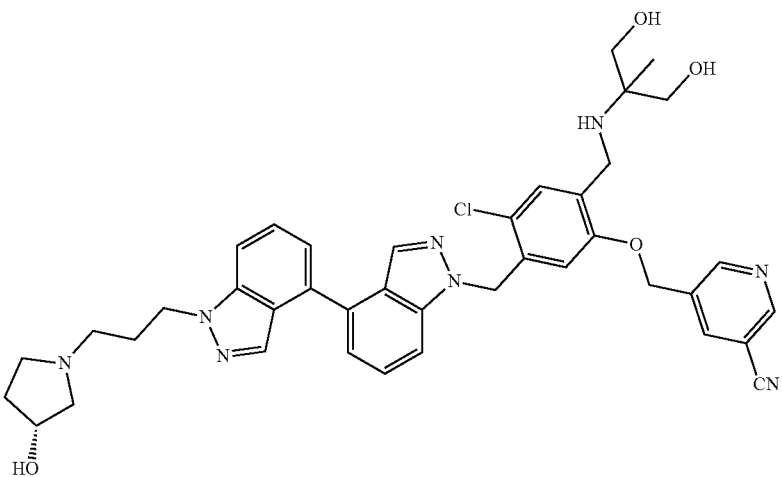 [SMILES: CC(CO)(CO)NCc1cc(Cl)c(Cn2ncc3c(-c4cccc5c4cnn5CCCN4CC[C@@H](O)C4)cccc32)cc1OCc1cncc(C#N)c1] |

| No. | Structure |
|---|---|
| 61 | 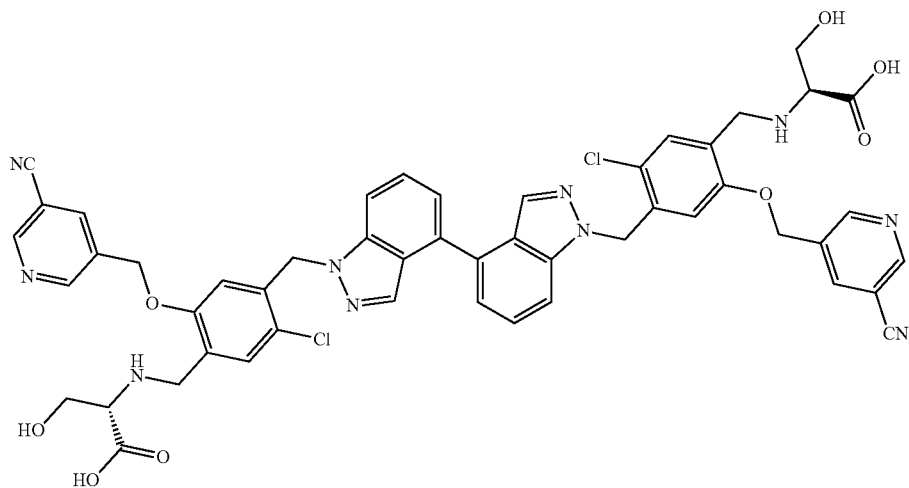 [SMILES: N#Cc1cncc(COc2cc(Cn3ncc4c(-c5cccc6c5cnn6Cc5cc(OCc6cncc(C#N)c6)c(CN[C@@H](CO)C(=O)O)cc5Cl)cccc43)c(Cl)cc2CN[C@@H](CO)C(=O)O)c1] |
| 62 | 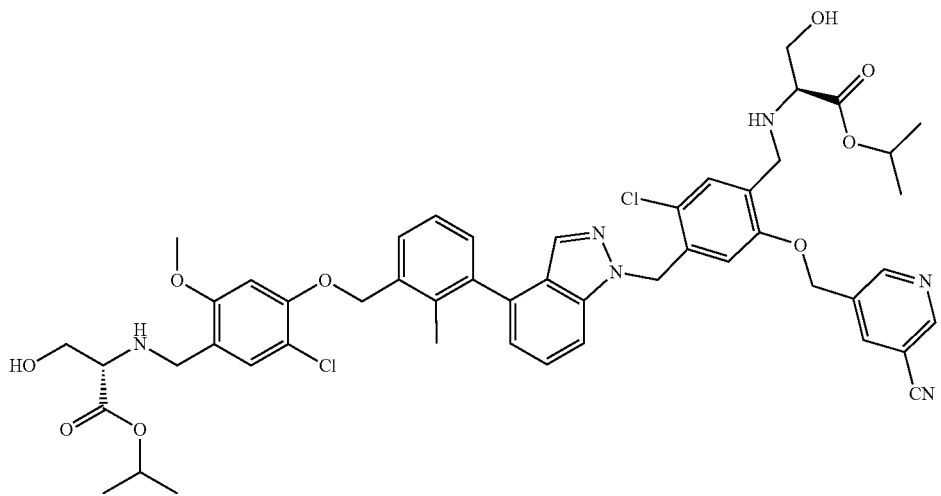 [SMILES: COc1cc(OCc2cccc(-c3cccc4c3cnn4Cc3cc(OCc4cncc(C#N)c4)c(CN[C@@H](CO)C(=O)OC(C)C)cc3Cl)c2C)c(Cl)cc1CN[C@@H](CO)C(=O)OC(C)C] |
| 63 | 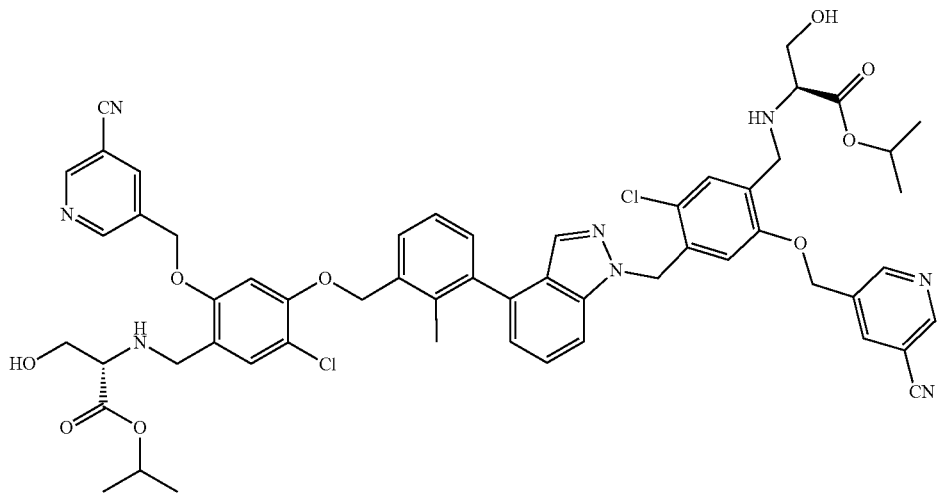 [SMILES: Cc1c(COc2cc(OCc3cncc(C#N)c3)c(CN[C@@H](CO)C(=O)OC(C)C)cc2Cl)cccc1-c1cccc2c1cnn2Cc1cc(OCc2cncc(C#N)c2)c(CN[C@@H](CO)C(=O)OC(C)C)cc1Cl] |

| No. | Structure |
|---|---|
| 64 | 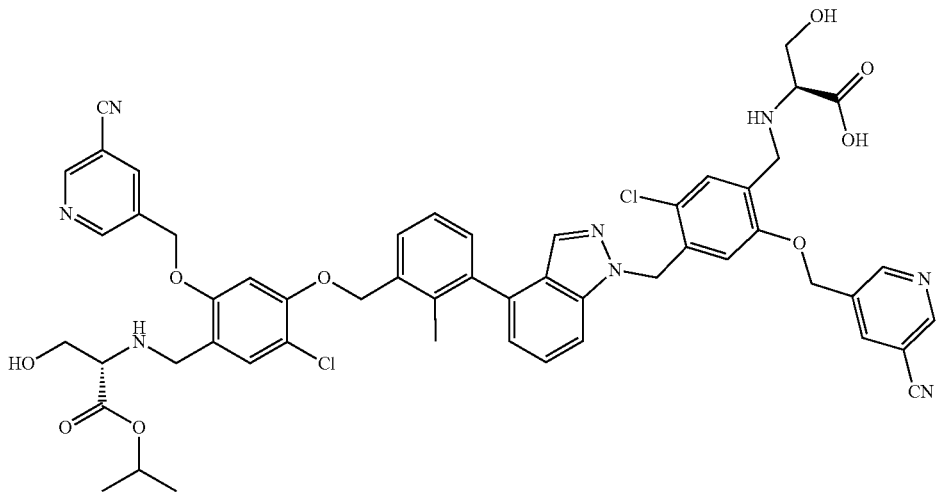 [SMILES: Cc1c(COc2cc(OCc3cncc(C#N)c3)c(CN[C@@H](CO)C(=O)OC(C)C)cc2Cl)cccc1-c1cccc2c1cnn2Cc1cc(OCc2cncc(C#N)c2)c(CN[C@@H](CO)C(=O)O)cc1Cl] |
| 65 | 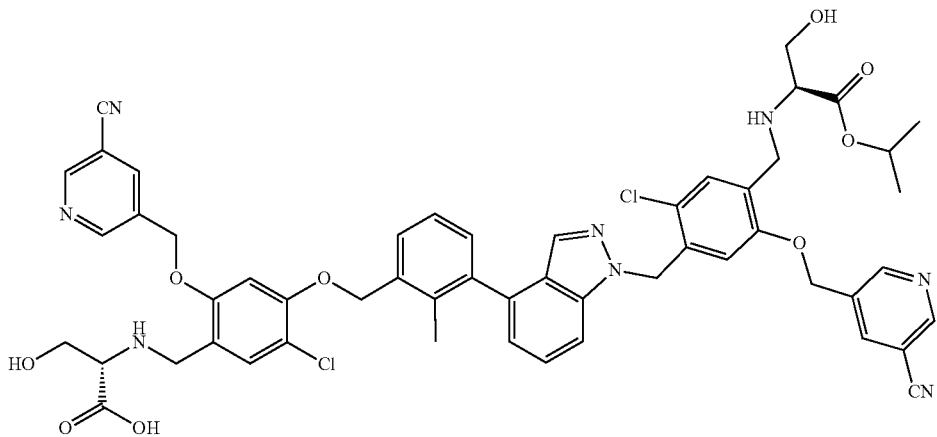 [SMILES: Cc1c(COc2cc(OCc3cncc(C#N)c3)c(CN[C@@H](CO)C(=O)O)cc2Cl)cccc1-c1cccc2c1cnn2Cc1cc(OCc2cncc(C#N)c2)c(CN[C@@H](CO)C(=O)OC(C)C)cc1Cl] |
| 66 | 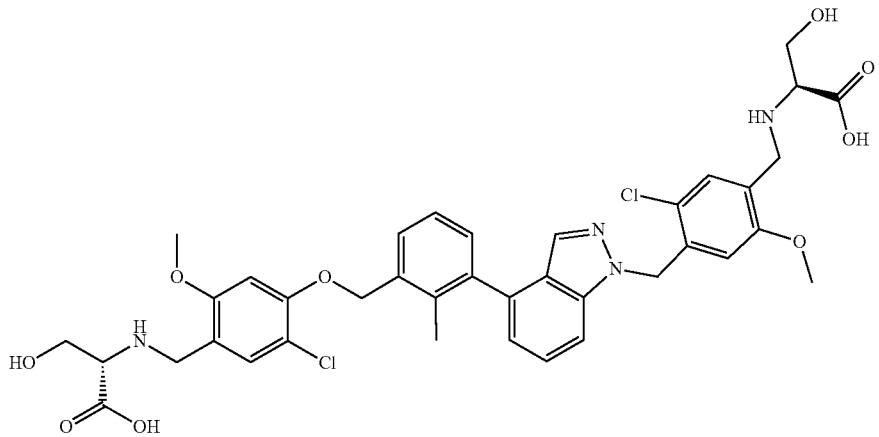 [SMILES: COc1cc(Cn2ncc3c(-c4cccc(COc5cc(OC)c(CN[C@@H](CO)C(=O)O)cc5Cl)c4C)cccc32)c(Cl)cc1CN[C@@H](CO)C(=O)O] |

| No. | Structure |
|---|---|
| 67 | 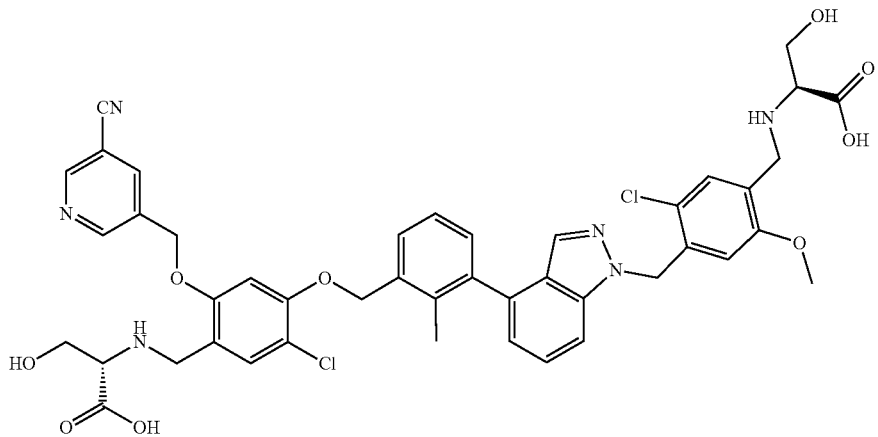 [SMILES: COc1cc(Cn2ncc3c(-c4cccc(COc5cc(OCc6cncc(C#N)c6)c(CN[C@@H](CO)C(=O)O)cc5Cl)c4C)cccc32)c(Cl)cc1CN[C@@H](CO)C(=O)O] |
| 68 | 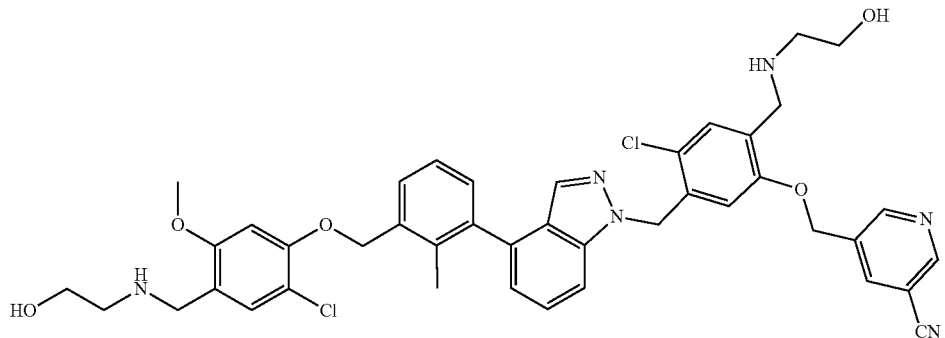 [SMILES: COc1cc(OCc2cccc(-c3cccc4c3cnn4Cc3cc(OCc4cncc(C#N)c4)c(CNCCO)cc3Cl)c2C)c(Cl)cc1CNCCO] |
| 69 | 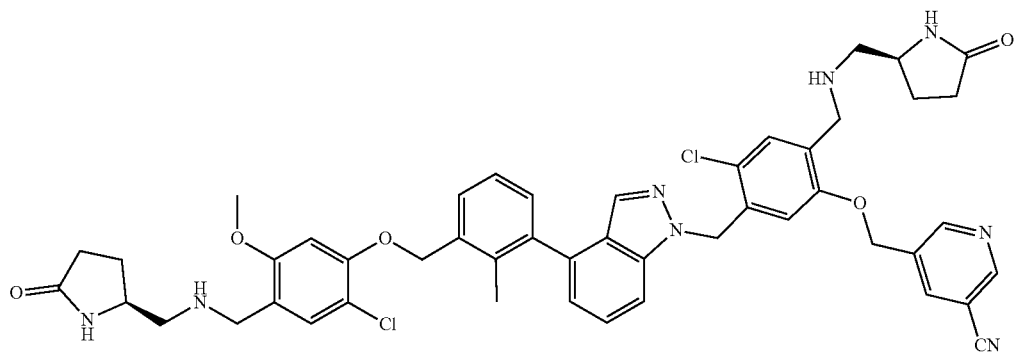 [SMILES: COc1cc(OCc2cccc(-c3cccc4c3cnn4Cc3cc(OCc4cncc(C#N)c4)c(CNC[C@@H]4CCC(=O)N4)cc3Cl)c2C)c(Cl)cc1CNC[C@@H]1CCC(=O)N1] |

-continued
| No. | Structure |
|---|---|
| 70 | 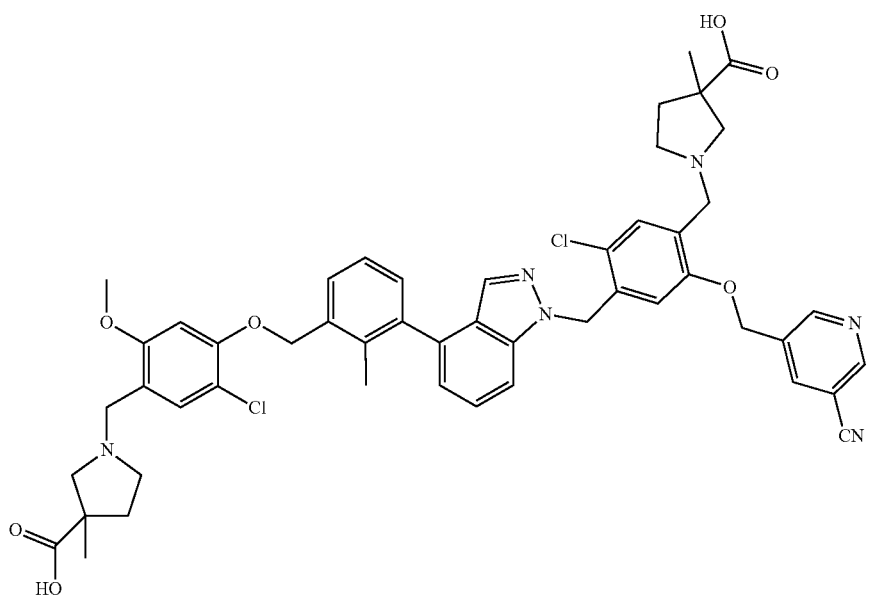 [SMILES: COc1cc(OCc2cccc(-c3cccc4c3cnn4Cc3cc(OCc4cncc(C#N)c4)c(CN4CCC(C)(C(=O)O)C4)cc3Cl)c2C)c(Cl)cc1CN1CCC(C)(C(=O)O)C1] |
| 71 | 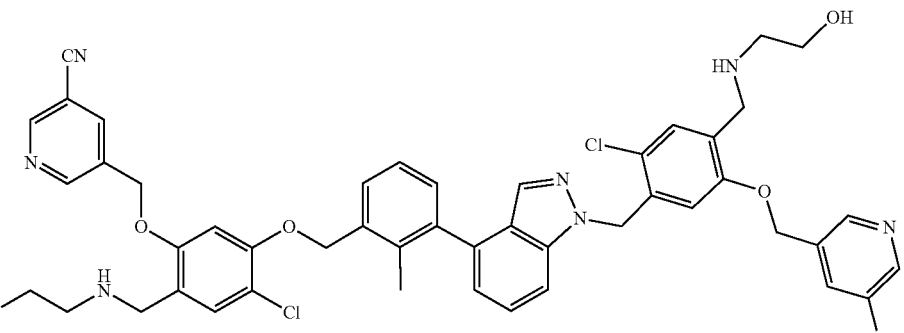 |
| 72 | 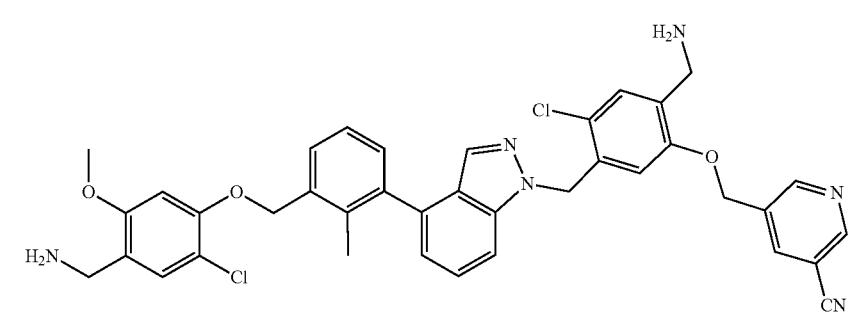 [SMILES: COc1cc(OCc2cccc(-c3cccc4c3cnn4Cc3cc(OCc4cncc(C#N)c4)c(CN)cc3Cl)c2C)c(Cl)cc1CN] |
| 73 | 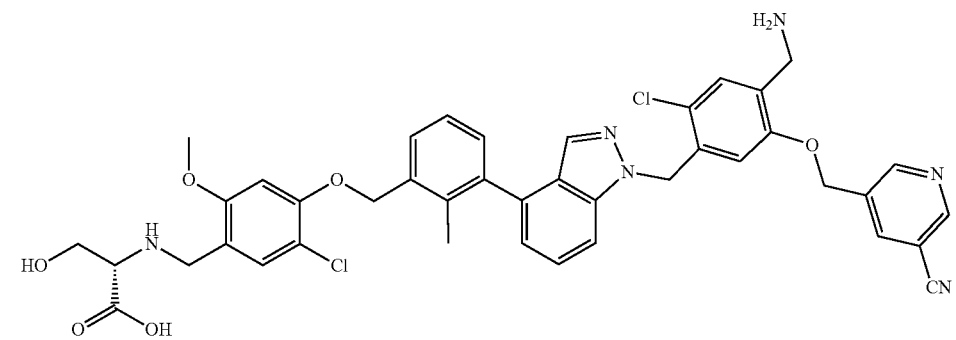 [SMILES: COc1cc(OCc2cccc(-c3cccc4c3cnn4Cc3cc(OCc4cncc(C#N)c4)c(CN)cc3Cl)c2C)c(Cl)cc1CN[C@@H](CO)C(=O)O] |

-continued
| No. | Structure |
|---|---|
| 74 | 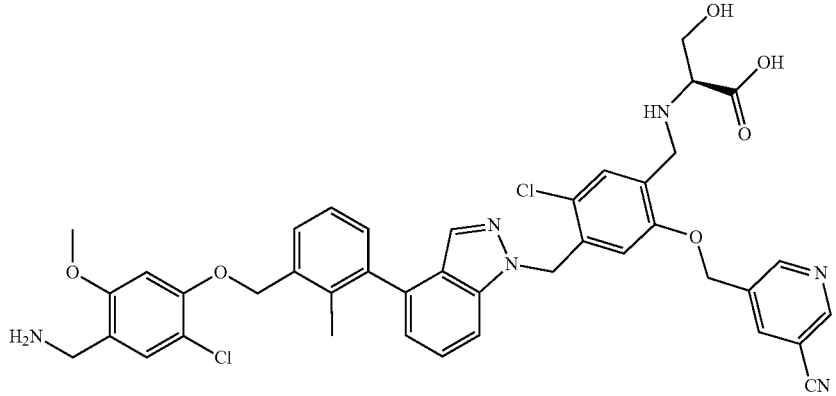 [SMILES: COc1cc(OCc2cccc(-c3cccc4c3cnn4Cc3cc(OCc4cncc(C#N)c4)c(CN[C@@H](CO)C(=O)O)cc3Cl)c2C)c(Cl)cc1CN] |
| 75 | 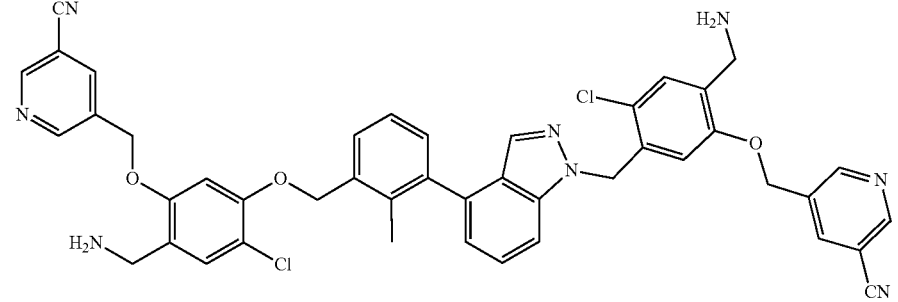 [SMILES: Cc1c(COc2cc(OCc3cncc(C#N)c3)c(CN)cc2Cl)cccc1-c1cccc2c1cnn2Cc1cc(OCc2cncc(C#N)c2)c(CN)cc1Cl] |
| 76 | 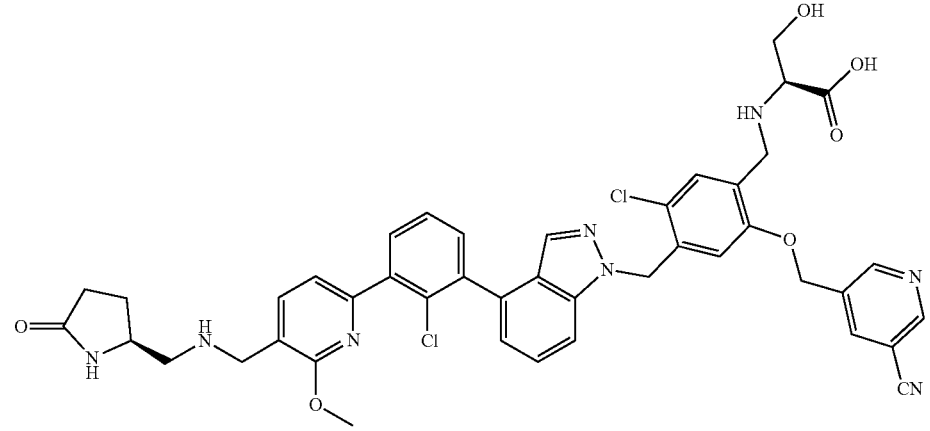 [SMILES: COc1nc(-c2cccc(-c3cccc4c3cnn4Cc3cc(OCc4cncc(C#N)c4)c(CN[C@@H](CO)C(=O)O)cc3Cl)c2Cl)ccc1CNC[C@@H]1CCC(=O)N1] |
| 77 | 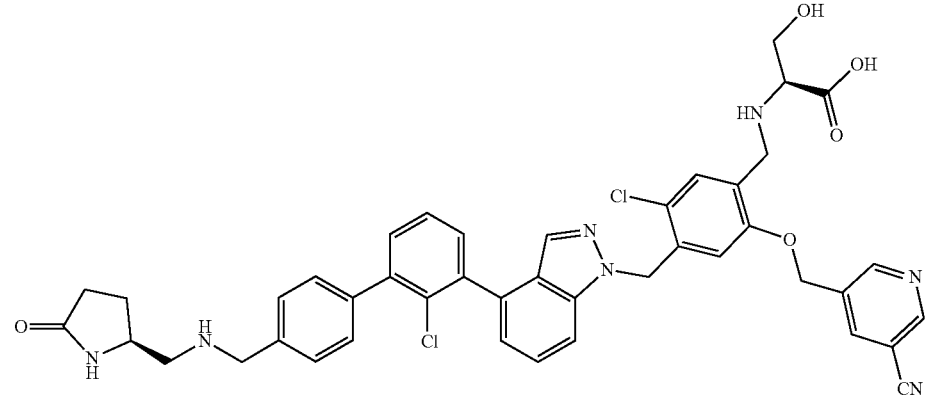 [SMILES: N#Cc1cncc(COc2cc(Cn3ncc4c(-c5cccc(-c6ccc(CNC[C@@H]7CCC(=O)N7)cc6)c5Cl)cccc43)c(Cl)cc2CN[C@@H](CO)C(=O)O)c1] |

| No. | Structure |
|---|---|
| 78 | 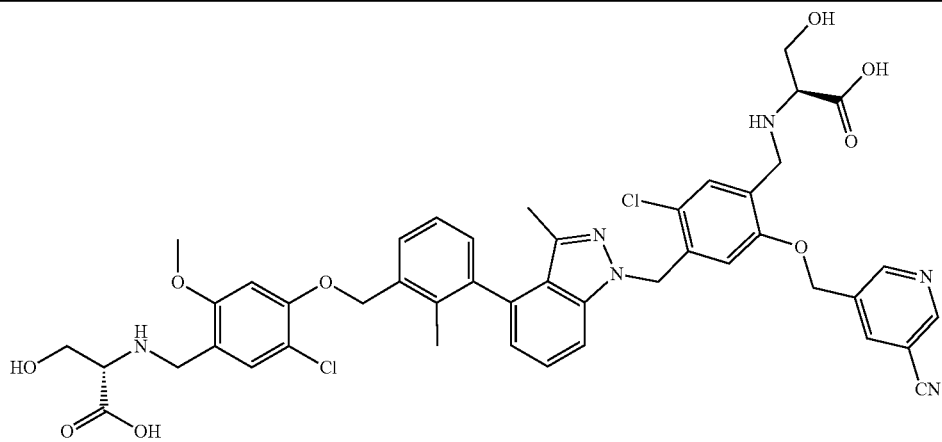 |
| 79 | 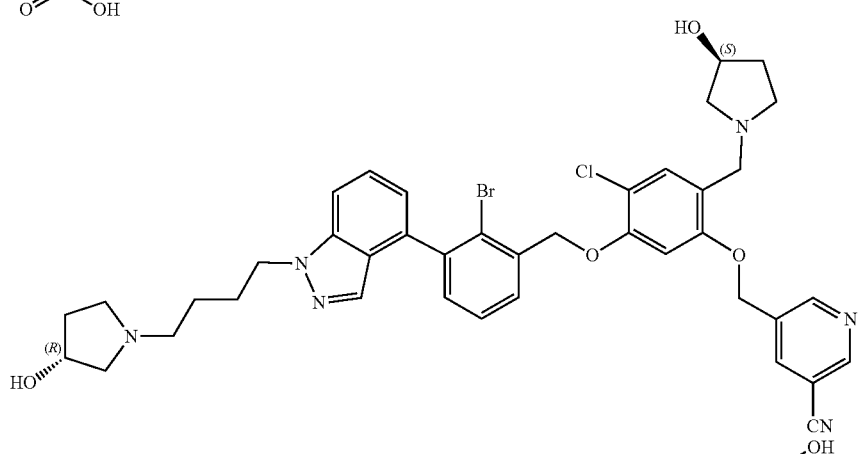 |
| 80 | 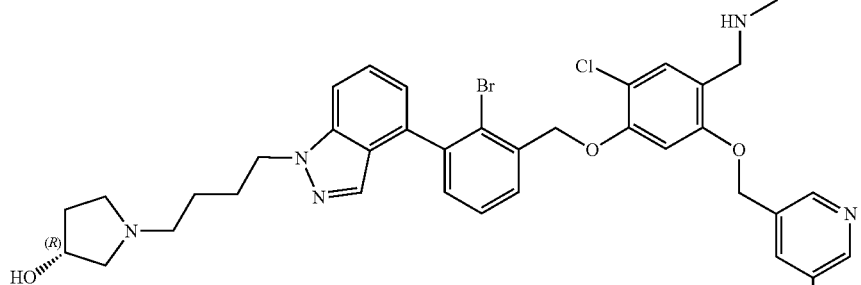 |
| 81 | 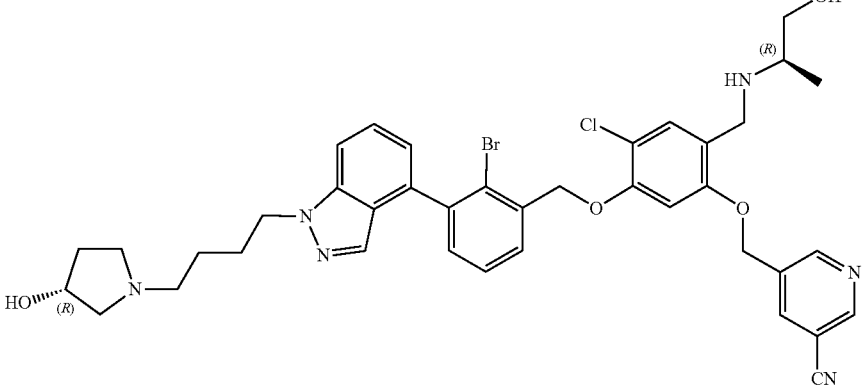 |

-continued
| No. | Structure |
|---|---|
| 82 | 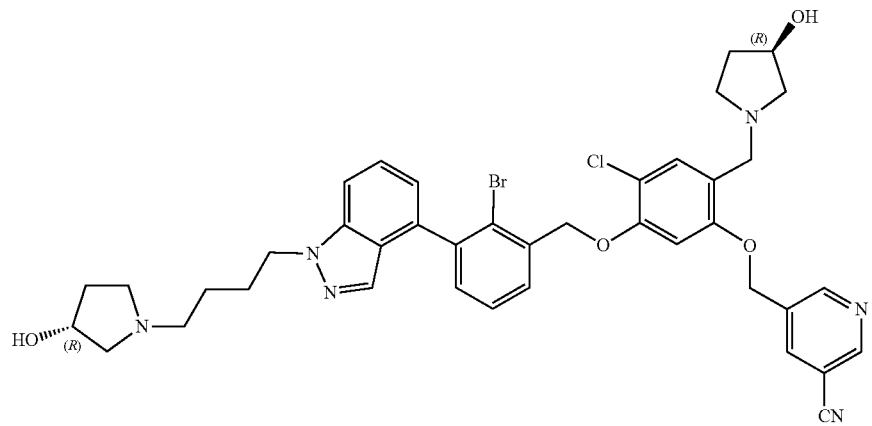 |
| 83 | 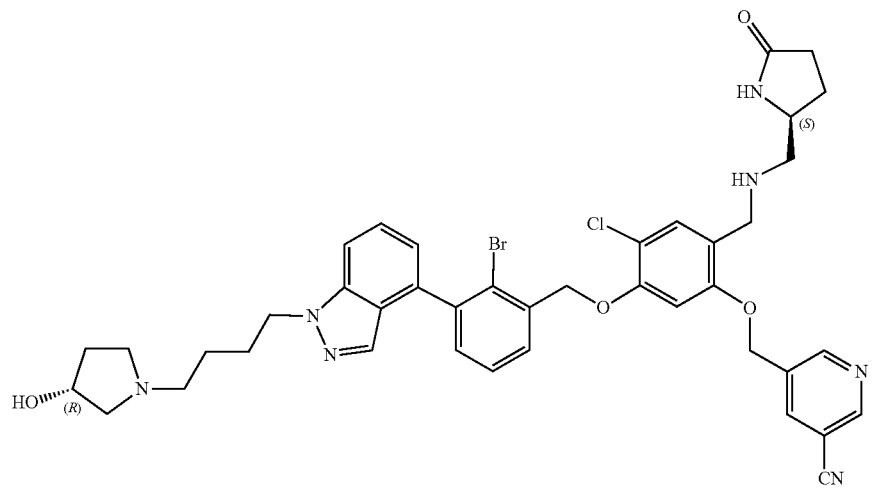 |
| 84 | 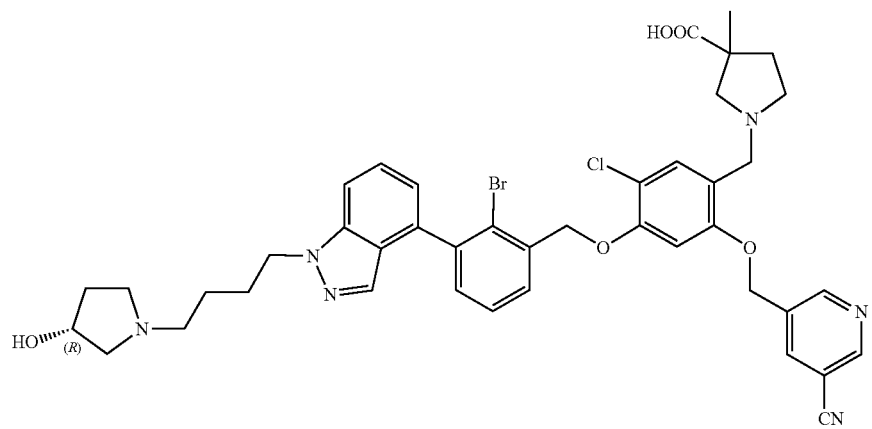 |

-continued

| No. | Structure |
|---|---|
| 85 | 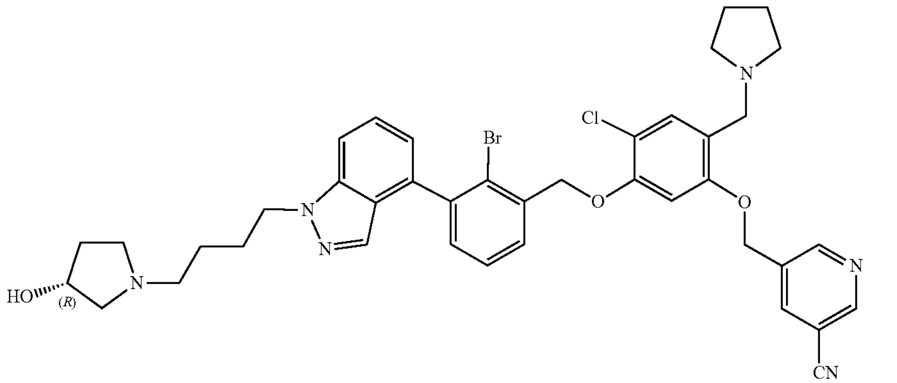 |
| 86 | 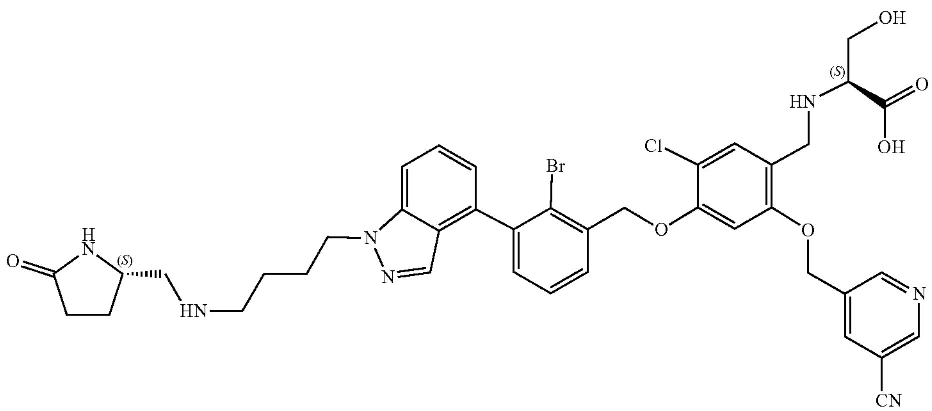 |
| 87 | 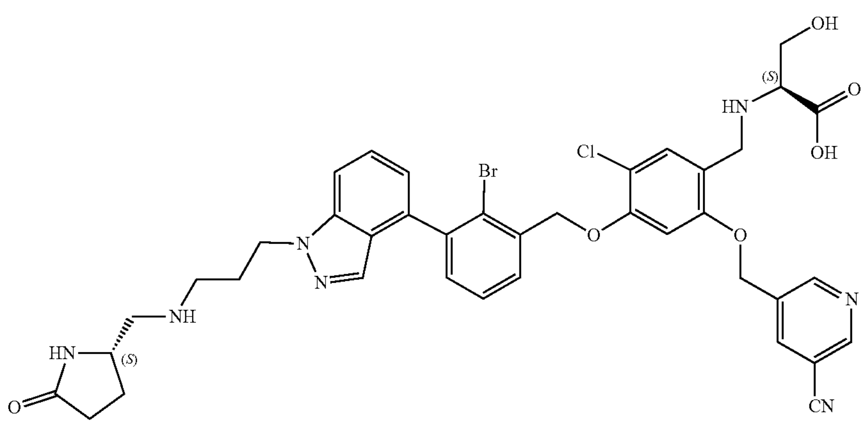 |
| 88 | 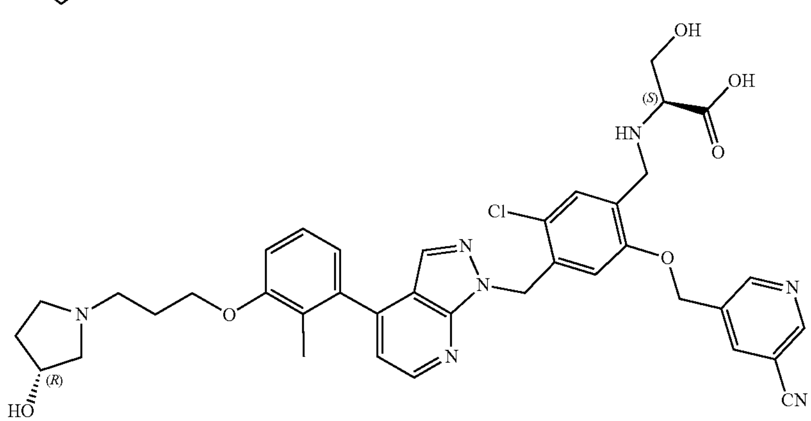 |

| No. | Structure |
|---|---|
| 89 | 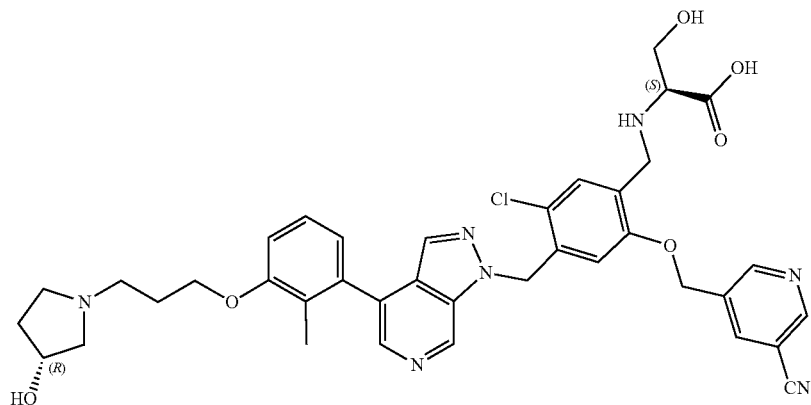 |
| 90 | 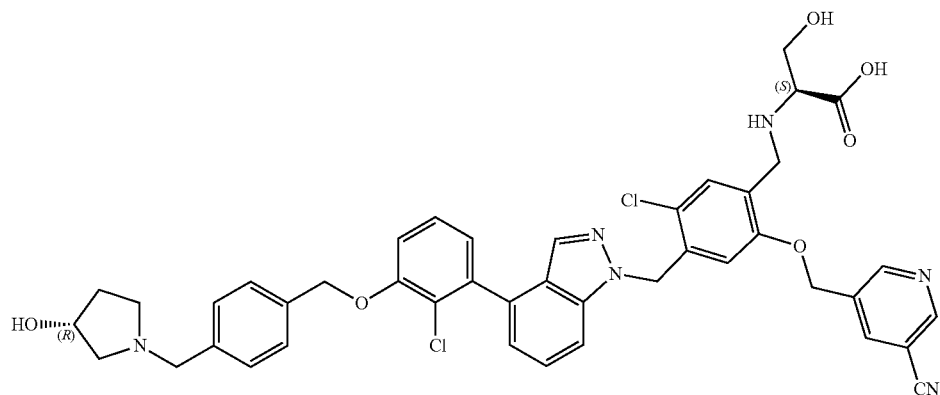 |
| 91 | 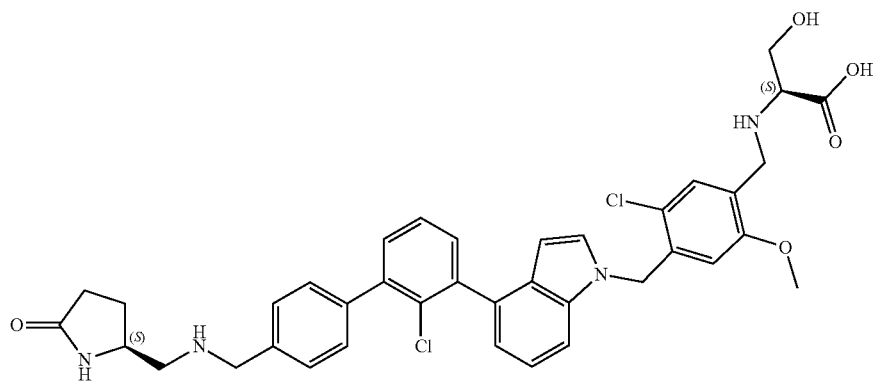 |
| 92 | 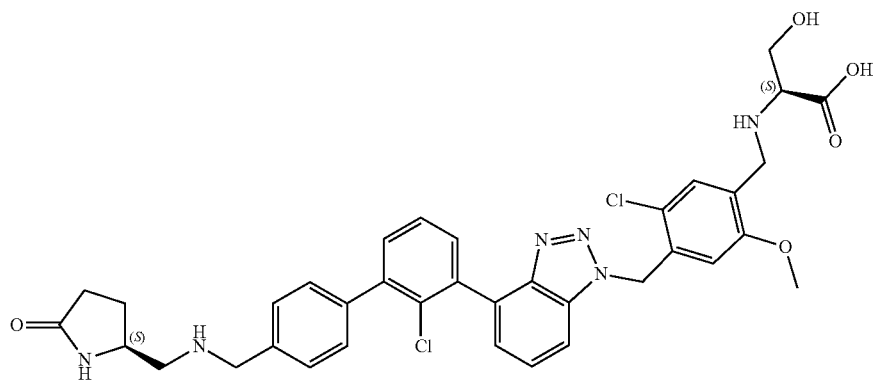 |

| No. | Structure |
|---|---|
| 93 | 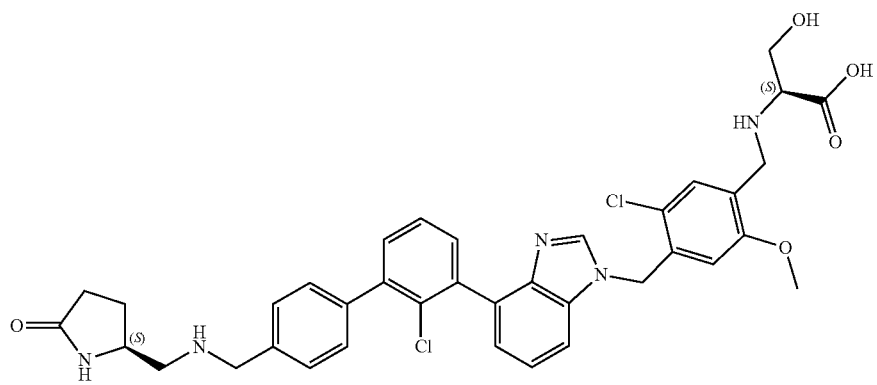 |
| 94 | 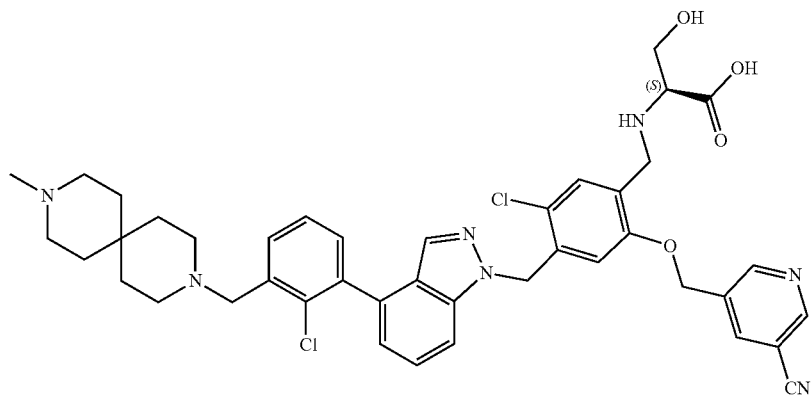 |
| 95 | 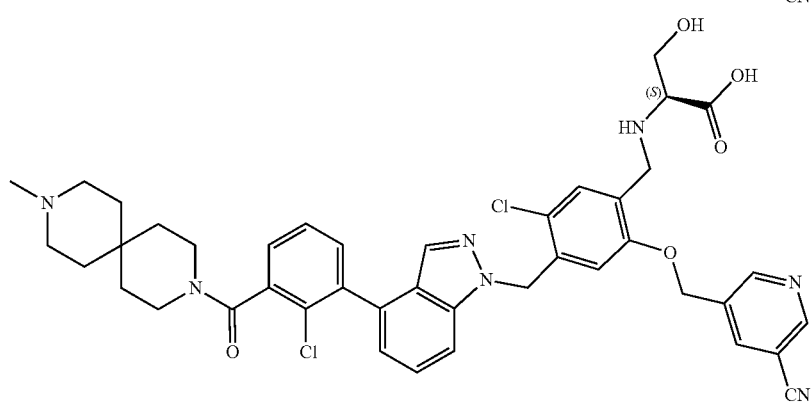 |
| 96 | 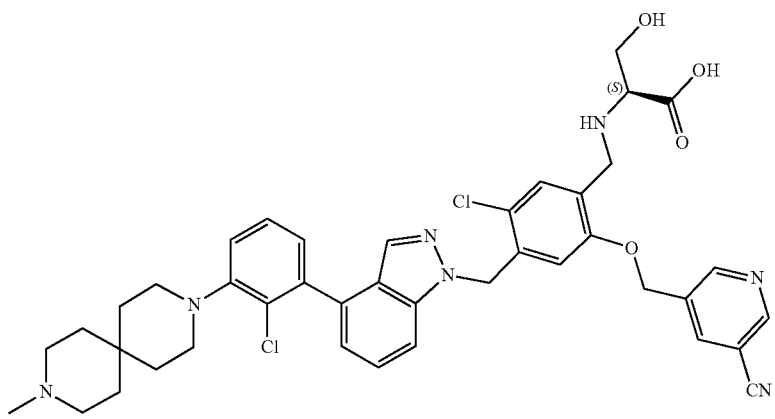 |

In addition, the present invention also provides a pharmaceutical composition including a compound of the present invention, and optionally further including an additional therapeutic agent and/or an immune checkpoint inhibitor. The pharmaceutical compositions of the present invention may include a pharmaceutically acceptable carrier.

In addition, the present invention also provides the use of a compound of the present invention or a pharmaceutical composition containing the compound of the present invention in the preparation of a medicament for the treatment of a disease or condition that can be treated by the inhibition of PD-L1 binding to PD-1. Preferably, the disease is selected from the group consisting of tumors, cancers, viral infections, inflammation-related diseases and autoimmune diseases.

The present invention also provides the use of a compound of the present invention or a pharmaceutical composition containing the compound of the present invention in the preparation of a medicament for the treatment of a disease or condition responsive to the inhibition of PD-L1 binding to PD-1. Preferably, the disease or condition is selected from the group consisting of tumors, cancers, viral infections, inflammation-related diseases and autoimmune diseases.

In addition, the present invention also provides a method for the treatment of a disease or condition (preferably tumors, cancers, viral infections, inflammation-related diseases, and autoimmune diseases) that can be treated by the inhibition of PD-L1 binding to PD-1, including administering to a mammal in need thereof a compound or a pharmaceutical composition of the present invention.

The present invention also provides a method for the treatment of a disease or condition responsive to the inhibition of PD-L1 binding to PD-1, including administering to a mammal in need thereof a compound or a pharmaceutical composition of the present invention. The term "disease or condition responsive to the inhibition of PD-L1 binding to PD-1" means any disease or condition in which: the disease progression may be altered by the inhibition of PD-L1 binding to PD-1, or may result in alleviation, inhibition, elimination, and amelioration of diseases, conditions, and disorders, or may prevent such diseases or conditions. Preferably, the disease or condition responsive to the inhibition of PD-L1 binding to PD-1 is selected from the group consisting of tumors, cancers, viral infections, inflammation-related diseases, and autoimmune diseases.

The present invention also provides a method for the inhibition of PD-L1 binding to PD-1, including exposing the compound or the pharmaceutical composition of the present invention to the PD-L1 and/or PD-1.

In the above-mentioned embodiments related to the compounds, pharmaceutical compositions and uses and methods of using the compounds or pharmaceutical compositions of the present invention, the compound of the present invention especially includes the form of a pharmaceutically acceptable salt thereof.

Representative examples of inflammatory diseases, autoimmune diseases, and immune-mediated diseases may include, but are not limited to, arthritis, rheumatoid arthritis, spondyloarthritis, gouty arthritis, osteoarthritis, juvenile arthritis, other arthritic conditions, lupus, systemic lupus erythematosus (SLE), skin-related diseases, psoriasis, eczema, dermatitis, allergic dermatitis, pain, lung disease, lung Inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia-reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenotransplantation, idiopathic thrombocytopenic purpura (ITP), Parkinson's disease, Alzheimer's disease, diabetes-related diseases, inflammation, pelvic inflammatory diseases, allergic rhinitis, allergic bronchitis, allergic sinusitis, leukemia, lymphoma, B-cell lymphoma, T-cell lymphoma, myeloma, acute lymphocytic leukemia (ALL), chronic lymphocytic leukemia (CLL), acute myelogenous leukemia (AML), chronic myelogenous leukemia (CML), hairy cell leukemia, Hodgkin's disease, non-Hodgkin's lymphoma, multiple myeloma, myelodysplastic syndrome (MDS), myeloproliferative tumor (MPN), diffuse large B-cell lymphoma, and follicular lymphoma.

Representative examples of cancers or tumors may include, but are not limited to, skin cancer, bladder cancer, ovarian cancer, breast cancer, gastric cancer, pancreatic cancer, prostate cancer, colon cancer, lung cancer, bone cancer, brain cancer, neurocytoma, rectal cancer, colon cancer, familial adenomatous polyposis cancer, hereditary nonpolyposis colorectal cancer, esophageal cancer, lip cancer, laryngeal cancer, hypopharyngeal cancer, tongue cancer, salivary gland cancer, gastric cancer, adenocarcinoma, medullary thyroid cancer, papillary thyroid cancer, renal cancer, carcinoma of renal parenchyma, ovarian cancer, cervical cancer, corpus carcinoma, endometrial cancer, choriocarcinoma, pancreatic cancer, prostate cancer, testicular cancer, carcinoma of urinary system, melanoma, brain tumors such as glioblastoma, astrocytoma, meningioma, medulloblastoma and peripheral neuroectodermal tumors, Hodgkin's lymphoma, non-Hodgkin's lymphoma, Burkitt's lymphoma, acute lymphoblastic leukemia (ALL), chronic lymphocytic leukemia (CLL), acute myelogenous leukemia (AML), chronic myelogenous leukemia (CML), adult T-cell leukemia lymphoma, diffuse large B-cell lymphoma (DLBCL), hepatocellular carcinoma, gallbladder carcinoma, bronchial carcinoma, small cell lung carcinoma, non-small cell lung carcinoma, multiple myeloma, basal cell tumor, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, or plasmacytoma.

When a compound of the present invention or a pharmaceutically acceptable salt thereof is administered in combination with another therapeutic agent or immune checkpoint inhibitor for the treatment of cancer or tumors, the compound of the present invention or a pharmaceutically acceptable salt thereof may provide an enhanced anticancer effect.

Representative examples of therapeutic agent for the treatment of a cancer or tumor may include, but are not limited to, cell signal transduction inhibitors, Chlorambucil, Melphalan, Cyclophosphamide, Ifosfamide, Busulfan, Carmustine, Lomustine, Streptozotocin, Cisplatin, Carboplatin, Oxaliplatin, Dacarbazine, Temozolomide, Procarbazine, Methotrexate, Fluorouracil, Cytarabine, Gemcitabine, Mercaptopurine, Fludarabine, Vinblastine, Vincristine, Vinorelbine, Paclitaxel, Docetaxel, Topotecan, Irinotecan, Etoposide, Trabectedin, Dactinomycin, Doxorubicin, Epirubicin, Daunorubicin, Mitoxantrone, Bleomycin, Mitomycin C, Ixabepilone, Tamoxifen, Flutamide, Gonadorelin Analogs, Megestrol, Prednisone, Dexamethasone, Methylprednisolone, Thalidomide, Interferon A, Calcium Folinate, Sirolimus, Sirolimus Lipide, Everolimus, Afatinib, Alisertib, Amuvatinib, Apatinib, Axitinib, Bortezomib, Bosutinib, Brivanib, Cabozantinib, Cediranib, Crenolanib, Crizotinib, Dabrafenib, Dacomitinib, Danusertib, Dasatinib, Dovitinib, Erlotinib, Foretinib, Ganetespib, Gefitinib, Ibrutinib, Icotinib, Imatinib, Iniparib, Lapatinib, Lenvatinib, Linifanib, Linsitinib, Masitinib, Momelotinib, Motesanib, Neratinib Nilotinib, Niraparib, Oprozomib, Olaparib, Pazopanib, Pictiliisib, Ponatinib, Quizartinib, Regorafenib, Rigosertib, Rucaparib, Ruxolitinib, Saracatinib, Saridegib, Sorafenib, Sunitinib, Telatinib, Tivantinib, Tivozanib, Tofacitinib, Trametinib, Vandetanib, Veliparib, Vemurafenib, Erivedge, Volasertib, Alemtuzumab, Bevacizumab, Brentuximab Vedotin, Catumaxomab, Cetuximab, Denosumab, Gemtuzumab, Ipilimumab, Nimotuzumab, Ofatumumab, Panitumumab, Rituximab, Tositumomab, Trastuzumab, PI3K inhibitors, CSF1R inhibitors, A2A and/or A2B receptor antagonists, IDO inhibitors, anti-PD-1 antibodies, LAG3 antibodies, TIM-3 antibodies, and anti-CTLA-4 antibodies, or any combination thereof.

When a compound of the present invention or a pharmaceutically acceptable salt thereof is administered in combination with another therapeutic agent for the treatment of inflammatory diseases, autoimmune diseases and immune-mediated diseases, the compound of the present invention or a pharmaceutically acceptable salt thereof may provide an enhanced therapeutic effect.

Representative examples of therapeutic agents for the treatment of inflammatory diseases, autoimmune diseases, and immune-mediated diseases may include, but are not limited to, steroidal drugs (e.g., prednisone, prednisolone, methylprednisolone, cortisone, hydroxycortisone, betamethasone, dexamethasone, etc.), methotrexate, leflunomide, anti-TNF a agents (e.g., etanercept, infliximab, adalimumab, etc.), calcineurin inhibitors (e.g., tacrolimus, pimecrolimus, etc.), and antihistamines (e.g., diphenhydramine, hydroxyzine, loratadine, ebastine, ketotifen, cetirizine, levocetirizine, fexofenadine, etc.), and at least one therapeutic agent selected therefrom may be included in the pharmaceutical compositions of the present invention.

The compound of the present invention or a pharmaceutically acceptable salt thereof can be administered orally or parenterally as an active ingredient in an effective amount ranging from 0.1 mg/kg body weight/day to 2,000 mg/kg body weight/day, preferably 1 mg/kg body weight/day to 1,000 mg/kg body weight/day in the case of mammals including humans (body weight about 70 kg), and administered in a single or four divided doses per day, or following/not following a predetermined time. The dosage of the active ingredient may be adjusted according to a number of relevant factors, such as the condition of the subject to be treated, the type and severity of the disease, the frequency of administration and the opinion of the physician). In some cases, amounts less than the above doses may be suitable. If it does not cause harmful side effects, an amount larger than the above dose can be used and the amount can be administered in divided doses per day.

In addition, the present invention also provides a method for the inhibition of PD-L1 binding to PD-1, including exposing the compound of the present invention, the pharmaceutically acceptable salt thereof or the pharmaceutical composition of the present invention to the PD-L1 and/or PD-1.

Definition of Terms:

It should be noted that, when reference is made herein to a "compound" having a specific structural formula, stereoisomers, diastereomers, enantiomers, racemic mixtures, and isotopic derivatives thereof, as well as pharmaceutically acceptable salts, solvates, and hydrates as alternative forms, are also generally contemplated. It is well known to those skilled in the art that a salt, solvate, hydrate of a compound is an alternative form of the compound that can be converted to the compound under conditions such that, as used herein, reference to a compound generally includes pharmaceutically acceptable salts thereof, and further includes solvates and hydrates thereof.

Similarly, when a compound is referred to herein, prodrugs, metabolites, and nitrogen oxides thereof are also generally included.

The pharmaceutically acceptable salt of the present invention may be formed using the an inorganic acid or an organic acid, the "pharmaceutically acceptable salt" means a salt that is, within the scope of sound medical judgment, suitable for use in contact with the tissues of humans and lower animals without undue toxicity, irritation, and allergic response, commensurate with a reasonable benefit/risk ratio. As outlined below, the salts may be prepared in situ during the final isolation and purification of the compounds of the present invention, or prepared by reacting the free base or free acid with a suitable reagent separately. For example, the free base may be reacted with a suitable acid. In addition, when the compounds of the present invention carry an acidic moiety, suitable pharmaceutically acceptable salts thereof may include metal salts, such as alkali metal salts (e.g., sodium or potassium salts); and alkaline earth metal salts (e.g., calcium or magnesium salts). Examples of pharmaceutically acceptable non-toxic acid addition salts are salts formed by amino groups with inorganic acids (e.g., hydrochloric acid, hydrobromic acid, phosphoric acid, sulfuric acid, and perchloric acid) or organic acids (e.g., acetic acid, oxalic acid, maleic acid, tartaric acid, citric acid, succinic acid, or malonic acid), or formed by using other methods known in the prior art such as ion exchange. Other pharmaceutically acceptable salts include adipate, sodium alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfonate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectate, persulfate, 3-phenylpropionate, phosphate, picrate, pivalate, propionate, stearate, succinate, sulfate, tartrate, thiocyanate, p-toluenesulfonate, undecanoate, and valerate. Representative alkali metal or alkaline earth metal salts include salts of sodium, lithium, potassium, calcium, and magnesium. Other pharmaceutically acceptable salts include, nontoxic ammonium salts (where appropriate), quaternary ammonium salts, and ammonium cations formed with counterions, for example, halides, hydroxides, carboxylates, sulfates, phosphates, nitrates, lower alkyl sulfonates, and aryl sulfonates.

The pharmaceutically acceptable salts of the present invention may be prepared by a conventional method, for example, by dissolving the compound of the present invention in a water-miscible organic solvent (e.g., acetone, methanol, ethanol, and acetonitrile), adding an excess of an aqueous organic or inorganic acid thereto to precipitate the salt from the resulting mixture, removing the solvent and remaining free acid therefrom, and then isolating the precipitated salt.

The precursors or metabolites of the present invention may be those known in the art as long as the precursors or metabolites are converted into compounds by metabolism in vivo. For example, "prodrugs" refer to those of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. The term "prodrugs" refer to compounds which yield the parent compounds of the above-mentioned formulae rapidly through transformation in vivo, for example, through metabolism in vivo, or N-demethylation of a compound of the present invention. "Solvate" of the present invention means a physical association of a compound of the present invention with one or more solvent molecules (whether organic or inorganic). The physical association includes hydrogen bonding. In some cases, for example when one or more solvent molecules are incorporated in the crystal lattice of the crystalline solid, the solvate will be capable of being isolated. The solvent molecules in the solvate may be present in a regular and/or disordered arrangement. Solvates may include stoichiometric or non-stoichiometric solvent molecules. "Solvate" encompasses both solution-phase and isolatable solvates. Exemplary solvates include, but are not limited to, hydrates, ethanolates, methanolates, and isopropanolates. Methods of solvation are well known in the art.

The "stereoisomerism" of the present invention is divided into conformational isomerism and configurational isomerism, and the configurational isomerism can also be divided into cis-trans isomerism and optical isomerism (i.e., optical isomerism). The conformational isomerism refers to a stereoisomerism phenomenon in which the rotation or distortion of the carbon-carbon single bond of an organic molecule with a certain configuration makes the atoms or atomic groups of the molecule produce different arrangements in space, and common examples include the structures of alkanes and cycloalkanes, such as chair and boat conformations as found in the cyclohexane structure. "Stereoisomers" means when the compounds of the present invention contain one or more asymmetric centers, thus they can be served as racemates and racemic mixtures, single enantiomers, diastereomeric mixtures, and single diastereomers. The compounds of the present invention may have asymmetric centers, each of which produces two optical isomers, and the scope of the present invention includes all possible optical isomers and diastereomeric mixtures and pure or partially pure compounds. The compounds of the present invention may exist in the form of tautomers, which have different linking points of hydrogen through the displacement of one or more double bonds. For example, ketone and its enol form are keto-enol tautomers. Each tautomer and mixtures thereof are included in the compounds of the present invention. All enantiomers, diastereomers, racemates, mesomers, cis-trans-isomers, tautomers, geometric isomers, epimers, and mixtures thereof of the compounds of Formula (I) are included within the scope of the present invention.

An "isotopic derivative" of the present invention refers to a molecule in which a compound is labeled with an isotope in this patent. Isotopes commonly used as isotopic labels are: hydrogen isotopes, $^2H$ and $^3H$; carbon isotope: $^{11}C$, $^{13}C$ and $^{14}C$; chlorine isotope: $^{35}Cl$ and $^{37}Cl$; fluorine isotope: $^{18}F$; iodine isotope: $^{123}I$ and $^{125}I$; nitrogen isotopes: $^{13}N$ and $^{15}N$; oxygen isotopes: $^{15}O$, $^{17}O$ and $^{18}O$ and sulfur isotope $^{35}S$. These isotopically labeled compounds can be used to study the distribution of pharmaceutical molecules in tissues. Deuterium $^2H$ and carbon $^{13}C$, in particular, are more widely used due to their ease of labeling and ease of detection. Substitution of certain heavy isotopes, such as heavy hydrogen ($^2H$), may enhance metabolic stability, prolong the half-life, and provide therapeutic advantages resulting from reduced dosage. Generally, starting from the labeled starting materials, isotopically-labeled compounds are synthesized by using known synthesis techniques in the same way as the synthesis of non-isotopically labeled compounds.

The compound or pharmaceutical compositions of the present invention may be formulated into dosage forms, such as tablets, granules, powders, capsules, syrups, emulsions, microemulsions, solutions or suspensions, for oral or parenteral administration (including intramuscular, intravenous and subcutaneous routes, and intratumoral injection) according to any of the conventional methods.

The pharmaceutical compositions of the present invention for oral administration may be prepared by mixing the active ingredient with carriers such as: cellulose, calcium silicate, corn starch, lactose, sucrose, dextrose, calcium phosphate, stearic acid, magnesium stearate, calcium stearate, gelatin, talc, surfactants, suspending agents, emulsifying agents, and diluents. Examples of carriers employed in the injectable compositions of the present invention consist of water, saline solutions, dextrose solutions, glucose-like solutions, alcohols, glycols, ethers (e.g., polyethylene glycol 400), oils, fatty acids, fatty acid esters, glycerides, surfactants, suspending agents, and emulsifying agents.

Additional features of the present invention will become apparent from the description of exemplary embodiments of the present invention which are presented for purposes of illustration and are not intended to be limiting thereof, and the following examples are prepared, isolated and characterized using the methods disclosed herein.

In the technical solution of the present invention, where ∿∿∿ represents an arbitrary connection position, for example, for A-$R^1$—X fragments, where $R^1$ is selected from the following group

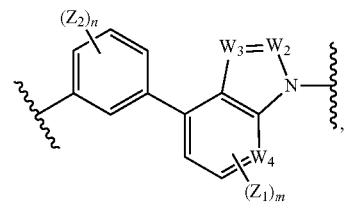

the A-$R^1$—X can represent either

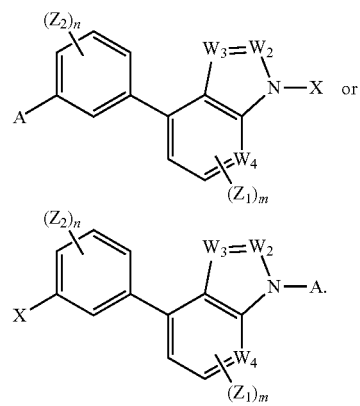

Terms used in the present invention, including the specification and claims, are defined as follows, unless otherwise indicated. It must be noted that, in the description and the appended claims, the singular forms "a", "an", and "the" include plural referents unless the context clearly dictates otherwise. If not stated otherwise, conventional methods of mass spectrometry, nuclear magnetic, HPLC, protein chemistry, biochemistry, recombinant DNA techniques and pharmacology are used. In this use, the use of "or" or "and" means "and/or" if not stated otherwise.

Throughout the specification and claims, a given chemical formula or name shall encompass all stereo and optical isomers and racemates in which such isomers exist. Unless otherwise indicated, all chiral (enantiomer and diastereoisomer) and racemic forms are within the scope of the present invention.

Many geometric isomers of C=C double bonds, C=N double bonds, and ring systems may also be present in the compounds, and all the above-mentioned stable isomers are encompassed in the present invention. Cis- and trans- (or E- and Z-) geometric isomers of the compounds of the present invention are described herein and may be isolated as mixtures of isomers or as separated isomeric forms. The compounds of the present invention may be isolated in optically active or racemic forms. All methods for preparing the compounds of the present invention and intermediates prepared therein are considered part of the present invention. In preparing enantiomeric or diastereomeric products, they can be isolated by conventional methods, for example, by chromatography or fractional crystallization. Depending on the process conditions, the final products of the present invention are obtained in free (neutral) or salt form. Both the free forms and salts of these end products are within the scope of the present invention. If desired, one form of the compound may be converted to another form. The free base or acid may be converted to a salt; the salt may be converted to the free compound or another salt; mixtures of isomeric compounds of the present invention may be isolated into the individual isomers. The compounds, free forms and salts thereof of the present invention, may exist in a variety of tautomeric forms in which hydrogen atoms are transposed onto other parts of the molecule and the chemical bonds between the atoms of the molecule are thus rearranged. It is to be understood that all tautomeric forms which may exist are included in the present invention.

Unless otherwise defined, the definitions of substituents of the present invention are each independent and not interrelated, e.g., for $R^a$ (or $R^b$) in substituents, they are each independent in the definition of different substituents. Specifically, when a definition of $R^a$ (or $R^b$) is selected in a substituent, it does not mean that $R^a$ (or $R^b$) has the same definition in other substituents. More specifically, for example (a non-exhaustive list) for $NR^aR^b$, when the definition of $R^a$ (or $R^b$) is selected from hydrogen, it does not mean that in —C(O)—$NR^aR^b$, $R^a$ (or $R^b$) must be hydrogen.

Unless otherwise defined, when a substituent is labeled "optionally substituted", the substituent is selected from, for example, the following substituents consisting of alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine group (in which two amino substituents are selected from alkyl, aryl or arylalkyl), alkanoylamino, aroylamino, aralkanoylamino, substituted alkanoylamino, substituted arylamino, substituted aralkanoylamino, thio, alkylthio, arylthio, arylalkylthio, arylthiocarbonyl, arylalkylthiocarbonyl, alkylsulfonyl, arylsulfonyl, arylalkylsulfonyl, sulfonamido such as —SO$_2$NH$_2$, substituted sulfonamido, nitro, cyano, carboxy, carbamoyl such as —CONH$_2$, substituted carbamoyl such as —CONH alkyl, —CONH aryl, —CONH arylalkyl or the case where there are two substituents selected from alkyl, aryl or arylalkyl on the nitrogen, alkoxycarbonyl, aryl, substituted aryl, guanidino, heterocyclyl such as indolyl, imidazolyl, furanyl, thienyl, thiazolyl, pyrrolidinyl, pyridyl, pyrimidinyl, pyrrolidinyl, piperidinyl, morpholinyl, piperazinyl, and homopiperazinyl, and substituted heterocyclyl.

As used herein, the term "alkyl" or "alkylene" is intended to include both branched and straight chain saturated aliphatic hydrocarbon groups having the specified number of carbon atoms. For example, "C1-C6 alkyl" denotes an alkyl group having 1 to 6 carbon atoms. Examples of alkyl groups include, but are not limited to, methyl (Me), ethyl (Et), n-propyl, isopropyl, n-butyl, isobutyl, tert-butyl, n-pentyl, isopentyl, and neopentyl.

The term "alkenyl" denotes a straight or branched chain hydrocarbon group containing one or more double bonds and typically 2 to 20 carbon atoms in length. For example, "C2-C6 alkenyl" contains 2 to 6 carbon atoms. Alkenyl groups include, but are not limited to, for example, ethenyl, propenyl, butenyl, and 1-methyl-2-buten-1-yl.

The term "alkynyl" denotes a straight or branched chain hydrocarbon group containing one or more triple bonds and typically 2 to 20 carbon atoms in length. For example, "C2-C6 alkynyl" contains 2 to 6 carbon atoms. Representative alkynyl groups include, but are not limited to, for example, ethynyl, 1-propynyl, and 1-butynyl.

The term "alkoxy" or "alkyloxy" refers to —O-alkyl. "C1-C6 alkoxy" (or alkyloxy) is intended to include C1, C2, C3, C4, C5, and C6 alkoxy. Examples of alkoxy groups include, but are not limited to, methoxy, ethoxy, propoxy (e.g., n-propoxy and isopropoxy), and t-butoxy. Similarly, "alkylthio" or "thioalkoxy" means an alkyl group, as defined above, with the specified number of carbon atoms linked via a sulfur bridge; for example, methyl-S— and ethyl-S—.

The term "carbonyl" refers to an organic functional group (C=O) composed of two carbon and oxygen atoms linked by a double bond.

The term "aryl", alone or as part of a larger moiety such as "aralkyl", "aralkoxy", or "aryloxyalkyl", refers to a monocyclic, bicyclic, or tricyclic ring system having a total of 5 to 12 ring members, where at least one ring in the system is aromatic and where each ring in the system contains 3 to 7 ring members. In certain embodiments of the present invention, "aryl" refers to an aromatic ring system including, but not limited to, phenyl, biphenyl, indanyl, 1-naphthyl, 2-naphthyl, and tetrahydronaphthyl. The term "aralkyl" or "arylalkyl" refers to an alkyl residue attached to an aryl ring. Non-limiting examples include benzyl, and phenethyl. The fused aryl group may be attached to another group at a suitable position on the cycloalkyl ring or the aromatic ring. For example, a dashed line drawn from a ring system indicates that the bond may be attached to any suitable ring atom.

The term "cycloalkyl" refers to a monocyclic or bicyclic alkyl group. Monocyclic alkyl refers to C3-C8 cyclic alkyl including, but not limited to, cyclopropyl, cyclobutyl, cyclopentyl, cyclohexyl, and norbornyl. Branched cycloalkyl such as 1-methylcyclopropyl and 2-methylcyclopropyl are included in the definition of "cycloalkyl". Bicyclic alkyl includes bridged, spiro, or fused cycloalkyl.

The term "cycloalkenyl" refers to a monocyclic or bicyclic alkenyl group. Monocyclic alkenyl refers to C3-C8 cyclic alkenyl including, but not limited to, cyclopropenyl, cyclobutenyl, cyclopentenyl, cyclohexenyl, and norbornenyl. Branched cycloalkenyl such as 1-methylcyclopropenyl and 2-methylcyclopropenyl are included in the definition of "cycloalkenyl". Bicyclic alkenyl includes bridged, spiro or fused cyclic alkenyl.

"Halo" or "halogen" includes fluoro, chloro, bromo and iodo. "Haloalkyl" is intended to include both branched and straight-chain saturated aliphatic hydrocarbon groups having the specified number of carbon atoms and substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" groups intended to include branched and straight chain saturated aliphatic hydrocarbon groups having the specified number of carbon atoms and substituted with one or more fluorine atoms.

"Haloalkoxy" or "haloalkyloxy" denotes a haloalkyl group, as defined above, having the indicated number of carbon atoms linked via an oxygen bridge. For example, "C1-C6 haloalkoxy" is intended to include C1, C2, C3, C4, C5, and C6 haloalkoxy. Examples of haloalkoxy include, but are not limited to, trifluoromethoxy, 2,2,2-trifluoroethoxy, and pentafluoroethoxy. Similarly, "haloalkylthio" or "thiohaloalkoxy" denotes a haloalkyl group, as defined above, having the indicated number of carbon atoms linked via a sulfur bridge; for example, trifluoromethyl-S— and pentafluoroethyl-S—.

In the present disclosure, the expression Cx1-Cx2 is used when referring to some substituent groups, which means that the number of carbon atoms in the substituent group may be x1 to x2. For example, C0-C8 means that the group contains 0, 1, 2, 3, 4, 5, 6, 7 or 8 carbon atoms, C1-C8 means that the group contains 1, 2, 3, 4, 5, 6, 7 or 8 carbon atoms, C2-C8 means that the group contains 2, 3, 4, 5, 6, 7 or 8 carbon atoms, C3-C8 means that the group contains 3, 4, 5, 6, 7 or 8 carbon atoms, C4-C8 means that the group contains 4, 5, 6, 7 or 8 carbon atoms, C0-C6 means that the group contains 0, 1, 2, 3, 4, 5 or 6 carbon atoms, C1-C6 means that the group contains 1, 2, 3, 4, 5 or 6 carbon atoms, C2-C6 means that the group contains 2, 3, 4, 5 or 6 carbon atoms, and C3-C6 means that the group contains 3, 4, 5 or 6 carbon atoms.

In the present disclosure, the expression "x1-x2 membered ring" is used when referring to cyclic groups such as aryl, heteroaryl, cycloalkyl and heterocycloalkyl, which means that the number of ring atoms of the group may be x1 to x2. For example, the 3- to 12-membered cyclic group may be a 3, 4, 5, 6, 7, 8, 9, 10, 11, or 12 membered ring, the number of ring atoms of which may be 3, 4, 5, 6, 7, 8, 9, 10, 11, or 12; the 3- to 6-membered ring means that the cyclic group may be a 3, 4, 5 or 6 membered ring, the number of ring atoms of which may be 3, 4, 5 or 6; the 3- to 8-membered ring means that the cyclic group may be a 3, 4, 5, 6, 7 or 8 membered ring, the number of ring atoms of which may be 3, 4, 5, 6, 7 or 8; the 3- to 9-membered ring means that the cyclic group may be a 3, 4, 5, 6, 7, 8 or 9 membered ring, the number of ring atoms of which may be 3, 4, 5, 6, 7, 8 or 9; the 4- to 7-membered ring means that the cyclic group may be a 4, 5, 6 or 7 membered ring, the number of ring atoms of which may be 4, 5, 6 or 7; the 5- to 8-membered ring means that the cyclic group may be a 5, 6, 7 or 8 membered ring, the number of ring atoms of which may be 5, 6, 7 or 8; the 5- to 12-membered ring means that the cyclic group may be a 5, 6, 7, 8, 9, 10, 11 or 12 membered ring, the number of ring atoms of which may be 5, 6, 7, 8, 9, 10, 11 or 12; and the 6- to 12-membered ring means that the cyclic group may be a 6, 7, 8, 9, 10, 11 or 12 membered ring, the number of ring atoms of which may be 6, 7, 8, 9, 10, 11 or 12. The ring atom may be a carbon atom or a heteroatom, for example, a heteroatom selected from N, O and S. When the ring is a heterocycle, the heterocycle may contain 1, 2, 3, 4, 5, 6, 7, 8, 9, 10 or more ring heteroatoms, for example, a heteroatom selected from N, O and S.

In the present invention, one or more halogens may each independently be selected from fluorine, chlorine, bromine, and iodine.

The term "heteroaryl" means a stable 3-, 4-, 5-, 6-, or 7-membered aromatic monocyclic or aromatic bicyclic or 7-, 8-, 9-, 10-, 11-, 12-membered aromatic polycyclic heterocycle, which is fully unsaturated, partially unsaturated, and contains carbon atoms and 1, 2, 3 or 4 heteroatoms independently selected from N, O and S; and includes any polycyclic group in which any heterocycle defined above is fused to a benzene ring. The nitrogen and sulfur heteroatoms may optionally be oxidized. The nitrogen atom is substituted or unsubstituted (i.e., N or NR, where R is H or another substituent if defined). The heterocycle may be attached to its pendant group at any heteroatom or carbon atom that results in a stable structure. If the resulting compound is stable, the heterocyclyl groups described herein may be substituted on a carbon or nitrogen atom. The nitrogen in the heterocycle may be optionally quaternized. Preferably, when the total number of S and O atoms in the heterocycle exceeds 1, then these heteroatoms are not adjacent to each other. Preferably, the total number of S and O atoms in the heterocycle is not greater than 1. When the term "heterocycle" is used, it is intended to include heteroaryl. Examples of heteroaryls include, but are not limited to, acridinyl, azetidinyl, azocinyl, benzimidazolyl, benzofuranyl, benzothiofuranyl, benzothienyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, imidazopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinyl, perimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl and xanthenyl, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydroquinoxalinyl and 1,2,3,4-tetrahydro-quinazolinyl. The term "heteroaryl" may also include biaryl structures formed from "aryl" and monocyclic "heteroaryl" as defined above, for example, but not limited to "-phenylbipyridyl-", "-phenylbipyrimidinyl", "-pyridylbiphenyl", "-pyridylbipyrimidinyl-", "-pyrimidinylbiphenyl-"; where the present invention also includes fused and spiro compounds containing, for example, the above-mentioned heterocycles.

As used herein, the term "heterocycloalkyl" refers to a monocyclic heterocycloalkyl system, or a bicyclic heterocycloalkyl system, and also includes spiroheterocycles or bridged heterocycloalkyl groups. The monocyclic heterocycloalkyl refers to a saturated or unsaturated but not aromatic 3- to 8-membered cyclic alkyl system containing at least one heteroatom selected from O, N, S, or P. The bicyclic heterocycloalkyl system refers to a heterocycloalkyl fused with a phenyl, or a cycloalkyl, or a cycloalkenyl, or a heterocycloalkyl, or a heteroaryl.

As used herein, the term "bridged cycloalkyl" refers to polycyclic compounds that share two or more carbon atoms, including bicyclic bridged cyclic hydrocarbons and polycyclic bridged cyclic hydrocarbons. The former are composed of two alicyclic rings sharing more than two carbon atoms; the latter are a bridged cyclic hydrocarbons consisting of more than three rings.

As used herein, the term "spirocycloalkyl" refers to polycyclic hydrocarbons that share one carbon atom (referred to as a spiro atom) between single rings.

As used herein, the term "bridged cycloheteryl" refers to polycyclic compounds that share two or more carbon atoms, and contain at least one atom selected from O, N, or S. including bicyclic bridged heterocycles and polycyclic bridged heterocycles.

As used herein, the term "heterospirocyclyl" refers to polycyclic hydrocarbons that share one carbon atom (referred to as a spiro atom) between single rings, and contain at least one heteroatom selected from O, N, or S.

As used herein, the term "substituted" means that at least one hydrogen atom is replaced with a non-hydrogen group, provided that normal valency is maintained and that the substitution results in a stable compound. As used herein, the ring double bond is a double bond (e.g., C=C, C=N, or N=N) formed between two adjacent ring atoms.

In the case where nitrogen atoms (e.g., amines) are present on the compounds of the present invention, these nitrogen atoms may be converted to N-oxides by treatment with an oxidizing agent (e.g., mCPBA and/or hydrogen peroxide) to obtain other compounds of the present invention. Thus, the nitrogen atoms shown and claimed are considered to encompass both the nitrogen shown and its N-oxides to obtain the derivatives of the present invention.

When any variable occurs more than once in any composition or formula of a compound, its definition at each occurrence is independent of its definition at every other occurrence. Thus, for example, if a group is shown to be substituted with 0-3 R, the group may be optionally substituted with up to three R groups, and at each occurrence R is independently selected from the definition of R. Furthermore, combinations of substituents and/or variables are permissible only if such combinations result in stable compounds.

As used herein, the term "patient" refers to an organism treated by the methods of the present invention. Such organisms preferably include, but are not limited to, mammals (e.g., murine, ape/monkey, equine, bovine, swine, canine, feline, etc.) and most preferably refer to humans.

As used herein, the term "effective amount" means an amount of a drug or pharmaceutical agent (i.e., a compound of the present invention) that will elicit the biological or medical response of a tissue, system, animal or human that is being sought, for example, by a researcher or clinician. Furthermore, the term "therapeutically effective amount" means an amount results in an improved treatment, cure, prevention or alleviation of a disease, condition or side effect, or a reduction in the rate of progression of a disease or condition, as compared to a corresponding subject not receiving such an amount. An effective amount can be administered in one or more dosing, administrations, or dosages and is not intended to be limited by the particular formulation or route of administration. The term also includes an amount effective that enhances normal physiological function within its scope.

As used herein, the term "treatment" includes its broad meaning and encompasses therapeutic and/or prophylactic treatment of a subject. Specifically, the term "treatment" includes any treatment that results in the alleviation, inhibition, elimination, and amelioration, and/or prevention of conditions, diseases, disorders, etc., such as the alleviation, reduction, modulation, amelioration, elimination, prevention, or amelioration of the symptoms thereof. The therapeutic treatment include alleviating, inhibiting, or ameliorating the symptoms or conditions of a disease; inhibiting the generation of complications; ameliorating potential metabolic syndrome; inhibiting the development of a disease or condition, such as controlling the development of a disease or condition; alleviating a disease or condition; reducing the disease or symptoms; alleviating complications resulting from the disease or condition, or treating symptoms resulting from the disease or condition. The prophylactic treatment includes prior treatment to prevent, block or delay, slow the occurrence or development of, or lessen the severity of the disease or condition.

Likewise, a "therapeutic agent" also includes a medicament or reagent that has a therapeutic and/or prophylactic treatment on a subject.

The term "medicinal" or "pharmaceutically acceptable" is used herein to refer to those compounds, materials, compositions, and/or dosage forms as follows: within the scope of sound medical judgment, suitable for use in contact with the tissues of humans and animals without undue toxicity, irritation, allergic response, and/or other problems or complications, commensurate with a reasonable benefit/risk ratio.

Specific Pharmaceutical and Medical Terms

The term "cancer", as used herein, refers to an uncontrolled abnormal growth of cells and is capable of metastasis (transmission) under certain conditions. This type of cancer includes, but is not limited to, solid tumors (e.g., bladder, bowel, brain, chest, uterus, heart, kidney, lung, lymphoid tissue (lymphoma), ovary, pancreas, or other endocrine organs (e.g., thyroid), prostate, skin (melanoma), or hematological tumors (e.g., aleukemic leukemia).

The term "administered in combination" or similar terms, as used herein, refers to the administration of several selected therapeutic agents to a patient in the same or different modes of administration at the same or different times.

The term "enhance" or "can enhance", as used herein, means that the desired result can be increased or prolonged in potency or duration. Thus, in enhancing the therapeutic effect of a drug, the term "can enhance" refers to the ability of the drug to increase or prolong potency or duration in the system. "Synergistic value", as used herein, refers to the ability to maximize the ability of another therapeutic agent in an ideal system.

The term "immunological disease" refers to a disease or condition that responds adversely or deleteriously to endogenous or exogenous antigens. The result is often a dysfunction of the cells, or thus destruction and dysfunction, or destruction of organs or tissues that may produce immune symptoms.

The term "kit" is synonymous with "product package".

The term "object", "subject" or "patient" includes mammals and non-mammals. Mammals include, but are not limited to, mammals: human, non-human primates such as chimpanzees, apes and monkeys; agricultural animals such as bovines, equines, goats, sheep, swines; domestic animals such as rabbits, canines; experimental animals include rodents, such as rats, mice, and guinea pigs. Non-mammalian animals include, but are not limited to, birds, and fish. In a preferred embodiment, the selected mammal is a human.

As used herein, a compound or pharmaceutical composition, upon administration, may result in amelioration of a disease, symptom, or condition, particularly amelioration of the severity, delay of the onset, alleviation of the progression, or reduction of the duration of the condition. Regardless of fixed administration or temporary administration, continuous administration or intermittent administration, it may be attributed to or related to the administration.

Route of Administration

Suitable routes of administration include, but are not limited to, oral, intravenous, rectal, aerosol, parenteral, ophthalmic, pulmonary, transdermal, vaginal, aural, nasal, and topical administration. In addition, by way of example only, parenteral administration includes intramuscular, subcutaneous, intravenous, intramedullary, ventricular, intraperitoneal, intralymphatic, and intranasal injections.

The compounds of the present invention may be administered topically. In particular embodiments, the prolonged action preparation is administered by implantation (e.g., subcutaneously or intramuscularly) or by intramuscular injection. Further, in another embodiment, the drug is administered by a targeted drug delivery system, for example, liposomes encapsulated by organ-specific antibodies. In this particular embodiment, the liposomes are selectively targeted to specific organs and absorbed.

Pharmaceutical Compositions and Dosages

As used herein, the phrase "pharmaceutically acceptable carrier" means a pharmaceutical material, composition or vehicle, such as a liquid or solid filler, diluent, excipient, manufacturing adjuvant (e.g., lubricant, talc, magnesium stearate, calcium stearate or zinc stearate or stearic acid), or solvent encapsulating material, which refers to carrying or transporting the subject compound from one organ or portion of the body to another organ or portion of the body. Each carrier must be "acceptable" in the sense of being compatible with the other ingredients of the formulation and not deleterious to the patient.

The term "pharmaceutical composition" means a composition including a compound of the present invention and optionally other pharmaceutically acceptable carrier. "Pharmaceutically acceptable carrier" means a medium generally accepted in the art for the delivery of a biologically active agent to an animal, particularly a mammal, and includes, i.e., adjuvants, excipients, or vehicles such as diluents, preservatives, fillers, flow regulating agents, disintegrating agents, wetting agents, emulsifying agents, suspending agents, sweetening agents, flavoring agents, perfuming agents, antibacterial agents, antifungal agents, lubricating agents, and dispersing agents. This depends on the mode of administration and the nature of the dosage form.

The pharmaceutical compositions of the present invention may include a therapeutically effective amount of one or more compounds of the present invention formulated together with optionally one or more pharmaceutically acceptable carriers (additives) and/or diluents, and optionally one or more of the other therapeutic agents described above. The compounds of the present invention may be administered for any of the above-mentioned uses by any suitable means, for example by orally, such as in the form of tablets, pills, powders, granules, elixirs, tinctures, suspensions (including nanosuspensions, microsuspensions, spray-dried dispersions), syrups and emulsions; by sublingually; by buccally; by parenterally, such as by subcutaneous, intravenous, intramuscular or intrasternal injection or infusion techniques (e.g., in the form of sterile injectable aqueous or nonaqueous solutions or suspensions); by nasally, including administration to the nasal mask, such as by inhalation spray; by topically, such as in the form of a cream or ointment; or by rectally, such as in the form of suppositories; or by intratumoral injection. They may be administered alone, but are generally administered using pharmaceutical acceptable carriers selected based on the chosen route of administration and standard pharmaceutical practice.

The pharmaceutical acceptable carriers are formulated according to a number of factors within the knowledge of those skilled in the art. These factors include, but are not limited to: types and properties of the formulated active agents; a subject to be administered the composition containing the active agent; the intended route of administration of the composition; and targeted therapeutic indications. The pharmaceutically acceptable carriers include aqueous and non-aqueous liquid media and various solid and semi-solid dosage forms.

The above-mentioned carrier may include many different ingredients and additives in addition to the active agent, and the above-mentioned other ingredients, for example, stabilizing active agent and binder, are included in the formulation for various reasons known to those skilled in the art. For a description of suitable pharmaceutical acceptable carriers and factors involved in the selection of carrier, see a number of readily available sources, such as Allen L. V. Jr. et al. Remington: The Science and Practice of Pharmacy (2 Volumes), 22nd Edition (2012), Pharmaceutical Press.

The dosage regimen for the compounds of the present invention will, of course, vary depending upon known factors such as the pharmacodynamic characteristics of the particular agent and its mode and route of administration; species, age, sex, health, medical condition and weight of the recipient; the nature and extent of symptoms; kind of concurrent treatment; treatment frequency; routes of administration, renal and hepatic function and desired effects in patients. According to general guidelines, when used for a given effect, the daily oral dosage of each active ingredient should be from about 0.001 mg/day to about 10-5000 mg/day, preferably from about 0.01 mg/day to about 1000 mg/day, and most preferably from about 0.1 mg/day to about 250 mg/day. During constant infusion, the most preferred intravenous dose should be from about 0.01 mg/kg/min to about 10 mg/kg/min. The compounds of the present invention may be administered in a single daily dose, or the total daily dose may be administered in divided doses of two, three or four times daily.

The compounds are generally administered in the form of a mixture of suitable pharmaceutical diluents, excipients, or carriers (collectively referred to herein as pharmaceutical acceptable carriers) suitably selected with respect to the intended form of administration (e.g., oral tablets, capsules, elixirs, and syrups) and consistent with conventional pharmaceutical practice.

Dosage forms (pharmaceutical compositions) suitable for administration may contain from about 1 mg to about 2000 mg of active ingredient per dosage unit. In these pharmaceutical compositions, the active ingredient will generally be present in an amount of about 0.1-95% by weight, based on a total weight of the composition.

Typical capsules for oral administration contain at least one compound of the present invention (250 mg), lactose (75 mg) and magnesium stearate (15 mg). The mixture was processed through a 60 meshes screen and packaged into No. 1 gelatin capsules.

A typical injectable formulation may be prepared as follows: at least one compound of the present invention (250 mg) was placed in a vial in a sterile manner, and lyophilized and sealed in a sterile manner. For use, the contents in the vial were mixed with 2 mL of normal saline to produce an injectable formulation.

The scope of the present invention includes (alone or in combination with a pharmaceutical acceptable carrier) pharmaceutical compositions containing a therapeutically effective amount of at least one compound of the present invention as an active ingredient. Optionally, the compounds of the present invention may be used alone, in combination with other compounds of the present invention, or in combination with one or more other therapeutic agents (e.g., anticancer agents or other pharmaceutically active agents).

Regardless of the selected route of administration, the compounds of the present invention (which may be used in suitable hydrated forms) and/or the pharmaceutical compositions of the present invention are formulated into pharmaceutically acceptable dosage forms by conventional methods known to those skilled in the art.

The actual dosage level of the active ingredient in the pharmaceutical compositions of the present invention may be varied so as to obtain an amount of the active ingredient that is effective to achieve the desired therapeutic response, composition, and mode of administration for a particular patient without being toxic to the patient.

The selected dosage level will depend upon a variety of factors, including the factors well known in the medical field such as the activity of the employed specific compound of the present invention, or an ester, salt or amide thereof; routes of administration; administration time; the discharge rate of the employed specific compound; the absorption rate and extent; duration of treatment; other drugs, compounds and/or substances used in combination with the employed specific compounds; the age, sex, weight, condition, general health and prior medical history of the patient being treated.

A physician or veterinarian having ordinary skill in the art can readily determine and prescribe an effective amount of the desired pharmaceutical composition. For example, to achieve the desired therapeutic effect, the physician or veterinarian may start a relatively small amount of the compound of the present invention used in the pharmaceutical composition below the desired level and gradually increase the dosage until the desired effect is achieved. In general, a suitable daily dose of a compound of the present invention will be that amount of the compound that is the lowest dose effective to produce a therapeutic effect. Such an effective dose will generally depend on such factors. In general, oral, intravenous, intracerebroventricular, and subcutaneous doses of a compound of the present invention for a patient range from about 0.01 to about 50 mg/kg body weight/day. If desired, an effective daily dose of the active compound may be administered in two, three, four, five, six or more sub-doses respectively at appropriate intervals throughout the day, optionally in unit dosage form. In certain aspects of the present invention, the medication is administered once a day.

Although the compound of the present invention may be administered alone, it is preferably administered in the form of a pharmaceutical preparation (composition).

Kit/Product Package

Kits/product packages are also described herein for the treatment of the above-mentioned indications. These kits may be composed of a conveyor, a medicine pack or a container box. The container box can be divided into multiple compartments to accommodate one or more containers, such as vials, and test tubes, where each container contains all a single component in the method. Suitable containers consist of bottles, vials, syringes, and test tubes. The container is made of an acceptable glass or plastic material.

For example, the container may contain one or more of the compounds described herein; the compound may exist either in the form of a pharmaceutical composition or may exist as a mixture with other ingredients described herein. The container may have a sterile outlet (e.g., the container may be an intravenous infusion bag or bottle and the stopper may be pierced by a hypodermic needle). Such kits may contain a compound and descriptions, labels or instructions for the method of use described herein.

A typical kit may include one or more containers, each containing one or more materials (e.g., reagents, concentrated stock solutions, and/or equipment) to accommodate commercial promotions and the needs of the user for the use of compounds. Such materials include, but are not limited to, buffers, diluents, filters, needles, syringes, conveyors, bags, containers, bottles, and/or tubes, with a list of contents and/or instructions for use, and with a build-in package. The entire set of instructions must be included.

The label may be displayed on or closely related to the container. The appearance of the label on the container means that the label letters, numbers or other features are pasted, molded, or engraved on the container; the label can also appear in the container box or shipping box containing a variety of containers, such as in the product insert. A label may be used to indicate a particular therapeutic use of the contents. The label may also indicate directions for the use of contents, such as described in the methods described above.

All of the features described in this specification (including any accompanying claims, abstract and drawings), and/or all of the steps involved in any method or process, may be present in any combination unless some features or steps are mutually exclusive in the same combination.

The features mentioned above, or the features mentioned in the embodiments mentioned herein, may be combined in any combination. All of the features disclosed in this specification may be combined in any combination, and each feature disclosed in this specification may be replaced by any alternative feature serving the same, equivalent or similar purpose. Thus, unless otherwise specified, the features disclosed are only general examples of equivalent or similar features.

The present invention will be described in detail below in connection with specific examples. It should be understood that these examples are only used to describe the present invention and are not intended to limit the scope of the present invention. The experimental methods in the following examples which are not specified with specific conditions are generally carried out according to conventional conditions or according to the conditions recommended by the manufacturer. All percentages, ratios, ratios, or parts are calculated by weight, unless otherwise stated.

The units in weight-volume percent in the present invention are well known to those skilled in the art and refer, for example, to the weight of solute in a 100 milliliters of solution. Unless otherwise defined, all professional and scientific terms used in the text have the same meaning as those familiar to those skilled in the art. In addition, any methods and materials similar or equivalent to those described can be used in the methods of the present invention. The preferred embodiments and materials described herein are exemplary only.

EXAMPLES

Intermediate I1: 4-((2-bromo-3-iodobenzyl)oxy)-5-chloro-2-hydroxybenzaldehyde

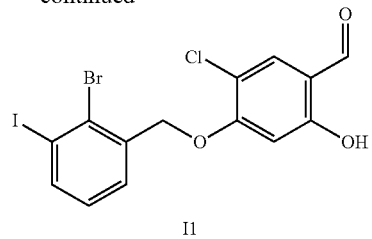

I1

The synthetic route of intermediate I1 is as follows:

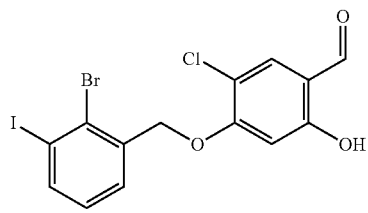

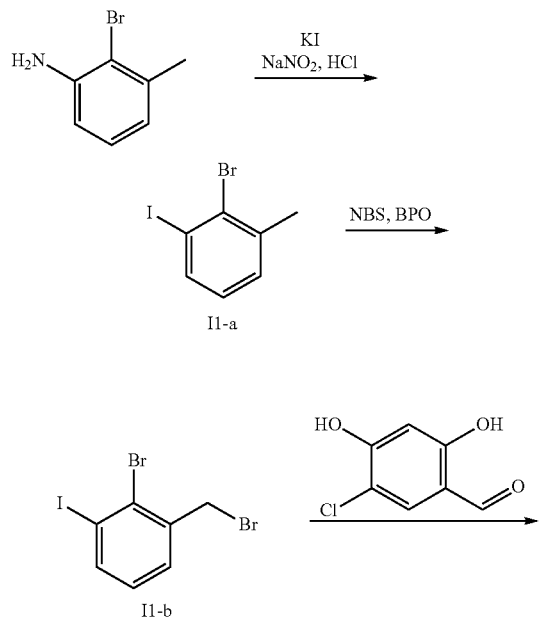

Step 1: A mixture of 2-bromo-3-methylaniline (31.5 g, 169.32 mmol) in concentrated HCl (100 mL) was stirred at room temperature for 20 min followed by the addition of crushed ice (250 g). After that, sodium nitrite (26.25 g, 380.43 mmol) was added to the above mixture slowly while keeping the temperature below 5° C.; and the mixture was further stirred at the same temperature for 1 h. Potassium iodide (112.89 g, 679.99 mmol) was add slowly and the mixture was stirred for 2 h at room temperature and another 1 h at 60° C. The resulting solution was cooled to room temperature and added with saturated sodium bisµLfite (200 mL). The mixture was extracted with petroleum ether (200 mL×3). The combined organic layers were washed with saturated sodium bicarbonate (200 mL) and brine (150 mL), dried over $Na_2SO_4$, filtered and concentrated. The residue was purified by silica gel column chromatography to obtain compound I1-a (36.0 g, 121.23 mmol, yield 71.6%) as light yellow oil.

Step 2: To a solution of compound I1-a (33.0 g, 111.14 mmol) in $CCl_4$ (400 mL), N-bromo succinimide (39.6 g, 222.27 mmol) and benzoyl peroxide (5.0 g, 20.66 mmol) was added. The mixture was stirred at refluxing temperature under nitrogen atmosphere for 16 h. The resulting mixture was cooled, filtered and concentrated. The residue was purified by silica gel column chromatography to obtain compound I1-b (28.0 g, 74.50 mmol, yield 67.0%) as light yellow oil.

Step 3: To a solution of compound I1-a and 5-chloro-2,4-dihydroxybenzaldehyde (6.43 g, 37.25 mmol) in acetonitrile (150 mL), sodium bicarbonate (39.6 g, 222.27 mmol) was added. The mixture was stirred at refluxing temperature for 16 h. The resulting mixture was cooled, added with water (150 mL) and then stirred for 20 min. Then the mixture was filtered and the cake was washed with water (20 mL×3), dried to give compound T1 (17.0 g, 36.36 mmol, yield 97.6%) as white solid.

Intermediate I2: 4-((5-((2-bromo-3-iodobenzyl)oxy)-4-chloro-2-formylphenoxy)methyl) picolinonitrile

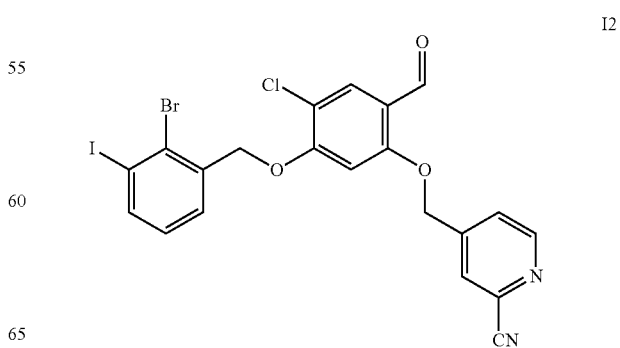

I2

The synthetic route of intermediate I2 is as follows:

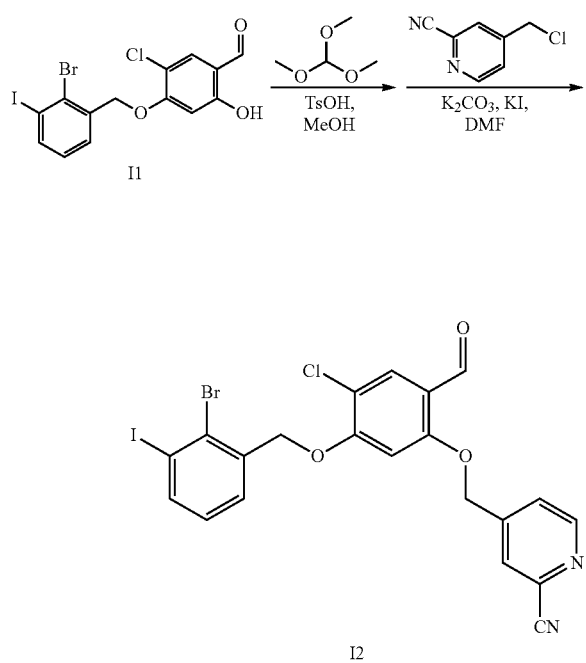

To a mixture of compound I1 (1.3 g, 3.68 mmol) in methanol (10 mL), trimethyl orthoformate (1.96 g, 18.42 mmol) and p-toluenesµLfonic acid (31.73 mg, 0.184 mmol) was added. The mixture was stirred at 50° C. for 16 h. The resulting mixture was concentrated. Then the residue was dissolved in DMF (10 mL) followed by the addition of potassium carbonate (1.53 g, 11.05 mmol), potassium iodide (61.17 mg, 0.368 mmol) and 4-(chloromethyl)picolinonitrile (1.3 g, 3.68 mmol). The mixture was stirred at 70° C. for 6 h. The resulting mixture was cooled, added with concentrated HCl (15 mL) and stirred for 20 min. After filtration, the cake was washed with water (10 mL×3), ethyl acetate (10 mL×2), dried to give compound I2 (0.97 g, 2.07 mmol, yield 56.1%) as light yellow solid.

Intermediate I3: 5-((5-((2-bromo-3-iodobenzyl)oxy)-4-chloro-2-formylphenoxy)methyl)nicotinonitrile

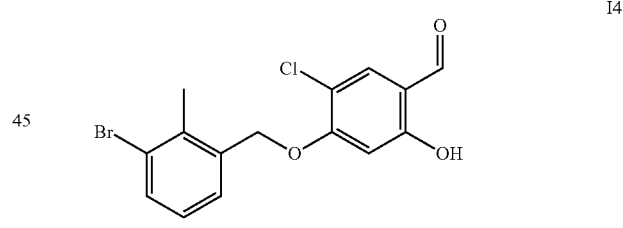

The synthetic route of intermediate I3 is as follows:

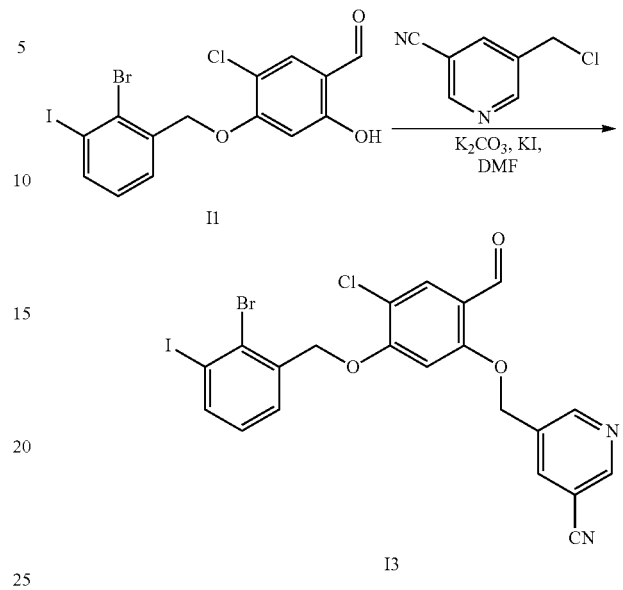

To a mixture of compound I1 (10.5 g, 29.53 mmol) in DMF (100 mL) was added with potassium carbonate (12.24 g, 88.58 mmol), potassium iodide (0.49 g, 2.95 mmol) and 5-(chloromethyl)nicotinonitrile (5.41 g, 35.43 mmol). The mixture was stirred at 70° C. for 6 h. The resulting mixture was cooled, added with water (100 mL) and stirred for 20 min. Then the mixture was filtered, and the cake was washed with water (50 mL×3), ethyl acetate (20 mL×2) and dried to give compound I3 (13.0 g, 27.56 mmol, yield 93.3%) as light yellow solid. MS (ESI): m/z 583.3 (M+H)⁺.

Intermediate I4: 4-((3-bromo-2-methylbenzyl)oxy)-5-chloro-2-hydroxybenzaldehyde

The synthetic route of intermediate I4 is as follows:

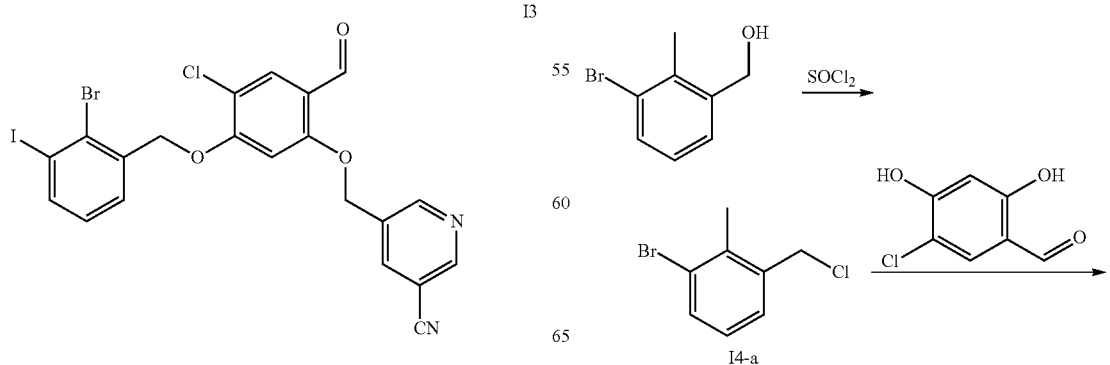

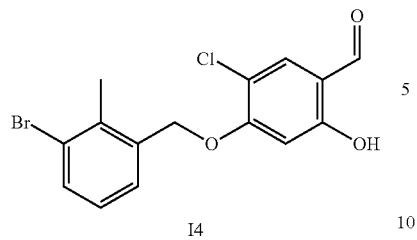

I4

Step 1: To a solution of (3-bromo-2-methylphenyl)methanol (10.0 g, 50.00 mmol) in DCM(100 mL), HCl (4 M in dioxane, 1.25 mL) and thionyl chloride (11.8 g, 100.00 mmol) was added in ice bath. The mixture was stirred at 70° C. for 3 h. The resulting mixture was cooled and concentrated. The residue was purified by silica gel column chromatography to obtain compound I4-a (10.05 g, 46.10 mmol, yield 92.2%) as light yellow solid.

Step 2: To a mixture of compound I4-a (10.05 g, 46.10 mmol) and 5-chloro-2,4-dihydroxybenzaldehyde (7.93 g, 46.10 mmol) in acetonitrile (200 mL), sodium bicarbonate (11.62 g, 119.05 mmol) was added. The mixture was stirred at refluxing temperature for 16 h. The resulting mixture was cooled, added with water (200 mL) and stirred for 20 min. Then the mixture was filtered, and the cake was washed with water (20 mL×3), ethyl acetate (20 mL×2) and dried to give compound I4 (14.71 g, 41.56 mmol, yield 90.2%) as a white solid. MS (ESI): m/z 353.2 (M−H)⁻.

Intermediate I5: 5-((5-((3-bromo-2-methylbenzyl)oxy)-4-chloro-2-formylphenoxy)methyl)nicotinonitrile

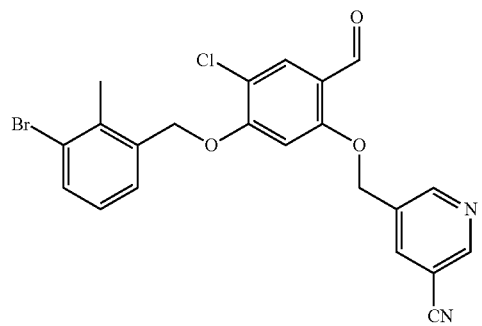

I5

The synthetic route of intermediate I5 is as follows:

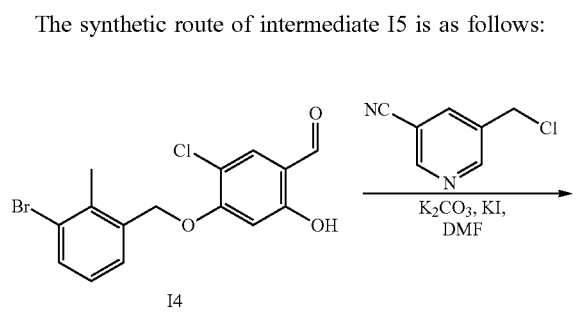

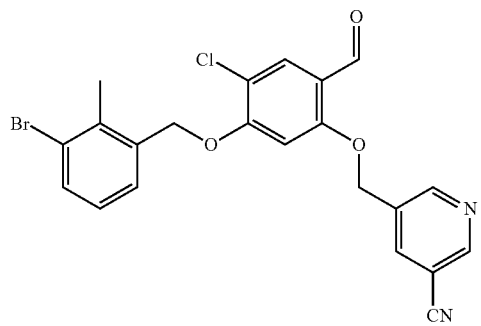

I5

To a mixture of compound I4 (10.0 g, 28.25 mmol) in DMF (100 mL), potassium carbonate (11.7 g, 84.75 mmol), potassium iodide (0.47 g, 2.83 mmol) and 5-(chloromethyl)nicotinonitrile (5.15 g, 33.90 mmol) was added. The mixture was stirred at 70° C. for 6 h. The resulting mixture was cooled, added with water (100 mL) and stirred for 20 min. Then the mixture was filtered, and the cake was washed with water (50 mL×3), ethyl acetate (20 mL×2) and dried to give compound I5 (12.4 g, 26.45 mmol, yield 93.6%) as light yellow solid. MS (ESI): m/z 471.2 (M+H)⁺.

Intermediate I6: (R)-1-(3-(4-(4,4,5,5-tetramethyl-1,3,2-dioxaborolan-2-yl)-1H-indazol-1-yl)propyl)pyrrolidin-3-ol

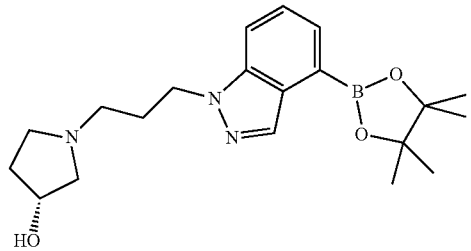

I6

The synthetic route of intermediate I6 is as follows:

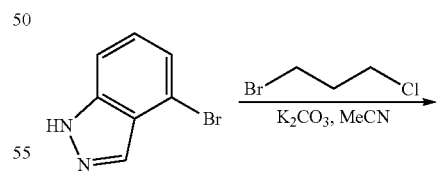

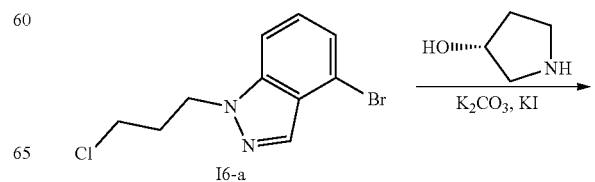

I6-a

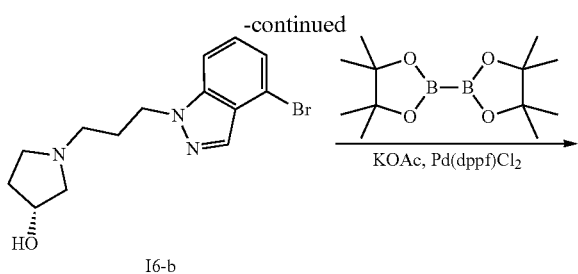

I6-b

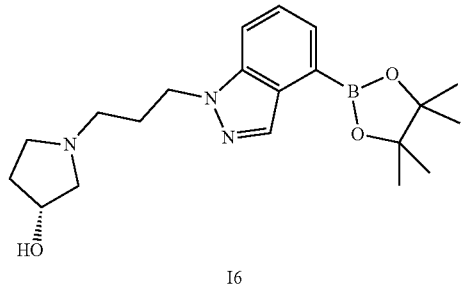

I6

Step 1: To a solution of 1-bromo-3-chloropropane (5.99 g, 38.06 mmol) and 4-bromo-1H-indazole (5.0 g, 25.38 mmol) in acetonitrile (50 mL), potassium carbonate (7.01 g, 50.75 mmol) was added. The mixture was stirred at 60° C. for 16 h. The resulting mixture was cooled, filtered and concentrated. The residue was purified by silica gel column chromatography to obtain compound I6-a (3.0 g, 10.97 mmol, yield 43.2%) as light yellow oil.

Step 2: To a solution of compound I6-a (1.5 g, 5.48 mmol) and (R)-pyrrolidin-3-ol (955.42 mg, 10.97 mmol) in acetonitrile (20 mL), potassium carbonate (3.03 g, 21.93 mmol) and potassium iodide (0.25 g, 1.48 mmol) were added. The mixture was stirred at 60° C. for 16 h. The resulting mixture was cooled, filtered and concentrated. The residue was dissolved in ethyl acetate (50 mL) and washed with water (20 mL×3), brine (20 mL), dried over Na$_2$SO$_4$, filtered and concentrated to obtain compound I6-b (1.78 g, 5.49 mmol, yield 100%) as light yellow oil. MS (ESI): m/z 324.4 (M+H)$^+$.

Step 3: To a solution of compound I6-b (1.78 g, 5.49 mmol) and bis(pinacolato)diboron (2.09 g, 8.24 mmol) in dioxane (20 mL), potassium acetate (1.62 g, 16.47 mmol) and Pd(dppf)Cl$_2$ (401.72 mg, 0.549 mmol) was added. The mixture was stirred under a nitrogen atmosphere at 90° C. for 16 h. The resulting mixture was cooled, added with ethyl acetate (100 mL) and filtered through celite. The filtrate was washed with water (50 mL×3), brine (50 mL), dried over Na$_2$SO$_4$, filtered and concentrated. The residue was purified by silica gel column chromatography to obtain compound I6 (1.38 g, 3.74 mmol, yield 68.1%) as light yellow oil. MS (ESI): m/z 372.4 (M+H)$^+$.

Intermediate I7~I17

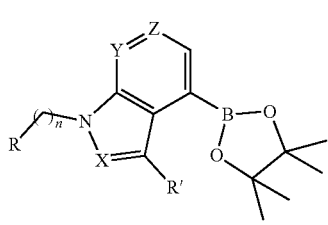

I7-I17

The synthetic route of intermediate I7-I17 is same as intermediate I6:

| INT | n | R | R' | X | Y | Z | m/z (M + H)$^+$ |
|---|---|---|---|---|---|---|---|
| I7 | 4 | (R)-3-hydroxypyrrolidinyl | H | N | CH | CH | 386.4 |
| I8 | 2 | (R)-3-hydroxypyrrolidinyl | H | N | CH | CH | 358.6 |
| I9 | 5 | (R)-3-hydroxypyrrolidinyl | H | N | CH | CH | 400.7 |
| I10 | 3 | (R)-3-hydroxypyrrolidinyl | H | CH | CH | CH | 371.4 |
| I11 | 3 | (R)-3-hydroxypyrrolidinyl | Me | N | CH | CH | 385.4 |
| I12 | 4 | 3-hydroxypyrrolidinyl | H | N | N | CH | 387.6 |
| I13 | 4 | (R)-3-hydroxypyrrolidinyl | H | N | CH | N | 387.6 |
| I14 | 4 | (S)-1-(tert-butoxycarbonyl)pyrrolidin-2-yl | H | N | CH | CH | 461.4 |
| I15 | 3 | 4-hydroxypiperidinyl | H | N | CH | CH | 386.7 |
| I16 | 4 | bis(2-hydroxyethyl)amino | H | N | CH | CH | 404.3 |
| I17 | 4 | (2-hydroxyethyl)amino | H | N | CH | CH | 360.6 |

Intermediate I18: (R)-1-((1r,4R)-4-(4-(4,4,5,5-tetramethyl-1,3,2-dioxaborolan-2-yl)-1H-indazol-1-yl)cyclohexyl)pyrrolidin-3-ol

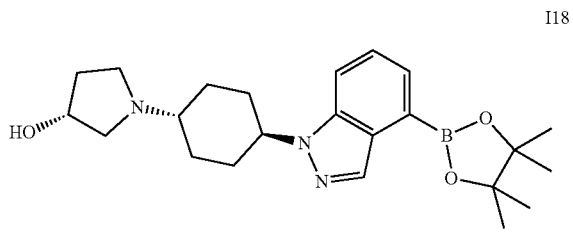 [SMILES: CC1(C)OB(c2cccc3c2cnn3[C@H]2CC[C@H](N3CC[C@@H](O)C3)CC2)OC1(C)C]

The synthetic route of intermediate I18 is as follows:

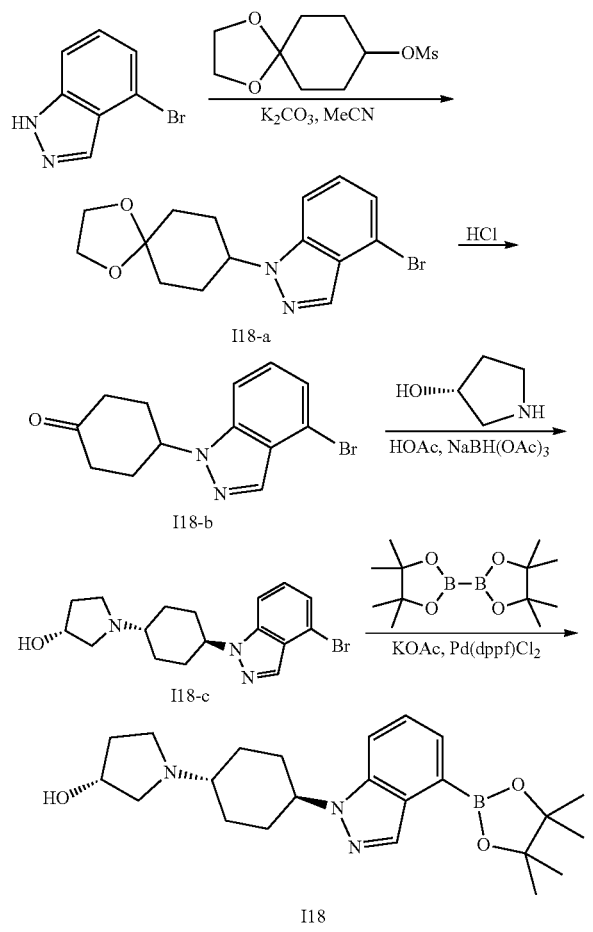

Step 1: To a solution of 1,4-dioxaspiro[4.5]decan-8-yl methanesµLfonate (7.5 g, 31.74 mmol) and 4-bromo-1H-indazole (4.17 g, 21.16 mmol) in DMF (60 mL), potassium carbonate (5.85 g, 42.32 mmol) was added. The mixture was stirred at 60° C. for 16 h. The resulting mixture was cooled and added with ethyl acetate (200 mL). The mixture was washed with water (100 mL×3) and brine (100 mL), dried over Na₂SO₄ and concentrated. The residue was purified by silica gel column to obtain compound I18-a (2.5 g, 7.41 mmol, yield 35.0%) as colorless oil. MS (ESI): m/z 337.4 (M+H)⁺.

Step 2: To a solution of compound I18-a (2.3 g, 6.82 mmol) in THF (10 mL), hydrochloric acid (4.0 M in water, 10 mL) was added. The mixture was stirred at room temperature for 2 h. The resulting mixture was added with saturated sodium bicarbonate until the pH=7 and then the THF was removed in vacuo. The mixture was extracted with ethyl acetate (20 mL×3). The combined organic layers were washed with water (20 mL) and brine (20 mL), dried over Na₂SO₄ and concentrated to give compound I18-b (1.6 g, 5.46 mmol, yield 80.0%) as white solid. MS (ESI): m/z 293.5 (M+H)⁺.

Step 3: To a solution of compound I18-b (150 mg, 511.67 µmol) and (R)-pyrrolidin-3-ol (89.15 mg, 1.02 mmol) in 1,2-dichloroethane (5 mL), acetic acid (0.05 mL) was added. The mixture was stirred at room temperature for 2 h followed by the addition of sodium triacetoxyborohydride (325.33 mg, 1.54 mmol). The mixture was further stirred at room temperature for 16 h. The resulting mixture was added with water (20 mL) and extracted with DCM (20 mL×2). The combined organic layers were washed with water (20 mL×2) and brine (20 mL), dried over Na₂SO₄ and concentrated. The residue was purified by silica gel column to obtain compound I18-c (150 mg, 411.77 µmol, yield 80.5%) as light yellow oil. MS (ESI): m/z 364.5 (M+H)⁺.

Step 4: To a solution of compound I18-c (1.3 g, 3.57 mmol) and bis(pinacolato)diboron (1.36 g, 5.35 mmol) in dioxane (15 mL), potassium acetate (1.05 g, 10.71 mmol) and Pd(dppf)Cl₂ (261.12 mg, 0.36 mmol) was added. The mixture was stirred under nitrogen atmosphere at 90° C. for 16 h. The resulting mixture was cooled, added with ethyl acetate (80 mL) and filtered through celite. The filtrate was washed with water (30 mL×3), brine (30 mL), dried over Na₂SO₄, filtered and concentrated. The residue was purified by silica gel column chromatography to obtain compound I18 (1.0 g, 2.43 mmol, yield 68.1%) as light yellow oil. MS (ESI): m/z m/z 412.3 (M+H)⁺.

Intermediate I19: 1-(1-(2,2-dimethyl-1,3-dioxan-5-yl)piperidin-4-yl)-4-(4,4,5,5-tetramethyl-1,3,2-dioxaborolan-2-yl)-1H-indazole

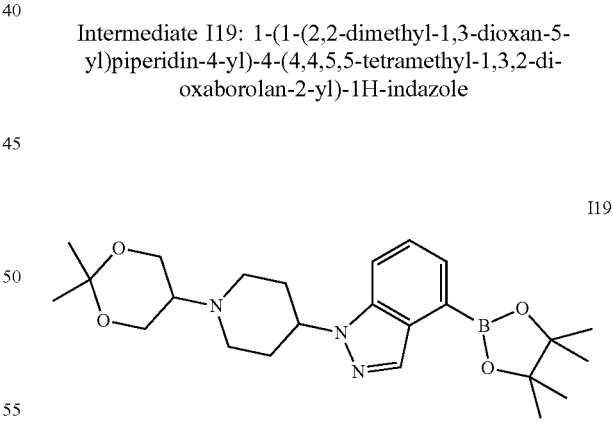

The synthetic route of intermediate I19 is as follows:

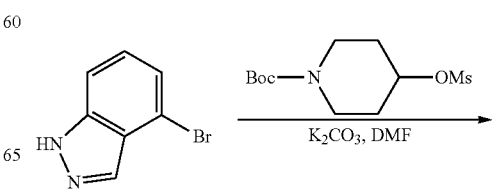

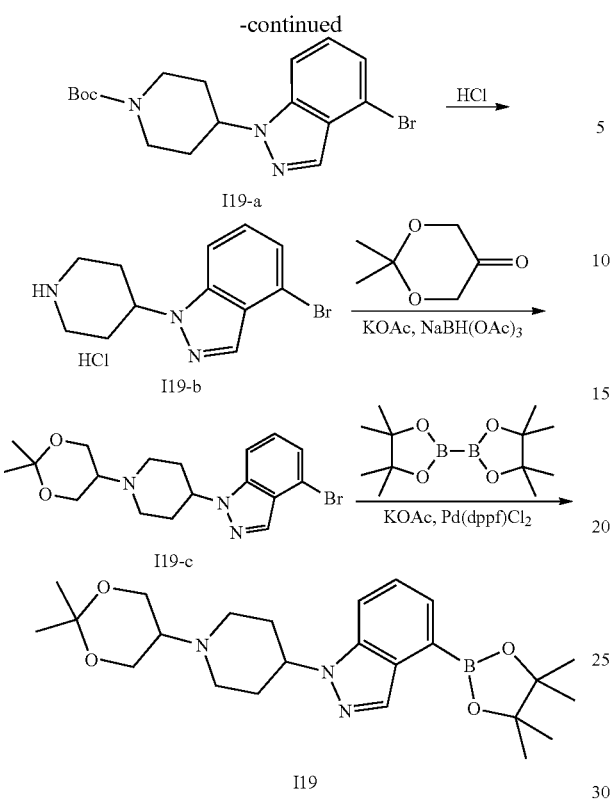

Step 1: To a solution of tert-butyl 4-((methylsµLfonyl) oxy) piperidine-1-carboxylate (6.38 g, 22.84 mmol) and 4-bromo-1H-indazole (3.0 g, 15.23 mmol) in DMF (40 mL), potassium carbonate (6.31 g, 45.68 mmol) was added. The mixture was stirred at 60° C. for 16 h. The resulting mixture was cooled and added with ethyl acetate (100 mL). Then the mixture was washed with water (50 mL×3) and brine (50 mL), dried over Na$_2$SO$_4$ and concentrated. The residue was purified by silica gel column to obtain compound I-19a (3.2 g, 8.41 mmol, yield 55.3%) as colorless oil. MS (ESI): m/z 380.6 (M+H)$^+$.

Step 2: To a solution of compound I-19a (3.2 g, 8.41 mmol) in dioxane (10 mL), HCl (4.0 M in dioxane, 10 mL) was added. The mixture was stirred at room temperature for 2 h. The resulting mixture was concentrated to give compound I19-b (2.6 g, 8.41 mmol, yield 100.0%) as white solid. MS (ESI): m/z 280.6 (M+H)$^+$.

Step 3: To a solution of compound I-19b (1.2 g, 4.28 mmol) and 2,2-dimethyl-1,3-dioxan-5-one (668.91 mg, 5.14 mmol) in 1,2-dichloroethane (10 mL), potassium acetate (1.26 g, 12.85 mmol) was added. The mixture was stirred at room temperature for 1 h followed by the addition of sodium triacetoxyborohydride (2.72 g, 12.85 mmol). The mixture was further stirred at room temperature for 16 h. The resulting mixture was added with water (20 mL) and extracted with DCM (20 mL×2). The combined organic layers were washed with water (20 mL×2) and brine (20 mL), dried over Na$_2$SO$_4$ and concentrated. The residue was purified by silica gel column to obtain compound I-19c (1.1 g, 2.79 mmol, yield 65.1%) as light yellow oil. MS (ESI): m/z 394.4 (M+H)$^+$.

Step 4: To a solution of compound I-19c (1.1 g, 2.79 mmol) and bis(pinacolato)diboron (1.06 g, 4.18 mmol) in dioxane (10 mL), potassium acetate (821.35 mg, 8.37 mmol) and Pd(dppf)Cl$_2$ (127 mg, 0.17 mmol) was added. The mixture was stirred under a nitrogen atmosphere at 90° C. for 16 h. The resulting mixture was cooled, added with ethyl acetate (70 mL) and filtered through celite. The filtrate was washed with water (20 mL×3), brine (20 mL), dried over Na$_2$SO$_4$, filtered and concentrated. The residue was purified by silica gel column chromatography to obtain compound I-19 (900 mg, 2.04 mmol, yield 73.1%) as light yellow oil. MS (ESI): m/z 442.6 (M+H)$^+$.

Intermediate I20 and I21: (R)-1-((1r,4R)-4-((4-(4,4,5,5-tetramethyl-1,3,2-dioxaborolan-2-yl)-1H-indazol-1-yl)methyl)cyclohexyl)pyrrolidin-3-ol and (R)-1-((1s,4S)-4-((4-(4,4,5,5-tetramethyl-1,3,2-dioxaborolan-2-yl)-1H-indazol-1-yl)methyl)cyclohexyl)pyrrolidin-3-ol

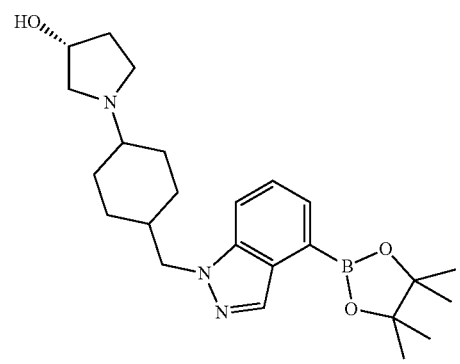

I20, trans-
I21, cis-

The synthetic route of intermediate I20 and intermediate I21 is as follows:

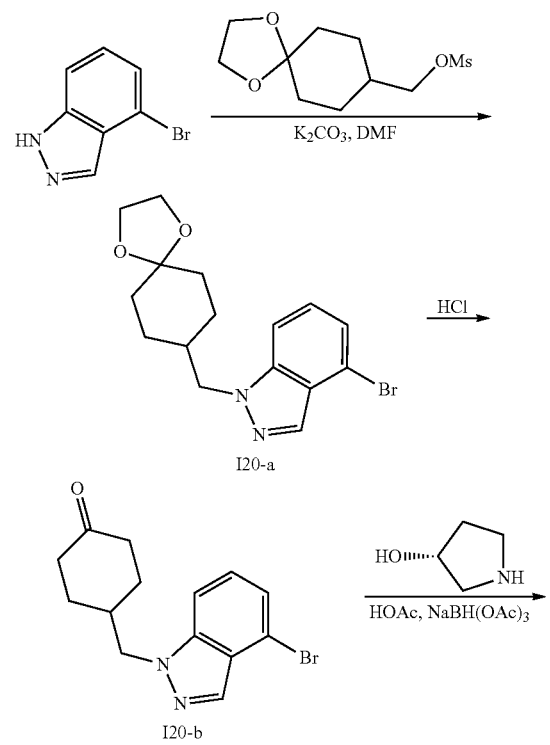

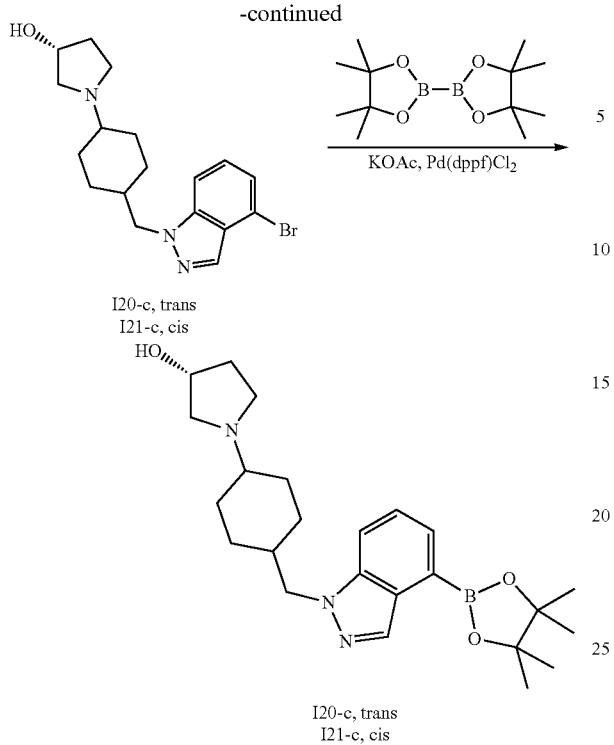

I20-c, trans
I21-c, cis

I20-c, trans
I21-c, cis

Step 1: To a solution of (1,4-dioxaspiro[4.5]decan-8-yl)methyl methanesμLfonate (7.93 g, 31.74 mmol) and 4-bromo-1H-indazole (4.17 g, 21.16 mmol) in DMF (60 mL), potassium carbonate (5.85 g, 42.32 mmol) was added. The mixture was stirred at 60° C. for 16 h. The resulting mixture was cooled and added with ethyl acetate (100 mL). The mixture was washed with water (50 mL×3) and brine (50 mL), dried over $Na_2SO_4$ and concentrated. The residue was purified by silica gel column to obtain compound I20-a (3.16 g, 9.03 mmol, yield 42.7%) as colorless oil. MS (ESI): m/z 351.4 $(M+H)^+$.

Step 2: To a solution of I20-a (3.16 g, 9.03 mmol) in THF (10 mL), hydrochloric acid (4.0 M in water, 10 mL) was added. The mixture was stirred at room temperature for 2 h. The resulting mixture was added with saturated sodium bicarbonate until the pH=7 and then the THF was removed in vacuo. The mixture was extracted with ethyl acetate (50 mL×3). The combined organic layers were washed with water (50 mL) and brine (50 mL), dried over $Na_2SO_4$ and concentrated to give compound I20-b (2.76 g, 9.03 mmol, yield 80.0%) as white solid. MS (ESI): m/z 307.6 $(M+H)^+$.

Step 3: To a solution of compound I20-b (2.5 g, 8.14 mmol) and (R)-pyrrolidin-3-ol (1.06 g, 12.21 mmol) in 1,2-dichloroethane (20 mL), acetic acid (1.47 g, 24.42 mmol) was added. The mixture was stirred at room temperature for 2 h followed by the addition of sodium triacetoxyborohydride (5.17 g, 24.42 mmol). The mixture was further stirred for 16 h. The resulting mixture was added with water (20 mL), extracted with DCM (20 mL×2). The combined organic layers were washed with water (20 mL) and brine (20 mL), dried over $Na_2SO_4$ and concentrated. The residue was purified by silica gel column to obtain compound I20-c (1.63 g, 4.32 mmol, yield 53.1%) as light yellow oil and compound I21-c (1.14 g, 3.02 mmol, yield 37.1%) as light yellow oil. I20-c MS (ESI): m/z 378.7 $(M+H)^+$. I21-c MS (ESI): m/z 378.7 $(M+H)^+$.

Step 4: To a solution of compound I20-c (1.63 g, 4.32 mmol) and bis(pinacolato)diboron (2.19 g, 8.64 mmol) in dioxane (20 mL), potassium acetate (1.27 g, 12.96 mmol) and $Pd(dppf)Cl_2$ (163 mg, 0.22 mmol) was added. The mixture was stirred under a nitrogen atmosphere at 90° C. for 16 h. The resulting mixture was cooled, added with ethyl acetate (50 mL) and filtered through celite. The filtrate was washed with water (20 mL×3), brine (20 mL), dried over $Na_2SO_4$, filtered and concentrated. The residue was purified by silica gel column chromatography to obtain compound I20 (1.30 g, 3.05 mmol, yield 70.6%) as light yellow oil. MS (ESI): m/z 426.7 $(M+H)^+$.

I21(1.02 g, 2.40 mmol, yield 79.5%) was obtained from I21-c by the same way as I20. MS (ESI): m/z 426.7 $(M+H)^+$.

Intermediate I22: (R)-1-(3-(2-methyl-3-(4,4,5,5-tetramethyl-1,3, 2-dioxaborolan-2-yl)phenoxy)propyl)pyrrolidin-3-ol

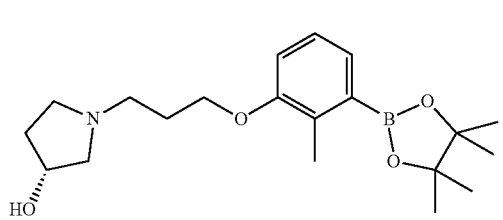

I22

The synthetic route of intermediate I22 is as follows:

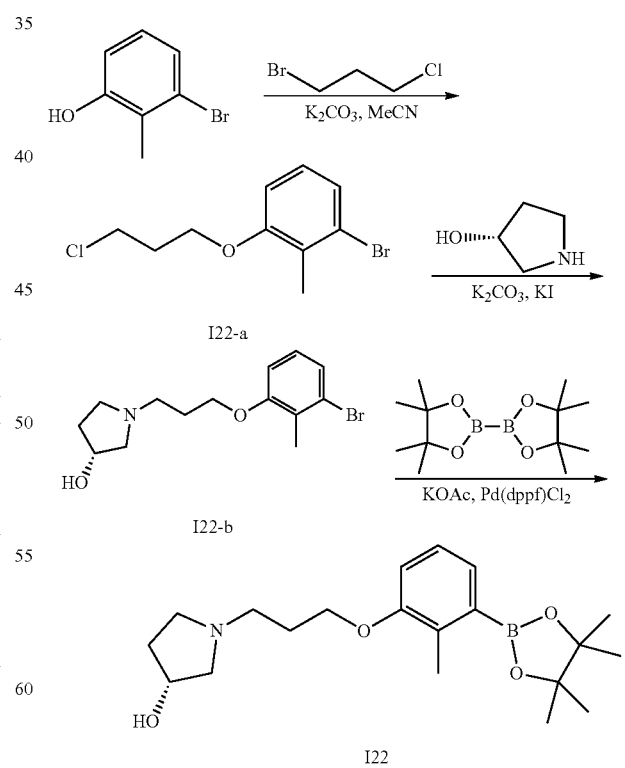

Step 1: To a solution of 1-bromo-3-chloropropane (101.01 g, 641.60 mmol) and 3-bromo-2-methylphenol (80.0 g, 427.73 mmol) in acetonitrile (80 mL), potassium carbonate (177.35 g, 1.28 mol) was added. The mixture was stirred at 60° C. for 16 h. The resulting mixture was cooled, filtered and concentrated to give compound I22-a (112.5 g, 427.73 mmol, yield 100%) as light yellow oil.

Step 2: To a solution of compound I22-a (112.5 g, 427.73 mmol) and (R)-pyrrolidin-3-ol (54.54 g, 626.05 mmol) in acetonitrile (1500 mL), potassium carbonate (173.05 g, 1.25 mol) and potassium iodide (6.93 g, 41.74 mmol) was added. The mixture was stirred at 60° C. for 16 h. The resulting mixture was cooled, filtered and concentrated. The residue was dissolved in ethyl acetate (1000 mL) and washed with water (200 mL×3), brine (200 mL), dried over Na$_2$SO$_4$, filtered and concentrated to obtain compound I22-b (130.0 g, 413.73 mmol, yield 99.1%) as light yellow oil. MS (ESI): m/z 314.6 (M+H)$^+$.

Step 3: To a solution of compound I22-b (130.0 g, 413.73 mmol) and bis(pinacolato)diboron (157.59 g, 620.59 mmol) in dioxane (500 mL), potassium acetate (104.26 g, 1.24 mol) and Pd(dppf)Cl$_2$ (15.14 g, 20.69 mmol) was added. The mixture was stirred under a nitrogen atmosphere at 90° C. for 16 h. The resulting mixture was cooled, added with ethyl acetate (500 mL) and filtered through celite. The filtrate was washed with water (100 mL×3), brine (100 mL), dried over Na$_2$SO$_4$, filtered and concentrated. The residue was purified by silica gel column chromatography to obtain compound I22 (63.7 g, 176.32 mmol, yield 42.6%) as light yellow oil. MS (ESI): m/z 362.6 (M+H).

Intermediate I23: (R)-1-(3-(2-bromo-3-(4,4,5,5-tetramethyl-1,3,2-dioxaborolan-2-yl)phenoxy) propyl)pyrrolidin-3-ol

I23

The synthetic route of intermediate I23 is same as intermediate I22

Intermediate I24: tert-butyl N-(4-((2-bromo-3-iodobenzyl)oxy)-5-chloro-2-hydroxybenzyl)-N-(tert-butoxycarbonyl)-O-(tert-butyl)-L-serinate

I24

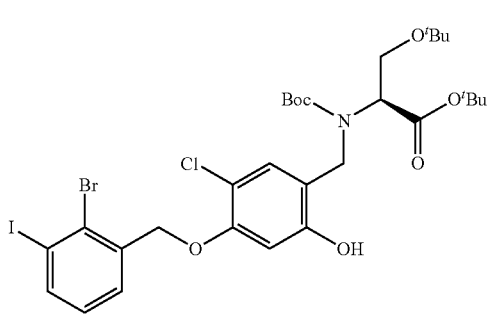

The synthetic route of intermediate I24 is as follows:

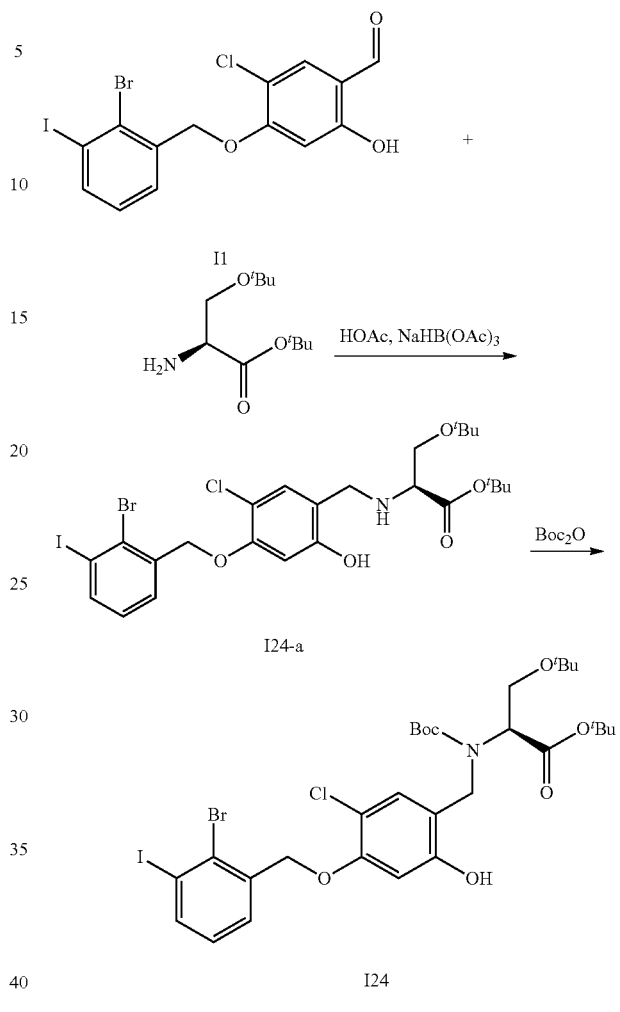

Step 1: To a solution of compound I1 (2.0 g, 4.28 mmol) in DMF (10 mL), tert-butyl O-(tert-butyl)-L-serinate (1.39 g, 6.42 mmol) and acetic acid (256.91 mg, 4.28 mmol) was added. The mixture was stirred at room temperature for 16 h followed by the addition of sodium triacetoxyborohydride (906.73 mg, 4.28 mmol). The mixture was stirred at room temperature for 3 h. The resulting mixture was added with water (20 mL) and extracted with ethyl acetate (50 mL×3). The combined organic layers were washed with water (30 mL×2) and brine (30 mL), dried over Na$_2$SO$_4$ and concentrated. The residue was purified by silica gel column to obtain compound I24-a (2.8 g, 4.19 mmol, yield 97.9%) as white solid. MS (ESI): m/z 668.6 (M+H)$^+$.

Step 2: To a solution of compound I24-a (2.8 g, 4.19 mmol) in DCM (20 mL), di-tert-butyl decarbonate (1.01 g, 4.61 mmol, 1.06 mL) was added in ice bath. The mixture was stirred from 0° C. to room temperature for 16 h. The resulting mixture was added with DCM (50 mL) and then washed with water (20 mL×2) and brine (20 mL), dried over Na$_2$SO$_4$ and concentrated. The residue was purified by silica gel column to obtain compound I24 (3.0 g, 3.90 mmol, yield 97.9%) as white solid. MS (ESI): m/z 768.4 (M+H)$^+$.

Intermediate I25: (S)-2-(5-((2-bromo-3-iodobenzyl)oxy)-2-(((tert-butoxycarbonyl)(1,3-di-tert-butoxy-1-oxopropan-2-yl)amino)methyl)-4-chlorophenoxy)acetic acid

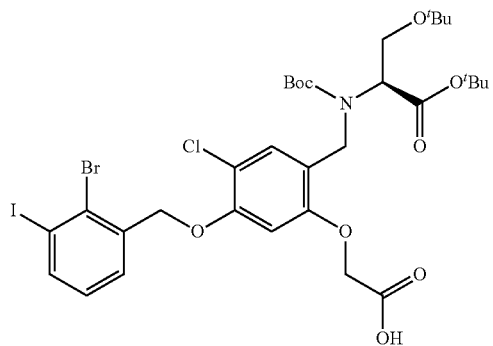

The synthetic route of intermediate I25 is as follows:

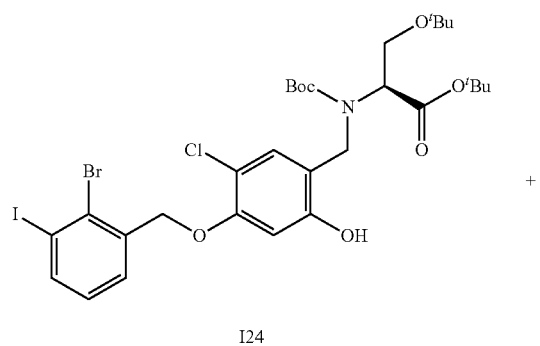

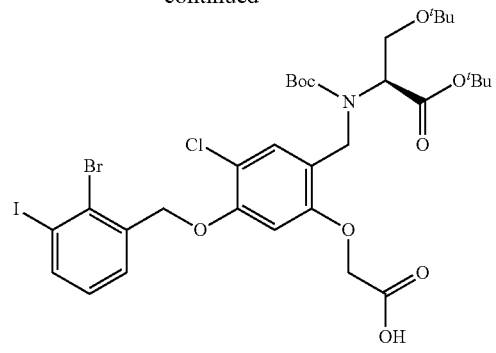

Step 1: To a solution of compound I24 (1.0 g, 1.30 mmol) in DMF (20 mL), methyl bromoacetate (298.43 mg, 1.95 mmol) and potassium carbonate (539.25 mg, 3.90 mmol) was added. The mixture was stirred at 50° C. for 6 h. The resulting mixture was cooled and added with ethyl acetate (60 mL). The mixture was washed with water (20 mL×2) and brine (20 mL), dried over Na$_2$SO$_4$, filtered and concentrated to give compound I25-a (1.09 g, 1.30 mmol, yield 100%) as light yellow oil.

Step 2: To a solution of I25-a (1.09 g, 1.30 mmol) in a mixture of THF (4 mL), methanol (4 mL) and water (4 mL), lithium hydroxide (108.88 mg, 2.59 mmol) was added. The mixture was stirred at 25° C. for 3 h. The resulting mixture was added with saturated citric acid until the pH=4 and then extracted with ethyl acetate (20 mL×3). The combined organic layers were washed with water (30 mL×2) and brine (30 mL), dried over Na$_2$SO$_4$, filtered and concentrated to give compound I25 (1.0 g, 1.21 mmol, yield 93.3%) as light yellow oil. MS (ESI): m/z 826.5 (M+H)$^+$.

Intermediate I40: tert-butyl N-(tert-butoxycarbonyl)-O-(tert-butyl)-N-(5-chloro-2-((5-cyanopyridin-3-yl)methoxy)-4-hydroxybenzyl)-L-serinate

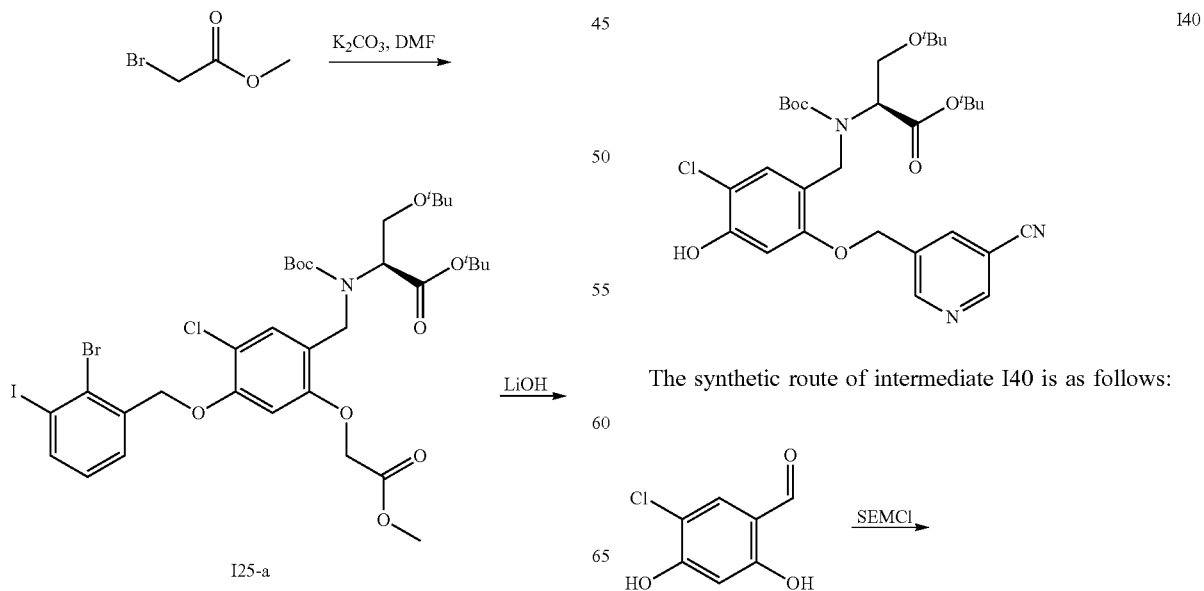

The synthetic route of intermediate I40 is as follows:

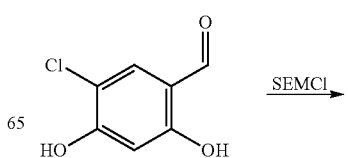

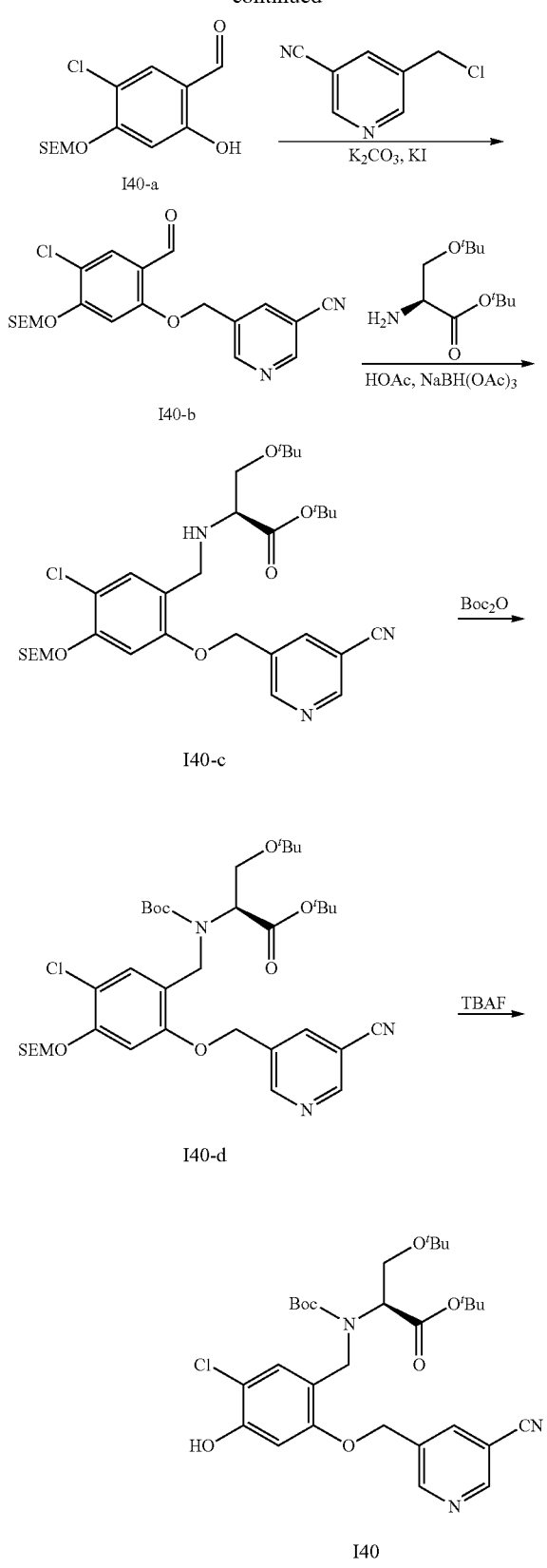

Step 1: To a solution of 5-chloro-2,4-dihydroxybenzaldehyde (5.0 g, 29.07 mmol) and N,N-diisopropylethylamine (5.62 g, 43.60 mmol) in THF (50 mL), 2-(Trimethylsilyl)ethoxymethyl chloride (5.79 g, 34.88 mmol) was slowly added in ice bath. The mixture was stirred at room temperature for 3 h. The resulting mixture was added with water (100 mL) and extracted with ethyl acetate (50 mL×2). The combined organic layers were washed with water (20 mL×2) and brine (20 mL), dried over $Na_2SO_4$ and concentrated. The residue was purified by silica gel column to obtain compound I40-a (150 mg, 411.77 μmol, yield 80.5%) as light yellow oil. MS (ESI): m/z 364.5 $(M+H)^+$.

Step 2: To a mixture of compound I40-a (5.5 g, 18.21 mmol) in DMF (50 mL), potassium carbonate (5.03 g, 36.42 mmol), potassium iodide (3.02 g, 18.21 mmol) and 5-(chloromethyl)nicotinonitrile (3.32 g, 21.85 mmol) was added. The mixture was stirred at 80° C. for 2 h. The resulting mixture was cooled, added with water (60 mL) and stirred for 20 min. Then the mixture was filtered, and the cake was washed with water (50 mL×3), ethyl acetate (20 mL×2) and dried to give compound I40-b (7.0 g, 16.75 mmol, yield 92.0%) as white solid. MS (ESI): m/z 419.4 $(M+H)^+$.

Step 3: To a solution of compound I40-b (4.0 g, 9.57 mmol) in DMF (20 mL), tert-butyl O-(tert-butyl)-L-serinate (2.49 g, 11.48 mmol) and acetic acid (1.15 g, 19.14 mmol) was added. The mixture was stirred at room temperature for 3 h followed by the addition of sodium triacetoxyborohydride (6.09 g, 28.71 mmol). The mixture further was stirred at room temperature for 16 h. The resulting mixture was added with water (50 mL) and extracted with ethyl acetate (50 mL×3). The combined organic layers were washed with water (30 mL×2) and brine (30 mL), dried over $Na_2SO_4$ and concentrated. The residue was purified by silica gel column to obtain compound I40-c (5.57 g, 8.99 mmol, 94.0%) as white solid. MS (ESI): m/z 620.4 $(M+H)^+$.

Step 4: To a solution of compound I40-c (5.57 g, 8.99 mmol) and triethylamine (2.72 g, 26.97 mmol) in THF (40 mL), di-tert-butyl decarbonate (3.92 g, 17.98 mmol) was added in ice bath. The mixture was warmed to room temperature while stirring and stirred at the same temperature for 16 h. The resulting mixture was added with water (60 mL) and extracted with ethyl acetate (50 mL×3). The combined organic layers were washed with brine (50 mL), dried over $Na_2SO_4$ and concentrated. The residue was purified by silica gel column to obtain compound I40-d (4.31 g, 5.99 mmol, yield 66.7%) as light yellow oil. MS (ESI): m/z 720.5 $(M+H)^+$.

Step 5: To a solution of compound I40-d (4.31 g, 5.99 mmol) in THF (50 mL), tetrabutylammonium fluoride (1.0 M in THF, 29.95 mL, 29.95 mmol) was added. The mixture was stirred at 50° C. for 16 h. The resulting mixture was cooled, added with saturated ammonium chloride (100 mL) and extracted with ethyl acetate (60 mL×3). The combined organic layers were washed with brine (50 mL), dried over $Na_2SO_4$ and concentrated. The residue was purified by silica gel column to obtain compound I40 (1.81 g, 3.07 mmol, yield 51.2%) as light yellow solid. MS (ESI): m/z 590.3 $(M+H)^+$.

Intermediate I41: 6-(2-chloro-3-(4,4,5,5-tetramethyl-1,3,2-dioxaborolan-2-yl)phenyl)-2-methoxynicotinaldehyde

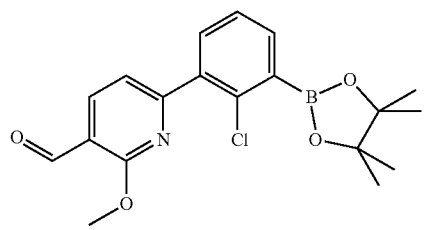

I41

The synthetic route of intermediate I41 is as follows:

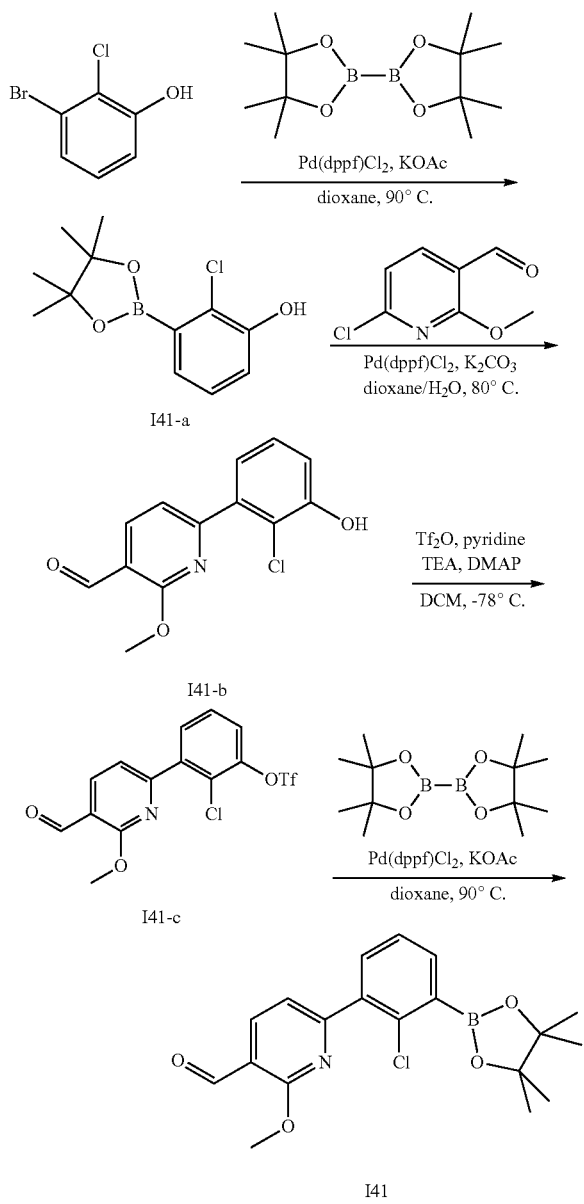

Step 1: To a solution of 3-bromo-2-chlorophenol (3.0 g, 14.46 mmol) and bis(pinacolato)diboron (4.41 g, 17.35 mmol) in dioxane (30 mL), potassium acetate (4.26 g, 43.38 mmol) and Pd(dppf)Cl$_2$ (529.06 mg, 723.06 μmol) was added. The mixture was stirred under a nitrogen atmosphere at 90° C. for 16 h. The resulting mixture was cooled, added with ethyl acetate (100 mL) and filtered through celite. The filtrate was concentrated. The residue was purified by silica gel column chromatography to obtain compound I41-a (3.17 g, 12.45 mmol, yield 86.1%) as white solid. MS (ESI): m/z 253.2 (M−H)⁻.

Step 2: To a solution of compound I41-a (890.02 mg, 3.50 mmol) and 6-chloro-2-methoxynicotinaldehyde (500 mg, 2.91 mmol) in a mixture of dioxane (10 mL) and water (2 mL), potassium carbonate (1.21 g, 8.74 mmol) and Pd(dppf)Cl$_2$ (106.61 mg, 145.70 μmol) was added. The mixture was stirred under a nitrogen atmosphere at 90° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by silica gel column chromatography to obtain compound I41-b (565 mg, 2.14 mmol, yield 73.5%) as light yellow solid. MS (ESI): m/z 262.1 (M−H)⁻. H NMR (500 MHz, DMSO-d$_6$) δ 10.39 (s, 1H), 10.29 (s, 1H), 8.17 (d, J=7.7 Hz, 1H), 7.40 (d, J=7.7 Hz, 1H), 7.27 (t, J=7.8 Hz, 1H), 7.13-7.05 (m, 2H), 4.03 (s, 3H).

Step 3: To a solution of I41-b (950 mg, 3.60 mmol) in dry DCM (20 mL), pyridine (740.97 mg, 9.37 mmol), 4-dimethylaminopyridine (44.02 mg, 360.29 μmol) and triethylamine (765.61 mg, 7.57 mmol, 1.05 mL) was added in sequence under a nitrogen atmosphere. Then the mixture was cooled to −78° C. followed the dropwise addition of triflic anhydride (1.17 g, 4.14 mmol, 695.83 μL). The mixture was stirred at −78° C. for 15 min and then further stirred at room temperature for 1 h. The resulting mixture added with ethyl acetate (200 mL) and washed with saturated citric acid (100 mL), brine (50 mL), dried over Na$_2$SO$_4$, filtered and concentrated. The residue was purified by silica gel column chromatography to obtain compound I41-c (1.1 g, 2.78 mmol, yield 77.2%) as light yellow solid. MS (ESI): m/z 396.3 (M+H)⁺. ¹H NMR (500 MHz, DMSO-d$_6$) δ 10.30 (s, 1H), 8.25 (d, J=7.6 Hz, 1H), 7.84 (dd, J=7.7, 1.5 Hz, 1H), 7.79 (dd, J=8.3, 1.5 Hz, 1H), 7.70 (t, J=8.0 Hz, 1H), 7.51 (d, J=7.7 Hz, 1H), 4.06 (s, 3H).

Step 4: To a solution of compound I41-c (500 mg, 1.26 mmol) and bis(pinacolato)diboron (385.01 mg, 1.52 mmol) in dioxane (10 mL), potassium acetate (371.99 mg, 3.79 mmol) and Pd(dppf)Cl$_2$ (92.45 mg, 126.35 μmol) was added. The mixture was stirred under a nitrogen atmosphere at 90° C. for 16 h. The resulting mixture was cooled, added with ethyl acetate (50 mL) and filtered through celite. The filtrate was concentrated. The residue was purified by silica gel column chromatography to obtain compound I41 (225 mg, 602.19 μmol, yield 47.7%) as light yellow solid. MS (ESI): m/z 374.2 (M+H)⁺.

Example 49: (4-((2-bromo-3-(1-(4-((R)-3-hydroxy-pyrrolidin-1-yl)butyl)-1H-indazol-4-yl)benzyl)oxy)-5-chloro-2-(2-((R)-3-hydroxypyrrolidin-1-yl)-2-oxo-ethoxy)benzyl)-L-serine
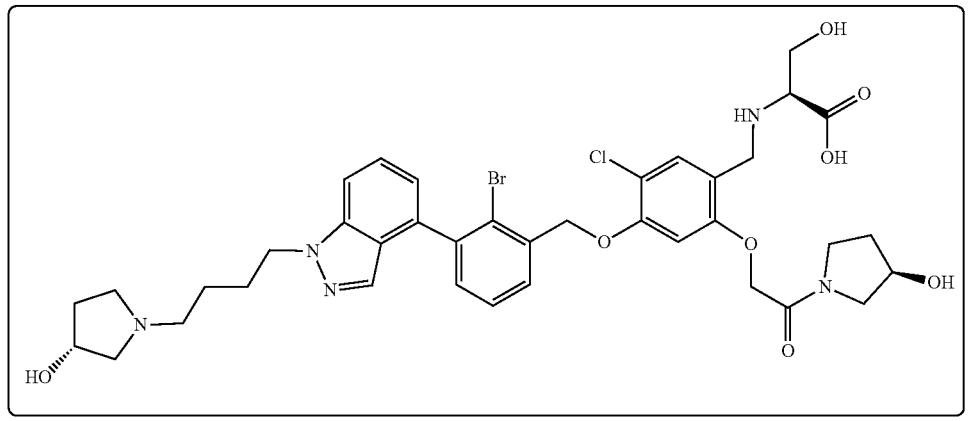
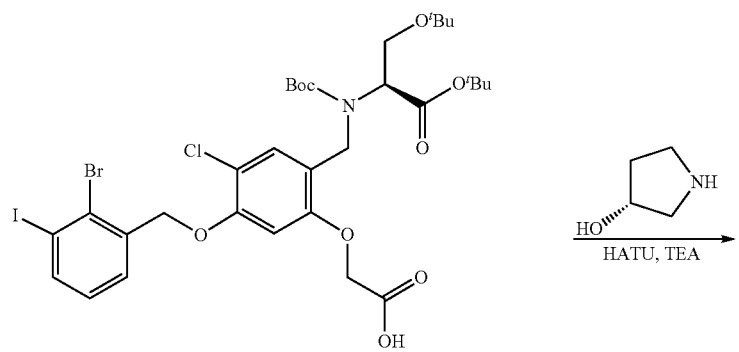
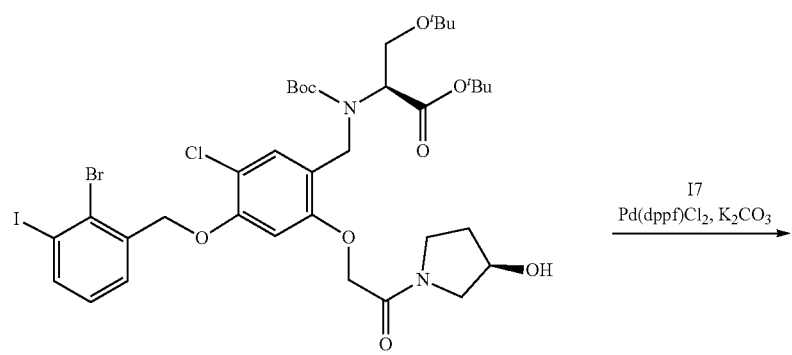

-continued

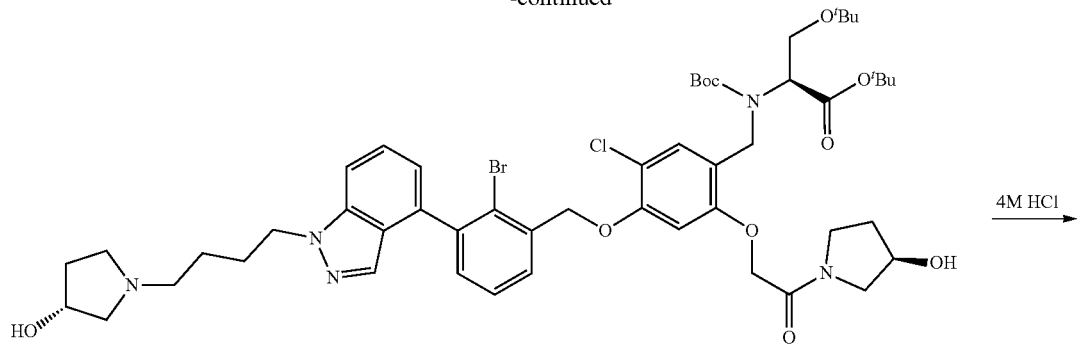

49b

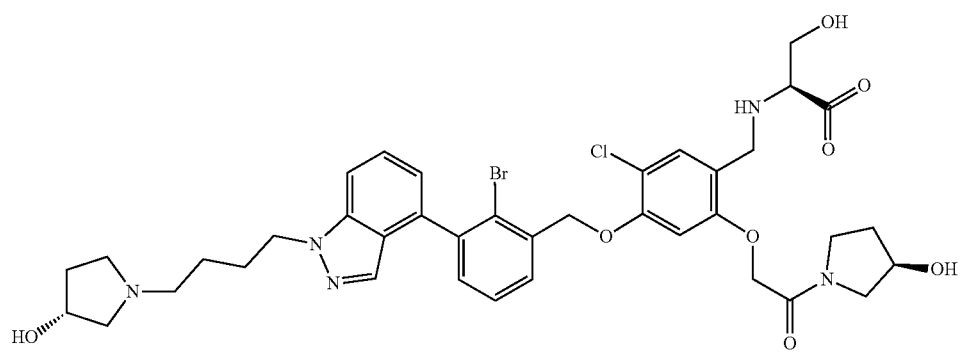

49

Step 1: To a solution of compound I25 (85 mg, 102.79 μmol) and (R)-pyrrolidin-3-ol (13.43 mg, 154.18 μmol) in DMF (3 mL), triethylamine (31.20 mg, 308.37 μmol) and HATU (58.63 mg, 154.18 μmol) was added. The mixture was stirred at room temperature for 0.5 h. The resulting mixture was added with water (20 mL) and extracted with ethyl acetate (20 mL×3). The combined organic layers were washed with water (10 mL) and brine (10 mL), dried over Na$_2$SO$_4$ and concentrated. The residue was purified by silica gel column to obtain compound 49a (90 mg, 100.44 μmol, yield 97.7%) as light yellow solid. MS (ESI): m/z 895.3 (M+H)$^+$.

Step 2: To a solution of compound 49a (90 mg, 100.44 μmol) and compound I7 (38.70 mg, 100.44 μmol) in a mixture of dioxane (4 mL) and water (0.4 mL), potassium carbonate (41.65 mg, 301.33 μmol) and Pd(dppf)Cl$_2$ (7.35 mg, 10.04 μmol) was added. The mixture was stirred under nitrogen atmosphere at 80° C. for 16 h. The resulting mixture was cooled, added with ethyl acetate (30 mL) and filtered through celite. The filtrate was washed with water (10 mL×3), brine (10 mL), dried over Na$_2$SO$_4$, filtered and concentrated. The residue was purified by silica gel column chromatography to obtain compound 49b (100 mg, 97.33 μmol, yield 96.9%) as light yellow solid. MS (ESI): m/z 1025.7 (M+H)$^+$.

Step 3: To a solution of compound 49b (100 mg, 97.33 μmol) in THF (3 mL), hydrochloric acid (4.0 M in water, 3 mL) was added. The mixture was stirred under at 50° C. for 16 h. The resulting mixture was cooled, added with sodium acetate until the pH=4, and concentrated. The residue was stirred in DMF (3 mL) and then filtered. The filtrate was purified by prep-HPLC to obtain compound 49 (15 mg, 18.40 μmol, yield 18.9%) as white solid. MS (ESI): m/z 814.1 (M+H)$^+$. $^1$H NMR (500 MHz, d$_6$-DMSO) δ 7.73 (d, J=8.5 Hz, 1H), 7.70 (d, J=7.5 Hz, 1H), 7.66 (s, 1H), 7.55 (t, J=7.5 Hz, 1H), 7.50-7.46 (m, 2H), 7.45-7.42 (m, 1H), 7.08-7.04 (m, 2H), 5.31 (s, 2H), 4.96 (s, 1H), 4.93-4.88 (m, 1H), 4.44 (t, J=7.0 Hz, 2H), 4.31 (s, 1H), 4.22 (s, 1H), 4.17 (s, 1H), 4.08-4.04 (m, 1H), 4.00-3.97 (m, 1H), 3.73-3.70 (m, 1H), 3.65-3.60 (m, 1H), 3.55-3.53 (m, 2H), 3.43-3.31 (m, 2H), 3.29-3.27 (m, 1H), 3.21-3.19 (m, 1H), 2.79-2.73 (m, 1H), 2.71-2.66 (m, 1H), 2.55-2.53 (m, 3H), 2.46-2.43 (m, 1H), 2.00-1.93 (m, 1H), 1.91-1.85 (m, 3H), 1.60-1.54 (m, 1H), 1.50-1.44 (m, 2H).

The following compounds were prepared from compound I25 using the similar procedures as described for compound 49.

| Compound | structure | MS (ESI): (M + H)+ | HNMR |
|---|---|---|---|
| 50 | 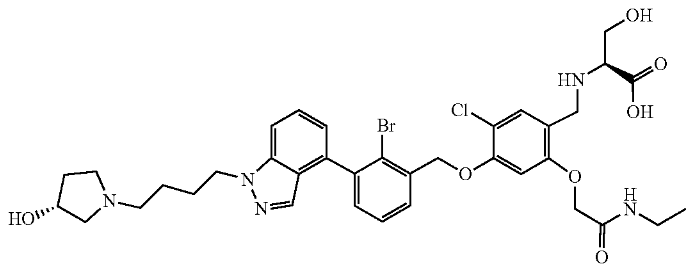 [SMILES: CCNC(=O)COc1cc(OCc2cccc(-c3cccc4c3cnn4CCCCN3CC[C@@H](O)C3)c2Br)c(Cl)cc1CN[C@@H](CO)C(=O)O] | 774.2 | ¹H NMR (500 MHz, d₆-DMSO) δ 8.65 (s, 1H), 7.76 – 7.71 (m, 2H), 7.69 (s, 1H), 7.57 (t, J = 7.5 Hz, 1H), 7.53 (s, 1H), 7.50 – 7.44 (m, 2H), 7.09 (d, J = 7.0 Hz, 1H), 7.01 (s, 1H), 5.37 (s, 2H), 4.68 – 4.57 (m, 3H), 4.46 (t, J = 7.0 Hz, 2H), 4.18 (s, 1H), 4.10 – 4.07 (m, 1H), 4.01 – 3.99 (m, 1H), 3.75 – 3.72 (m, 1H), 3.66 – 3.64 (m 1H), 3.22 – 3.16 (m, 3H), 2.75 – 2.69 (m, 2H), 2.66 – 2.59 (s, 2H), 2.42 – 2.34 (m, 1H), 1.98 – 1.93 (m, 1H), 1.91 – 1.85 (m, 2H), 1.55 (s, 1H), 1.46 (s, 2H), 1.06 (t, J = 7.0 Hz, 3H). |
| 51 | 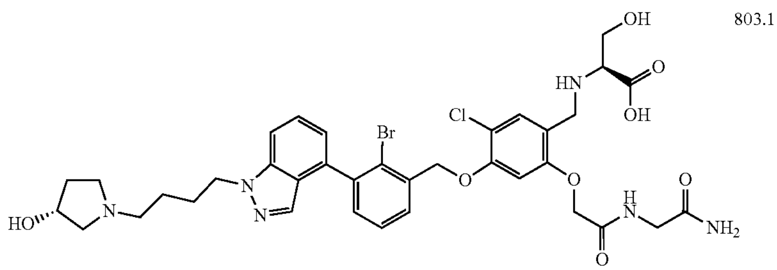 | 803.1 | ¹H (500 MHz, d₆-DMSO) δ 9.03 (s, 1H), 7.87 (s, 1H), 7.76 – 7.74 (m, 2H), 7.69 (s, 1H), 7.59 – 7.56 (m, 2H), 7.50 – 7.45 (m, 2H), 7.09 (d, J = 7.0 Hz, 1H), 7.07 (s, 1H), 6.99 (s, 1H), 5.39 (s, 2H), 4.67 (s, 2H), 4.46 (t, J = 7.0 Hz, 2H), 4.23 – 4.17 (m, 2H), 4.16 – 4.11 (m, 2H), 3.77 – 3.69 (m, 3H), 3.68 – 3.60 (m, 2H), 3.20 (s, 1H), 2.79 (s, 1H), 2.71 (s, 1H), 2.57 (s, 3H), 2.00 – 1.93 (m, 1H), 1.91 – 1.85 (m, 2H), 1.58 (s, 1H), 1.50 – 1.44 (m, 2H). |
| 52 | 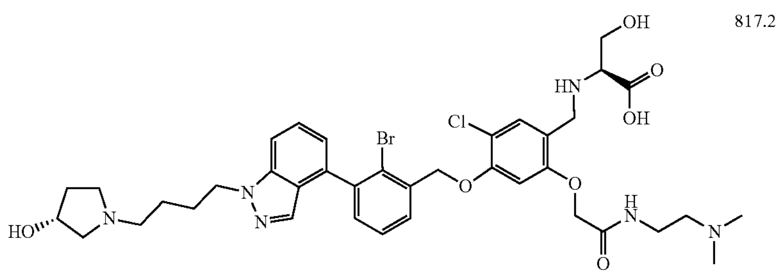 | 817.2 | ¹H NMR (500 MHz, d₆-DMSO) δ 7.75 (d, J = 8.0 Hz, 2H), 7.68 (s, 1H), 7.60 – 7.56 (m, 2H), 7.51 – 7.45 (m, 2H), 7.14 (s, 1H), 7.09 (d, J = 7.0 Hz, 1H), 5.37 (s, 2H), 4.97 – 4.94 (m, 1H), 4.87 – 4.84 (m, 1H), 4.46 (t, J = 7.0 Hz, 2H), 4.21 – 4.19 (m, 2H), 4.03 – 4.01 (m, 1H), 3.78 – 3.74 (m, 1H), 3.66 – 3.59 (m, 3H), 3.19 (s, 1H), 3.07 (s, 1H), 3.04 (s, 3H), 2.77 (s, 1H), 2.68 (s, 1H), 2.52 (s, 6H), 2.45 (s, 2H), 1.99 – 1.94 (m, 1H), 1.90 – 1.85 (m, 2H), 1.56 (s, 1H), 1.49 – 1.43 (m, 2H). |
| 53 | 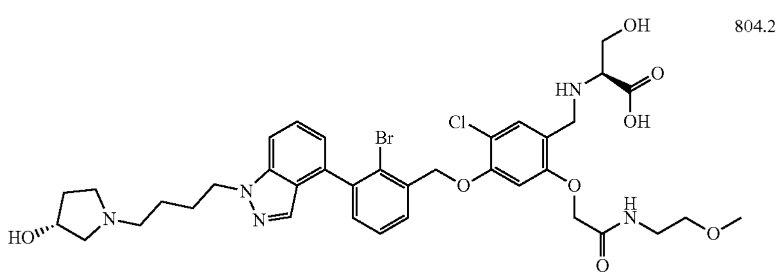 | 804.2 | ¹H NMR (500 MHz, d₆-DMSO) δ 8.65 (s, 1H), 7.74 (t, J = 8.0 Hz, 2H), 7.69 (s, 1H), 7.57 (t, J = 7.5 Hz, 1H), 7.53 (s, 1H), 7.51 – 7.44 (m, 2H), 7.09 (d, J = 7.0 Hz, 1H), 7.01 (s, 1H), 5.36 (s, 2H), 4.69 – 4.60 (m, 2H), 4.46 (t, J = 7.0 Hz, 2H), 4.17 (s, 1H), 4.09 – 4.06 (m, 1H), 4.01 – 3.98 (m, 1H), 3.75 – 3.71 (m, 1H), 3.66 – 3.62 (m, 1H), 3.42 (t, J = 6.0 Hz, 2H), 3.35 – 3.29 (m, 2H), 3.21 (s, 3H), 3.19 – 3.18 (m, 1H), 2.74 – 2.69 (m, 1H), 2.64 – 2.59 (m, 1H), 2.48 – 2.47 (m, 1H), 2.38 – 2.36 (m, 1H), 1.97 – 1.93 (m, 1H), 1.91 – 1.85 (m, 2H), 1.57 – 1.51 (m, 1H), 1.48 – 1.42 (m, 2H). |

Example 54: (5-chloro-2-((5-cyanopyridin-3-yl)methoxy)-4-((4-(3-(3-((R)-3-hydroxypyrrolidin-1-yl)propoxy)-2-methylphenyl)-1H-indazol-1-yl)methyl)benzyl)-L-serine
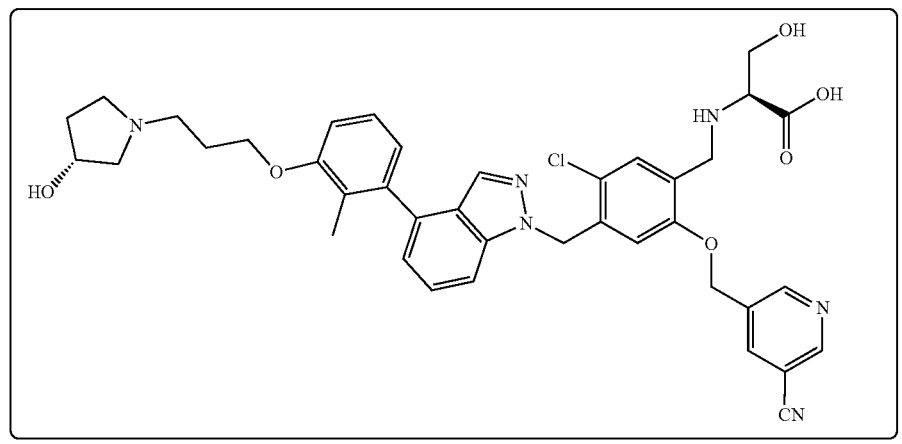
54
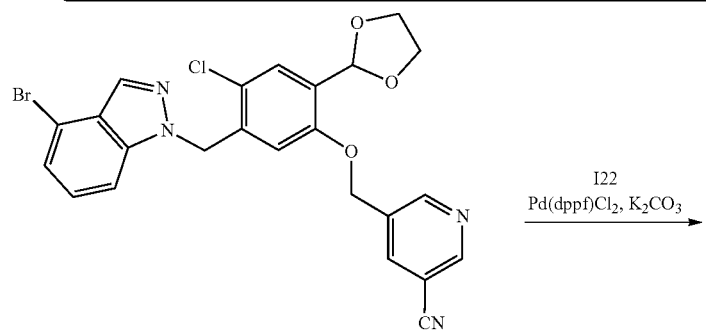
I22
Pd(dppf)Cl₂, K₂CO₃
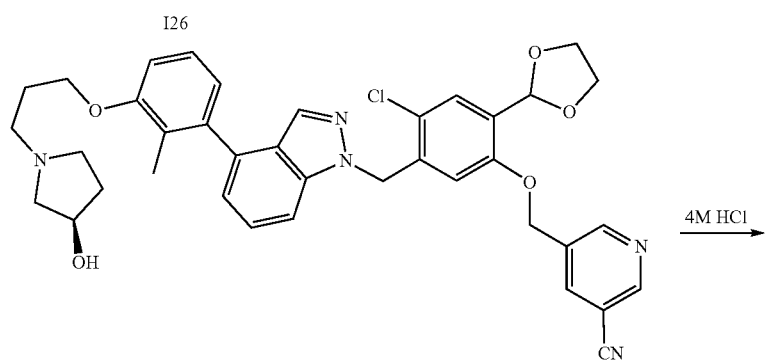
4M HCl
54a
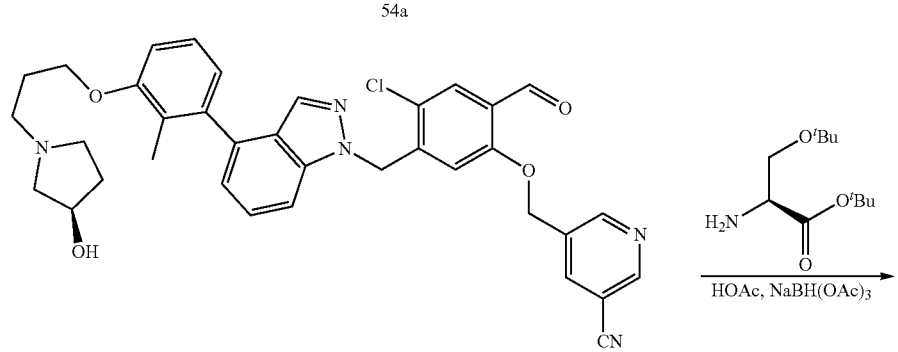
HOAc, NaBH(OAc)₃
54b -continued

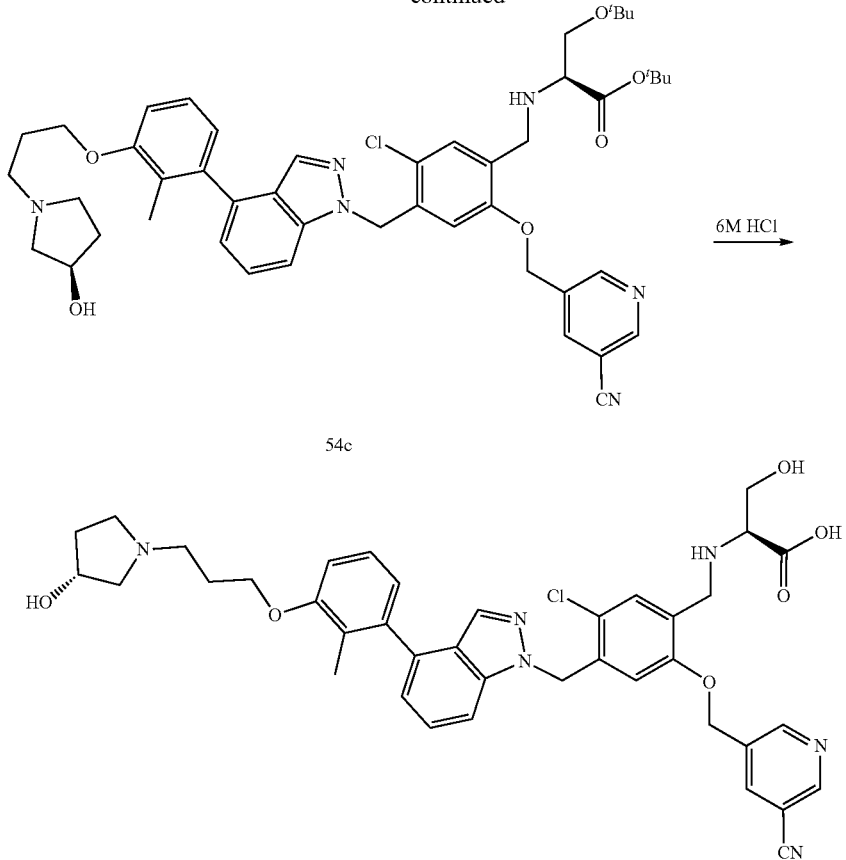

Step 1: To a solution of compound I26 (1.5 g, 912.93 μmol) and compound I22 (494.74 mg, 1.37 mmol) in a mixture of dioxane (10 mL) and water (2 mL), potassium carbonate (630.88 mg, 4.56 mmol) and Pd(dppf)Cl₂ (66.80 mg, 91.29 μmol) were added. The mixture was stirred under nitrogen atmosphere at 90° C. for 3 h. The resulting mixture was cooled, added with ethyl acetate (50 mL) and filtered through celite. The filtrate was washed with water (20 mL×3), brine (20 mL), dried over Na₂SO₄, filtered and concentrated to give the crude compound 54a (0.62 g, 913.10 μmol, yield 100%) as light yellow solid. MS (ESI): m/z 680.3 (M+H)⁺.

Step 2: To a solution of 54a (0.6 g, 882.11 μmol) in THF (10 mL), hydrochloric acid (4.0 M in water, 1.85 mL) was added. The mixture was stirred at room temperature for 0.5 h. The resulting mixture was added with saturated sodium bicarbonate until the pH=7, and then the THF was removed in vacuo. The mixture was extracted with ethyl acetate (30 mL×2). The combined organic layers were washed with brine (20 mL), dried over Na₂SO₄ and concentrated to give compound 54b (0.56 g, 881.19 μmol, yield 99.8%) as light yellow solid. MS (ESI): m/z 636.3 (M+H)⁺.

Step 3: To a solution of 54b (0.1 g, 157.20 μmol) in DMF (2 mL), tert-butyl O-(tert-butyl)-L-serinate (0.09 g, 414.17 μmol) and acetic acid (262.50 mg, 4.37 mmol, 0.25 mL) was added. The mixture was stirred at room temperature for 2 h followed by the addition of sodium triacetoxyborohydride (199.90 mg, 943.19 μmol) and further stirred at room temperature for 1 h. The resulting mixture was added with water (20 mL) and extracted with ethyl acetate (30 mL×2). The combined organic layers were washed with brine (10 mL), dried over Na₂SO₄ and concentrated. The residue was purified by prep-TLC to give compound 54c (90 mg, 107.66 μmol, yield 68.4%) as light yellow solid. MS (ESI): m/z 837.6 (M+H)⁺.

Step 4: To a solution of compound 54c (0.08 g, 95.53 μmol) in THF (6 mL), hydrochloric acid (6.0 M in water, 6 mL) was added. The mixture was stirred at 50° C. for 3 h. The resulting mixture was cooled, added with sodium acetate until the pH=4 and concentrated. The residue was stirred in DMF (3 mL) and then filtered. The filtrate was purified by prep-HPLC to obtain compound 54 (20 mg, 27.62 μmol, yield 28.9%) as white solid. MS (ESI): m/z 725.9 (M+H)⁺. ¹H NMR (500 MHz, d₆-DMSO) δ 8.95 (d, J=2.0 Hz, 1H), 8.85 (d, J=2.0 Hz, 1H), 8.34 (s, 1H), 7.69 (s, 1H), 7.65 (d, J=8.5 Hz, 1H), 7.55 (s, 1H), 7.44 (dd, J=8.5, 7.0 Hz, 1H), 7.26 (t, J=8.0 Hz, 1H), 7.01 (t, J=7.5 Hz, 2H), 6.91 (d, J=7.5 Hz, 1H), 6.86 (s, 1H), 5.70 (s, 2H), 5.15-5.05 (m, 2H), 4.21 (s, 1H), 4.08 (t, J=6.0 Hz, 2H), 3.94 (d, J=14.0 Hz, 1H), 3.87 (d, J=14.0 Hz, 1H), 3.64-3.57 (m, 3H), 3.16-3.12 (m, 1H), 2.81-2.76 (m, 1H), 2.72-2.60 (m, 3H), 2.58-2.52 (m, 1H), 2.46-2.34 (m, 2H), 2.05-1.85 (m, 6H), 1.61-1.53 (m, 1H).

Example 55: (4-((4-(2-bromo-3-(3-((R)-3-hydroxy-pyrrolidin-1-yl)propoxy)phenyl)-1H-indazol-1-yl)methyl)-5-chloro-2-((5-cyanopyridin-3-yl)methoxy)benzyl)-L-serine

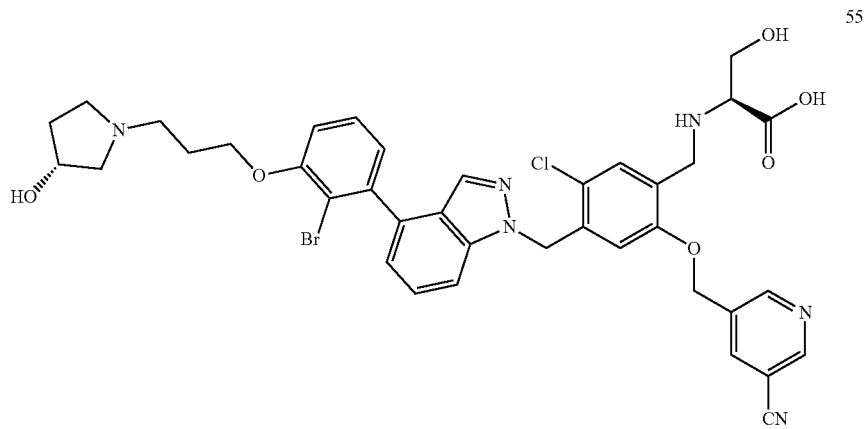 [SMILES: N#Cc1cncc(COc2cc(Cn3ncc4c(-c5cccc(OCCCN6CC[C@@H](O)C6)c5Br)cccc43)c(Cl)cc2CN[C@@H](CO)C(=O)O)c1]

Compound 55 was prepared using similar procedures as described for compound 54 with compound I23 replacing compound I22. MS (ESI): m/z 790.0 (M+H)$^+$. $^1$H NMR (500 MHz, d$_6$-DMSO) δ 8.95 (d, J=2.0 Hz, 1H), 8.85 (d, J=2.0 Hz, 1H), 8.34 (s, 1H), 8.21 (s, 1H), 7.73-7.65 (m, 2H), 7.55 (s, 1H), 7.48-7.41 (m, 2H), 7.18 (dd, J=8.5, 1.0 Hz, 1H), 7.06 (d, J=7.0 Hz, 1H), 7.03 (dd, J=7.5, 1.0 Hz, 1H), 6.82 (s, 1H), 5.71 (s, 2H), 5.13-5.04 (m, 2H), 4.20 (s, 1H), 4.16 (t, J=6.0 Hz, 2H), 3.94 (d, J=14.5 Hz, 1H), 3.86 (d, J=14.5 Hz, 1H), 3.64 (dd, J=11.0, 4.0 Hz, 1H), 3.58 (dd, J=11.0, 6.0 Hz, 1H), 3.16-3.12 (m, 1H), 2.76 (s, 1H), 2.70-2.60 (m, 3H), 2.40 (s, 1H), 2.03-1.90 (m, 3H), 1.56 (s, 1H).

Example 56: (4-((3-(1-(4-(((((S)-1-carboxy-2-hydroxyethyl)amino)methyl)-2-chloro-5-((5-cyanopyridin-3-yl)methoxy)benzyl)-1H-indazol-4-yl)-2-methylbenzyl)oxy)-5-chloro-2-methoxybenzyl)-L-serine

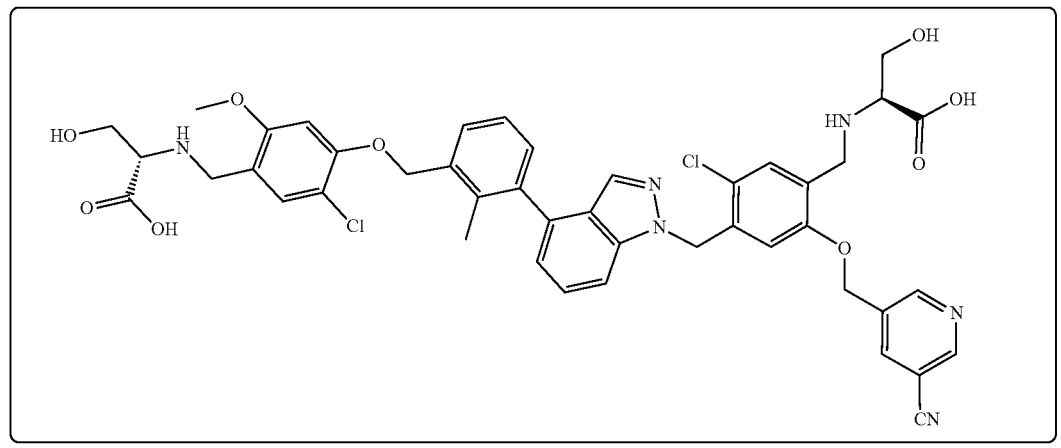

-continued
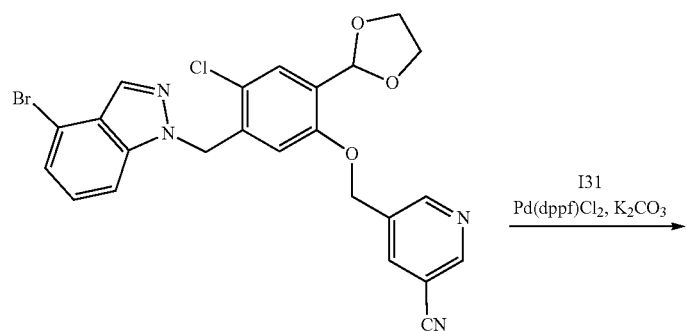
I26
Pd(dppf)Cl₂, K₂CO₃
I31
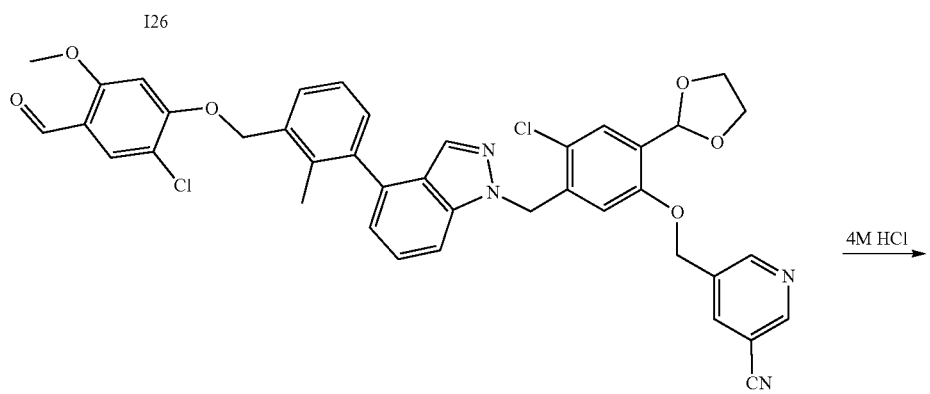
56a
4M HCl
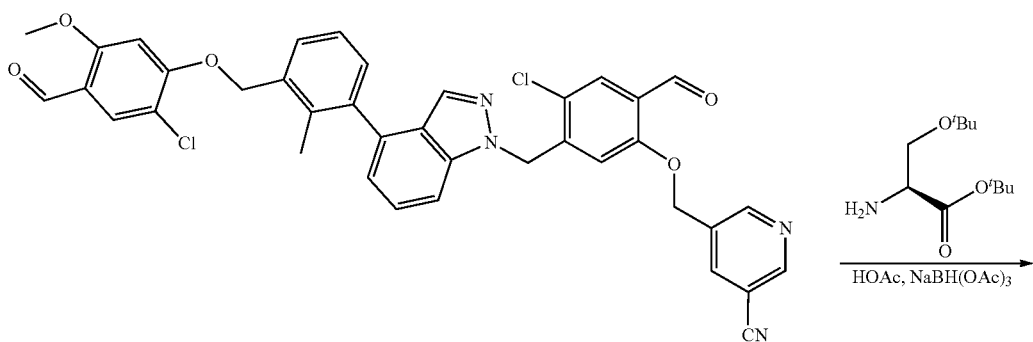
56b
HOAc, NaBH(OAc)₃
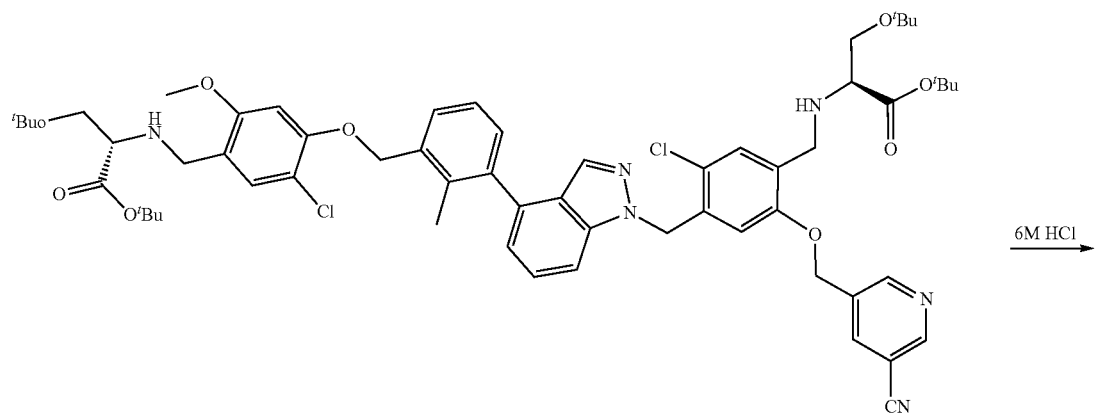
56c
6M HCl

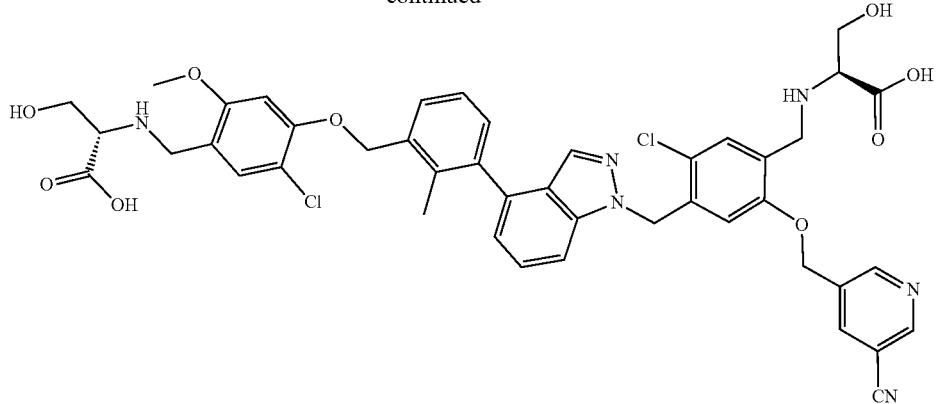

56

Step 1: To a solution of compound I26 (0.45 g, 855.87 μmol) and compound I31 (0.4 g, 959.92 μmol) in a mixture of dioxane (10 mL) and water (2 mL), potassium carbonate (354.87 mg, 2.57 mmol) and Pd(dppf)Cl$_2$ (31.31 mg, 42.79 μmol) was added. The mixture was stirred under a nitrogen atmosphere at 100° C. for 16 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by silica gel column chromatography to obtain compound 56a (0.38 g, 516.58 μmol, yield 60.4%) as light yellow solid. MS (ESI): m/z 736.2 (M+H)$^+$.

Step 2: To a solution of 56a (0.38 g, 516.58 μmol) in THF (5 mL), hydrochloric acid (4.0 M in water, 1 mL) was added. The mixture was stirred at room temperature for 1 h. The resulting mixture was added with saturated sodium bicarbonate until the pH=7, and then the THF was removed in vacuo. The mixture was extracted with ethyl acetate (30 mL×2). The combined organic layers were washed with brine (10 mL), dried over Na$_2$SO$_4$ and concentrated to give compound 56b (0.35 g, 506.10 μmol, yield 98.0%) as light yellow solid. MS (ESI): m/z 691.7 (M+H)$^+$.

Step 3: To a solution of compound 56b (0.35 g, 506.10 μmol) in DMF (5 mL), tert-butyl O-(tert-butyl)-L-serinate (241.95 mg, 1.11 mmol) and acetic acid (121.57 mg, 2.02 mmol, 115.78 μL) was added. The mixture was stirred at room temperature for 16 h followed by the addition of sodium triacetoxyborohydride (429.05 mg, 2.02 mmol) and further stirred at room temperature for 1 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 56c (0.35 g, 319.88 μmol, yield 63.2%) as light yellow solid. MS (ESI): m/z 548.6 (M/2+H)$^+$.

Step 4: To a solution of compound 56c (0.35 g, 319.88 μmol) in THF (2 mL), hydrochloric acid (6.0 M in water, 2 mL) was added. The mixture was stirred at 50° C. for 3 h. The resulting mixture was cooled, added with sodium acetate until the pH=4 and concentrated. The residue was stirred in DMF (3 mL) and then filtered. The filtrate was purified by prep-HPLC to obtain compound 56 (0.11 g, 126.47 μmol, yield 39.5%) as white solid. MS (ESI): m/z 869.7 (M+H)$^+$. $^1$H NMR (500 MHz, d$_6$-DMSO) δ 8.96 (d, J=2.0 Hz, 1H), 8.86 (d, J=2.0 Hz, 1H), 8.35 (s, 1H), 8.16 (HCOOH, s, 0.3H), 7.68 (d, J=10.5 Hz, 2H), 7.63 (d, J=6.0 Hz, 1H), 7.57 (s, 1H), 7.50-7.46 (m, 2H), 7.42-7.32 (m, 2H), 7.06 (d, J=7.0 Hz, 1H), 7.04 (s, 1H), 6.88 (s, 1H), 5.73 (s, 2H), 5.36 (s, 2H), 5.12 (q, J=12.5 Hz, 2H), 4.07-3.81 (m, 7H), 3.74-3.59 (m, 4H), 3.22-3.15 (m, 2H), 2.18 (s, 3H).

Example 57: (4-((3-(1-(4-((((S)-1-carboxy-2-hydroxyethyl)amino)methyl)-2-chloro-5-((5-cyanopyridin-3-yl)methoxy)benzyl)-1H-indazol-4-yl)-2-methylbenzyl)oxy)-5-chloro-2-((5-cyanopyridin-3-yl) methoxy) benzyl)-L-serine
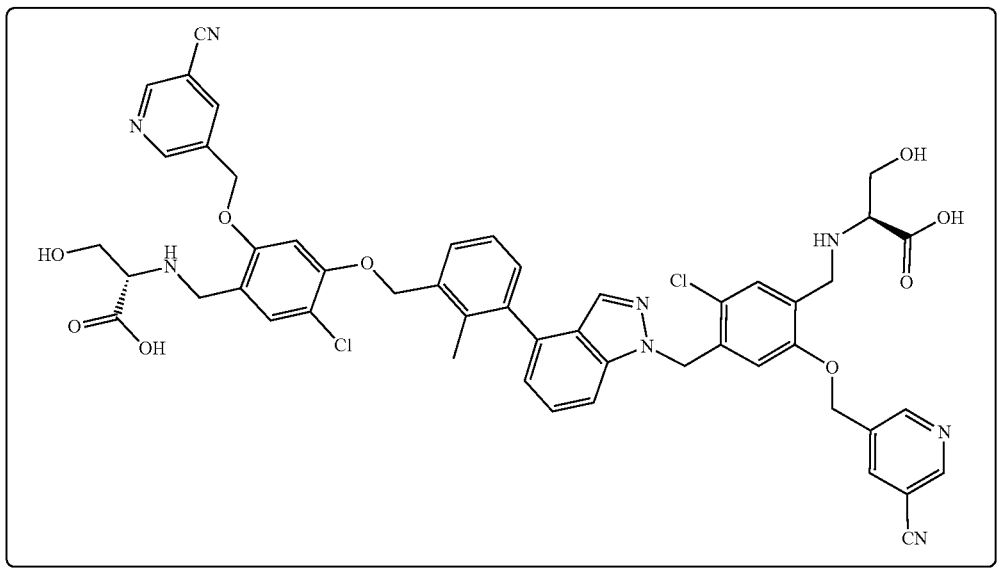
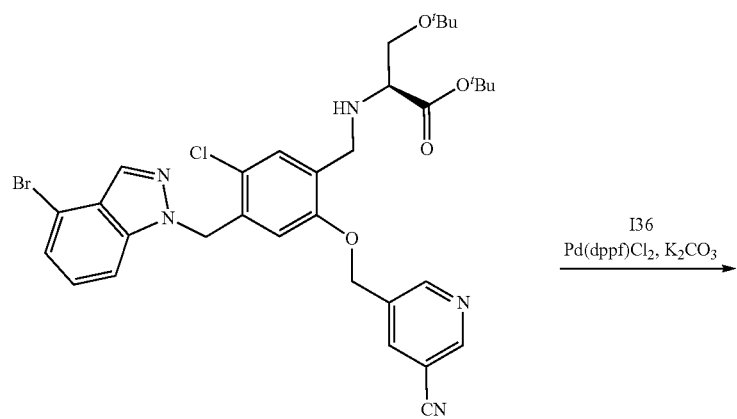

-continued

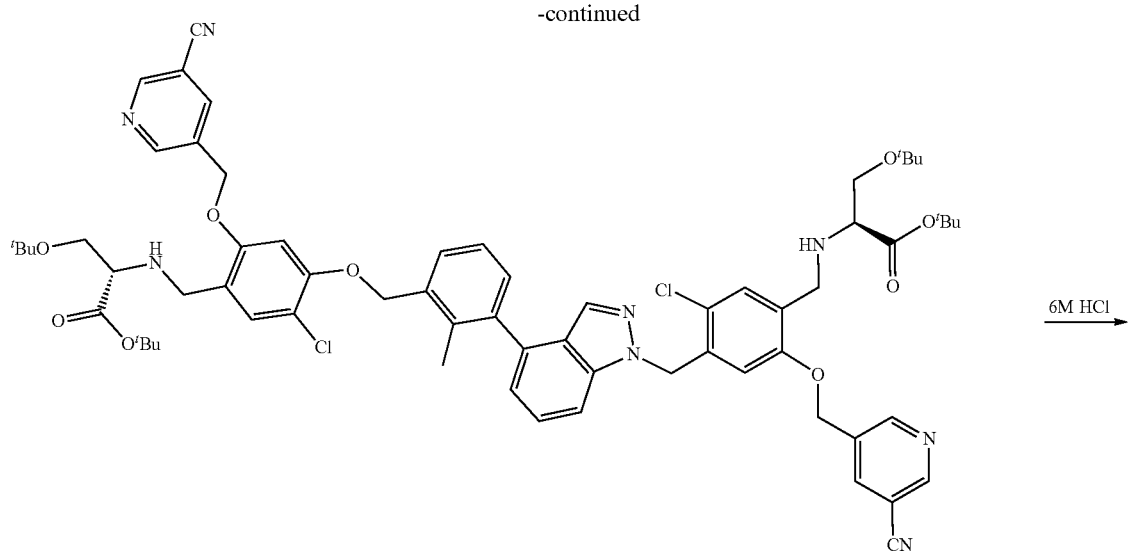

57a

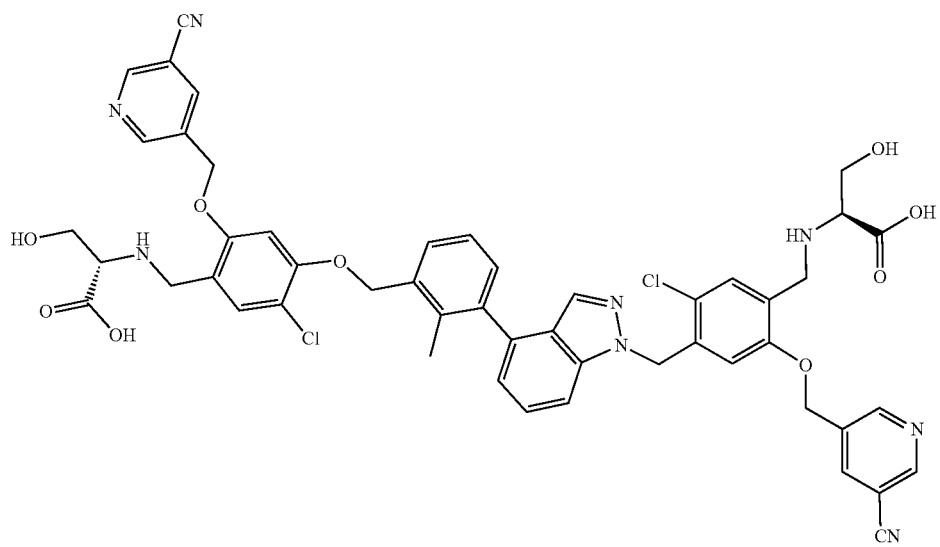

57

Step 1: To a solution of compound I34 (120 mg, 175.69 μmol) and compound I36 (151.81 mg, 210.82 μmol) in a mixture of dioxane (10 mL) and water (2 mL), potassium carbonate (72.84 mg, 527.06 μmol) and Pd(dppf)Cl$_2$ (12.86 mg, 17.57 μmol) was added. The mixture was stirred under a nitrogen atmosphere at 100° C. for 16 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by prep-TLC to obtain compound 57a (130 mg, 108.67 μmol, yield 61.9%) as light yellow oil. MS (ESI): m/z 598.0 (M/2+H)$^+$.

Step 2: To a solution of compound 57a (130 mg, 108.67 μmol) in THF (3 mL), hydrochloric acid (6.0 M in water, 3 mL) was added. The mixture was stirred at 50° C. for 16 h. The resulting mixture was cooled, added with sodium acetate until the pH=4 and concentrated. The residue was stirred in DMF (3 mL) and then filtered. The filtrate was purified by prep-HPLC to obtain compound 57 (25 mg, 25.72 μmol, yield 23.7%) as white solid. MS (ESI): m/z 971.7 (M+H)$^+$. $^1$H NMR (500 MHz, d$_6$-DMSO) δ 9.03 (dd, J=5.0, 1.5 Hz, 2H), 8.95 (d, J=2.0 Hz, 1H), 8.86 (s, 1H), 8.53 (s, 1H), 8.35 (s, 1H), 8.27 (HCCOH, s, 1H), 7.70-7.68 (m, 2H), 7.58 (dd, J=6.0, 3.0 Hz, 1H), 7.55 (s, 1H), 7.51 (s, 1H), 7.48 (t, J=6.0 Hz, 1H), 7.40-7.34 (m, 2H), 7.17 (s, 1H), 7.06 (d, J=7.0 Hz, 1H), 6.87 (s, 1H), 5.72 (s, 2H), 5.42-5.31 (m, 4H), 5.18-5.06 (m, 2H), 3.95-3.84 (m, 4H), 3.63-3.57 (m, 4H), 3.13-3.07 (m, 2H), 2.17 (s, 3H).

Example 58: (4-((4-(2-bromo-3-((4-((((S)-1-carboxy-2-hydroxyethyl)amino)methyl)-2-chloro-5-((5-cyanopyridin-3-yl)methoxy)phenoxy)methyl)phenyl)-1H-indazol-1-yl)methyl)benzyl)-L-serine
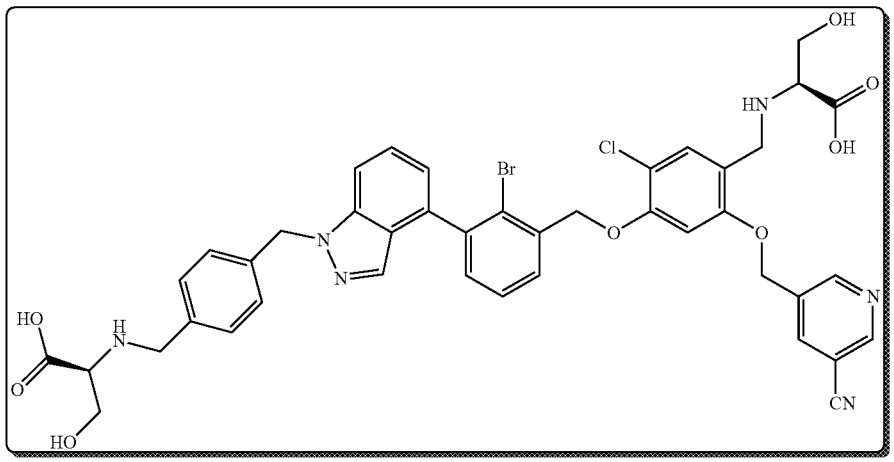
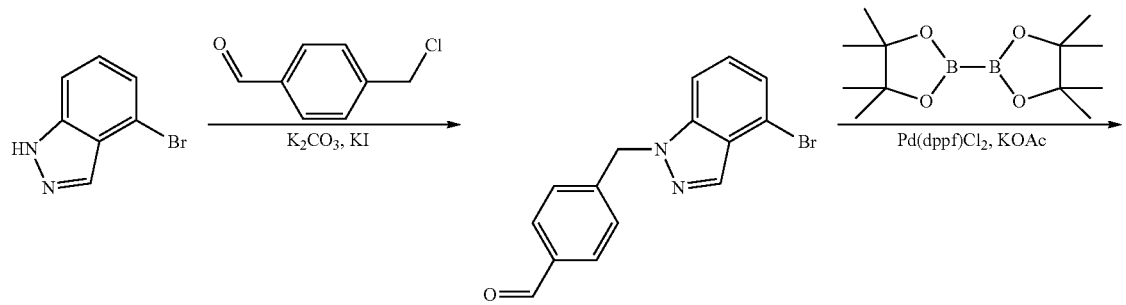
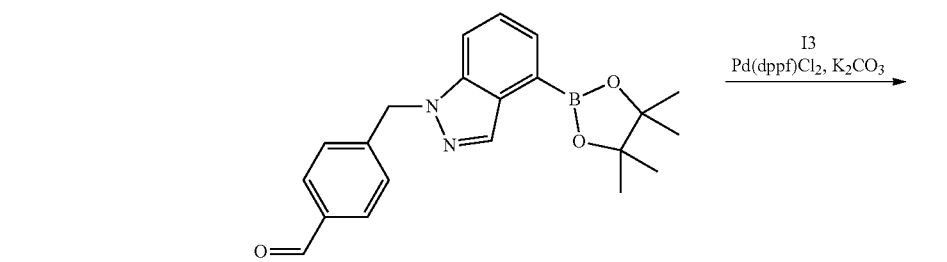
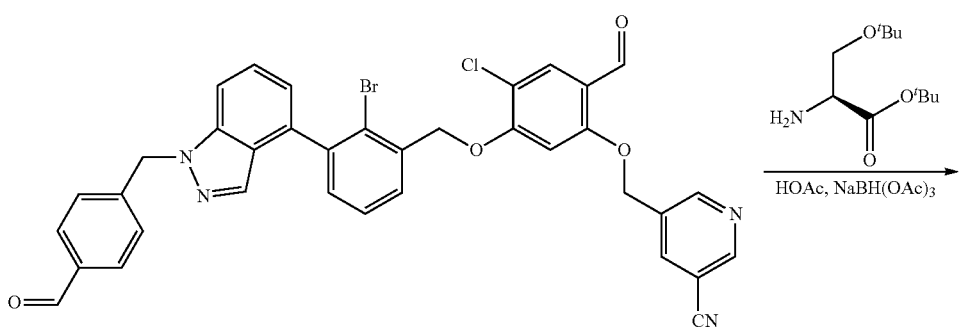

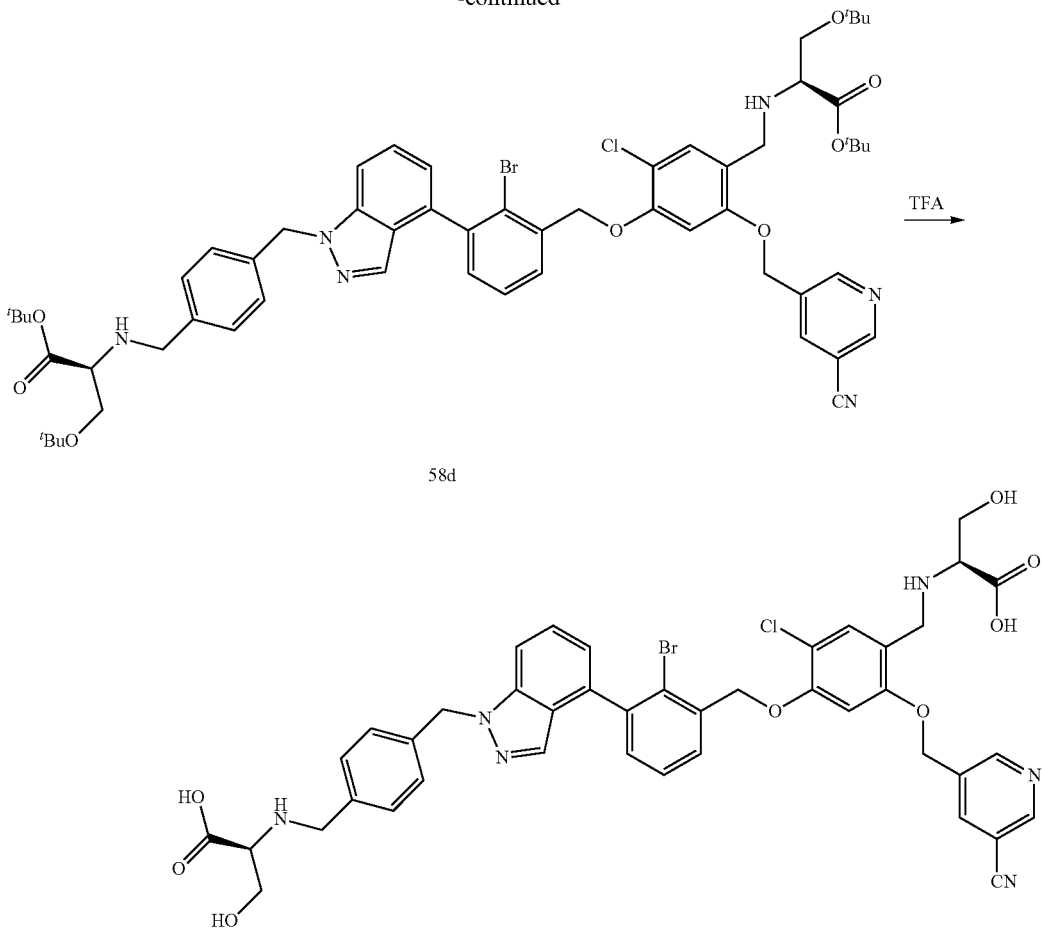

Step 1: To a solution of 4-(chloromethyl)benzaldehyde (1.0 g, 6.47 mmol) and 4-bromo-1H-indazole (1.2 g, 6.09 mmol) in acetonitrile (10 mL), potassium carbonate (1.01 g, 6.09 mmol) was added. The mixture was stirred at 70° C. for 18 h. The resulting mixture was cooled, filtered and concentrated. The residue was purified by silica gel column chromatography to obtain compound 58a (800 mg, 2.54 mmol, yield 41.7%) as light yellow solid.

Step 2: To a solution of compound 58a (400 mg, 1.27 mmol) and bis(pinacolato)diboron (386.75 mg, 1.52 mmol) in dioxane (10 mL), potassium acetate (374.17 mg, 3.81 mmol) and Pd(dppf)Cl$_2$ (92.87 mg, 126.92 μmol) was added. The mixture was stirred under a nitrogen atmosphere at 100° C. for 16 h. The resulting mixture was cooled, added with ethyl acetate (50 mL), filtered through celite and concentrated. The residue was purified by silica gel column chromatography to obtain compound 58b (300 mg, 828.21 μmol, yield 65.3%) as light yellow solid. MS (ESI): m/z 363.2 (M+H)$^+$.

Step 3: To a solution of compound 58b (150 mg, 414.10 μmol) and compound I3 (230 mg, 394.11 μmol) in a mixture of dioxane (10 mL) and water (2 mL), potassium carbonate (163.41 mg, 1.18 mmol) and Pd(dppf)Cl$_2$ (28.84 mg, 39.41 μmol) was added. The mixture was stirred under a nitrogen atmosphere at 80° C. for 16 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by prep-TLC to obtain compound 58c (140 mg, 202.33 μmol, yield 51.3%) as light yellow solid. MS (ESI): m/z 691.2 (M+H)$^+$.

Step 4: To a solution of compound 58c (110 mg, 158.97 μmol) in DMF (3 mL), tert-butyl O-(tert-butyl)-L-serinate (103.63 mg, 476.91 μmol) and acetic acid (105.00 mg, 1.75 mmol, 0.1 mL) was added. The mixture was stirred at room temperature for 2 h followed by the addition of sodium triacetoxyborohydride (200 mg, 943.66 μmol) and further stirred at room temperature for 1 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 58d (120 mg, 109.63 μmol, yield 69.0%) as light yellow oil. MS (ESI): m/z 547.1 (M/2+H)$^+$.

Step 5: To a solution of compound 58d (120 mg, 109.63 μmol) in THF (3 mL), hydrochloric acid (6.0 M in water, 3 mL) was added. The mixture was stirred at 50° C. for 16 h. The resulting mixture was cooled, added with sodium acetate until the pH=4 and concentrated. The residue was stirred in DMF (3 mL) and then filtered. The filtrate was purified by prep-HPLC to obtain compound 58 (5 mg, 5.75 μmol, yield 5.2%) as white solid. MS (ESI): m/z 869.5 (M+H)$^+$. $^1$H NMR (500 MHz, d$_6$-DMSO) δ 8.94 (s, 1H), 8.91 (s, 1H), 8.44 (s, 1H), 7.70 (d, J=8.5 Hz, 1H), 7.65 (d, J=7.6 Hz, 2H), 7.51-7.45 (m, 2H), 7.42-7.36 (m, 2H), 7.30 (d, J=7.7 Hz, 2H), 7.21 (d, J=7.8 Hz, 2H), 7.03 (s, 1H), 7.02 (s, 1H), 5.62 (s, 2H), 5.32-5.26 (m, 4H), 3.94-3.79 (m, 9H), 3.08 (s, 1H), 3.02 (s, 1H).

Example 59: (4-((4-(2-bromo-3-((4-((((S)-1-car-boxy-2-hydroxyethyl)amino)methyl)-2-chloro-5-((5-cyanopyridin-3-yl)methoxy)phenoxy)methyl)phenyl)-1H-indazol-1-yl)methyl)-3-chlorobenzyl)-L-serine

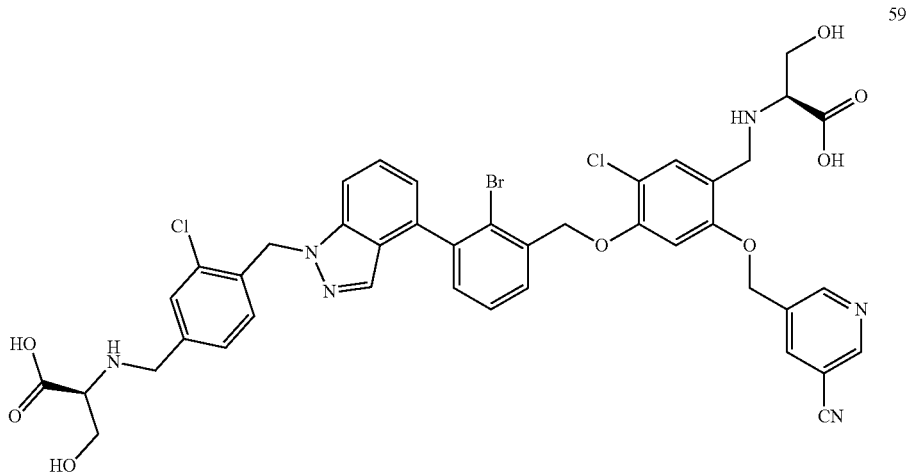 [SMILES: N#Cc1cncc(COc2cc(OCc3cccc(-c4cccc5c4cnn5Cc4ccc(CN[C@@H](CO)C(=O)O)cc4Cl)c3Br)c(Cl)cc2CN[C@@H](CO)C(=O)O)c1]

Compound 59 was prepared using similar procedures as described for compound 58. MS (ESI): m/z 903.5 (M+H)⁺. ¹H NMR (500 MHz, d₆-DMSO) δ 9.03-8.96 (m, 2H), 8.49 (s, 1H), 8.20 (s, 0.5H), 7.74 (t, J=4.0 Hz, 2H), 7.70 (d, J=7.5 Hz, 1H), 7.57-7.53 (m, 3H), 7.50-7.45 (m, 2H), 7.25 (d, J=8.0 Hz, 1H), 7.11 (d, J=8.0 Hz, 2H), 6.91 (d, J=8.0 Hz, 1H), 5.75 (s, 2H), 5.40-5.28 (m, 4H), 3.98 (t, J=14.0 Hz, 2H), 3.90 (d, J=13.5 Hz, 2H), 3.80 (d, J=14.0 Hz, 2H), 3.15 (s, 2H), 3.09 (s, 2H).

Example 60: (R)-5-((4-chloro-2-(((1,3-dihydroxy-2-methylpropan-2-yl)amino)methyl)-5-((1'-(3-(3-hydroxypyrrolidin-1-yl)propyl)-1H,1'H-[4,4'-biindazol]-1-yl)methyl)phenoxy)methyl)nicotinonitrile Compound 60 was prepared using similar procedures as described for compound 54 with compound I6 and 2-amino-2-methylpropane-1,3-diol replacing compound I22 and tert-butyl O-(tert-butyl)-L-serinate. MS (ESI): m/z 735.5 (M+H)⁺. ¹H NMR (500 MHz, d₆-DMSO) δ 8.94 (s, 1H), 8.86 (s, 1H), 8.32 (s, 1H), 8.04 (d, J=6.0 Hz, 2H), 7.77 (d, J=8.5 Hz, 1H), 7.72 (d, J=8.5 Hz, 1H), 7.61-7.50 (m, 3H), 7.48-7.40 (m, 2H), 6.88 (s, 1H), 5.75 (s, 2H), 5.13 (s, 2H), 4.53 (t, J=6.5 Hz, 2H), 4.21 (s, 2H), 3.79 (s, 2H), 3.70-3.63 (m, 2H), 2.76-2.73 (m, 1H), 2.68-2.63 (m, 1H), 2.47-2.40 (m, 3H), 2.06-1.96 (m, 3H), 1.62-1.56 (m, 1H), 0.95 (s, 3H).

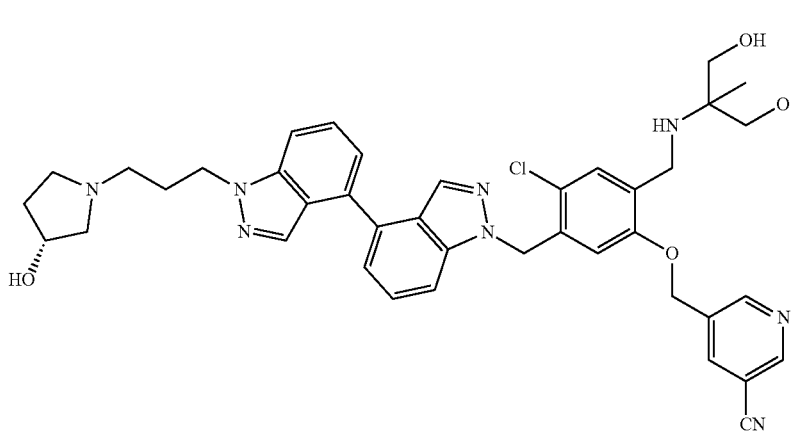

Example 61: (2S,2'S)-2,2'-((((1H,1'H-[4,4'-biindazole]-1,1'-diylbis(methylene)) bis(5-chloro-2-((5-cyanopyridin-3-yl)methoxy)-4,1-phenylene)) bis(methylene))bis(azanediyl))bis(3-hydroxypropanoic acid)
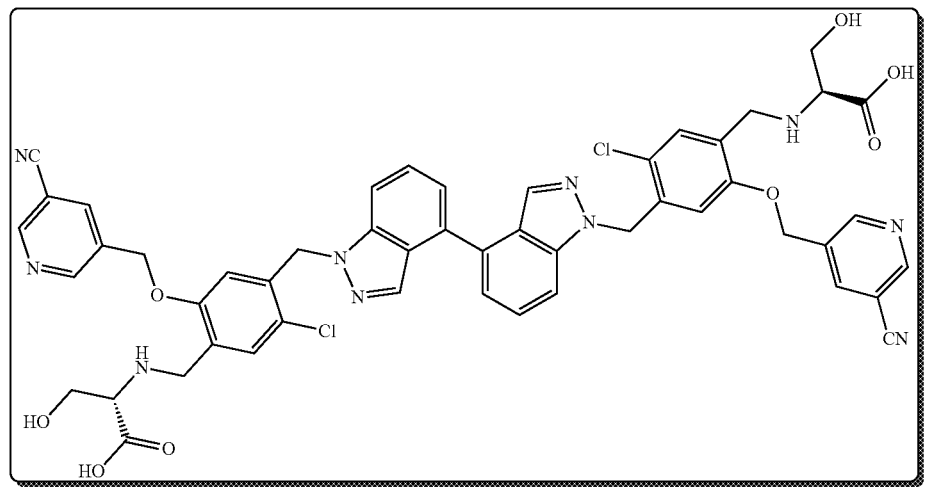
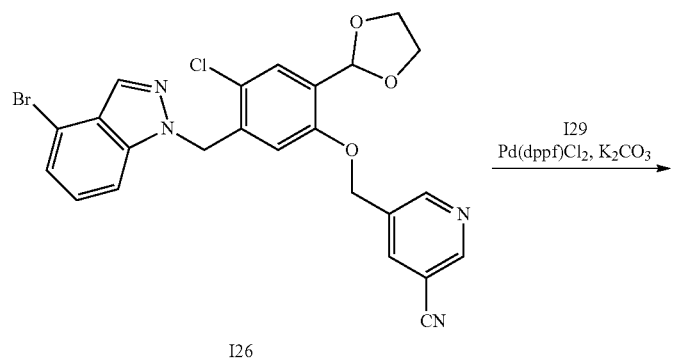
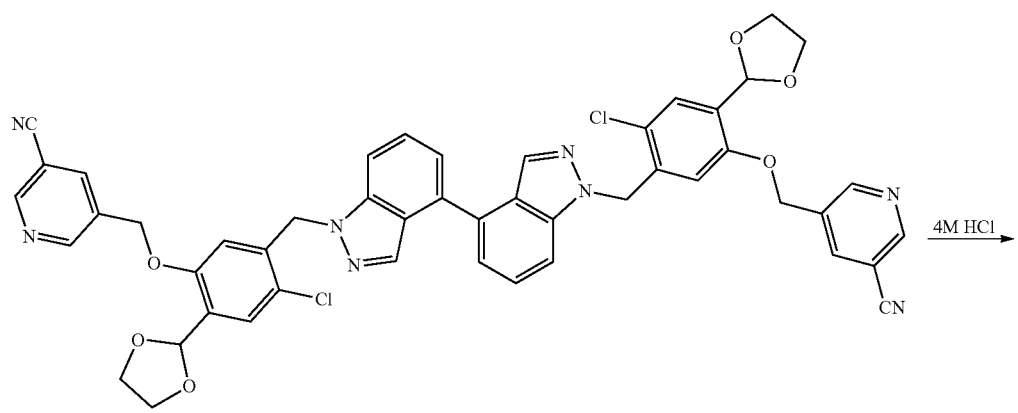

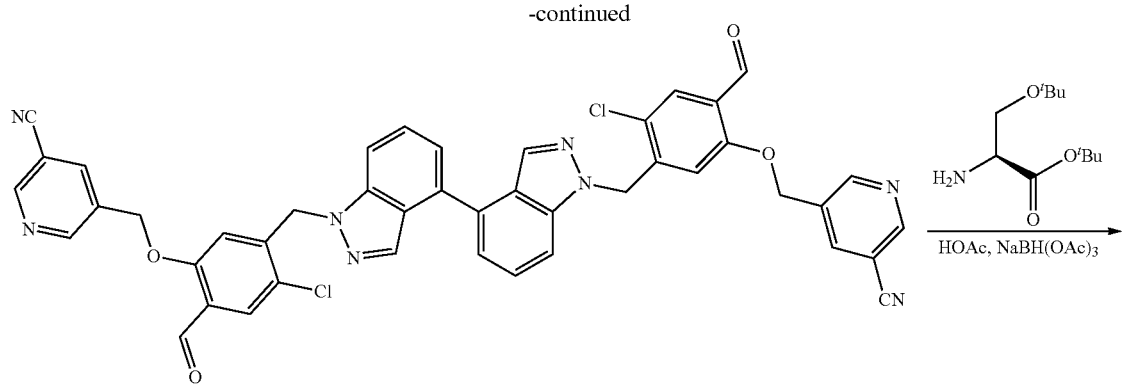

61b

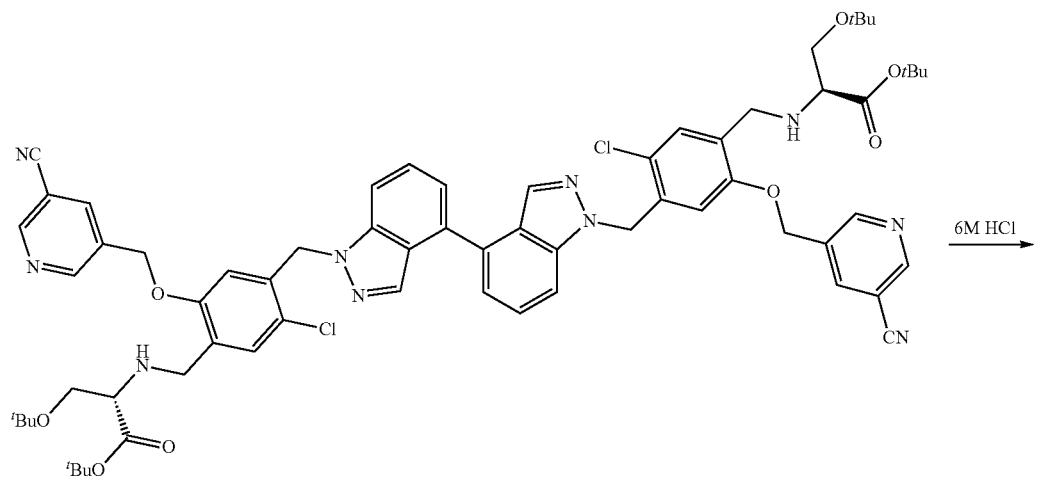

61c

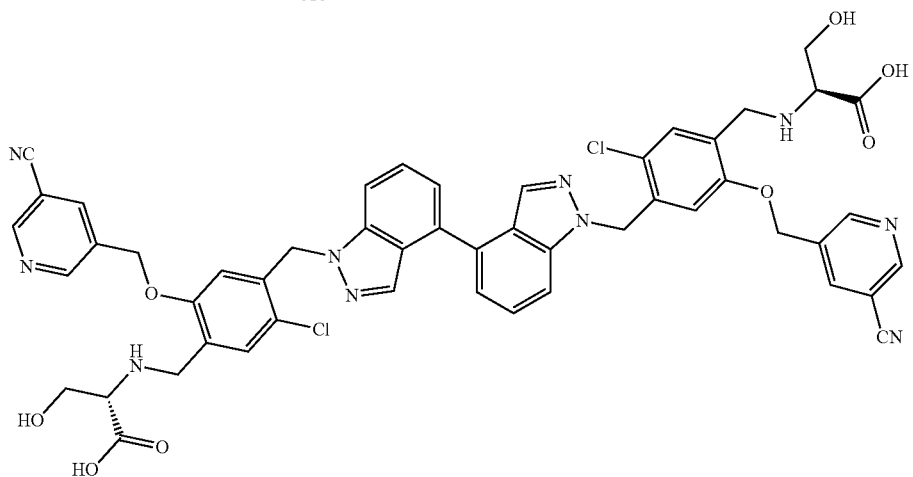

61

Step 1: To a solution of compound I26 (0.3 g, 572.52 μmol) and compound I29 (0.39 g, 687.02 μmol) in a mixture of dioxane (10 mL) and water (2 mL), potassium carbonate (158.7 mg, 1.15 mmol) and Pd(dppf)Cl$_2$ (41.67 mg, 0.057 mmol) was added. The mixture was stirred under a nitrogen atmosphere at 100° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated to give crude compound 61a (413 mg, 464.31 μmol, yield 81.1%) as black solid. MS (ESI): m/z 891.2 (M+H)$^+$.

Step 2: To a solution of 61a (413 mg, 464.31 μmol) in THF (5 mL), hydrochloric acid (4.0 M in water, 1 mL) was added. The mixture was stirred at room temperature for 0.5 h. The resulting mixture was added with saturated sodium bicarbonate until the pH=7, and then the THF was removed in vacuo. The mixture was extracted with ethyl acetate (30 mL×2). The combined organic layers were washed with brine (10 mL), dried over Na$_2$SO$_4$ and concentrated to give compound 61b (359 mg, 447.59 μmol, yield 96.4%) as light yellow solid. MS (ESI): m/z 803.8 (M+H)$^+$.

Step 3: To a solution of compound 61b (359 mg, 447.59 μmol) in DMF (5 mL), tert-butyl O-(tert-butyl)-L-serinate (242.82 mg, 1.12 mmol) and acetic acid (107.42 mg, 1.79 mmol) was added. The mixture was stirred at room temperature for 2 h followed by the addition of sodium triacetoxyborohydride (379.56 mg, 1.79 mmol) and further stirred at room temperature for 1 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 61c (0.25 g, 207.64 μmol, yield 46.4%) as light yellow solid. MS (ESI): m/z 603.2 (M/2+H)$^+$.

Step 4: To a solution of compound 61c (0.2 g, 165.80 μmol) in THF (5 mL), hydrochloric acid (6.0 M in water, 5 mL) was added. The mixture was stirred at 50° C. for 3 h. The resulting mixture was cooled, added with sodium acetate until the pH=4 and concentrated. The residue was stirred in DMF (3 mL) and then filtered. The filtrate was purified by prep-HPLC to obtain compound 61 (25 mg, 25.51 μmol, yield 15.4%) as white solid. MS (ESI): m/z 981.3 (M+H)$^+$. $^1$H NMR (500 MHz, d$_6$-DMSO) δ 8.92 (d, J=1.5 Hz, 2H), 8.83 (s, 2H), 8.32 (s, 2H), 8.21 (HCOOH, s, 0.27H), 8.07 (s, 2H), 7.73 (d, J=8.5 Hz, 2H), 7.65-7.51 (m, 4H), 7.47 (d, J=7.0 Hz, 2H), 6.87 (s, 2H), 5.75 (s, 4H), 5.20-5.06 (m, 4H), 3.97 (d, J=14.5 Hz, 2H), 3.89 (d, J=14.5 Hz, 2H), 3.66 (dd, J=11.0, 4.5 Hz, 2H), 3.62-3.59 (m, 2H), 3.17 (d, J=5.0 Hz, 2H).

Example 62: Isopropyl (5-chloro-4-((3-(1-(2-chloro-5-((5-cyanopyridin-3-yl) methoxy)-4-((((S)-3-hydroxy-1-isopropoxy-1-oxopropan-2-yl)amino) methyl)benzyl)-1H-indazol-4-yl)-2-methylbenzyl) oxy)-2-methoxybenzyl)-L-serinate

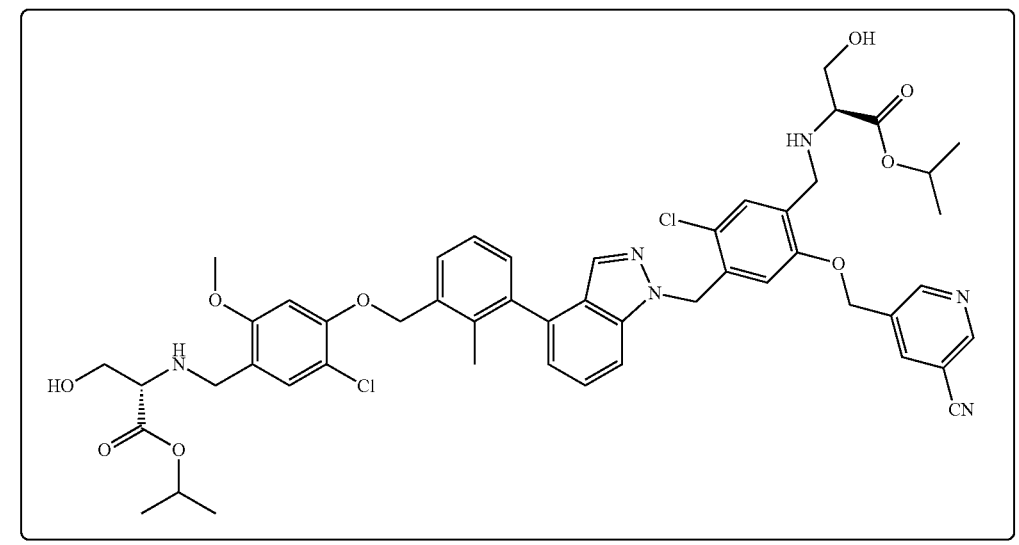

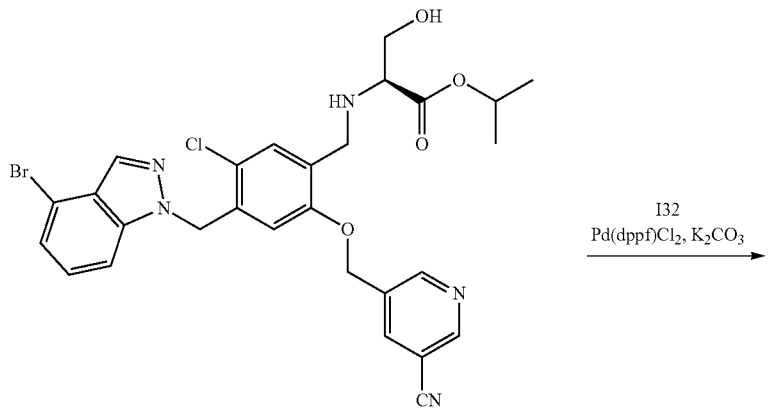

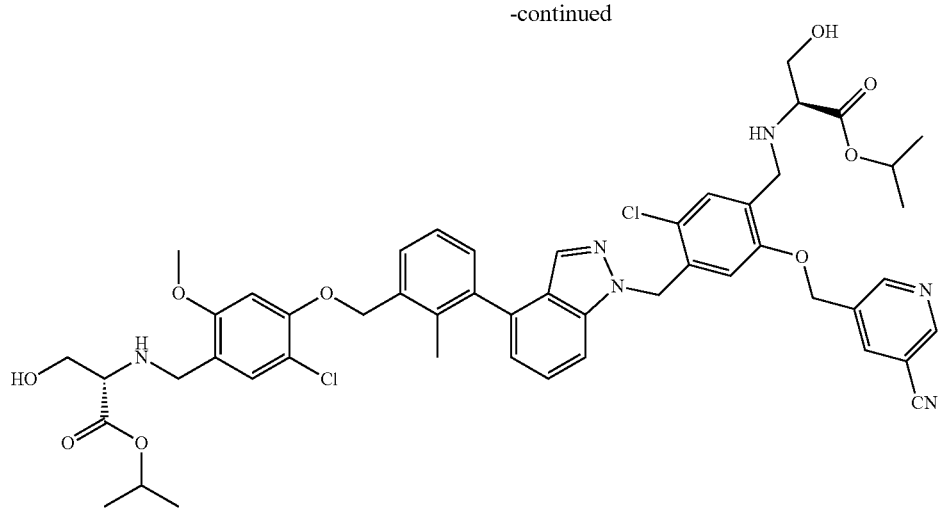

62

Step 1: To a solution of compound I35 (200 mg, 327.33 μmol) and compound I32 (215 mg, 392.80 μmol) in a mixture of dioxane (10 mL) and water (2 mL), potassium carbonate (90 mg, 654.66 μmol) and Pd(dppf)Cl$_2$ (24 mg, 32.73 μmol) was added. The mixture was stirred under nitrogen atmosphere at 80° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by prep-HPLC to obtain compound 62 (153 mg, 160.71 μmol, yield 49.1%) as white solid. MS (ESI): m/z 953.8 (M+H)$^+$. $^1$H NMR (500 MHz, d$_6$-DMSO) δ 8.96 (d, J=1.5 Hz, 1H), 8.84 (d, J=1.5 Hz, 1H), 8.32 (t, J=1.5 Hz, 1H), 7.68 (t, J=4.0 Hz, 2H), 7.61 (d, J=7.0 Hz, 1H), 7.52-7.45 (m, 2H), 7.39-7.31 m, 3H), 7.05 (d, J=7.0 Hz, 1H), 6.97 (s, 1H), 6.87 (s, 1H), 5.71 (s, 2H), 5.32 (s, 2H), 5.14-5.07 (m, 2H), 4.85-4.81 (m, 2H), 3.84 (s, 3H), 3.77 (d, J=14.5 Hz, 1H), 3.66-3.62 (m, 2H), 3.57-3.53 (m, 5H), 3.21-3.17 (m, 2H), 2.18 (s, 3H), 1.17-1.15 (m, 6H), 1.11 (d, J=6.0 Hz, 3H), 1.08 (d, J=6.0 Hz, 3H).

Example 63: Isopropyl (5-chloro-4-((3-(1-(2-chloro-5-((5-cyanopyridin-3-yl) methoxy)-4-(((((S)-3-hydroxy-1-isopropoxy-1-oxopropan-2-yl)amino) methyl)benzyl)-1H-indazol-4-yl)-2-methylbenzyl) oxy)-2-((5-cyanopyridin-3-yl)methoxy)benzyl)-L-serinate

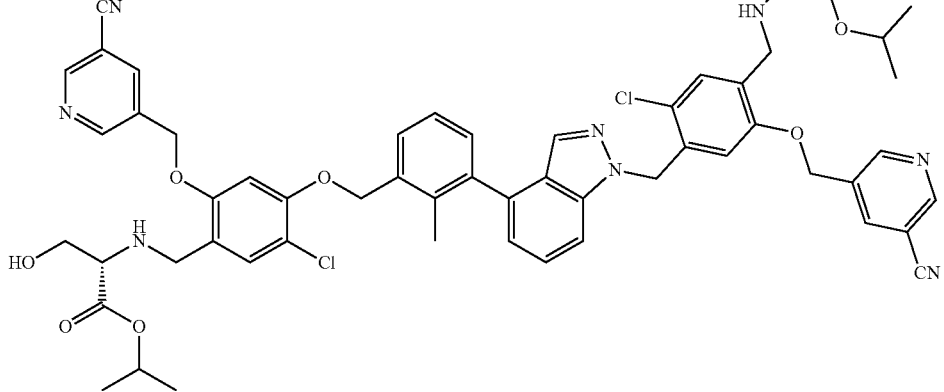

63

Compound 63 was prepared using similar procedures as described for compound 62 with compound I37 replacing compound I32. MS (ESI): m/z 1055.5 (M+H)$^+$. $^1$H NMR (500 MHz, d$_6$-DMSO) δ 9.02 (d, J=2.0 Hz, 1H), 8.98 (d, J=2.0 Hz, 1H), 8.94 (d, J=2.0 Hz, 1H), 8.84 (d, J=2.0 Hz, 1H), 8.44 (t, J=2.0 Hz, 1H), 8.34 (t, J=2.0 Hz, 1H), 7.68-7.66 (m, 2H), 7.60-7.55 (m, 1H), 7.53 (s, 1H), 7.50-7.44 (m, 1H), 7.40-7.32 (m, 3H), 7.12 (s, 1H), 7.05 (d, J=6.5 Hz, 1H), 6.85 (s, 1H), 5.72 (s, 2H), 5.32-5.30 (m, 4H), 5.13-5.07 (m, 2H), 4.88-4.83 (m, 2H), 3.90-3.83 (m, 2H), 3.74-3.71 (m, 1H), 3.60-3.53 (m, 4H), 3.20 (t, J=5.0 Hz, 2H), 3.06-3.04 (m, 1H), 2.17 (s, 3H), 1.13-1.10 (m, 12H).

Example 64: (5-chloro-4-((4-(3-((2-chloro-5-((5-cyanopyridin-3-yl)methoxy)-4-((((S)-3-hydroxy-1-isopropoxy-1-oxopropan-2-yl)amino)methyl) phenoxy)methyl)-2-methylphenyl)-1H-indazol-1-yl) methyl)-2-((5-cyanopyridin-3-yl)methoxy)benzyl)-L-serine
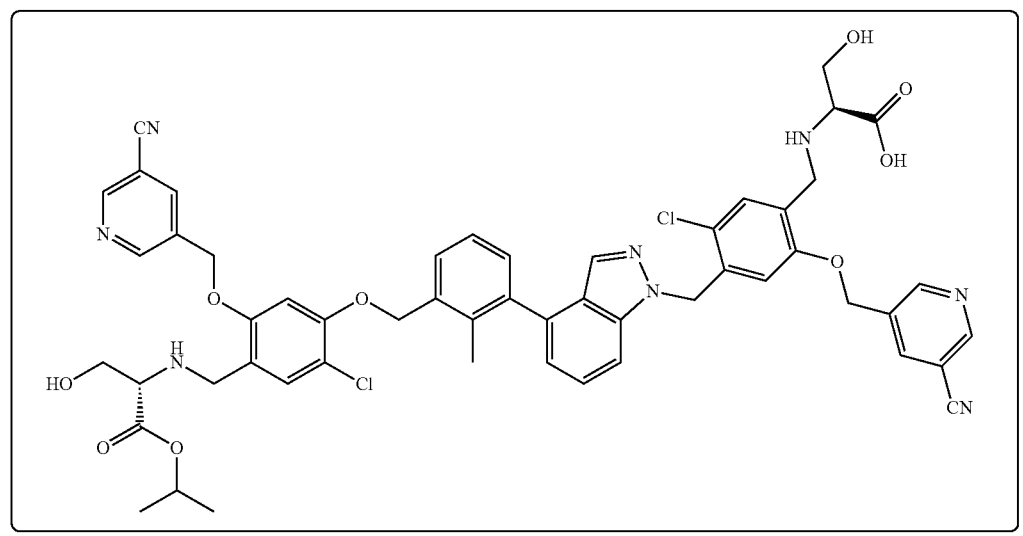
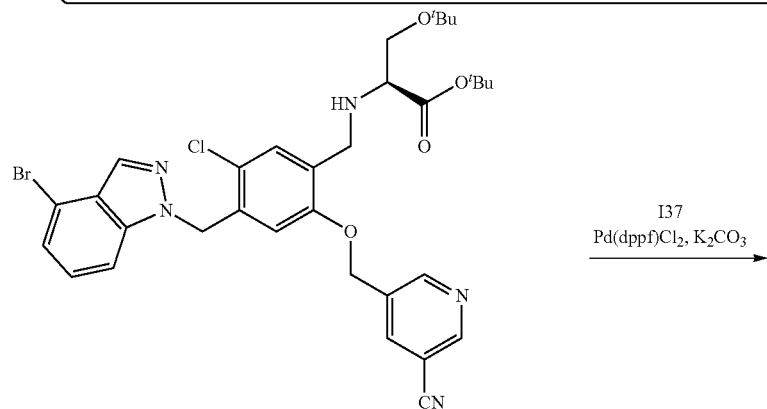
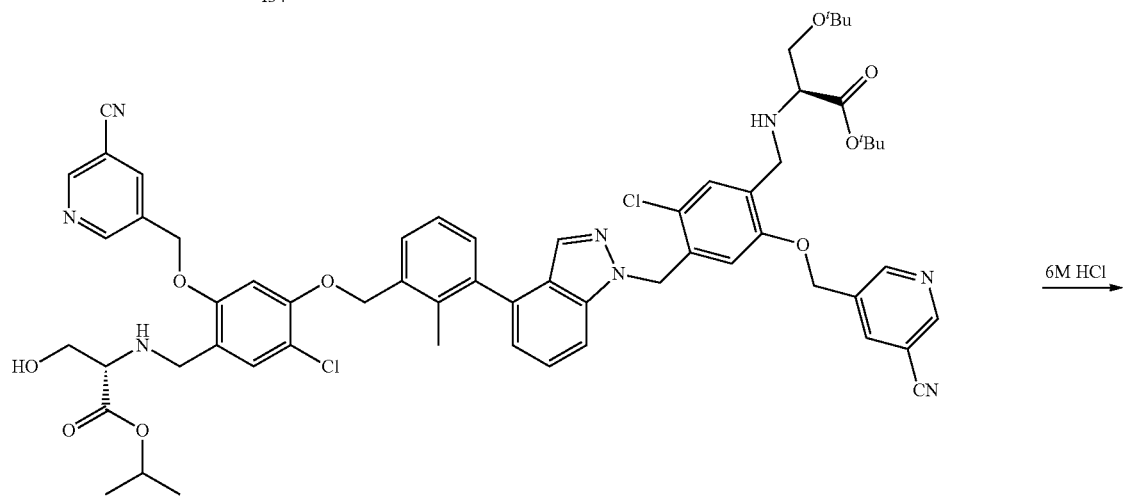

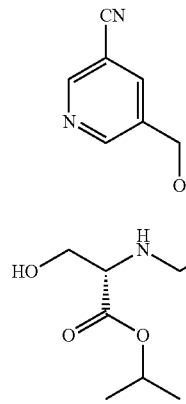
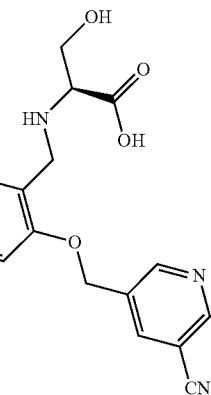

64

Step 1: To a solution of compound I34 (200 mg, 293.68 µmol) and compound I37 (229 mg, 352.42 µmol) in a mixture of dioxane (10 mL) and water (2 mL), potassium carbonate (81 mg, 587.36 µmol) and Pd(dppf)Cl$_2$ (22 mg, 29.37 µmol) was added. The mixture was stirred under a nitrogen atmosphere at 80° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by prep-TLC to obtain compound 64a (185 mg, 164.59 µmol, yield 56.0%) as light yellow solid. MS (ESI): m/z 563.4 (M/2+H)$^+$.

Step 2: To a solution of compound 64a (185 mg, 164.59 µmol) in THF (2 mL), hydrochloric acid (6.0 M in water, 2 mL) was added. The mixture was stirred at 50° C. for 16 h. The resulting mixture was cooled, added with sodium acetate until the pH=4 and concentrated. The residue was stirred in DMF (4 mL) and then filtered. The filtrate was purified by prep-HPLC to obtain compound 64 (124 mg, 122.53 µmol, yield 74.4%) as white solid. MS (ESI): m/z 1013.5 (M+H)$^+$. $^1$H NMR (500 MHz, d$_6$-DMSO) δ 9.02 (d, J=2.0 Hz, 1H), 8.98 (d, J=2.0 Hz, 1H), 8.94 (d, J=2.0 Hz, 1H), 8.84 (d, J=2.0 Hz, 1H), 8.44 (t, J=2.0 Hz, 1H), 8.34 (t, J=2.0 Hz, 1H), 7.68-7.66 (m, 2H), 7.60-7.55 (m, 1H), 7.53 (s, 1H), 7.50-7.44 (m, 1H), 7.40-7.32 (m, 3H), 7.12 (s, 1H), 7.05 (d, J=6.5 Hz, 1H), 6.85 (s, 1H), 5.72 (s, 2H), 5.32-5.30 (m, 4H), 5.13-5.07 (m, 2H), 4.88-4.83 (m, 1H), 3.90-3.83 (m, 2H), 3.74-3.71 (m, 1H), 3.60-3.53 (m, 5H), 3.20 (t, J=5.0 Hz, 1H), 3.06-3.04 (m, 1H), 2.17 (s, 3H), 1.13-1.10 (m, 6H).

Example 65: (5-chloro-4-((3-(1-(2-chloro-5-((5-cyanopyridin-3-yl)methoxy)-4-((((S)-3-hydroxy-1-isopropoxy-1-oxopropan-2-yl)amino)methyl) benzyl)-1H-indazol-4-yl)-2-methylbenzyl)oxy)-2-((5-cyanopyridin-3-yl)methoxy)benzyl)-L-serine

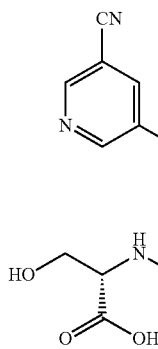
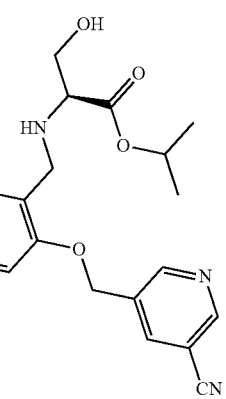

65

Compound 65 was prepared using similar procedures as described for compound 64 with compound I35 and compound I36 replacing compound I34 and compound I37. MS (ESI): m/z 1013.5 (M+H)$^+$. $^1$H NMR (500 MHz, d$_6$-DMSO) δ 9.03 (d, J=2.0 Hz, 1H), 9.02 (d, J=2.0 Hz, 1H), 8.95 (d, J=2.0 Hz, 1H), 8.83 (d, J=2.0 Hz, 1H), 8.52 (t, J=2.0 Hz, 1H), 8.30 (t, J=2.0 Hz, 1H), 7.69-7.66 (m, 2H), 7.57 (dd, J=7.0, 2.0 Hz, 1H), 7.52 (s, 1H), 7.50-7.44 (m, 2H), 7.38-7.32 (m, 2H), 7.17 (s, 1H), 7.05 (d, J=7.0 Hz, 1H), 6.86 (s, 1H), 5.71 (s, 2H), 5.41-5.28 (m, 4H), 5.09 (s, 2H), 4.83 (q, J=6.0 Hz, 1H), 3.96 (s, 2H), 3.79-3.76 (m, 1H), 3.70-3.58 (m, 3H), 3.54 (d, J=5.5 Hz, 2H), 3.19 (t, J=5.5 Hz, 1H), 3.15 (t, J=5.5 Hz, 1H), 2.17 (s, 3H), 1.11 (d, J=6.0 Hz, 3H), 1.08 (d, J=6.0 Hz, 3H).
Example 66: (4-((3-(1-(4-((((S)-1-carboxy-2-hydroxyethyl)amino)methyl)-2-chloro-5-methoxybenzyl)-1H-indazol-4-yl)-2-methylbenzyl)oxy)-5-chloro-2-methoxybenzyl)-L-serine
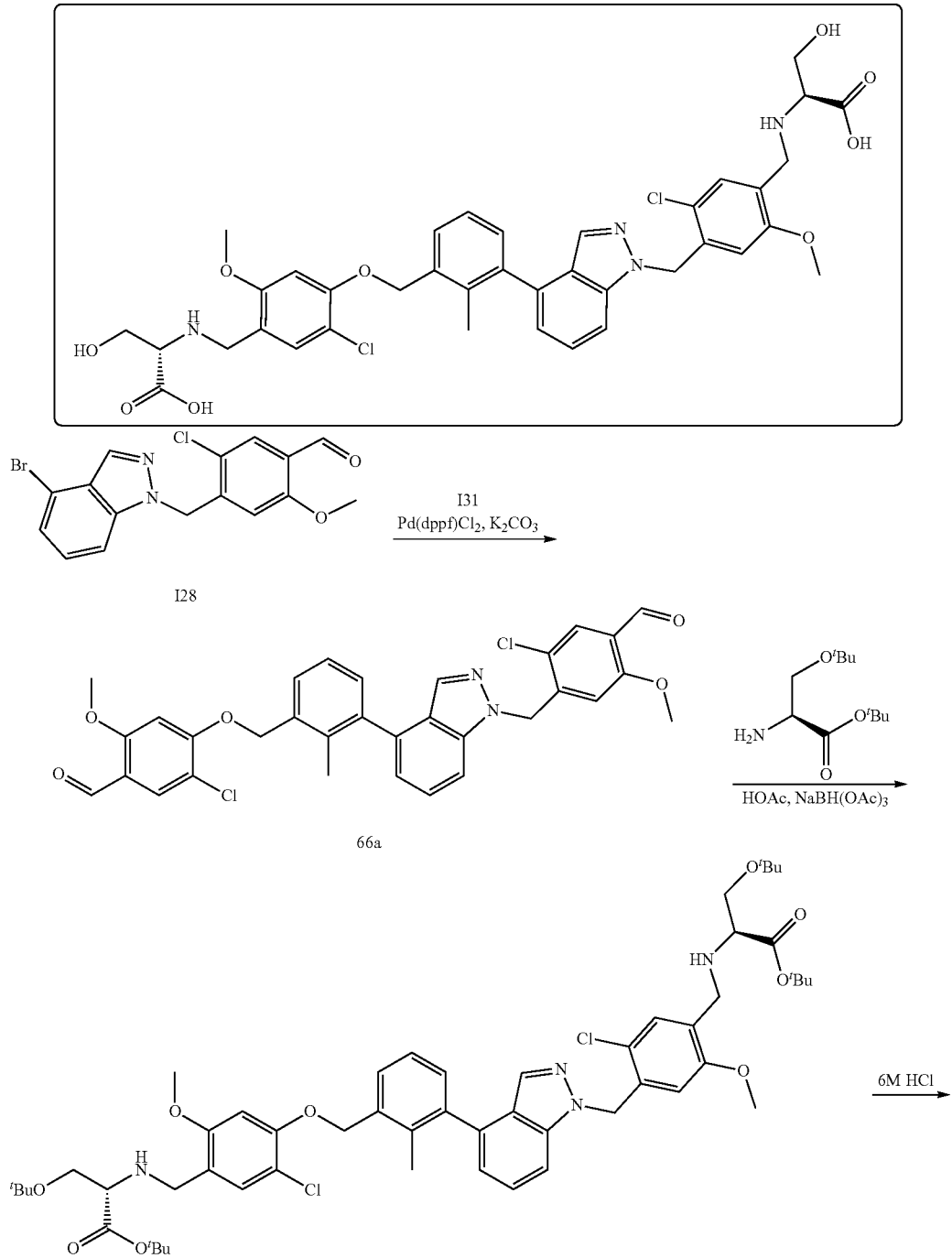

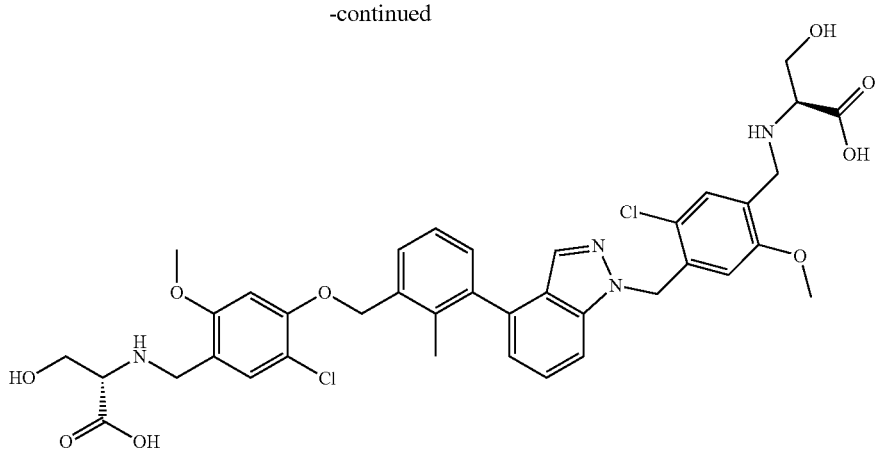

66

Step 1: To a solution of compound I28 (200 mg, 529.10 μmol) and compound I31 (264 mg, 634.92 μmol) in a mixture of dioxane (10 mL) and water (2 mL), potassium carbonate (147 mg, 1.06 mmol) and Pd(dppf)Cl$_2$ (39 mg, 52.91 μmol) was added. The mixture was stirred under a nitrogen atmosphere at 80° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by prep-TLC to obtain compound 66a (203 mg, 345.24 μmol, yield 65.3%) as light yellow solid. MS (ESI): m/z 589.4 (M+H)$^+$.

Step 2: To a solution of compound 66a (203 mg, 345.24 μmol) in DMF (3 mL), tert-butyl O-(tert-butyl)-L-serinate (180 mg, 828.58 μmol) and acetic acid (83 mg, 1.38 mmol) was added. The mixture was stirred at room temperature for 2 h followed by the addition of sodium triacetoxyborohydride (439 mg, 2.07 mmol) and further stirred at room temperature for 1 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 66b (310 mg, 313.13 μmol, yield 90.7%) as light yellow solid. MS (ESI): m/z 991.4 (M+H)$^+$.

Step 3: To a solution of 66b (100 mg, 101.01 μmol) in THF (5 mL), hydrochloric acid (6.0 M in water, 5 mL) was added. The mixture was stirred at 50° C. for 16 h. The resulting mixture was cooled, added with sodium acetate until the pH=4 and concentrated. The residue was stirred in DMF (4 mL) and then filtered. The filtrate was purified by prep-HPLC to obtain compound 66 (23.24 mg, 30.34 μmol, yield 30.0%) as white solid. MS (ESI): m/z 767.5 (M+H)$^+$. $^1$H NMR (500 MHz, d$_6$-DMSO) δ 7.72 (d, J=8.5 Hz, 1H), 7.67 (s, 1H), 7.59 (d, J=7.5 Hz, 1H), 7.51-7.47 (m, 2H), 7.47-7.44 (m, 1H), 7.37-7.28 (m, 2H), 7.03 (d, J=7.0 Hz, 1H), 7.01 (s, 1H), 6.68 (s, 1H), 5.72 (s, 2H), 5.33 (s, 2H), 3.91-3.79 (m, 7H), 3.71-3.59 (m, 7H), 3.14 (t, J=5.5 Hz, 2H), 2.14 (s, 3H).

Example 67: (4-((4-(3-((4-(((((S)-1-carboxy-2-hydroxyethyl)amino)methyl)-2-chloro-5-((5-cyanopyridin-3-yl)methoxy)phenoxy)methyl)-2-methylphenyl)-1H-indazol-1-yl)methyl)-5-chloro-2-methoxybenzyl)-L-serine

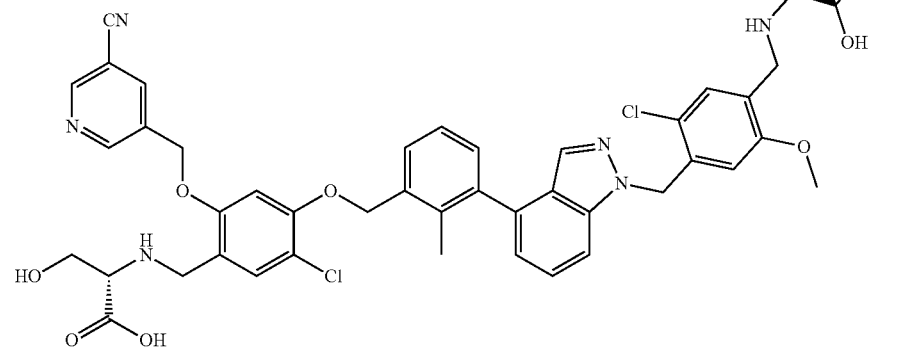

67

Compound 67 was prepared using similar procedures as described for compound 66 with compound I38 replacing compound I31. MS (ESI): m/z 869.5 (M+H)+. ¹H NMR (500 MHz, d₆-DMSO) δ 9.02 (dd, J=4.5, 1.9 Hz, 2H), 8.53 (d, J=2.0 Hz, 1H), 7.74 (d, J=8.5 Hz, 1H), 7.71 (s, 1H), 7.59-7.55 (m, 1H), 7.54-7.49 (m, 3H), 7.37-7.31 (m, 2H), 7.17 (s, 1H), 7.06 (d, J=7.0 Hz, 1H), 6.70 (s, 1H), 5.74 (s, 2H), 5.39-5.30 (m, 4H), 4.02-3.95 (m, 2H), 3.91-3.86 (m, 1H), 3.83-3.78 (m, 1H), 3.72-3.60 (m, 7H), 3.16 (q, J=6.0 Hz, 2H), 2.16 (s, 3H).

Example 68: 5-((4-chloro-5-((4-(3-((2-chloro-4-(((2-hydroxyethyl)amino)methyl)-5-methoxyphenoxy)methyl)-2-methylphenyl)-1H-indazol-1-yl)methyl)-2-(((2-hydroxyethyl)amino)methyl)phenoxy)methyl)nicotinonitrile Step 1: To a solution of compound 56b (100 mg, 144.93 μmol) in DMF (3 mL), ethanolamine (22 mg, 347.83 μmol) and acetic acid (35 mg, 579.72 mmol) was added. The mixture was stirred at room temperature for 3 h followed by the addition of sodium triacetoxyborohydride (184 mg, 869.58 μmol) and further stirred at room temperature for 16 h. The resulting mixture was added with water (20 mL) and extracted with ethyl acetate (30 mL×2). The combined organic layers were washed with brine (10 mL), dried over Na₂SO₄ and concentrated. The residue was purified by prep-HPLC to give compound 68 (25.63 mg, 32.86 μmol, yield 22.7%) as white solid. MS (ESI): m/z 781.4 (M+H)+. ¹H NMR (500 MHz, d₆-DMSO) δ 9.04 (d, J=2.0 Hz, 1H), 8.92 (d, J=2.0 Hz, 1H), 8.39 (s, 1H), 7.81-7.74 (m, 2H), 7.70 (d, J=7.5 Hz, 1H), 7.61-7.53 (m, 2H), 7.52-7.38 (m, 3H), 7.13 (d, J=7.0 Hz, 1H), 7.08 (s, 1H), 6.95 (s, 1H), 5.80 (s, 2H), 5.42 (s, 2H), 5.19 (s, 2H), 3.95 (s, 3H), 3.83 (s, 2H), 3.80 (s, 2H), 3.60-3.58 (m, 2H), 3.57-3.54 (m, 2H), 2.76-2.70 (m, 2H), 2.70-2.64 (m, 2H), 2.26 (s, 3H).

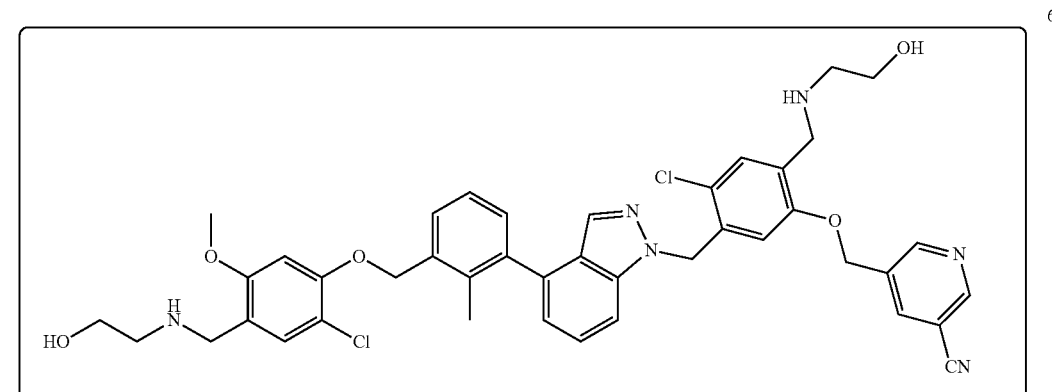

68

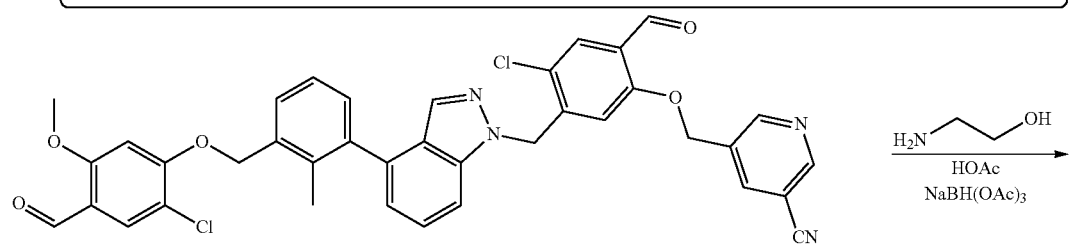

56b

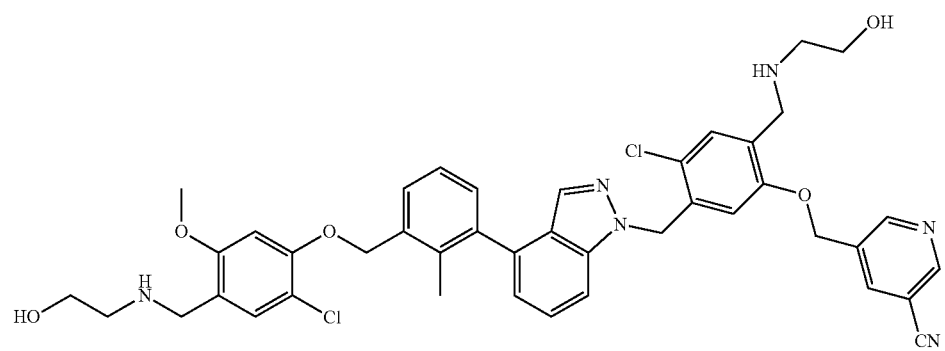

68

Example 69: 5-((4-chloro-5-((4-(3-((2-chloro-5-methoxy-4-(((((S)-5-oxopyrrolidin-2-yl)methyl)amino)methyl)p henoxy)methyl)-2-methylphenyl)-1H-indazol-1-yl)methyl)-2-(((((S)-5-oxopyrrolidin-2-yl)methyl) amino) methyl)phenoxy)methyl) nicotinonitrile

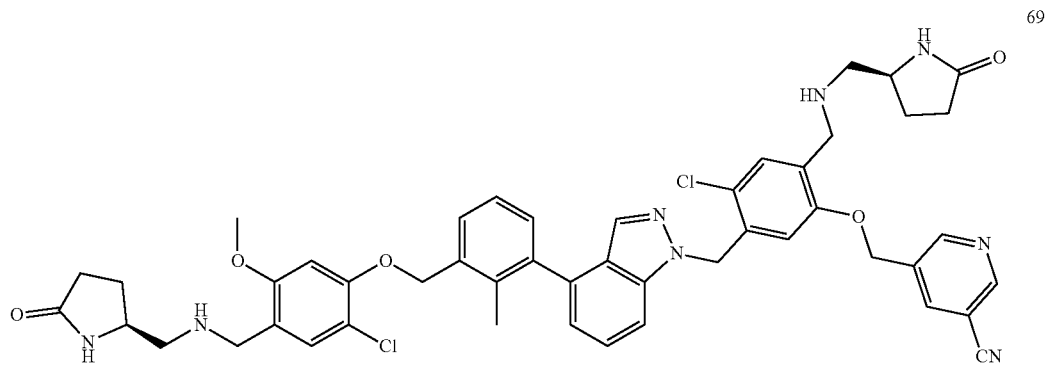 [SMILES: COc1cc(OCc2cccc(-c3cccc4c3cnn4Cc3cc(OCc4cncc(C#N)c4)c(CNC[C@@H]4CCC(=O)N4)cc3Cl)c2C)c(Cl)cc1CNC[C@@H]1CCC(=O)N1]

Compound 69 was prepared using similar procedures as described for compound 68 with (S)-5-(aminomethyl)pyrrolidin-2-one replacing ethanolamine. MS (ESI): m/z 887.5 (M+H)⁺. ¹H NMR (500 MHz, $d_6$-DMSO) δ 8.96 (d, J=2.0 Hz, 1H), 8.86 (d, J=2.0 Hz, 1H), 8.35 (s, 1H), 7.81 (s, 2H), 7.68 (d, J=10.5 Hz, 2H), 7.63 (d, J=6.0 Hz, 1H), 7.57 (s, 1H), 7.50-7.46 (m, 2H), 7.42-7.32 (m, 2H), 7.06 (d, J=7.0 Hz, 1H), 7.04 (s, 1H), 6.88 (s, 1H), 5.73 (s, 2H), 5.36 (s, 2H), 5.12 (q, J=12.5 Hz, 2H), 4.07-3.81 (m, 8H), 3.74-3.59 (m, 5H), 3.22-3.15 (m, 4H), 2.18 (s, 3H), 2.01-1.91 (m, 4H).

Example 70: 1-(4-((3-(1-(4-((3-carboxy-3-methylpyrrolidin-1-yl)methyl)-2-chloro-5-((5-cyanopyridin-3-yl)methoxy)benzyl)-1H-indazol-4-yl)-2-methylbenzyl)oxy)-5-chloro-2-methoxybenzyl)-3-methylpyrrolidine-3-carboxylic acid

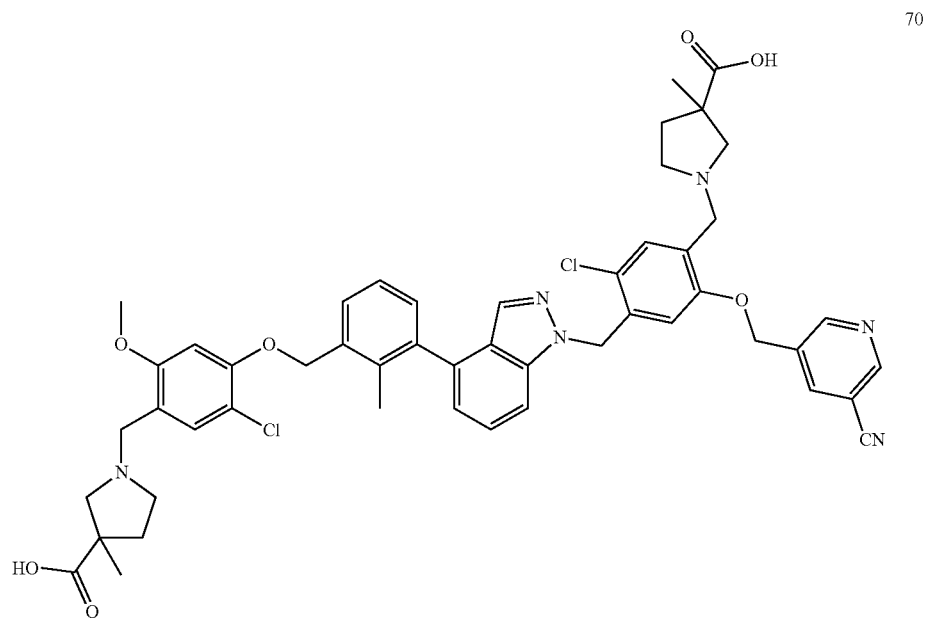 [SMILES: COc1cc(OCc2cccc(-c3cccc4c3cnn4Cc3cc(OCc4cncc(C#N)c4)c(CN4CCC(C)(C(=O)O)C4)cc3Cl)c2C)c(Cl)cc1CN1CCC(C)(C(=O)O)C1]

Compound 70 was prepared using similar procedures as described for compound 68 with 3-methylpyrrolidine-3-carboxylic acid replacing ethanolamine. MS (ESI): m/z 917.5 (M+H)+. $^1$H NMR (500 MHz, d$_6$-DMSO) δ 8.96 (d, J=2.0 Hz, 1H), 8.86 (d, J=2.0 Hz, 1H), 8.35 (s, 1H), 7.68 (d, J=10.5 Hz, 2H), 7.63 (d, J=6.0 Hz, 1H), 7.57 (s, 1H), 7.50-7.46 (m, 2H), 7.42-7.32 (m, 2H), 7.06 (d, J=7.0 Hz, 1H), 7.04 (s, 1H), 6.88 (s, 1H), 5.73 (s, 2H), 5.36 (s, 2H), 5.12 (q, J=12.5 Hz, 2H), 4.07-3.81 (m, 8H), 3.74 (s, 3H), 2.40-2.30 (m, 4H), 2.18 (s, 3H), 1.89-1.74 (m, 4H), 1.27 (s, 6H).

Example 87: (4-((2-bromo-3-(1-(3-(((((S)-5-oxopyr-rolidin-2-yl)methyl)amino)propyl)-1H-indazol-4-yl)benzyl)oxy)-5-chloro-2-((5-cyanopyridin-3-yl)methoxy)benzyl)-L-serine

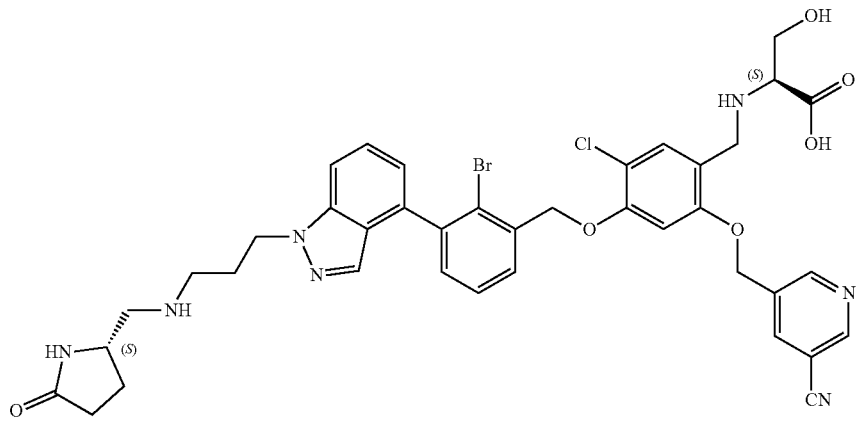

87

Compound 87 was prepared using similar procedures as described for compound 86 with 1-bromo-3-chloropropane replacing 1-bromo-4-chlorobutane. MS (ESI): m/z 816.4 (M+H)+. $^1$H NMR (500 MHz, DMSO-d$_6$) δ 9.06-8.98 (m, 2H), 8.56-8.44 (m, 1H), 7.79-7.70 (m, 4H), 7.61-7.54 (m, 2H), 7.50 (t, J=8.0 Hz, 1H), 7.47-7.41 (m, 1H), 7.16-7.07 (m, 2H), 5.40-5.31 (m, 4H), 4.53 (t, J=6.5 Hz, 2H), 4.01 (s, 2H), 3.74-3.62 (m, 3H), 3.19 (s, 1H), 2.70-2.59 (m, 4H), 2.14-2.04 (m, 5H), 1.73-1.63 (m, 1H).

Example 88: (5-chloro-2-((5-cyanopyridin-3-yl)methoxy)-4-((4-(3-(3-((R)-3-hydroxypyrrolidin-1-yl)propoxy)-2-methylphenyl)-1H-pyrazolo[3,4-b]pyridin-1-yl)methyl)benzyl)-L-serine

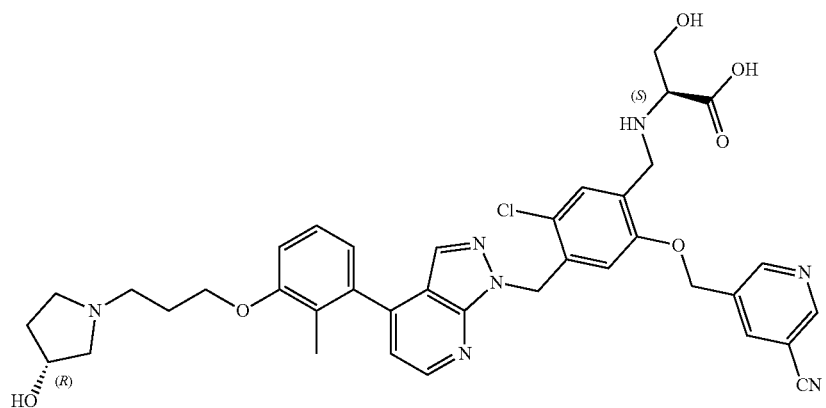

88

Compound 88 was prepared using similar procedures as described for compound 54 with 4-bromo-1H-pyrazolo[3,4-b]pyridine replacing 4-bromo-1H-indazole. MS (ESI): m/z 726.6 (M+H)+. 1H NMR (500 MHz, DMSO-d6) δ 8.92 (d, J=2.0 Hz, 1H), 8.82 (d, J=2.0 Hz, 1H), 8.59 (d, J=4.5 Hz, 1H), 8.32 (t, J=2.0 Hz, 1H), 7.88 (s, 1H), 7.53 (s, 1H), 7.30 (t, J=8.0 Hz, 1H), 7.15 (d, J=4.5 Hz, 1H), 7.07 (d, J=8.0 Hz, 1H), 6.96 (d, J=7.5 Hz, 1H), 6.89 (s, 1H), 5.74 (s, 2H), 5.13-5.05 (m, 2H), 4.26-4.17 (m, 1H), 4.08 (t, J=6.0 Hz, 2H), 3.96-3.84 (m, 2H), 3.66-3.55 (m, 2H), 3.14 (t, J=5.5 Hz, 1H), 2.89-2.82 (m, 1H), 2.82-2.68 (m, 3H), 2.67-2.59 (m, 1H), 2.56-2.49 (m, 1H), 2.01 (s, 3H), 1.99-1.93 (m, 3H), 1.63-1.56 (m, 1H).

Example 89: (5-chloro-2-((5-cyanopyridin-3-yl)methoxy)-4-((4-(3-(3-((R)-3-hydroxypyrrolidin-1-yl)propoxy)-2-methylphenyl)-1H-pyrazolo[3,4-c]pyridin-1-yl)methyl)benzyl)-L-serine

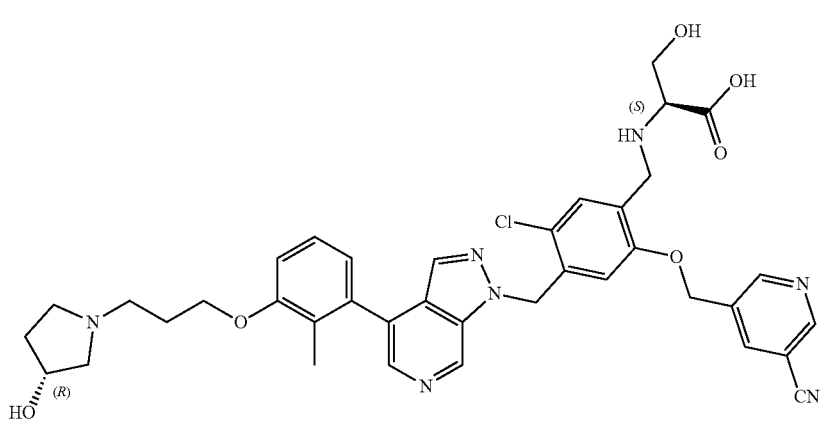

89

Compound 89 was prepared using similar procedures as described for compound 54 with 4-bromo-1H-pyrazolo[3,4-c]pyridine replacing 4-bromo-1H-indazole. MS (ESI): m/z 726.6 (M+H)+. 1H NMR (500 MHz, DMSO-d6) δ 9.20 (s, 1H), 8.96 (d, J=2.0 Hz, 1H), 8.90 (d, J=2.0 Hz, 1H), 8.40 (t, J=2.0 Hz, 1H), 8.14 (s, 1H), 7.91 (s, 1H), 7.55 (s, 1H), 7.29 (t, J=8.0 Hz, 1H), 7.11-7.04 (m, 2H), 6.94 (d, J=7.5 Hz, 1H), 5.85 (s, 2H), 5.21-5.14 (m, 2H), 4.23-4.16 (m, 1H), 4.08 (t, J=6.0 Hz, 2H), 3.96-3.82 (m, 2H), 3.62-3.54 (m, 2H), 3.10 (t, J=5.5 Hz, 1H), 2.73 (dd, J=9.5, 6.0 Hz, 1H), 2.65-2.56 (m, 3H), 2.47-2.44 (m, 1H), 2.36 (dd, J=9.5, 3.5 Hz, 1H), 1.99 (s, 3H), 1.98-1.90 (m, 3H), 1.58-1.51 (m, 1H).

Example 90: (5-chloro-4-((4-(2-chloro-3-((4-(((R)-3-hydroxypyrrolidin-1-yl)methyl) benzyl)oxy)phenyl)-1H-indazol-1-yl)methyl)-2-((5-cyanopyridin-3-yl) methoxy)benzyl)-L-serine

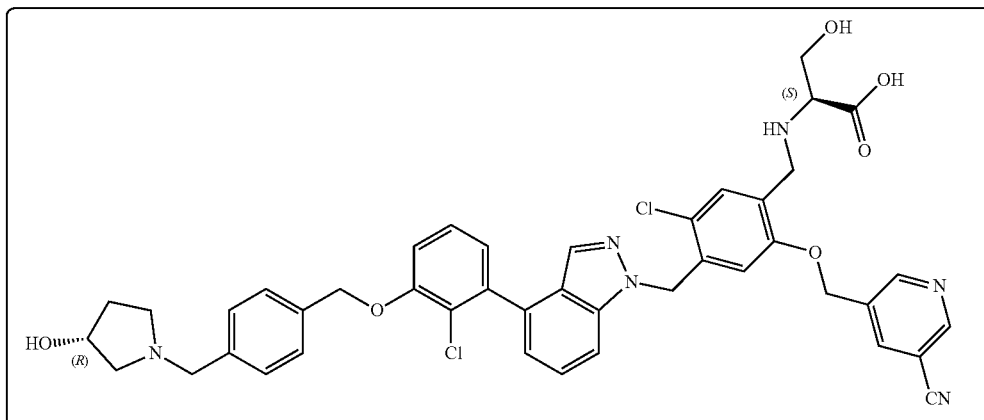

90

-continued
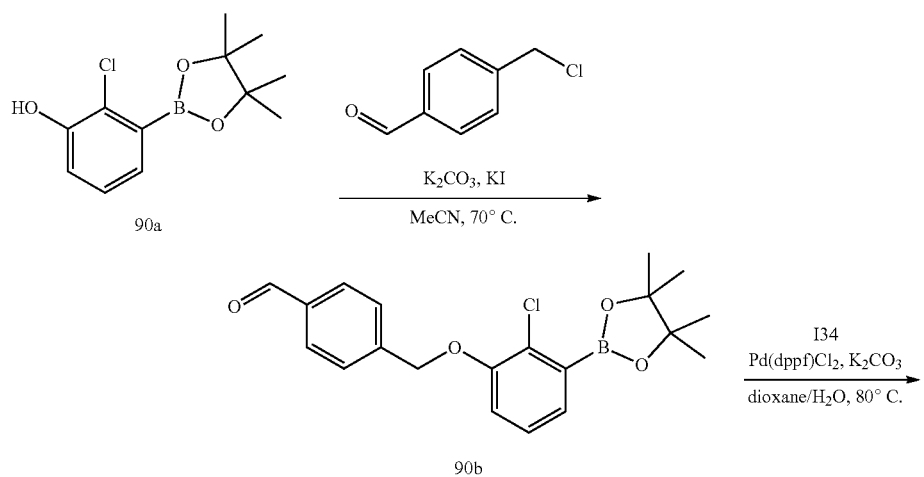
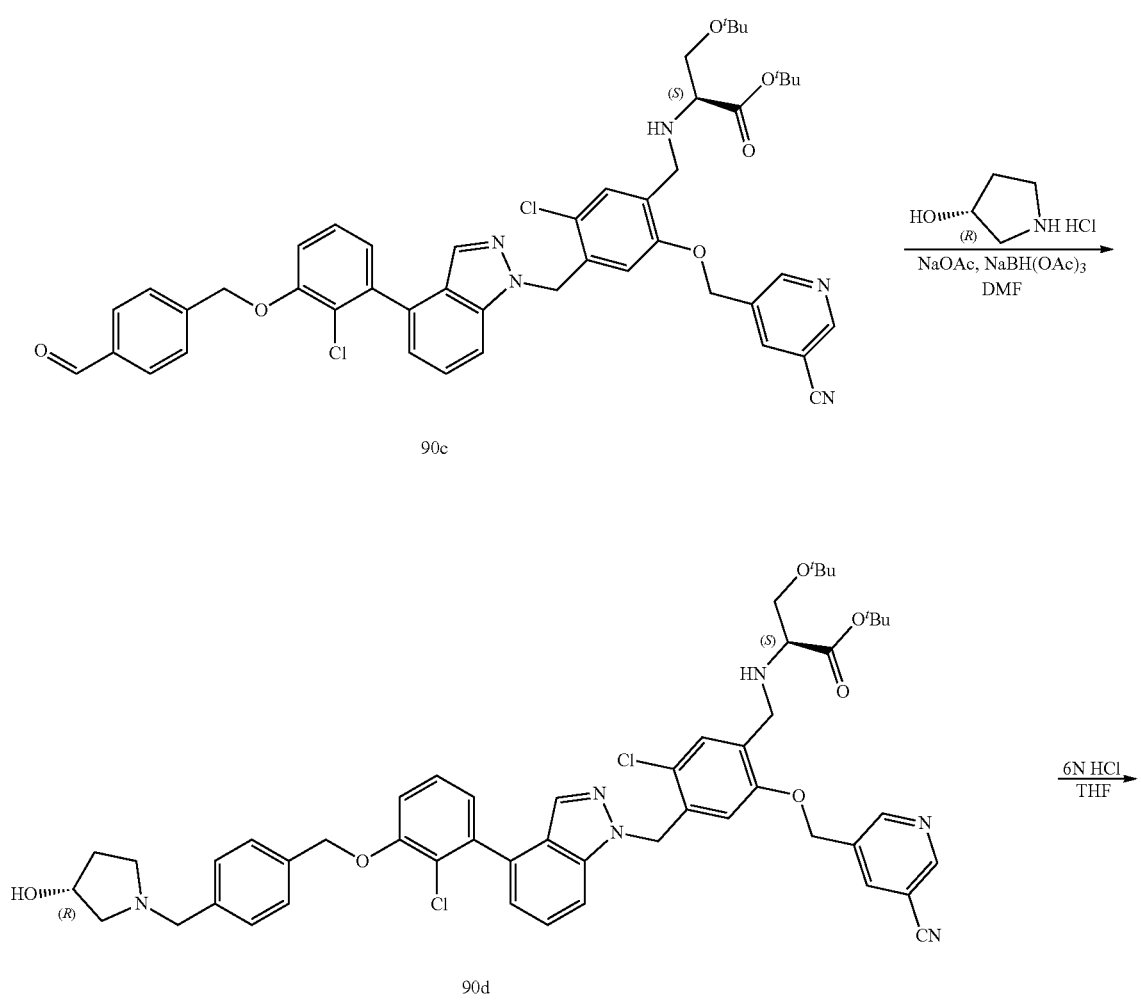

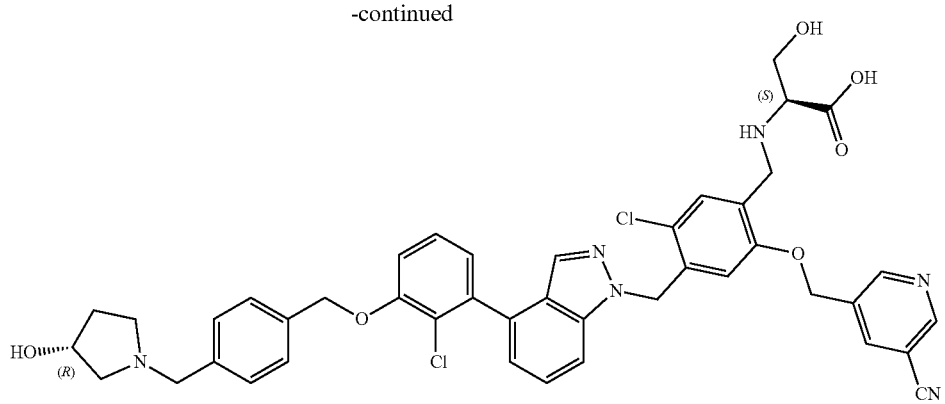

90

Step 1: To a solution of 90a (260 mg, 1.02 mmol) and 4-(chloromethyl)benzaldehyde (189.51-99-mg, 1.23 mmol) in acetonitrile (10 mL), potassium carbonate (282.37 mg, 2.04 mmol) and potassium iodide (67.83 mg, 408.62 μmol) was added. The mixture was stirred at 70° C. for 16 h. The resulting mixture was added with water (20 mL) and extracted with ethyl acetate (30 mL×2). The combined organic layers were washed with brine (20 mL), dried over Na₂SO₄ and concentrated. The residue was purified by prep-TLC to give compound 90b (207 mg, 555.48 μmol, yield 54.4%) as white solid. MS (ESI): m/z 547.1 (M/2+H)⁺.

Step 2: To a solution of compound I34 (50 mg, 73.20 μmol) and compound 90b (32.73 mg, 87.84 μmol) in a mixture of dioxane (5 mL) and water (1 mL), potassium carbonate (20.23 mg, 146.41 μmol) and Pd(dppf)Cl₂ (5.36 mg, 7.32 μmol) was added. The mixture was stirred under a nitrogen atmosphere at 80° C. for 3 h. The resulting mixture was cooled, added with ethyl acetate (50 mL) and filtered through celite. The filtrate was washed with water (20 mL×3), brine (20 mL), dried over Na₂SO₄, filtered and concentrated. The residue was purified by prep-TLC to obtain compound 90c (53 mg, 62.44 μmol, yield 85.3%) as light yellow solid. MS (ESI): m/z 848.4 (M+H)⁺.

Step 3: To a solution of compound 90c (53 mg, 62.44 μmol) in DMF (2 mL), (R)-3-pyrrolidinol hydrochloride (23.15 mg, 187.32 μmol) and sodium acetate (15.36 mg, 187.32 μmol) was added. The mixture was stirred at room temperature for 2 h followed by the addition of sodium triacetoxyborohydride (42.31 mg, 374.64 μmol) and further stirred at room temperature for 2 h. The resulting mixture was added with water (10 mL) and extracted with ethyl acetate (20 mL×2). The combined organic layers were washed with brine (20 mL), dried over Na₂SO₄ and concentrated. The residue was purified by prep-TLC to give compound 90d (19 mg, 20.65 μmol, yield 33.1%) as light yellow oil. MS (ESI): m/z 919.8 (M+H)⁺.

Step 4: To a solution of compound 90d (19 mg, 20.65 μmol) in THF (1 mL), hydrochloric acid (6.0 M in water, 1 mL) was added. The mixture was stirred at 50° C. for 16 h. The resulting mixture was cooled, added with sodium acetate until the pH=4 and concentrated. The residue was stirred in DMF (3 mL) and then filtered. The filtrate was purified by prep-HPLC to obtain compound 90 (5.31 mg, 6.57 μmol, yield 31.8%) as white solid. MS (ESI): m/z 869.5 (M+H)⁺. MS (ESI): m/z 807.5 (M+H)⁺. ¹H NMR (500 MHz, DMSO-d₆) δ 8.95 (s, 1H), 8.84 (s, 1H), 8.33 (t, J=2.0 Hz, 1H), 7.75-7.73 (m, 1H), 7.71-7.66 (m, 1H), 7.53 (s, 1H), 7.48-7.44 (m, 4H), 7.44-7.40 (m, 1H), 7.37-7.32 (m, 3H), 7.13-7.08 (m, 2H), 5.74-5.68 (m, 2H), 5.25 (s, 2H), 5.13-5.05 (m, 2H), 4.21-4.15 (m, 1H), 3.77-3.72 (m, 1H), 3.63-3.51 (m, 6H), 2.70-2.63 (m, 2H), 2.44-2.35 (m, 1H), 2.33-2.28 (m, 1H), 2.02-1.95 (m, 1H), 1.57-1.49 (m, 1H).

Example 91: (5-chloro-4-((4-(2-chloro-4'-(((((S)-5-oxopyrrolidin-2-yl)methyl)amino) methyl)-[1,1'-biphenyl]-3-yl)-1H-indol-1-yl)methyl)-2-methoxy-benzyl)-L-serine

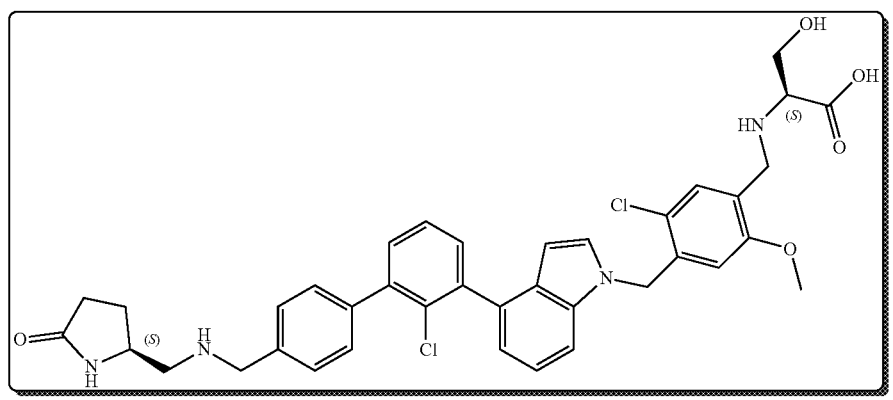

91

-continued
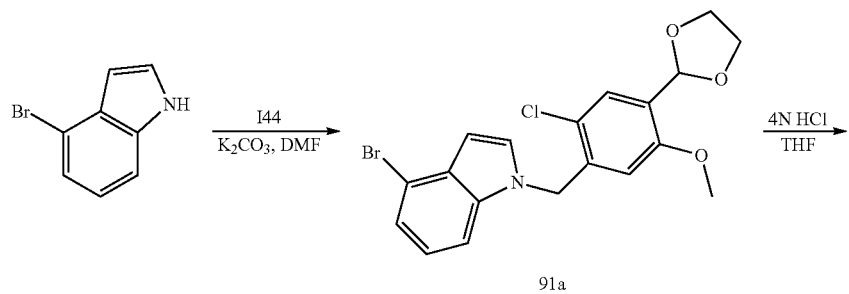
91a
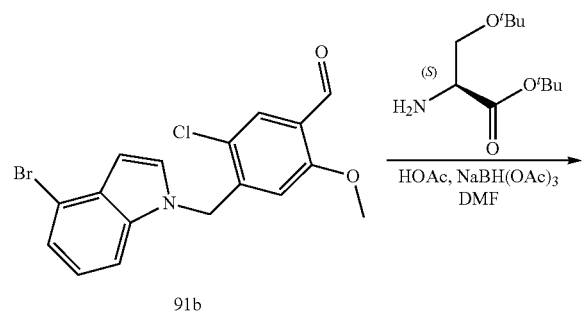
91b
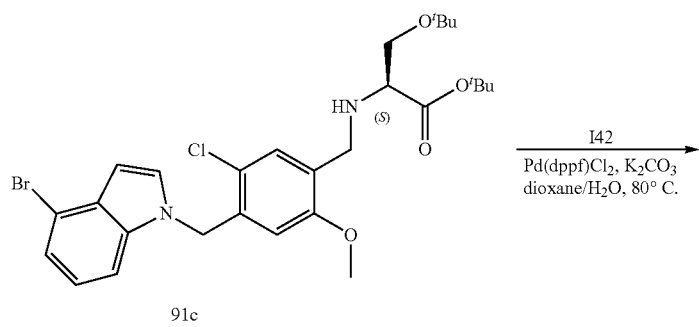
91c
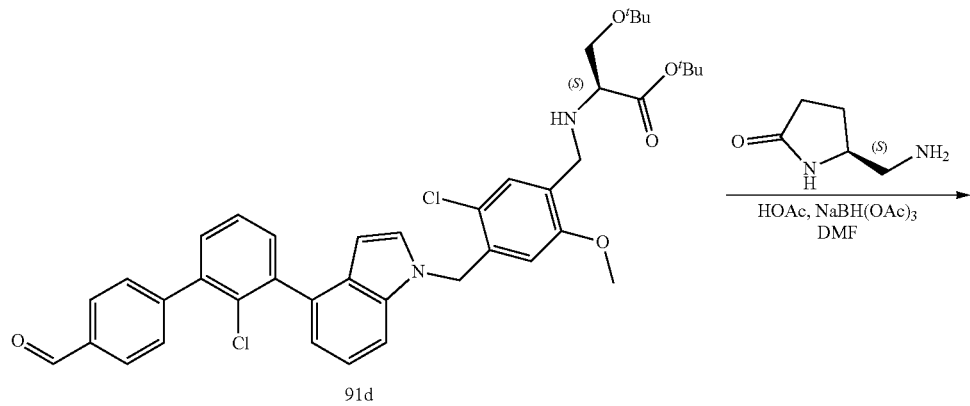
91d

-continued

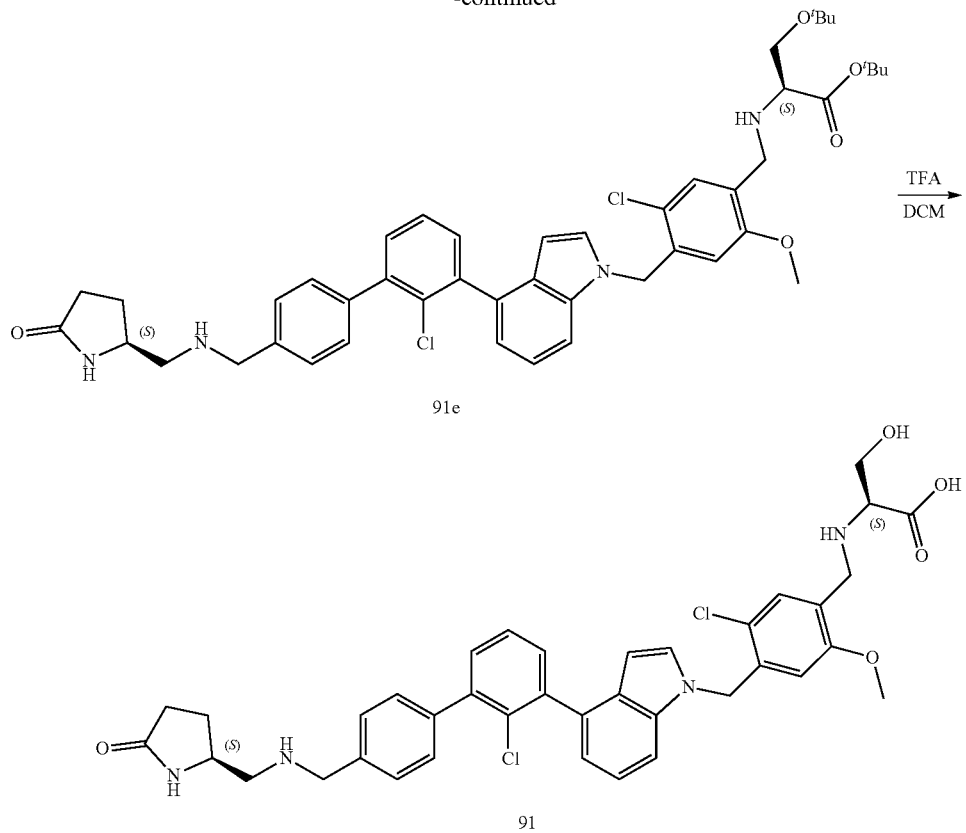

Step 1: To a solution of compound I44 (268.43 mg, 1.02 mmol) and 4-bromo-1H-indole (200 mg, 1.02 mmol) in DMF (5 mL), potassium carbonate (281.99 mg, 2.04 mmol) was added. The mixture was stirred at 60° C. for 3 h. The resulting mixture was added with water (20 mL) and extracted with ethyl acetate (30 mL×2). The combined organic layers were washed with brine (10 mL), dried over $Na_2SO_4$ and concentrated. The residue was purified by prep-TLC to give compound 91a (120 mg, 283.89 μmol, yield 27.8%) as light yellow oil. MS (ESI): m/z 422.1 $(M+H)^+$.

Step 2: To a solution of 91a (120 mg, 283.89 μmol) in THF (3 mL), hydrochloric acid (4.0 M in water, 1 mL) was added. The mixture was stirred at room temperature for 1 h. The resulting mixture was added with saturated sodium bicarbonate until the pH=7, and then the THF was removed in vacuo. The mixture was extracted with ethyl acetate (30 mL×2). The combined organic layers were washed with brine (10 mL), dried over $Na_2SO_4$ and concentrated to give compound 91b (100 mg, 264.10 μmol, yield 93.0%) as light yellow solid. MS (ESI): m/z 378.3 $(M+H)^+$.

Step 3: To a solution of compound 91b (100 mg, 264.10 μmol) in DMF (3 mL), tert-butyl O-(tert-butyl)-L-serinate (68.87 mg, 316.92 μmol) and acetic acid (19.02 mg, 316.92 μmol) was added. The mixture was stirred at room temperature for 1 h followed by the addition of sodium triacetoxyborohydride (447.78 mg, 2.11 mmol) and further stirred at room temperature for 1 h. The resulting mixture was added with water (20 mL) and extracted with ethyl acetate (30 mL×2). The combined organic layers were washed with brine (10 mL), dried over $Na_2SO_4$ and concentrated. The residue was purified by prep-TLC to give compound 91c (86 mg, 148.29 μmol, yield 56.1%) as light yellow solid. MS (ESI): m/z 579.1 $(M+H)^+$.

Step 4: To a solution of compound 91c (86 mg, 148.29 μmol) and compound I42 (60.97 mg, 177.95 μmol) in a mixture of dioxane (5 mL) and water (0.5 mL), potassium carbonate (40.93 mg, 296.58 μmol) and $Pd(dppf)Cl_2$ (10.84 mg, 14.83 μmol) was added. The mixture was stirred under a nitrogen atmosphere at 80° C. for 3 h. The resulting mixture was cooled, added with ethyl acetate (50 mL) and filtered through celite. The filtrate was washed with water (20 mL×3), brine (20 mL), dried over $Na_2SO_4$, filtered and concentrated. The residue was purified by silica gel column chromatography to obtain compound 91d (76 mg, 106.04 μmol, yield 71.5%) as light yellow solid. MS (ESI): m/z 716.5 $(M+H)^+$.

Step 5: To a solution of compound 91d (76 mg, 106.04 μmol) in DMF (5 mL), (S)-5-(aminomethyl)pyrrolidin-2-one (18.16 mg, 159.06 μmol) and acetic acid (9.54 mg, 159.06 μmol) was added. The mixture was stirred at room temperature for 16 h followed by the addition of sodium triacetoxyborohydride (44.95 mg, 212.08 μmol) and further stirred at room temperature for 3 h. The resulting mixture was added with water (20 mL) and extracted with ethyl acetate (30 mL×2). The combined organic layers were washed with brine (10 mL), dried over $Na_2SO_4$ and concentrated. The residue was purified by prep-TLC to give compound 91e (45 mg, 55.29 μmol, yield 52.1%) as light yellow solid. MS (ESI): m/z 813.1 $(M+H)^+$.

Step 6: To a solution of compound 91e (45 mg, 55.29 μmol) in DCM (1 mL), TFA (2 mL) was added. The mixture was stirred at 25° C. for 4 h. The resulting mixture was concentrated. The residue was stirred in DMF (3 mL) and then filtered. The filtrate was purified by prep-HPLC to obtain compound 91 (13.75 mg, 19.60 μmol, yield 35.4%) as white solid. MS (ESI): m/z 701.6 (M+H)+. $^1$H NMR (500 MHz, DMSO-d$_6$) δ 7.68 (s, H), 7.55 (d, J=2.0 Hz, 1H), 7.50-7.40 (m, 10H), 7.22 (t, J=8.0 Hz, 1H), 7.04 (d, J=8.0 Hz, 1H), 6.22 (t, J=3.0 Hz, 1H), 5.50 (s, 2H), 3.77 (m, 2H), 3.65-3.63 (m, 5H), 3.55-3.53 (m, 3H), 1.71-1.68 (m, 1H).

Example 92: (5-chloro-4-((4-(2-chloro-4'-(((((S)-5-oxopyrrolidin-2-yl)methyl)amino) methyl)-[1,1'-biphenyl]-3-yl)-1H-benzo[d][1,2,3]triazol-1-yl) methyl)-2-methoxybenzyl)-L-serine

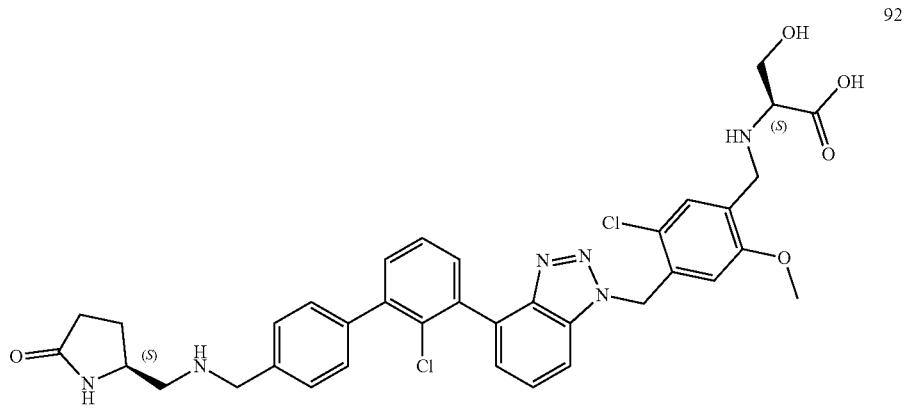

Compound 92 was prepared using similar procedures as described for compound 91 with 4-bromo-1H-benzo[d][1,2,3]triazole replacing 4-bromo-1H-indazole. MS (ESI): m/z 703.4 (M+H)+. $^1$H NMR (500 MHz, DMSO-d$_6$) δ 7.86 (d, J=8.4 Hz, 1H), 7.68 (s, 1H), 7.64 (t, J=7.7 Hz, 1H), 7.55-7.52 (m, 3H), 7.49-7.45 (m, 5H), 7.41 (d, J=7.1 Hz, 1H), 7.11 (s, 1H), 6.05 (s, 2H), 3.89 (d, J=14.5 Hz, 1H), 3.84-3.77 (m, 3H), 3.74 (s, 3H), 3.67-3.64 (m, 2H), 3.62-3.58 (m, 1H), 3.18-3.15 (m, 1H), 2.59 (d, J=6.1 Hz, 2H), 2.14-2.08 (m, 3H), 1.73-1.68 (m, 1H).

Example 93: (5-chloro-4-((4-(2-chloro-4'-(((((S)-5-oxopyrrolidin-2-yl)methyl)amino) methyl)-[1,1'-biphenyl]-3-yl)-1H-benzo[d]imidazol-1-yl)methyl)-2-methoxybenzyl)-L-serine

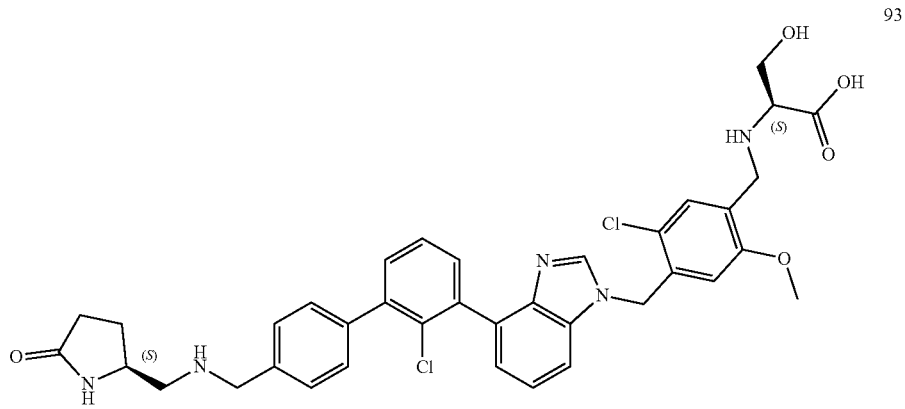

Compound 93 was prepared using similar procedures as described for compound 91 with 4-bromo-1H-benzo[d]imidazole replacing 4-bromo-1H-indazole. MS (ESI): m/z 702.7 (M+H)+. $^1$H NMR (500 MHz, DMSO-$d_6$) δ 8.32 (s, 1H), 7.67 (s, 1H), 7.62 (d, J=8.0 Hz, 1H), 7.52 (s, 1H), 7.47-7.41 (m, 7H), 7.32 (t, J=7.5 Hz, 1H), 7.21 (d, J=7.0 Hz, 1H), 7.05 (s, 1H), 5.58 (s, 2H), 3.90-3.85 (m, 1H), 3.81-3.75 (m, 3H), 3.71 (s, 3H), 3.66-3.59 (m, 3H), 3.14 (s, 1H), 2.56 (d, J=6.0 Hz, 2H), 2.13-2.08 (m, 3H), 1.72-1.68 (m, 1H).
Example 94: (5-chloro-4-((4-(2-chloro-3-((9-methyl-3,9-diazaspiro[5.5]undecan-3-yl)methyl)phenyl)-1H-indazol-1-yl)methyl)-2-((5-cyanopyridin-3-yl)methoxy)benzyl)-L-serine
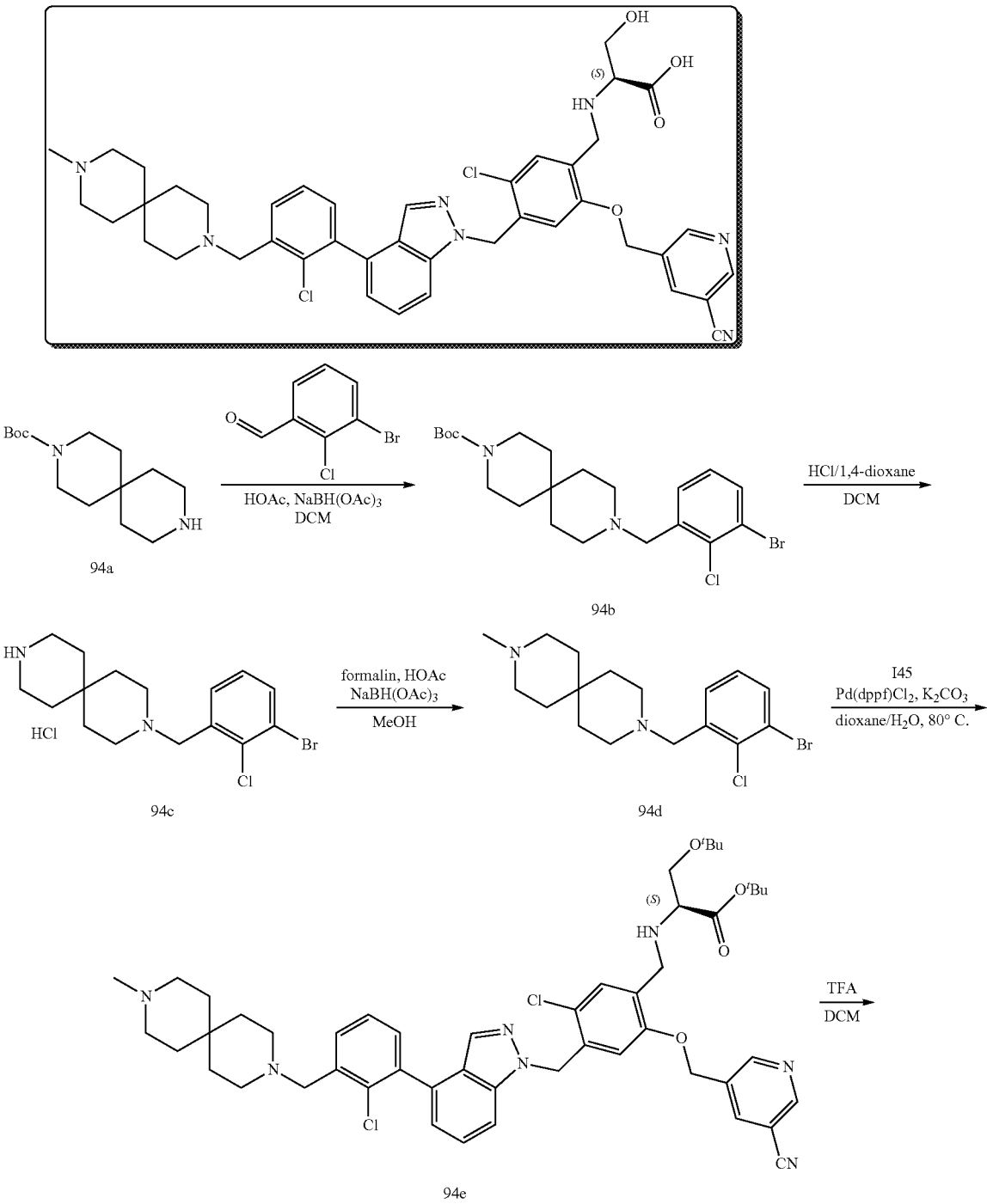

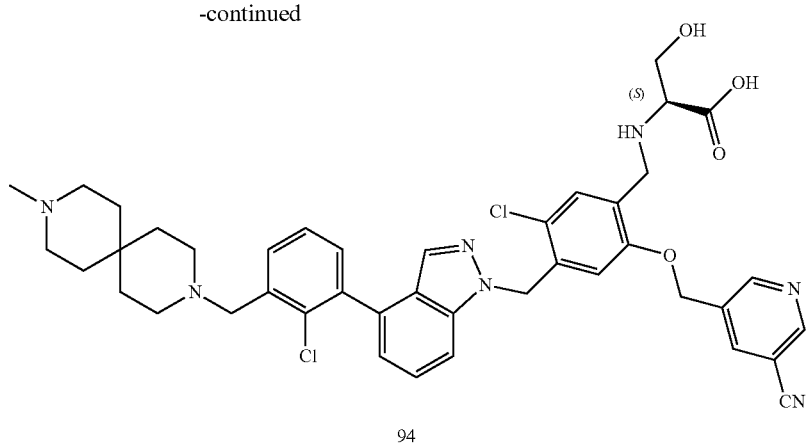

94

Step 1: To a solution of compound 94a (200 mg, 786.26 µmol) in DCM (3 mL), 3-bromo-2-chlorobenzaldehyde (224.32 mg, 1.02 mmol) and acetic acid (94.43 mg, 1.57 mmol) was added. The mixture was stirred at room temperature for 16 h followed by the addition of sodium triacetoxyborohydride (666.56 mg, 3.15 mmol) and further stirred at room temperature for 3 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 94b (200 mg, 436.84 µmol, yield 55.6%) as light yellow solid. MS (ESI): m/z 457.4 (M+H)$^+$.

Step 2: To a solution of 94b (200 mg, 436.84 µmol) in DCM (3 mL), hydrochloric acid (4.0 M in dioxane, 1 mL) was added. The mixture was stirred at room temperature for 3 h. The resulting mixture was concentrated to give compound 94c (172 mg, 436.35 µmol, yield 99.9%) as light yellow solid. MS (ESI): m/z 357.4 (M+H)$^+$.

Step 3: To a solution of compound 94c (172 mg, 436.35 µmol) in methanol (3 mL), formalin (141.66 mg, 1.75 mmol, 129.96 uL) and acetic acid (52.41 mg, 872.71 µmol) was added. The mixture was stirred at room temperature for 1 h followed by the addition of sodium triacetoxyborohydride (369.92 mg, 1.75 mmol) and further stirred at room temperature for 3 h. The mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 94d (160 mg, 430.41 µmol, yield 98.6%) as light yellow solid. MS (ESI): m/z 371.2 (M+H)$^+$.

Step 4: To a solution of compound 94d (32.66 mg, 87.84 µmol) and compound I45 (50 mg, 73.20 µmol) in a mixture of dioxane (3 mL) and water (0.3 mL), potassium carbonate (30.35 mg, 219.61 µmol) and Pd(dppf)Cl$_2$ (5.36 mg, 7.32 µmol) was added. The mixture was stirred under nitrogen atmosphere at 80° C. for 3 h. The resulting mixture was cooled, added with ethyl acetate (50 mL) and filtered through celite. The filtrate was washed with water (20 mL×3), brine (20 mL), dried over Na$_2$SO$_4$, filtered and concentrated. The residue was purified by silica gel column chromatography to obtain compound 94e (20 mg, 22.35 µmol, yield 30.5%) as light yellow solid. MS (ESI): m/z 895.0 (M+H)$^+$.

Step 5: To a solution of compound 94e (20 mg, 22.35 µmol) in DCM (2 mL), TFA (2 mL) was added. The mixture was stirred at 25° C. for 4 h. The resulting mixture was concentrated. The residue was stirred in DMF (3 mL) and then filtered. The filtrate was purified by prep-HPLC to obtain compound 94 (5 mg, 6.39 µmol, yield 28.6%) as white solid. MS (ESI): m/z 782.7 (M+H). $^1$H NMR (500 MHz, DMSO-d$_6$) δ 8.94 (d, J=1.9 Hz, 1H), 8.84 (d, J=2.1 Hz, 1H), 8.32 (t, J=2.2 Hz, 1H), 7.74-7.65 (m, 2H), 7.58 (dd, J=7.6, 1.9 Hz, 1H), 7.54 (s, 1H), 7.45 (t, J=7.6 Hz, 2H), 7.39 (dd, J=7.6, 1.8 Hz, 1H), 7.10 (d, J=7.0 Hz, 1H), 6.80 (s, 1H), 5.70 (s, 2H), 5.14-5.02 (m, 2H), 3.95-3.88 (m, 2H), 3.65 (s, 2H), 3.60-3.55 (m, 2H), 3.15-3.09 (m, 1H), 2.61-2.54 (m, 2H), 2.48-2.41 (m, 5H), 2.39-2.26 (m, 4H), 1.55-1.43 (m, 8H).

Example 95: (5-chloro-4-((4-(2-chloro-3-(9-methyl-3,9-diazaspiro[5.5]undecane-3-carbonyl)phenyl)-1H-indazol-1-yl)methyl)-2-((5-cyanopyridin-3-yl)methoxy)benzyl)-L-serine
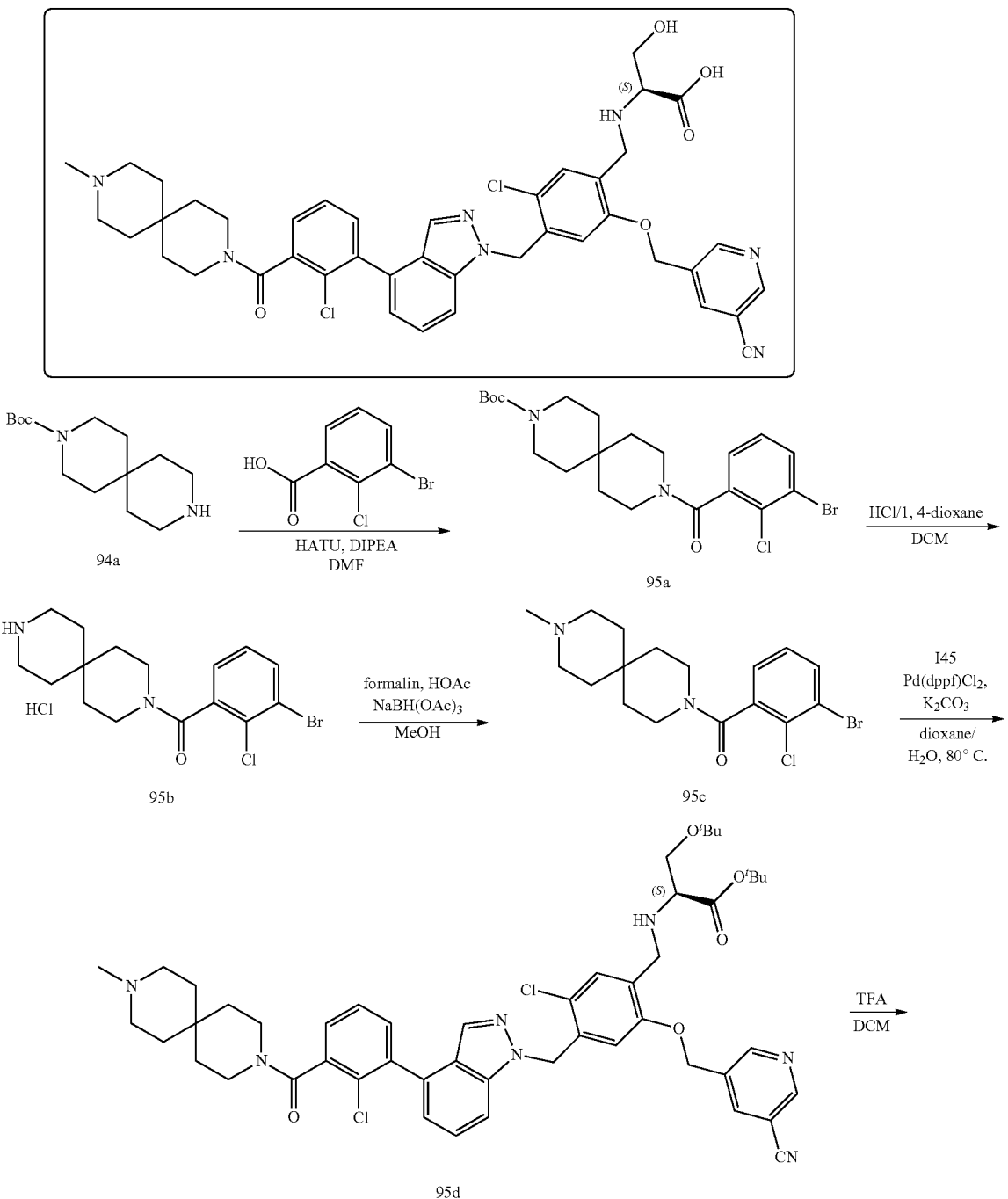

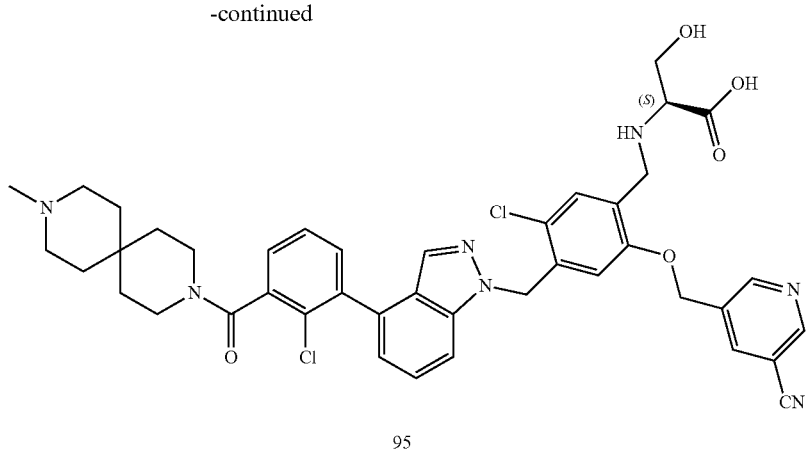

95

Step 1: To a solution of compound 94a (200 mg, 786.26 μmol) and 3-bromo-2-chlorobenzoic acid (224.32 mg, 1.02 mmol) in DMF (3 mL), N,N-diisopropylethylamine and HATU (298.96 mg, 786.26 μmol) was added. The mixture was stirred at room temperature for 16 h. The resulting mixture was added with water (20 mL) and extracted with ethyl acetate (30 mL×2). The combined organic layers were washed with brine (10 mL), dried over $Na_2SO_4$ and concentrated. The residue was purified by prep-TLC to give compound 95a (240 mg, 508.67 μmol, yield 64.7%) as light yellow oil. MS (ESI): m/z 471.3 (M+H)+.

From compound 95a, compound 95 was prepared following the procedures for compound 94 (7 mg, 8.79 μmol) as white solid. MS (ESI): m/z 796.7 (M+H)+. $^1$H NMR (500 MHz, DMSO-$d_6$) δ 8.94 (d, J=2.1 Hz, 1H), 8.83 (d, J=2.1 Hz, 1H), 8.32 (s, 1H), 7.76 (s, 1H), 7.72 (d, J=8.5 Hz, 1H), 7.58-7.49 (m, 3H), 7.48-7.41 (m, 2H), 7.15 (d, J=7.0 Hz, 1H), 6.79 (s, 1H), 5.72 (s, 2H), 5.08 (d, J=3.9 Hz, 2H), 3.92-3.85 (m, 2H), 3.73-3.70 (m, 2H), 3.57-3.56 (m, 2H), 3.21-3.19 (m, 2H), 3.05-3.03 (m, 1H), 2.36-2.30 (m, 4H), 2.19 (s, 3H), 1.50-1.38 (m, 8H).

Example 96: (5-chloro-4-((4-(2-chloro-3-(9-methyl-3,9-diazaspiro[5.5]undecan-3-yl)phenyl)-1H-indazol-1-yl) methyl)-2-((5-cyanopyridin-3-yl)methoxy) benzyl)-L-serine

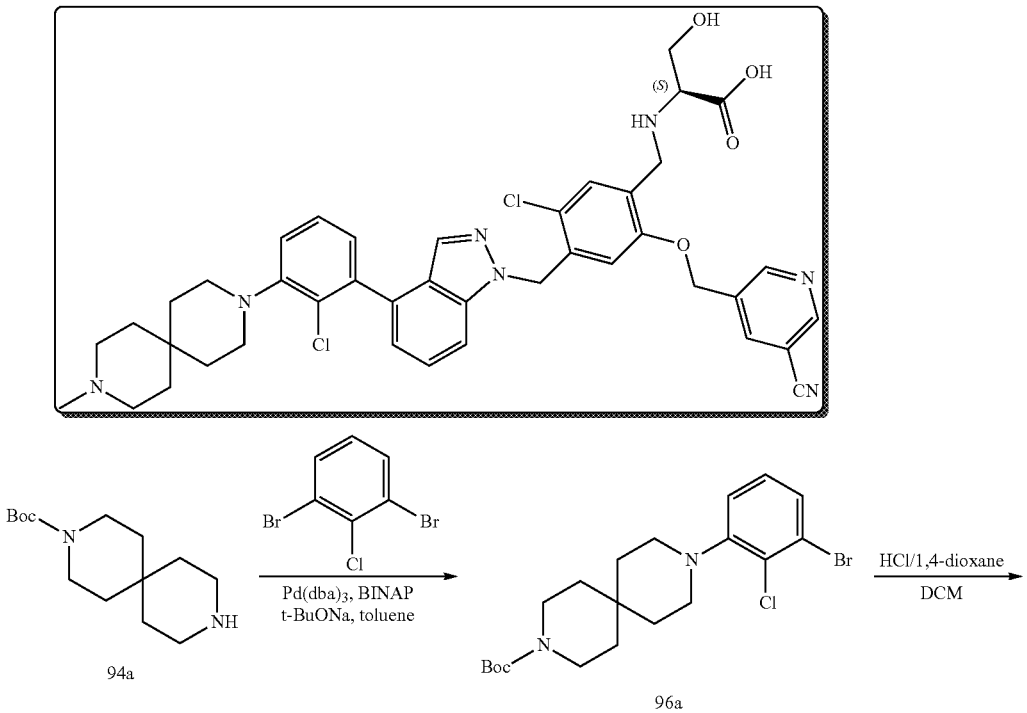

96

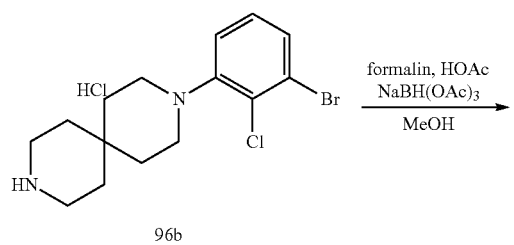

96b

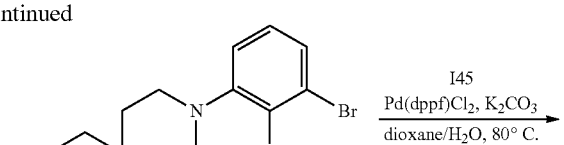

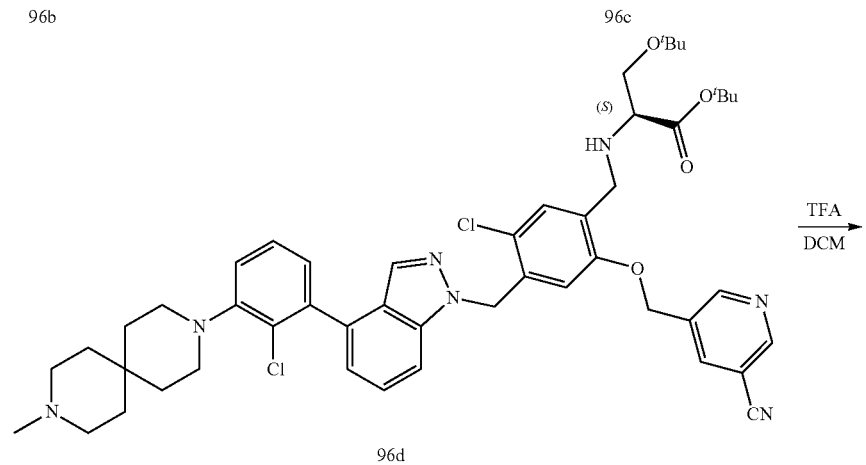

96c

96d

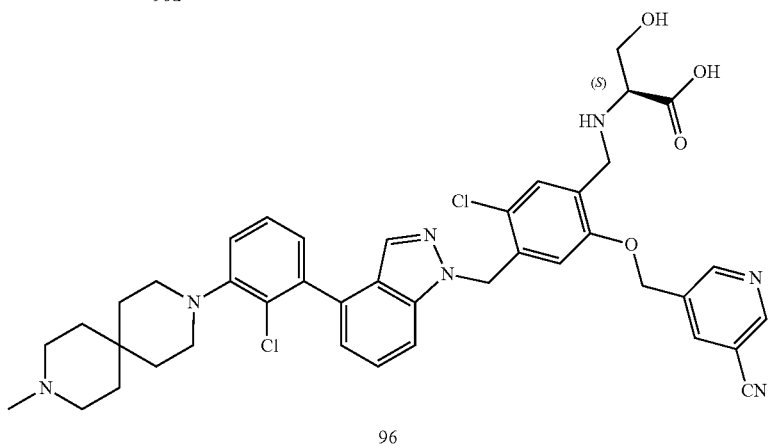

96

Step 1: To a solution of compound 94a (200 mg, 786.26 μmol) and 1,3-dibromo-2-chlorobenzene (212.57 mg, 786.26 μmol) in Toluene (3 mL), Pd$_2$(dba)$_3$ (36.00 mg, 39.31 μmol), BINAP (48.93 mg, 78.62 μmol) and sodium tert-butoxide (75.56 mg, 786.26 μmol) was added. The mixture was stirred under a nitrogen atmosphere at 100° C. for 16 h. The resulting mixture was added with water (20 mL) and extracted with ethyl acetate (30 mL×2). The combined organic layers were washed with brine (10 mL), dried over Na$_2$SO$_4$ and concentrated. The residue was purified by prep-TLC to give compound 96a (250 mg, 563.31 μmol, yield 71.6%) as light yellow oil. MS (ESI): m/z 443.3 (M+H)$^+$.

From compound 96a, compound 96 was prepared following the procedures for compound 94 (10 mg, 13.01 μmol) as white solid. MS (ESI): m/z 782.7 (M+H)$^+$. $^1$H NMR (500 MHz, DMSO-d$_6$) δ 8.95 (d, J=2.1 Hz, 2H), 8.84 (d, J=2.0 Hz, 1H), 8.32 (t, J=2.1 Hz, 1H), 7.72 (s, 1H), 7.67 (d, J=8.5 Hz, 1H), 7.54 (s, 1H), 7.48-7.36 (m, 2H), 7.27 (dd, J=8.2, 1.6 Hz, 1H), 7.16-7.06 (m, 2H), 6.78 (s, 1H), 5.71 (s, 2H), 5.13-5.03 (m, 2H), 3.97-3.73 (m, 2H), 3.65-3.55 (m, 2H), 3.15-3.09 (m, 1H), 3.00 (t, J=5.5 Hz, 4H), 2.50-2.38 (m, 4H), 2.32-2.24 (m, 3H), 1.64-1.49 (m, 8H).

Cell Based PD-1/PD-L1 NFAT Reporter Assay

Compounds of the present patent were tested in a cell based PD-1/PD-L1 NFAT reporter assay.

Background

The cell-based luciferase reporter assay is used for monitoring the PD-1/PD-L1 inhibitor by characterizing the biological activity of PD-1: PD-L1 interactions in cellular context. PD-1/NFAT-Reporter-Jurkat cells stably over-expressing human PD-1 with NFAT reporter are used as effector cells. TCR activator/PD-L1—CHO cells over-expressing PD-L1 and an engineered T cell receptor (TCR) activator are used as target cells. When these two cells are co-cultivated, TCR complexes on effector cells are activated by TCR activator on target cells, resulting in expression of the NFAT luciferase reporter. However, PD1 and PD-L1 (or PD-L2) ligation prevents TCR activation and suppresses the NFAT-responsive luciferase activity. This inhibition can be specifically reversed by anti-PD1 or anti-PD-L1 inhibitors. PD1/PD-L1 inhibitors block PD1:PD-L1 interaction and promote TCR activation, resulting in reactivation of the NFAT responsive luciferase reporter.

Materials and Equipment

PD-1/NFAT—Reporter—Jurkat cell (Cat: 60535) and TCR activator/PD-L1—CHO cell (Cat: 60536) were purchased from BPS Bioscience. Anti-human PD-L1 antibody (Atezolizumab, Cat: A2004) was purchased from Selleck; luciferase reporter gene expression detection kit (ONE-Glo™ Luciferase Assay System, Cat: E6120) was purchased from Promega; multifunction plate reader (SpectraMax i3x) was purchased from Molecular Devices.

Procedures

PD-1/NFAT—Reporter—Jurkat cells and TCR activator/PD-L1—CHO cells were cultured in recommended media respectively.

Harvest TCR activator/PD-L1-CHO cells from culture and seed cells at a density of 35,000 cells per well into 96-well microplate in 100 1 of growth medium. Incubate cells at 37° C. in a CO2 incubator overnight. Next day, discard the culture media, add diluted compound in assay medium for 30 min. Anti-PD-L1 antibody (Atezolizumab, final concentration 10 nM) and 0.1% DMSO were the positive and negative control, respectively. Harvest the PD-1/NFAT-reporter-Jurkat cells by centrifugation and add to the wells. After 6 hour incubation, perform luciferase assay using the ONE-Glo™ Luciferase Assay System, following the manufacturer's assay protocol.

Anti-PD-L1 antibody (Atezolizumnab, 10 nM) was used as positive control to calibrate the inhibition rate using the following equation:

% inhibition=(Sample luminescence/Average vehicle group luminescence−1)/(Average PD-L1 group luminescence/Average vehicle group luminescence−1)×100%.

Representative data are shown in the Table below

| No. | Absolute EC50 (μM) |
|---|---|
| 1 | 0.34 |
| 2 | 0.31 |
| 3 | 2.382 |
| 4 | 5.492 |
| 5 | 0.241 |
| 6 | 0.266 |
| 7 | 0.338 |
| 8 | 1.155 |
| 9 | 0.367 |
| 10 | 0.412 |
| 11 | 0.142 |
| 12 | 0.289 |
| 13 | 0.242 |
| 14 | 0.323 |
| 15 | 3.235 |
| 16 | 9.355 |
| 17 | 1.762 |
| 18 | 0.235 |
| 19 | 0.764 |
| 20 | 0.876 |
| 21 | 3.54 |
| 22 | 1.126 |
| 23 | 0.608 |
| 24 | >10 |
| 25 | 0.138 |
| 26 | 1.828 |
| 27 | 0.643 |
| 28 | 0.726 |
| 29 | >1.1 |
| 31 | >10 |
| 32 | 0.724 |
| 33 | >0.37 |
| 34 | 5.783 |
| 35 | 1.537 |
| 36 | 2.34 |
| 37 | 1.915 |
| 38 | 7.638 |
| 39 | >10 |
| 40 | >10 |
| 41 | 0.606 |
| 42 | >10 |
| 44 | 0.153 |
| 45 | 2.721 |
| 46 | 0.846 |
| 47 | 0.261 |
| 48 | 0.997 |
| 49 | >10 |
| 50 | 2.82 |
| 51 | 3.081 |
| 52 | >10 |
| 53 | >10 |
| 54 | 0.339 |
| 55 | 1.153 |
| 56 | 0.163 |
| 57 | 0.053 |
| 58 | 1.71 |
| 59 | 0.22 |
| 60 | 1.846 |
| 61 | 0.124 |
| 64 | 0.55 |
| 65 | 0.418 |
| 66 | 0.307 |
| 67 | 0.089 |
| 68 | 0.348 |
| 69 | 0.157 |
| 70 | 5.849 |
| 71 | 0.134 |
| 72 | >1.11 |
| 73 | 0.448 |
| 74 | 2.702 |
| 75 | 2.83 |
| 76 | 0.034 |
| 77 | 0.028 |
| 78 | 1.605 |
| 79 | >0.37 |
| 80 | 0.318 |
| 81 | 0.221 |
| 82 | 0.339 |
| 83 | 0.232 |
| 84 | 1.749 |
| 85 | >0.37 |
| 86 | 0.214 |
| 87 | 0.098 |
| 88 | 1.034 |
| 89 | 5.447 |
| 90 | 1.063 |
| 91 | 0.518 |
| 92 | 0.416 |
| 93 | 2.129 |
| 94 | >10 |
| 95 | >10 |
| 96 | 2.451 |

The above data show that compounds of the present disclosure are generally effective at blocking the PD-1/PD-L1 interaction.

The invention claimed is:
1. A compound of Formula (I),

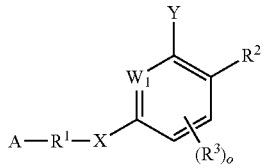

Formula (I)

wherein,
R$^1$ is selected from the following groups:

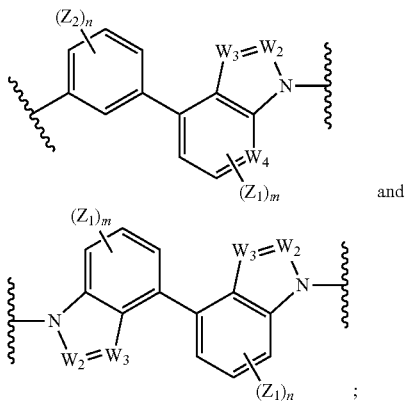

and wherein W$_1$, W$_2$, W$_3$, and W$_4$ each independently represent CR$^c$ or N; Z$_1$ and Z$_2$ each independently represent hydrogen, (C$_1$-C$_6$) alkyl, (C$_3$-C$_6$) cycloalkyl, halo (C$_1$-C$_6$) alkyl, halo, —OR$^a$, —C(O)OR$^a$, (C$_1$-C$_6$) alkoxy, —NR$^a$R$^b$, —SO$_2$R$^a$, cyano, or nitro;

R$^2$ represents —(C$_0$-C$_6$ alkylene) NR$^A$R$^B$ or —O (C$_0$-C$_6$ alkylene) NR$^A$R$^B$;

R$^3$ represents hydrogen, (C$_1$-C$_6$) alkyl, (C$_3$-C$_6$) cycloalkyl, (C$_1$-C$_6$) haloalkyl, halogen, —OR$^a$, —C(O)OR$^a$, (C$_1$-C$_6$) alkoxy, —NR$^a$R$^b$, —SO$_2$R$^a$, cyano, or nitro;

X represents —(C$_0$-C$_6$ alkylene)-, —(C$_0$-C$_6$ alkylene)O—, or —O (C$_0$-C$_6$ alkylene)-;

Y represents —(C$_0$-C$_6$ alkylene)(C$_6$-C$_{10}$ aryl), —(C$_0$-C$_6$ alkylene)(5- to 10-membered heteroaryl), —O(C$_1$-C$_6$) alkyl, —O(C$_0$-C$_6$ alkylene)(C$_6$-C$_{10}$ aryl), —O(C$_0$-C$_6$ alkylene)(5- to 10-membered heteroaryl), —(C$_0$-C$_6$ alkylene)((C$_6$-C$_{10}$ aryl), —(C$_0$-C$_6$ alkylene)O(5- to 10-membered heteroaryl), —O(C$_0$-C$_6$ alkylene)(C$_3$-C$_6$ cycloalkyl), or —O(C$_0$-C$_6$ alkylene)(3- to 6-membered heterocycloalkyl);

for alkylene, alkyl, cycloalkyl, heterocycloalkyl, aryl, heteroaryl in the above-mentioned definition of Y, they are optionally substituted by 0, 1, 2 or 3 substituents selected from the group consisting of: —OR$^a$, cyano, oxo(=O), halogen, C$_1$-C$_6$ alkyl, —(C$_1$-C$_6$ alkylene)OR$^a$, C$_1$-C$_6$ cyanoalkyl, C$_1$-C$_6$ haloalkyl, C$_3$-C$_8$ cycloalkyl, —C(O)R$^a$, —(C$_1$-C$_6$ alkylene)C(O)R$^a$, —C(O)OR$^a$, —(C$_1$-C$_6$ alkyl)C(O)OR$^a$, —NR$^a$R$^b$, —(C$_1$-C$_6$ alkylene)NR$^a$R$^b$, —C(O)NR$^a$R$^b$, SO$_2$R$^a$, —C(O)NR$^a$SO$_2$R$^b$; or —NR$^a$C(O)R$^b$;

or Y represents —O(C$_0$-C$_6$ alkylene)CONR$^A$R$^B$;

A represents —(C$_0$-C$_6$ alkylene)NR$^A$R$^B$, —O(C$_0$-C$_6$ alkylene)NR$^A$R$^B$, —C(O)(C$_0$-C$_6$ alkylene)NR$^A$R$^B$, —(C$_0$-C$_6$ alkylene)(C$_3$-C$_6$ cycloalkyl)NR$^A$R$^B$, or -(3- to 6-membered heterocycloalkyl)CHR$^A$R$^B$;

or A represents

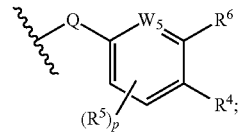

wherein Q represents —(C$_0$-C$_6$ alkylene)-, —(C$_0$-C$_6$ alkylene)O—, or —O(C$_0$-C$_6$ alkylene)-;

W$_5$ represents CH or N;

R$^4$ represents —(C$_0$-C$_6$ alkylene)NR$^A$R$^B$, —O(C$_0$-C$_6$ alkylene)NR$^A$R$^B$, or —C(O)NR$^A$R$^B$;

R$^5$ represents hydrogen, (C$_1$-C$_6$) alkyl, (C$_3$-C$_6$) cycloalkyl, (C$_1$-C$_6$) haloalkyl, halogen, —OR$^a$, —C(O)OR$^a$, (C$_1$-C$_6$) alkoxy, —NR$^a$R$^b$, —SO$_2$R$^a$, cyano, or nitro;

R$^6$ represents hydrogen, —(C$_0$-C$_6$ alkylene)(C$_6$-C$_{10}$ aryl), —(C$_0$-C$_6$ alkylene)(5- to 10-membered heteroaryl), —O(C$_1$-C$_6$)alkyl, —O(C$_0$-C$_6$ alkylene)CONR$^A$R$^B$, —O(C$_0$-C$_6$ alkylene)(C$_6$-C$_{10}$ aryl), —O(C$_0$-C$_6$ alkylene)(5- to 10-membered heteroaryl), —(C$_0$-C$_6$ alkylene)O(C$_6$-C$_{10}$ aryl), —(C$_0$-C$_6$ alkylene)O(5- to 10-membered heteroaryl), —O(C$_0$-C$_6$ alkylene)(C$_3$-C$_6$ cycloalkyl), or —O(C$_0$-C$_6$ alkylene)(3- to 6-membered heterocycloalkyl);

for alkylene, alkyl, cycloalkyl, heterocycloalkyl, aryl, and heteroaryl in the above-mentioned definition of R$^6$, they are optionally substituted by 0, 1, 2 or 3 substituents selected from the group consisting of: —OR$^a$, cyano, halogen, C$_1$-C$_6$ alkyl, —(C$_1$-C$_6$ alkylene)OR$^a$, C$_1$-C$_6$ cyanoalkyl, C$_1$-C$_6$ haloalkyl, C$_3$-C$_8$ cycloalkyl, —C(O)R$^a$, —(C$_1$-C$_6$ alkylene)C(O)R$^a$, —C(O)OR$^a$, —(C$_1$-C$_6$ alkyl)C(O)OR$^a$, —NR$^a$R$^b$, —(C$_1$-C$_6$ alkylene)NR$^a$R$^b$, —C(O)NR$^a$R$^b$, —SO$_2$R$^a$, —C(O)NR$^a$SO$_2$R$^b$, or —NR$^a$C(O)R$^b$;

$\sim\sim\sim$ represents an arbitrary connection position;

m, n, o, and p are selected from 0, 1, 2, and 3;

R$^A$ and R$^B$ each independently represent hydrogen, C$_1$-C$_6$ alkyl, C$_2$-C$_6$ alkenyl, C$_2$-C$_6$ alkynyl, —(C$_0$-C$_6$ alkylene)(C$_3$-C$_6$ cycloalkyl), —(C$_0$-C$_6$ alkylene)(3- to 6-membered heterocycloalkyl), —(C$_0$-C$_6$ alkylene)(C$_6$-C$_{10}$ aryl), —(C$_0$-C$_6$ alkylene)(5- to 10-membered heteroaryl), —(C$_0$-C$_6$ aryl)C(O)OR$^a$, —SO$_2$R$^a$, —SO$_2$NR$^a$R$^b$, or —C(O)NR$^a$SO$_2$R$^b$;

for alkylene, alkyl, alkenyl, alkynyl, cycloalkyl, heterocycloalkyl, aryl, and heteroaryl in the above-mentioned definition of R$^A$ and R$^B$, they are optionally substituted with 0, 1, 2 or 3 substituents selected from the group consisting of: —OR$^a$, cyano, oxo, halogen, C$_1$-C$_6$ alkyl, —(C$_1$-C$_6$ alkylene)OR$^a$, C$_1$-C$_6$ cyanoalkyl, C$_1$-C$_6$ haloalkyl, C$_3$-C$_8$ cycloalkyl, —C(O)R$^a$, —(C$_1$-C$_6$ alkylene)C(O)R$^a$, —C(O)OR$^a$, —(C$_1$-C$_6$ alkyl)C(O)OR$^a$, —NR$^a$R$^b$, —(C$_1$-C$_6$ alkylene)NR$^a$R$^b$, —C(O)NR$^a$R$^b$, —SO$_2$R$^a$, —C(O)NR$^a$SO$_2$R$^b$, or —NR$^a$C(O)R$^b$;

or R$^A$ and R$^B$ together with atoms bound thereto are optionally cyclized to each other into a 5- to 7-membered ring, and the ring also optionally has 0, 1, 2 or 3 heteroatoms selected from O, N, S, further the ring is optionally substituted by 0, 1, 2 or 3 substituents selected from the group consisting of: oxo, cyano, C$_1$-C$_6$ alkyl, C$_3$-C$_6$ cycloalkyl, C$_2$-C$_6$ alkenyl, C$_2$-C$_6$ alkynyl, —OR$^a$, —C(O)OR$^a$, —(C$_1$-C$_6$) cyanoalkyl, ($C_1$-$C_6$) haloalkyl, —($C_1$-$C_6$ alkylene)OR$^a$, —C(O)R$^a$, —NR$^a$R$^b$, —($C_1$-$C_6$ alkylene)NR$^a$R$^b$, —C(O)NR$^a$R$^b$, —($C_1$-$C_6$ alkylene)C(O)NR$^a$R$^b$, —SO$_2$R$^a$, —($C_1$-$C_6$ alkylene)SO$_2$R$^a$, —SO$_2$NR$^a$R$^b$, or —($C_1$-$C_6$ alkylene)SO$_2$NR$^a$R$^b$;

R$^a$ and R$^b$ are each independently selected from the group consisting of hydrogen, $C_1$-$C_6$ alkyl, —($C_0$-$C_6$ alkylene) ($C_3$-$C_6$ cycloalkyl), —($C_0$-$C_6$ alkylene)($C_3$-$C_6$ heterocycloalkyl), —($C_0$-$C_6$ alkylene)($C_6$-$C_{10}$ aryl), or —($C_0$-$C_6$ alkylene)(5- to 10-membered heteroaryl);

or R$^a$ and R$^b$ together with atoms bound thereto are optionally cyclized to each other into a 5- to 7-membered ring, and the ring also optionally has 0, 1, 2 or 3 heteroatoms selected from O, N, S, further the ring is optionally substituted by 0, 1, 2 or 3 substituents selected from the group consisting of: oxo, cyano, $C_1$-$C_6$ alkyl, $C_3$-$C_6$ cycloalkyl, $C_2$-$C_6$ alkenyl, $C_2$-$C_6$ alkynyl, —OR$^d$, —C(O)OR$^d$, —($C_1$-$C_6$) cyanoalkyl, ($C_1$-$C_6$) haloalkyl, —($C_1$-$C_6$ alkylene)OR$^d$, —C(O)R$^d$, —NR$^d$R$^e$, —($C_1$-$C_6$ alkylene)NR$^d$R$^e$, —C(O)NR$^d$R$^e$, —($C_1$-$C_6$ alkylene)C(O)NR$^d$R$^e$, —SO$_2$R$^d$, —($C_1$-$C_6$ alkylene)SO$_2$R$^d$, —SO$_2$NR$^d$R$^e$, or —($C_1$-$C_6$ alkylene)SO$_2$NR$^d$R$^e$;

wherein R$^c$, R$^d$, and R$^e$ each independently represent hydrogen, $C_1$-$C_6$ alkyl, or $C_3$-$C_6$ cycloalkyl.

2. The compound according to claim 1, having the following structure of Formula (II), or Formula (III), or Formula (IV):

Formula (II)

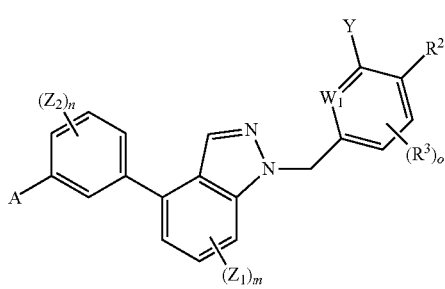

wherein R$^2$, R$^3$, A, W$_1$, Z$_1$, Z$_2$, Y, m, n, and o are as defined in claim 1;

Formula (III)

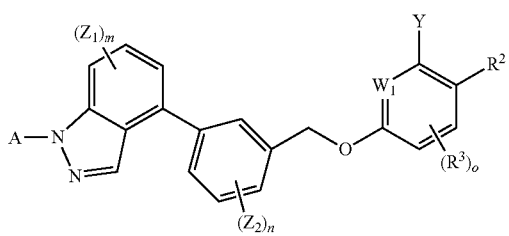

wherein R$^2$, R$^3$, A, Z$_1$, Z$_2$, W$_1$, Y, m, n, and o are as defined in claim 1;

Formula (IV)

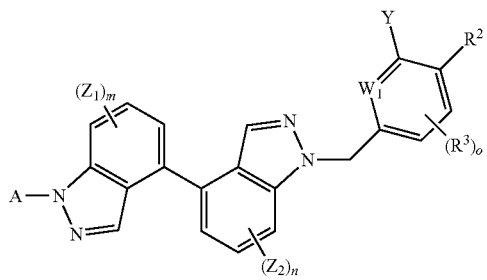

wherein R$^2$, R$^3$, A, Z$_1$, Z$_2$, W$_1$, Y, m, n, and o are as defined in claim 1.

3. The compound according to claim 1, wherein R$^2$ represents —(C$_0$-C$_6$ alkylene)NR$^A$R$^B$, wherein R$^A$ and R$^B$ each independently represent hydrogen or represent $C_1$-$C_6$ alkyl substituted by —OR$^a$, —C(O)R$^a$, or —C(O)OR$^a$, wherein R$^a$ and R$^b$ each independently represent hydrogen or $C_1$-$C_6$ alkyl.

4. The compound according to claim 1, wherein Y represents —O($C_1$-$C_6$)alkyl, —O(C$_0$-$C_6$ alkylene)(C$_6$-$C_{10}$ aryl), —O(C$_0$-$C_6$ alkylene)(5- to 10-membered heteroaryl), —(C$_0$-$C_6$ alkylene)O(C$_6$-$C_{10}$ aryl), or —(C$_0$-$C_6$ alkylene)O (5- to 10-membered heteroaryl) substituted by —OR$^a$, cyano, halogen, $C_1$-$C_6$ alkyl, —($C_1$-$C_6$ alkylene)OR$^a$, $C_1$-$C_6$ cyanoalkyl, —C(O)OR$^a$, —NR$^a$R$^b$, —C(O)NR$^a$R$^b$, SO$_2$R$^a$, —C(O)NR$^a$SO$_2$R$^b$, or —NR$^a$C(O)R$^b$, wherein R$^a$ and R$^b$ each independently represent hydrogen or $C_1$-$C_6$ alkyl.

5. The compound according to claim 1, wherein Y is selected from —O—($C_1$-$C_6$ alkyl), wherein the $C_1$-$C_6$ alkyl is optionally substituted by 0, 1, or 2 cyano, halogen, hydroxy, —C(O)NH$_2$, amino, sulfo, or carboxyl.

6. The compound according to claim 1, wherein Y is selected from —O (C$_0$-$C_6$ alkylene) (3- to 6-membered heterocycloalkyl), wherein the 3- to 6-membered heterocycloalkyl is optionally substituted by oxo, $C_1$-$C_6$ alkyl, or hydroxy.

7. The compound according to claim 1, wherein Y is selected from the group consisting of

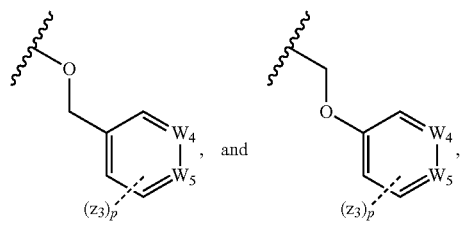

wherein W$_4$ and W$_5$ each independently represent CH or N; p represents 0, 1, 2 or 3; Z$_3$ represents hydrogen, ($C_1$-$C_6$) alkyl, ($C_3$-$C_6$) cycloalkyl, halo ($C_1$-$C_6$) alkyl, halogen, —OR$^a$, —C(O)OR$^a$, ($C_1$-$C_6$) alkoxy, —NR$^a$R$^b$, —SO$_2$R$^a$, cyano, or nitro; R$^a$ and R$^b$ represent hydrogen or $C_1$-$C_6$ alkyl.

8. The compound according to claim 1, wherein Y is selected from

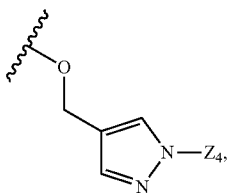

wherein $Z_4$ represents hydrogen, $C_1$-$C_6$ alkyl, cyano, cyanomethyl or $C_3$-$C_6$ cycloalkyl.

9. The compound according to claim 1, wherein Y represents —O($C_0$-$C_6$ alkylene)CONR$^A$R$^B$, wherein R$^A$ and R$^B$ each independently represent hydrogen or $C_1$-$C_6$ alkyl optionally substituted by —OR$^a$, —NR$^a$R$^b$, or —C(O)NR$^a$R$^b$, wherein R$^a$ and R$^b$ each independently represent hydrogen or $C_1$-$C_6$ alkyl.

10. The compound according to claim 1, wherein Y represents —O ($C_0$-$C_6$ alkylene)CONR$^A$R$^B$, wherein R$^A$ and R$^B$ together with nitrogen atom bound thereto are optionally cyclized to each other into a 5- to 7-membered ring, and the ring also optionally has 0, 1, 2 or 3 heteroatoms selected from O, N, S, further the ring is also optionally substituted by 0, 1, 2 or 3 substituents selected from the group consisting of: cyano, $C_1$-$C_6$ alkyl, $C_3$-$C_6$ cycloalkyl, $C_2$-$C_6$ alkenyl, $C_2$-$C_6$ alkynyl, —OR$^a$, —C(O)OR$^a$, —($C_1$-$C_6$) cyanoalkyl, ($C_1$-$C_6$) haloalkyl, —($C_1$-$C_6$ alkylene)OR$^a$, —C(O)R$^a$, and —NR$^a$R$^b$, wherein R$^a$ and R$^b$ each independently represent hydrogen or $C_1$-$C_6$ alkyl.

11. The compound according to claim 1, wherein A represents —($C_0$-$C_6$ alkylene)NR$^A$R$^B$, wherein R$^A$ and R$^B$ together with atoms bound thereto are optionally cyclized to each other into a 5- to 7-membered ring, and the ring also optionally has 0, 1, 2 or 3 heteroatoms selected from O, N, S, further the ring may also be optionally substituted by 0, 1, 2 or 3 substituents selected from the group consisting of: oxo, cyano, $C_1$-$C_6$ alkyl, $C_3$-$C_6$ cycloalkyl, $C_2$-$C_6$ alkenyl, $C_2$-$C_6$ alkynyl, —OR$^a$, —C(O)OR$^a$, —($C_1$-$C_6$)cyanoalkyl, ($C_1$-$C_6$)haloalkyl, —($C_1$-$C_6$ alkylene)OR$^a$, —C(O)R$^a$, —NR$^a$R$^b$, —($C_1$-$C_6$ alkylene)NR$^a$R$^b$, —C(O)NR$^a$R$^b$, —($C_1$-$C_6$ alkylene)C(O)NR$^a$R$^b$, —SO$_2$R$^a$, —($C_1$-$C_6$ alkylene)SO$_2$R$^a$, —SO$_2$NR$^a$R$^b$, or —($C_1$-$C_6$ alkylene) SO$_2$NR$^a$R, wherein R$^a$ and R$^b$ each independently represents hydrogen or $C_1$-$C_6$ alkyl.

12. The compound according to claim 1, wherein A is selected from the group consisting of:

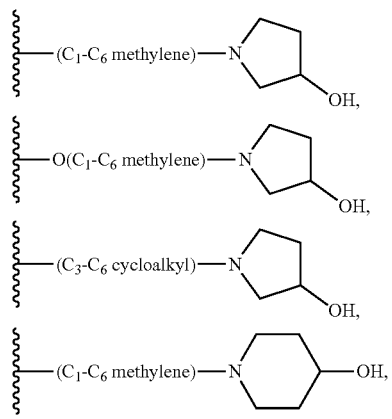

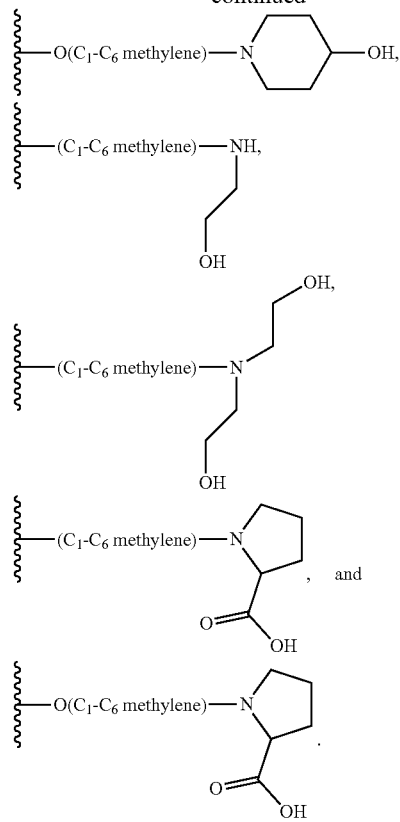

13. The compound according to claim 1, wherein A represents

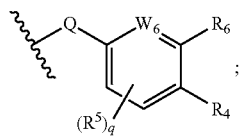

wherein,
Q represents —($C_0$-$C_6$ alkylene)-, —($C_0$-$C_6$ alkylene)O—, or —O($C_0$-$C_6$ alkylene)-;
$W_6$ represents CH or N;
$R^4$ represents —($C_0$-$C_6$ alkylene)NR$^A$R$^B$;
wherein R$^A$ and R$^B$ each independently represent hydrogen or $C_1$-$C_6$ alkyl substituted by —OR$^a$, —C(O)R$^a$, —C(O)OR$^a$, —C(O)NR$^a$R$^b$, —SO$_2$R$^a$, —C(O)NR$^a$SO$_2$R$^b$, or —NR$^a$C(O)R$^b$;
$R^5$ represents hydrogen, ($C_1$-$C_6$) alkyl, ($C_3$-$C_6$) cycloalkyl, ($C_1$-$C_6$) haloalkyl, halogen, —OR$^a$, —C(O)OR$^a$, ($C_1$-$C_6$) alkoxy, —NR$^a$R$^b$, —SO$_2$R$^a$, cyano, or nitro;
$R^6$ represents hydrogen or —O($C_1$-$C_6$) alkyl, —O($C_0$-$C_6$ alkylene)($C_6$-$C_{10}$ aryl), or —O($C_0$-$C_6$ alkylene)(5- to 10-membered heteroaryl) substituted by the group consisting of: —OR$^a$, cyano, halogen, $C_1$-$C_6$ alkyl, —($C_1$-$C_6$ alkylene)OR$^a$, $C_1$-$C_6$ cyanoalkyl, —C(O)OR$^a$, —NR$^a$R$^b$, —C(O)NR$^a$R$^b$, SO$_2$R$^a$, —C(O)NR$^a$SO$_2$R$^b$, or —NR$^a$C(O)R$^b$;
R$^a$ and R$^b$ are each independently selected from hydrogen or $C_1$-$C_6$ alkyl;
q represents 0, 1, 2 or 3.

14. The compound according to claim 1, wherein R² is selected from the group consisting of
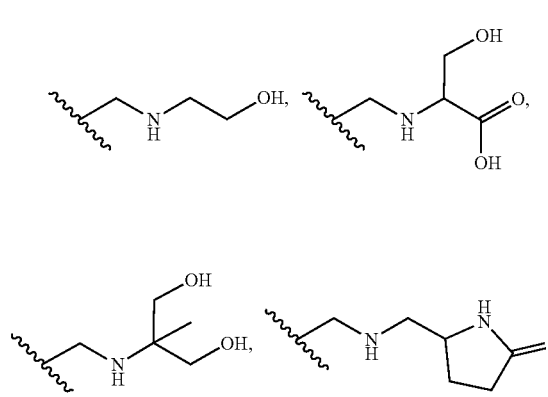
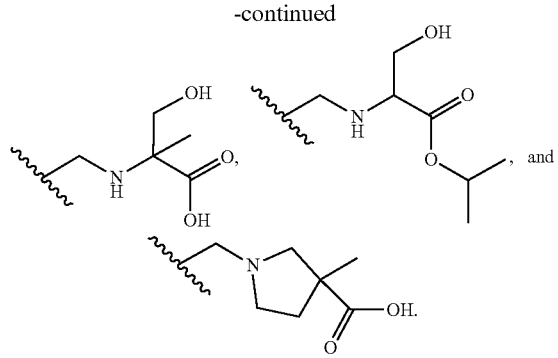
15. The compound according to claim 1, wherein W₅ represents CH.
16. The compound according to claim 1, wherein $Z_1$ or $Z_2$ represents hydrogen, halogen, cyano, or $C_1$-$C_6$ alkyl.
17. The compound according to claim 1, having one of the following structures:
| No. | Structure |
|---|---|
| 1 | 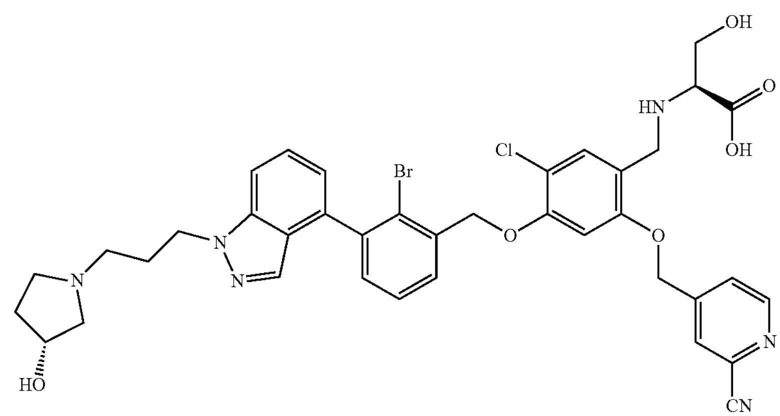 [SMILES: N#Cc1cc(COc2cc(OCc3cccc(-c4cccc5c4cnn5CCCN4CC[C@@H](O)C4)c3Br)c(Cl)cc2CN[C@@H](CO)C(=O)O)ccn1] |
| 2 | 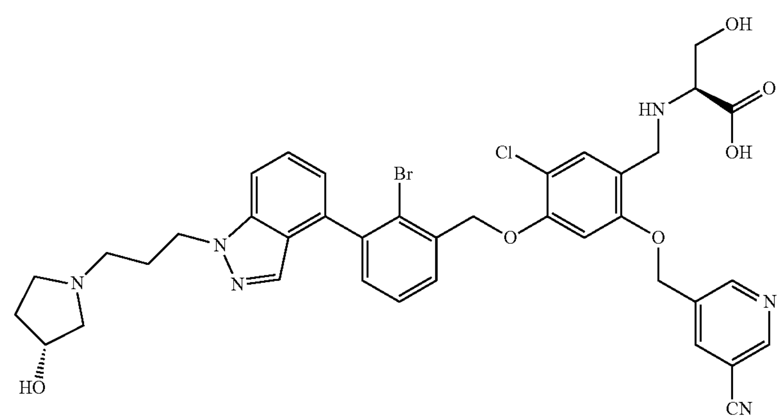 |

| No. | Structure |
|---|---|
| 3 | 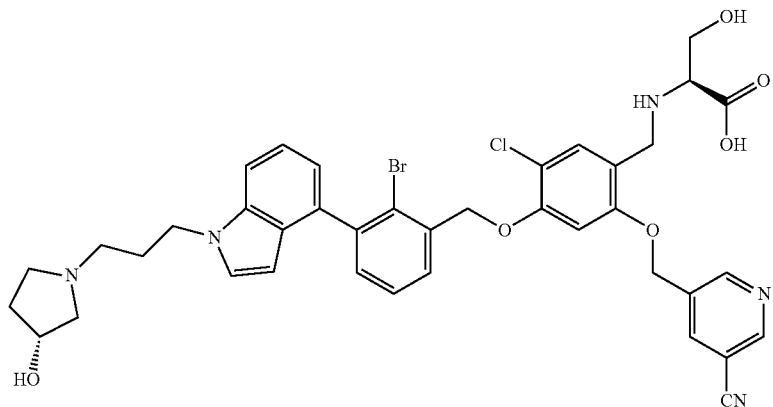 [SMILES: N#Cc1cncc(COc2cc(OCc3cccc(-c4cccc5c4ccn5CCCN4CC[C@@H](O)C4)c3Br)c(Cl)cc2CN[C@@H](CO)C(=O)O)c1] |
| 4 | 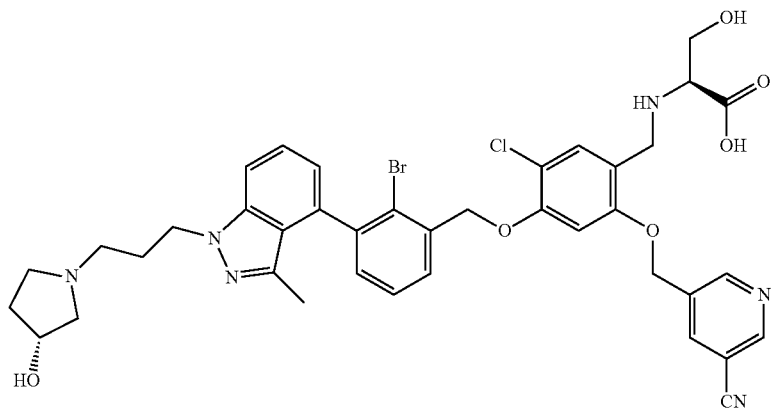 [SMILES: Cc1nn(CCCN2CC[C@@H](O)C2)c2cccc(-c3cccc(COc4cc(OCc5cncc(C#N)c5)c(CN[C@@H](CO)C(=O)O)cc4Cl)c3Br)c12] |
| 5 | 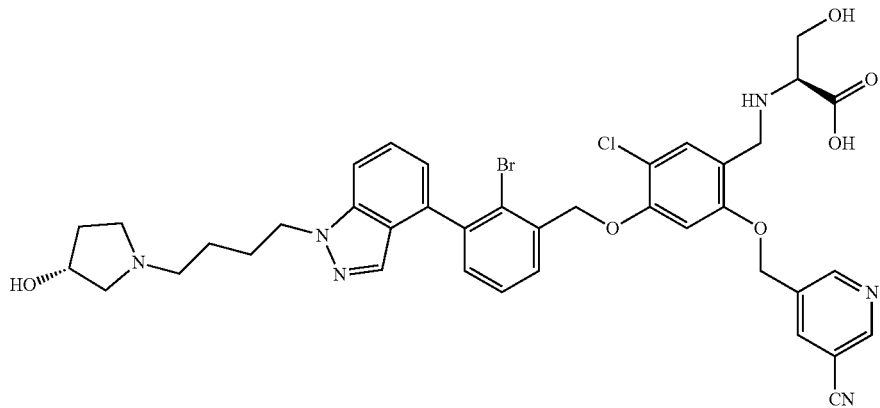 [SMILES: N#Cc1cncc(COc2cc(OCc3cccc(-c4cccc5c4cnn5CCCCN4CC[C@@H](O)C4)c3Br)c(Cl)cc2CN[C@@H](CO)C(=O)O)c1] |

| No. | Structure |
|---|---|
| 6 | 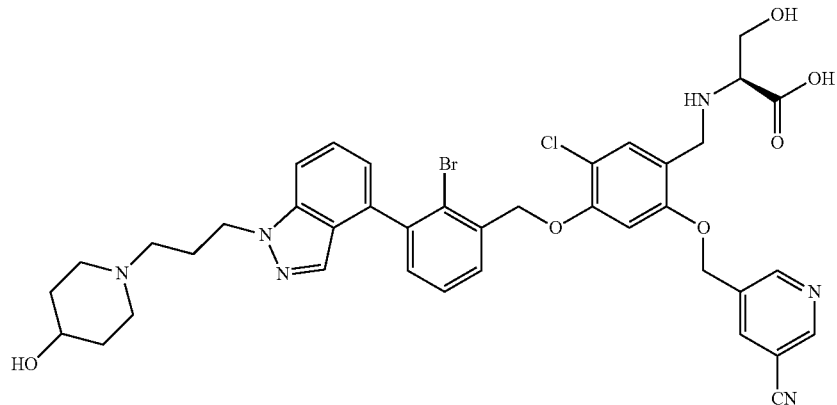 [SMILES: N#Cc1cncc(COc2cc(OCc3cccc(-c4cccc5c4cnn5CCCN4CCC(O)CC4)c3Br)c(Cl)cc2CN[C@@H](CO)C(=O)O)c1] |
| 7 | 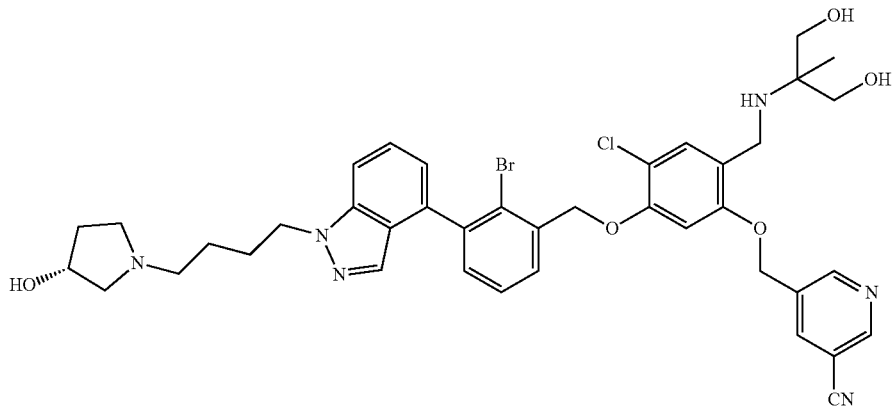 [SMILES: CC(CO)(CO)NCc1cc(Cl)c(OCc2cccc(-c3cccc4c3cnn4CCCCN3CC[C@@H](O)C3)c2Br)cc1OCc1cncc(C#N)c1] |
| 8 | 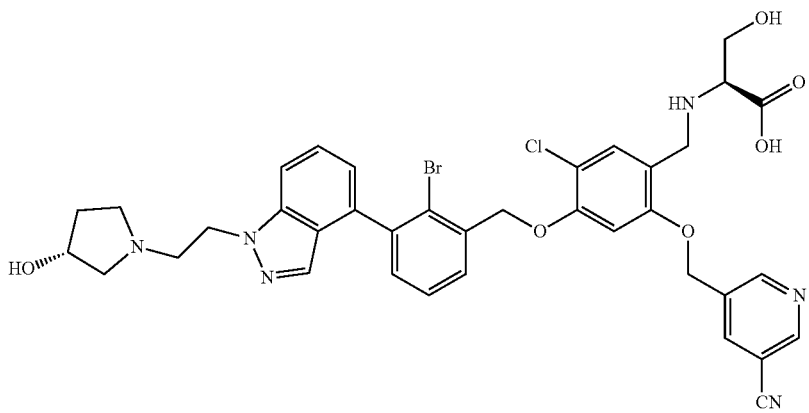 [SMILES: N#Cc1cncc(COc2cc(OCc3cccc(-c4cccc5c4cnn5CCN4CC[C@@H](O)C4)c3Br)c(Cl)cc2CN[C@@H](CO)C(=O)O)c1] |

| No. | Structure |
|---|---|
| 9 | 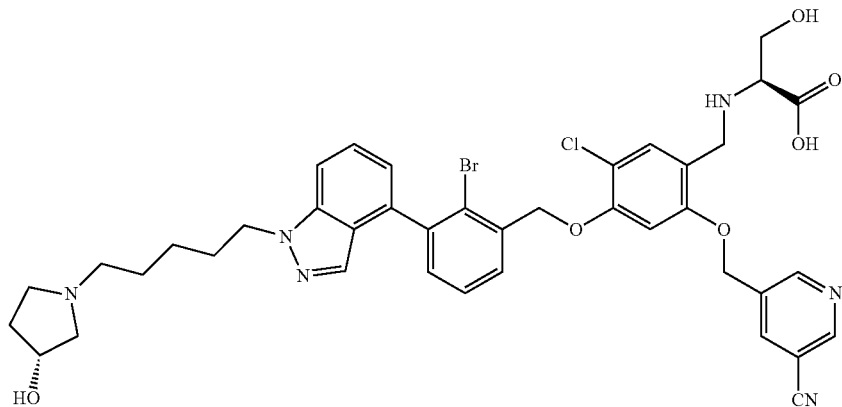 [SMILES: N#Cc1cncc(COc2cc(OCc3cccc(-c4cccc5c4cnn5CCCCCN4CC[C@@H](O)C4)c3Br)c(Cl)cc2CN[C@@H](CO)C(=O)O)c1] |
| 10 | 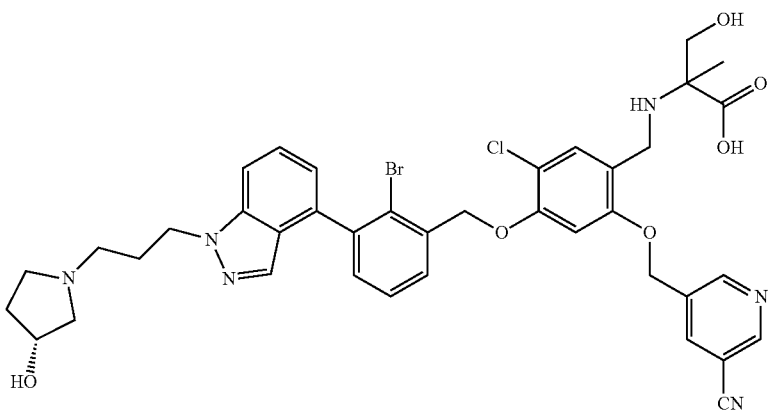 [SMILES: CC(CO)(NCc1cc(Cl)c(OCc2cccc(-c3cccc4c3cnn4CCCN3CC[C@@H](O)C3)c2Br)cc1OCc1cncc(C#N)c1)C(=O)O] |
| 11 | 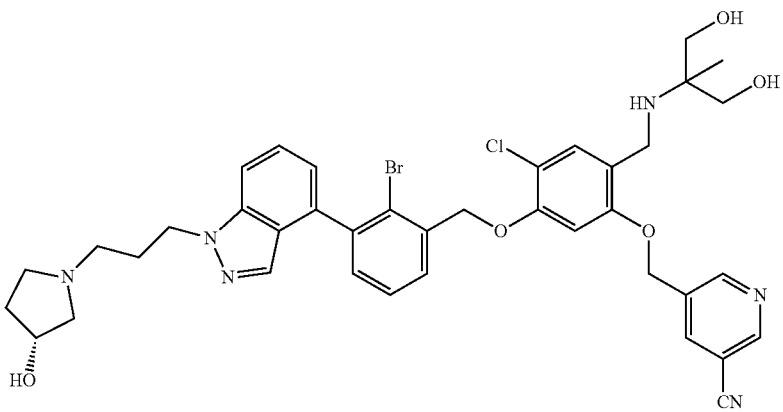 [SMILES: CC(CO)(CO)NCc1cc(Cl)c(OCc2cccc(-c3cccc4c3cnn4CCCN3CC[C@@H](O)C3)c2Br)cc1OCc1cncc(C#N)c1] |

| No. | Structure |
|---|---|
| 12 | 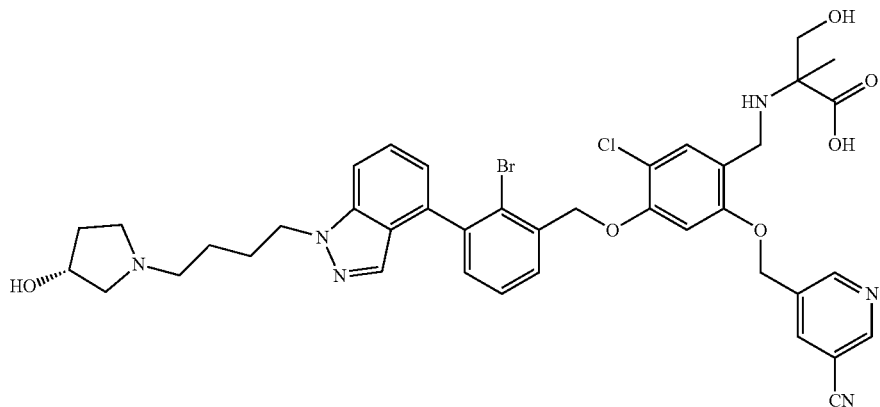 [SMILES: CC(CO)(NCc1cc(Cl)c(OCc2cccc(-c3cccc4c3cnn4CCCCN3CC[C@@H](O)C3)c2Br)cc1OCc1cncc(C#N)c1)C(=O)O] |
| 13 | 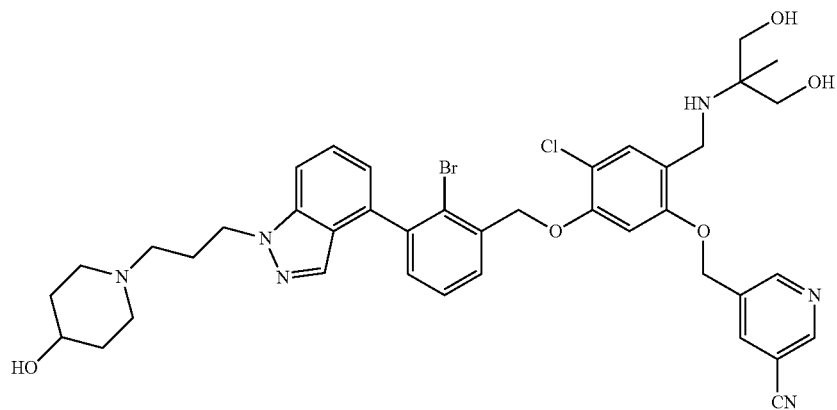 [SMILES: CC(CO)(CO)NCc1cc(Cl)c(OCc2cccc(-c3cccc4c3cnn4CCCN3CCC(O)CC3)c2Br)cc1OCc1cncc(C#N)c1] |
| 14 | 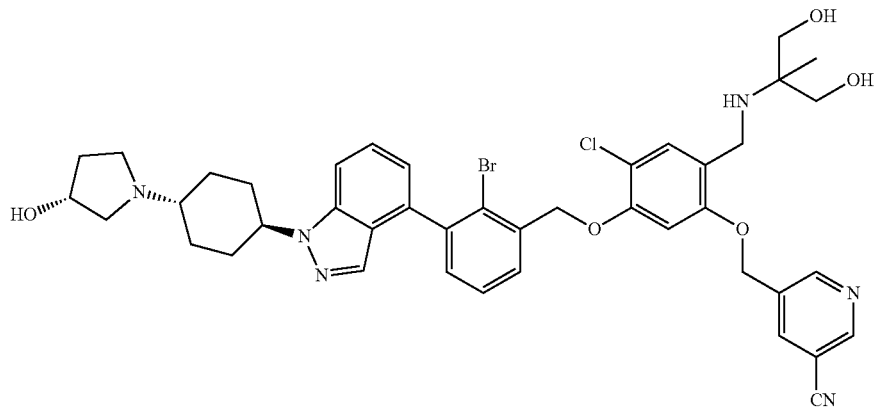 [SMILES: CC(CO)(CO)NCc1cc(Cl)c(OCc2cccc(-c3cccc4c3cnn4[C@H]3CC[C@H](N4CC[C@@H](O)C4)CC3)c2Br)cc1OCc1cncc(C#N)c1] |

| No. | Structure |
|---|---|
| 15 | 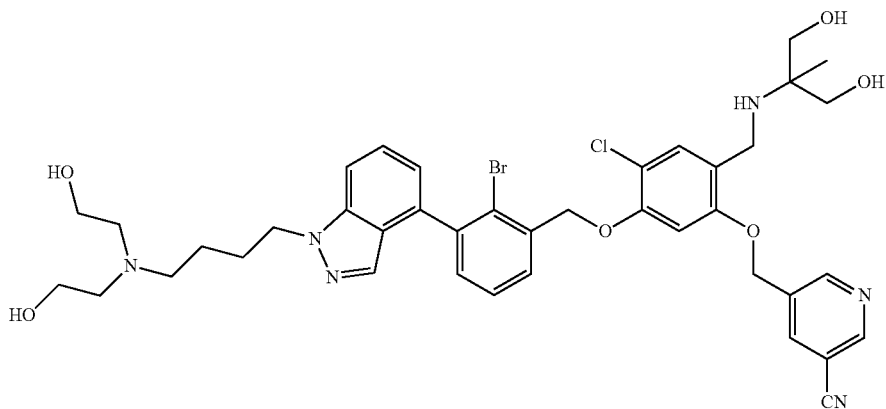 [SMILES: CC(CO)(CO)NCc1cc(Cl)c(OCc2cccc(-c3cccc4c3cnn4CCCCN(CCO)CCO)c2Br)cc1OCc1cncc(C#N)c1] |
| 16 | 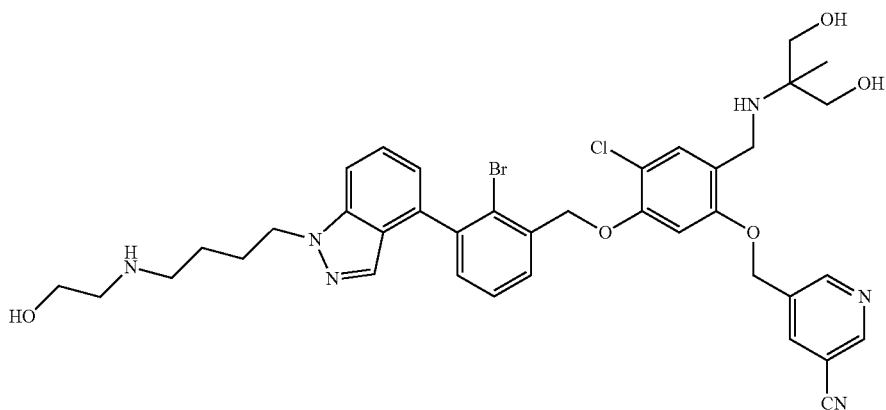 [SMILES: CC(CO)(CO)NCc1cc(Cl)c(OCc2cccc(-c3cccc4c3cnn4CCCCNCCO)c2Br)cc1OCc1cncc(C#N)c1] |
| 17 | 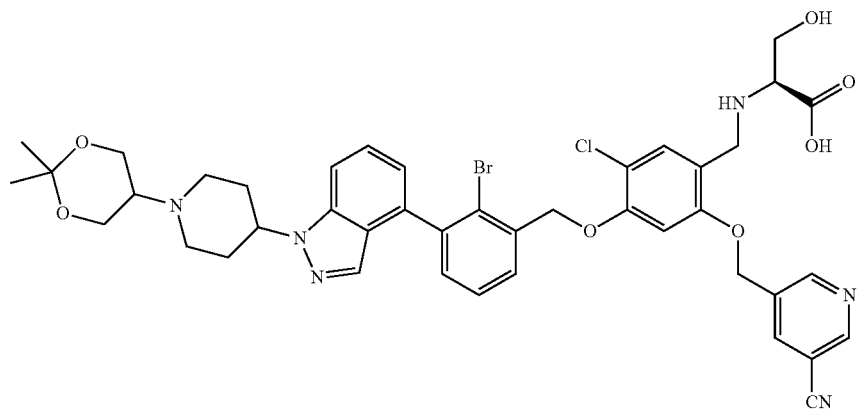 [SMILES: CC1(C)OCC(N2CCC(n3ncc4c(-c5cccc(COc6cc(OCc7cncc(C#N)c7)c(CN[C@@H](CO)C(=O)O)cc6Cl)c5Br)cccc43)CC2)CO1] |

| No. | Structure |
|---|---|
| 18 | 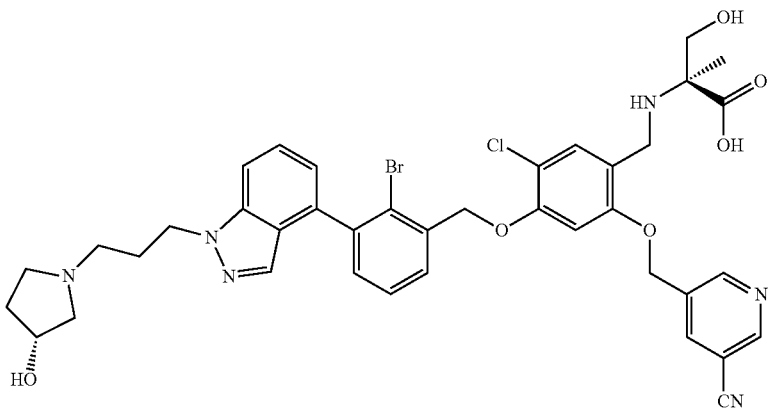 [SMILES: C[C@@](CO)(NCc1cc(Cl)c(OCc2cccc(-c3cccc4c3cnn4CCCN3CC[C@@H](O)C3)c2Br)cc1OCc1cncc(C#N)c1)C(=O)O] |
| 19 | 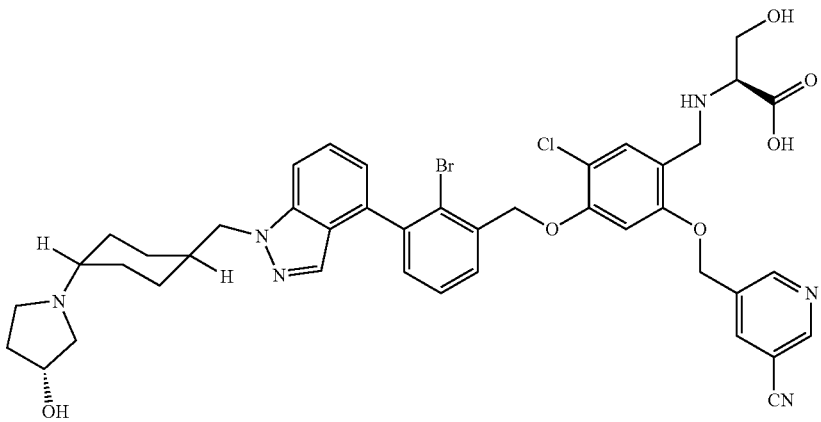 [SMILES: N#Cc1cncc(COc2cc(OCc3cccc(-c4cccc5c4cnn5CC4CCC(N5CC[C@@H](O)C5)CC4)c3Br)c(Cl)cc2CN[C@@H](CO)C(=O)O)c1] |
| 20 | 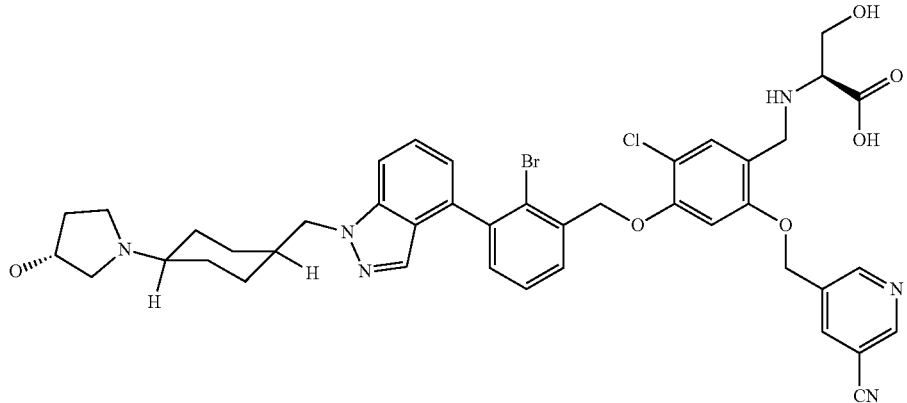 [SMILES: N#Cc1cncc(COc2cc(OCc3cccc(-c4cccc5c4cnn5CC4CCC(N5CC[C@@H](O)C5)CC4)c3Br)c(Cl)cc2CN[C@@H](CO)C(=O)O)c1] |

| No. | Structure |
|---|---|
| 21 | 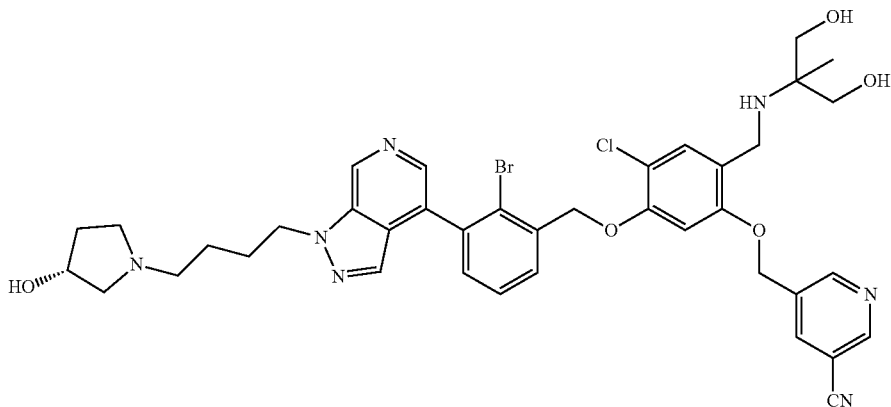 [SMILES: CC(CO)(CO)NCc1cc(Cl)c(OCc2cccc(-c3cncc4c3cnn4CCCCN3CC[C@@H](O)C3)c2Br)cc1OCc1cncc(C#N)c1] |
| 22 | 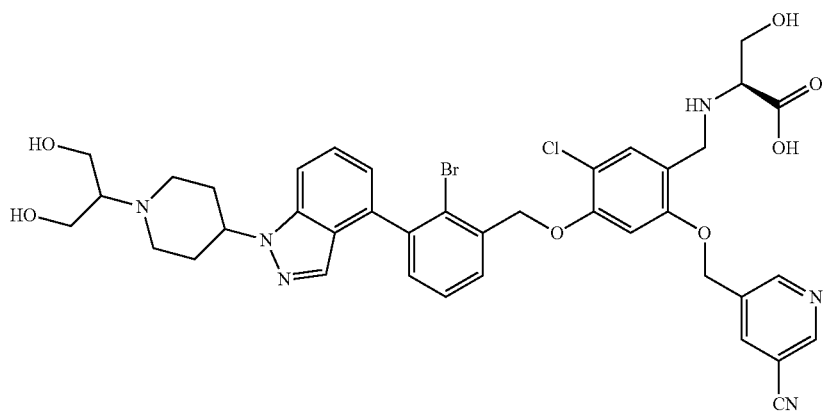 [SMILES: N#Cc1cncc(COc2cc(OCc3cccc(-c4cccc5c4cnn5C4CCN(C(CO)CO)CC4)c3Br)c(Cl)cc2CN[C@@H](CO)C(=O)O)c1] |
| 23 | 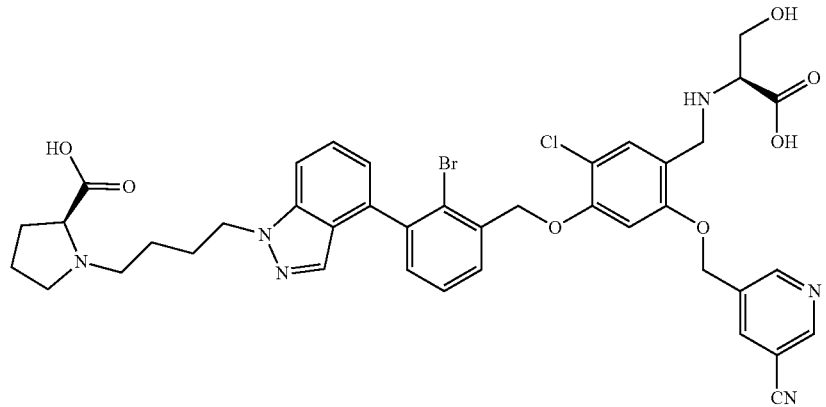 [SMILES: N#Cc1cncc(COc2cc(OCc3cccc(-c4cccc5c4cnn5CCCCN4CCC[C@H]4C(=O)O)c3Br)c(Cl)cc2CN[C@@H](CO)C(=O)O)c1] |

| No. | Structure |
|---|---|
| 24 | 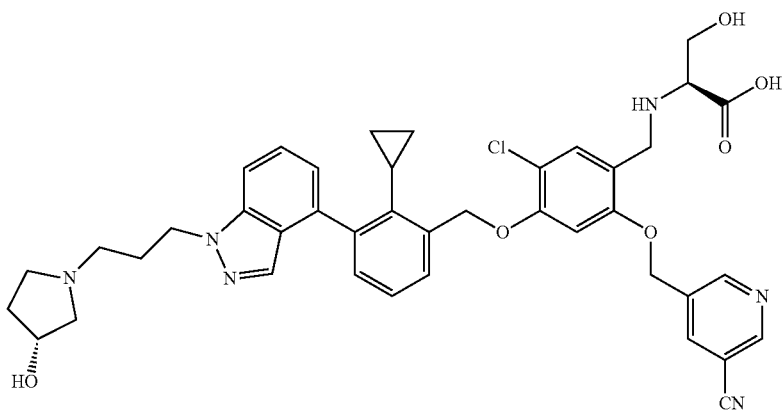 [SMILES: N#Cc1cncc(COc2cc(OCc3cccc(-c4cccc5c4cnn5CCCN4CC[C@@H](O)C4)c3C3CC3)c(Cl)cc2CN[C@@H](CO)C(=O)O)c1] |
| 25 | 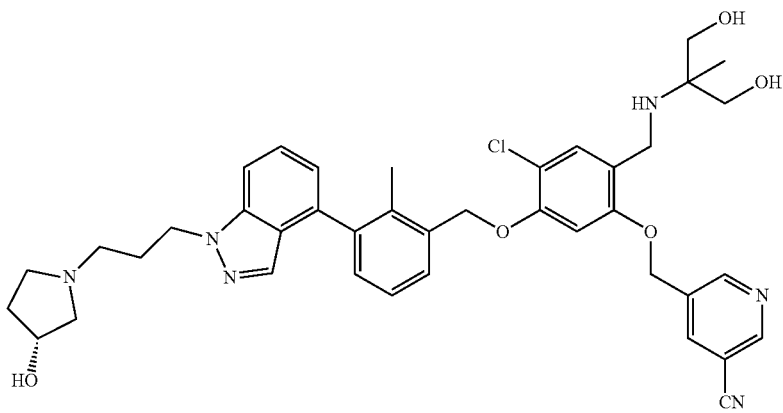 [SMILES: Cc1c(COc2cc(OCc3cncc(C#N)c3)c(CNC(C)(CO)CO)cc2Cl)cccc1-c1cccc2c1cnn2CCCN1CC[C@@H](O)C1] |
| 26 | 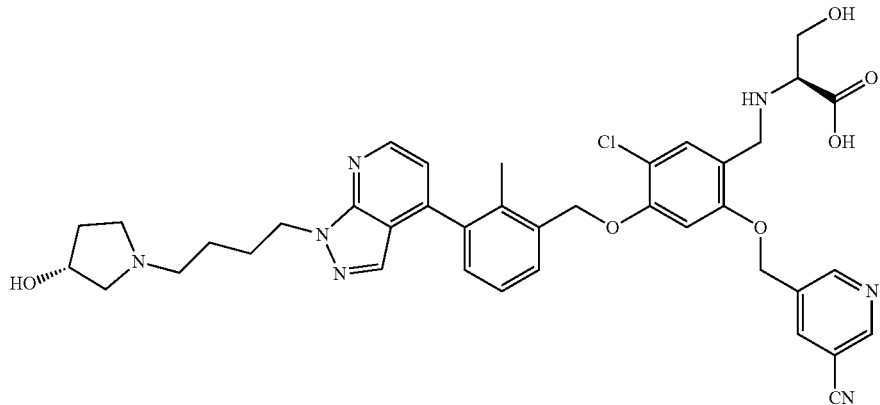 [SMILES: Cc1c(COc2cc(OCc3cncc(C#N)c3)c(CN[C@@H](CO)C(=O)O)cc2Cl)cccc1-c1ccnc2c1cnn2CCCCN1CC[C@@H](O)C1] |

| No. | Structure |
|---|---|
| 27 | 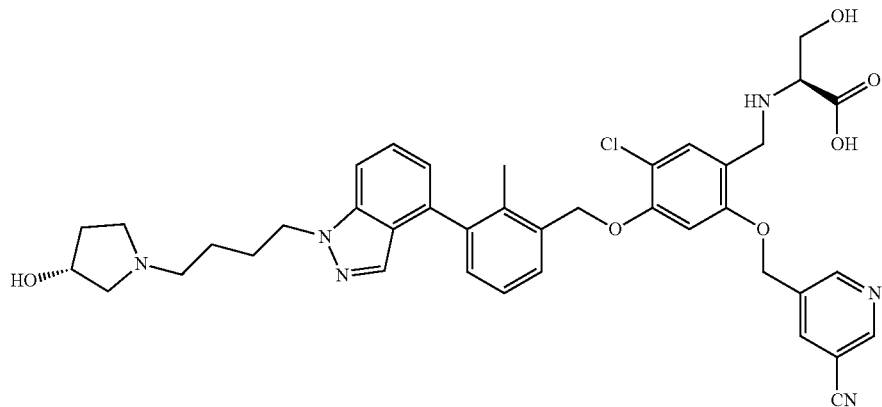 [SMILES: Cc1c(COc2cc(OCc3cncc(C#N)c3)c(CN[C@@H](CO)C(=O)O)cc2Cl)cccc1-c1cccc2c1cnn2CCCCN1CC[C@@H](O)C1] |
| 28 | 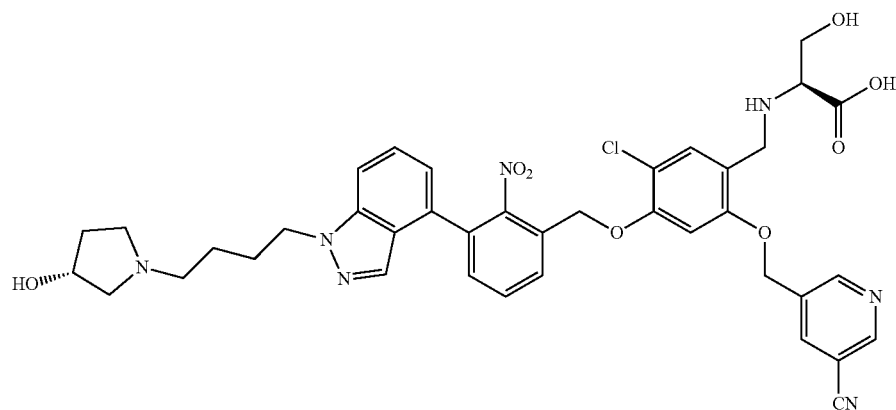 [SMILES: N#Cc1cncc(COc2cc(OCc3cccc(-c4cccc5c4cnn5CCCCN4CC[C@@H](O)C4)c3[N+](=O)[O-])c(Cl)cc2CN[C@@H](CO)C(=O)O)c1] |
| 29 | 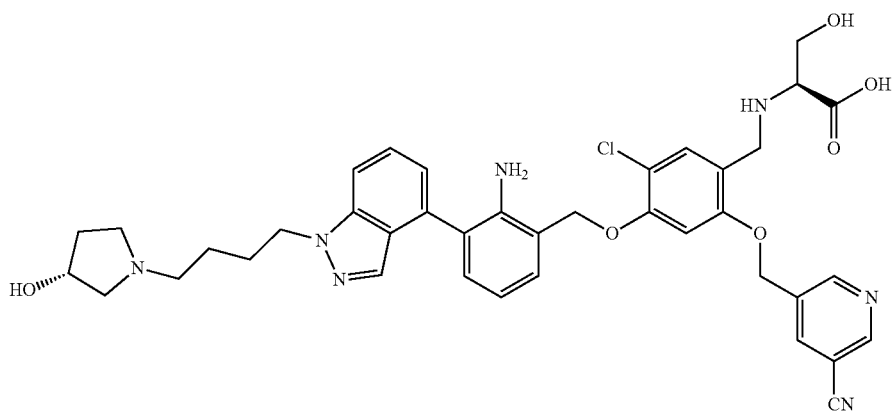 [SMILES: N#Cc1cncc(COc2cc(OCc3cccc(-c4cccc5c4cnn5CCCCN4CC[C@@H](O)C4)c3N)c(Cl)cc2CN[C@@H](CO)C(=O)O)c1] |

-continued

| No. | Structure |
|---|---|
| 30 | 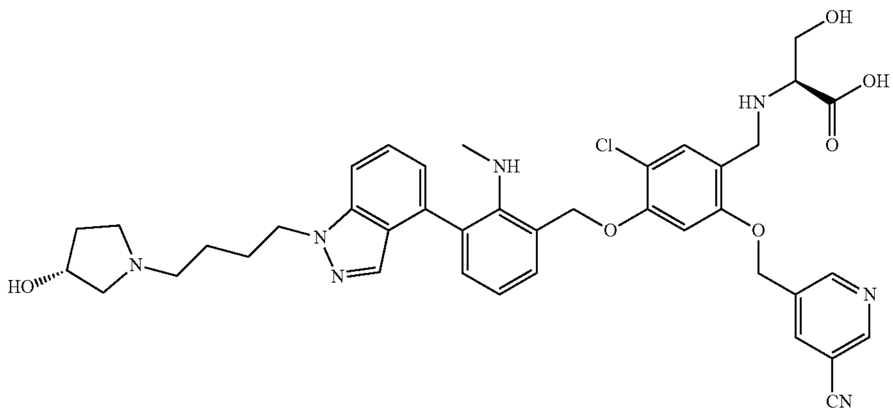 [SMILES: CNc1c(COc2cc(OCc3cncc(C#N)c3)c(CN[C@@H](CO)C(=O)O)cc2Cl)cccc1-c1cccc2c1cnn2CCCCN1CC[C@@H](O)C1] |
| 31 | 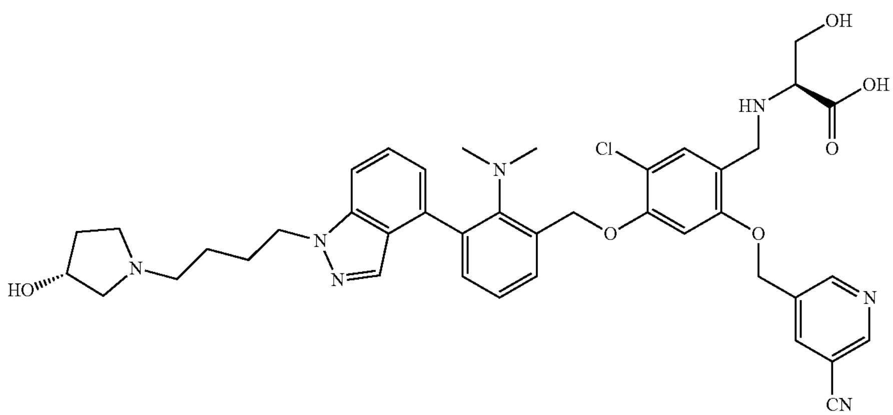 [SMILES: CN(C)c1c(COc2cc(OCc3cncc(C#N)c3)c(CN[C@@H](CO)C(=O)O)cc2Cl)cccc1-c1cccc2c1cnn2CCCCN1CC[C@@H](O)C1] |
| 32 | 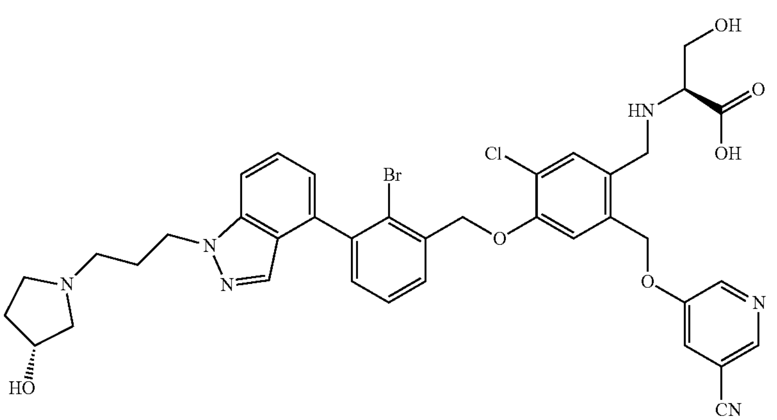 [SMILES: N#Cc1cncc(OCc2cc(OCc3cccc(-c4cccc5c4cnn5CCCN4CC[C@@H](O)C4)c3Br)c(Cl)cc2CN[C@@H](CO)C(=O)O)c1] |

-continued

| No. | Structure |
|---|---|
| 33 | 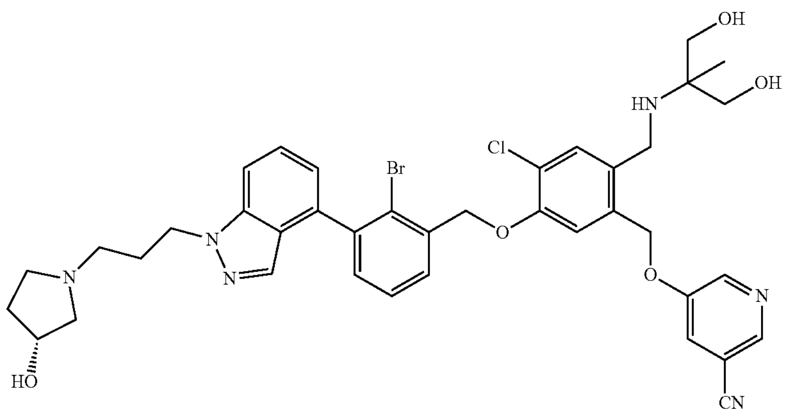 [SMILES: CC(CO)(CO)NCc1cc(Cl)c(OCc2cccc(-c3cccc4c3cnn4CCCN3CC[C@@H](O)C3)c2Br)cc1COc1cncc(C#N)c1] |
| 34 | 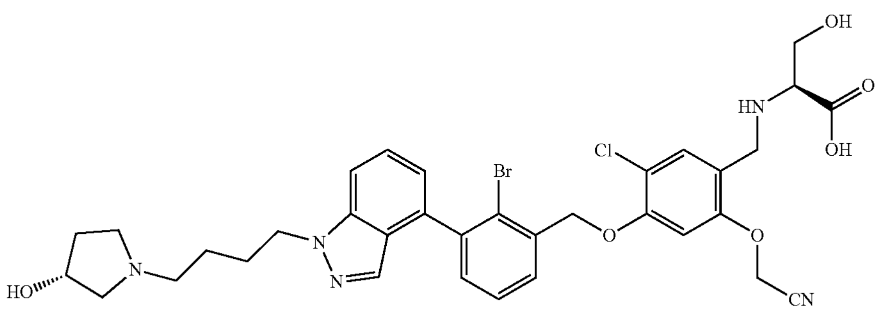 [SMILES: N#CCOc1cc(OCc2cccc(-c3cccc4c3cnn4CCCCN3CC[C@@H](O)C3)c2Br)c(Cl)cc1CN[C@@H](CO)C(=O)O] |
| 35 | 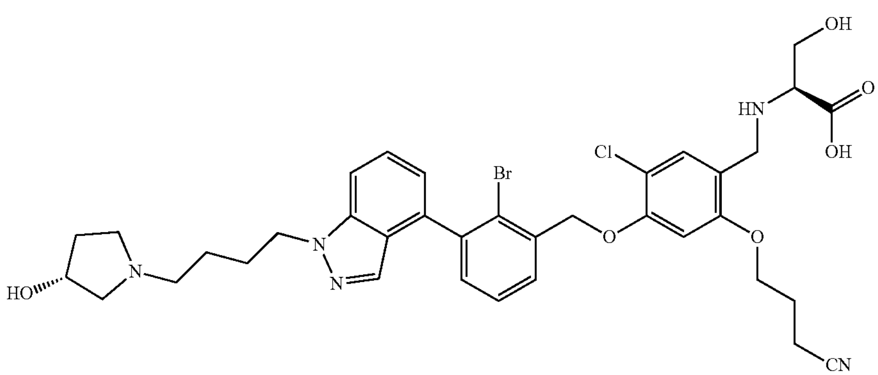 [SMILES: N#CCCCOc1cc(OCc2cccc(-c3cccc4c3cnn4CCCCN3CC[C@@H](O)C3)c2Br)c(Cl)cc1CN[C@@H](CO)C(=O)O] |
| 36 | 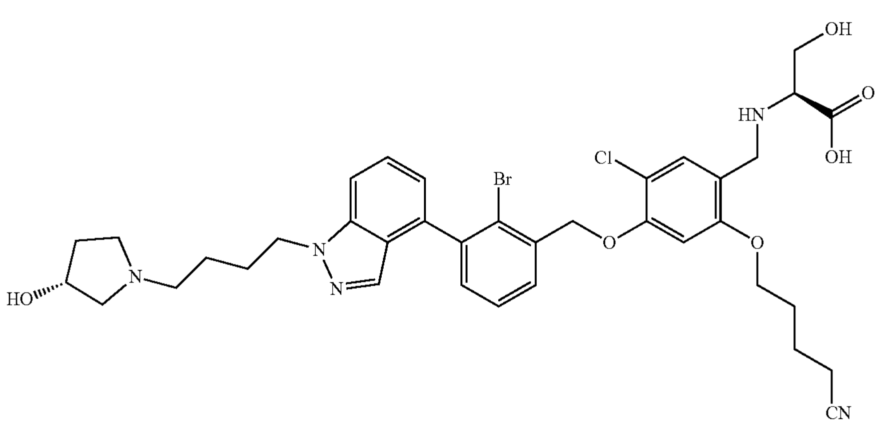 [SMILES: N#CCCCCOc1cc(OCc2cccc(-c3cccc4c3cnn4CCCCN3CC[C@@H](O)C3)c2Br)c(Cl)cc1CN[C@@H](CO)C(=O)O] |

| No. | Structure |
|---|---|
| 37 | 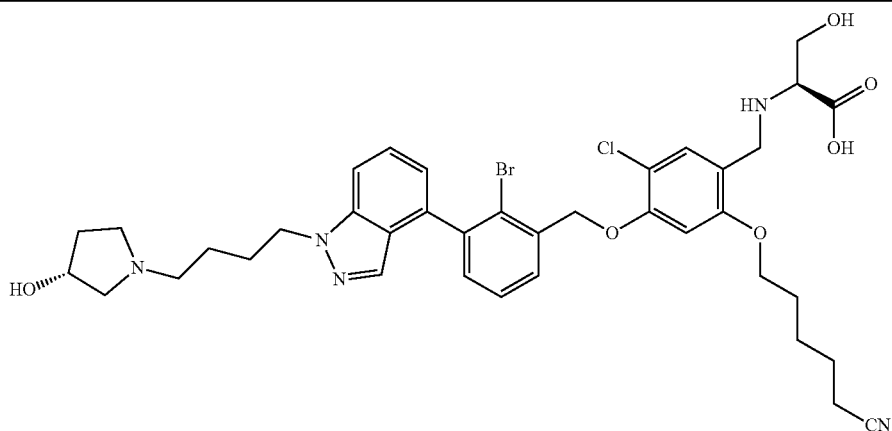 |
| 38 | 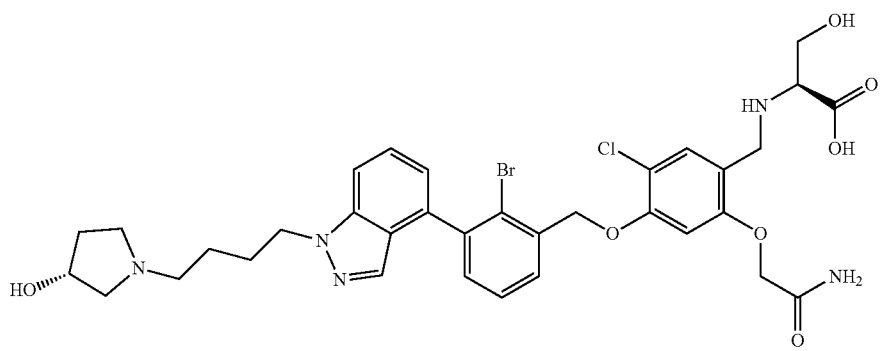 [SMILES: NC(=O)COc1cc(OCc2cccc(-c3cccc4c3cnn4CCCCN3CC[C@@H](O)C3)c2Br)c(Cl)cc1CN[C@@H](CO)C(=O)O] |
| 39 | 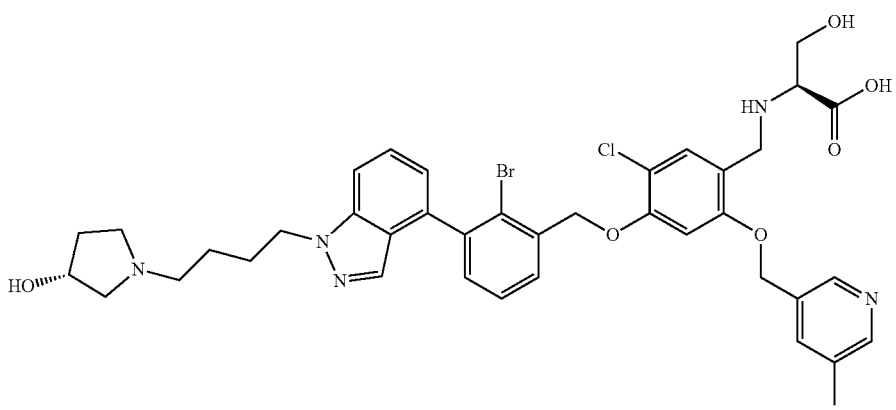 [SMILES: Cc1cncc(COc2cc(OCc3cccc(-c4cccc5c4cnn5CCCCN4CC[C@@H](O)C4)c3Br)c(Cl)cc2CN[C@@H](CO)C(=O)O)c1] |
| 40 | 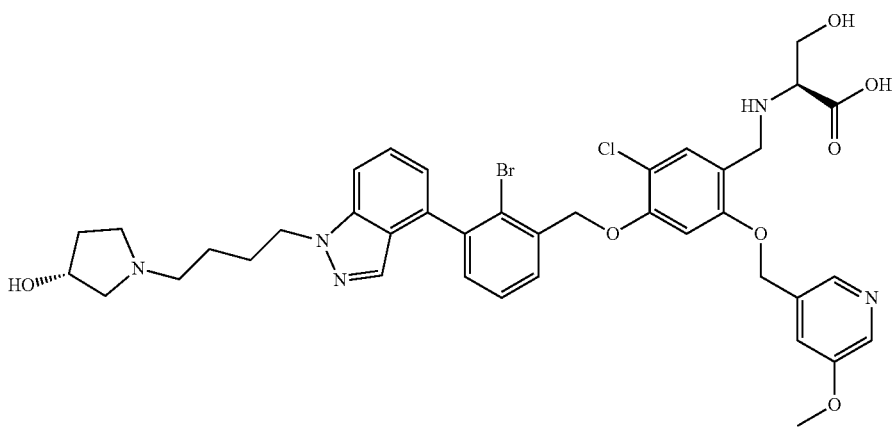 [SMILES: COc1cncc(COc2cc(OCc3cccc(-c4cccc5c4cnn5CCCCN4CC[C@@H](O)C4)c3Br)c(Cl)cc2CN[C@@H](CO)C(=O)O)c1] |

| No. | Structure |
|---|---|
| 41 | 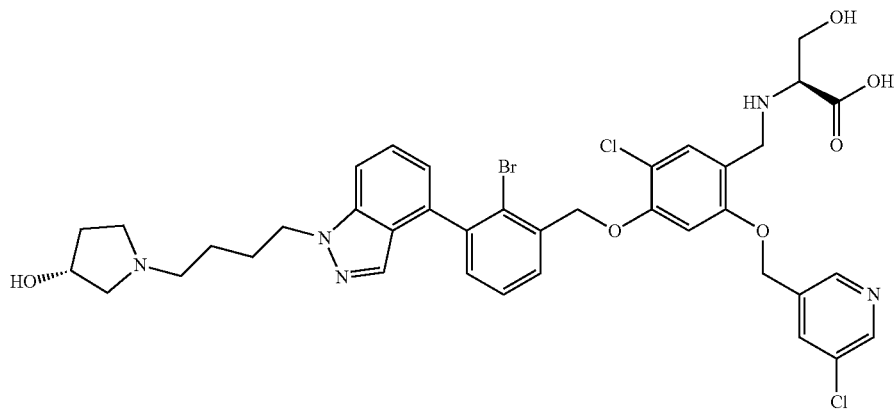 [SMILES: O=C(O)[C@H](CO)NCc1cc(Cl)c(OCc2cccc(-c3cccc4c3cnn4CCCCN3CC[C@@H](O)C3)c2Br)cc1OCc1cncc(Cl)c1] |
| 42 | 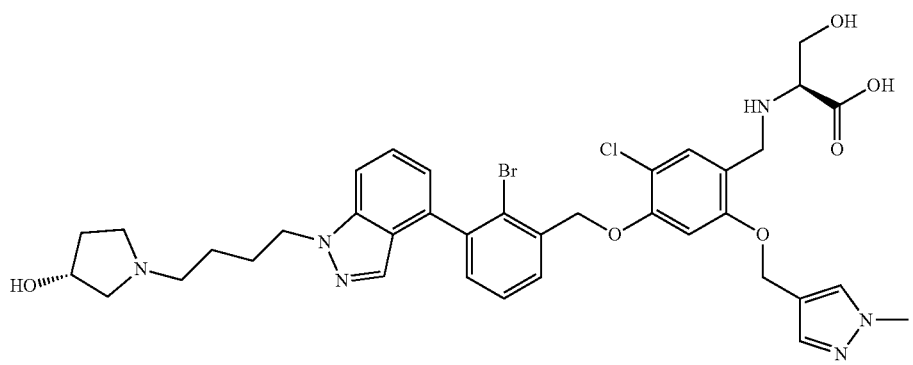 [SMILES: Cn1cc(COc2cc(OCc3cccc(-c4cccc5c4cnn5CCCCN4CC[C@@H](O)C4)c3Br)c(Cl)cc2CN[C@@H](CO)C(=O)O)cn1] |
| 43 | 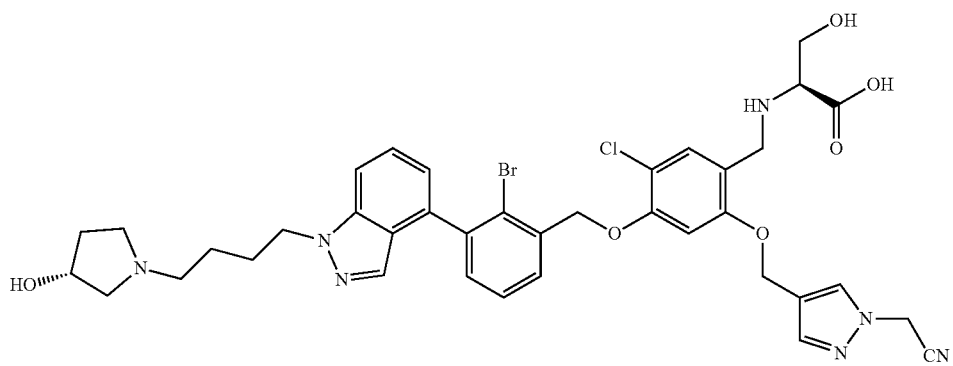 [SMILES: N#CCn1cc(COc2cc(OCc3cccc(-c4cccc5c4cnn5CCCCN4CC[C@@H](O)C4)c3Br)c(Cl)cc2CN[C@@H](CO)C(=O)O)cn1] |
| 44 | 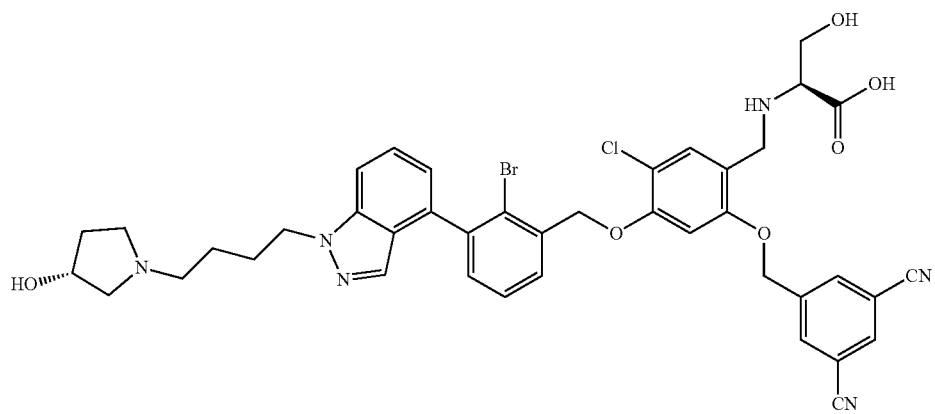 [SMILES: N#Cc1cc(C#N)cc(COc2cc(OCc3cccc(-c4cccc5c4cnn5CCCCN4CC[C@@H](O)C4)c3Br)c(Cl)cc2CN[C@@H](CO)C(=O)O)c1] |

| No. | Structure |
|---|---|
| 45 | 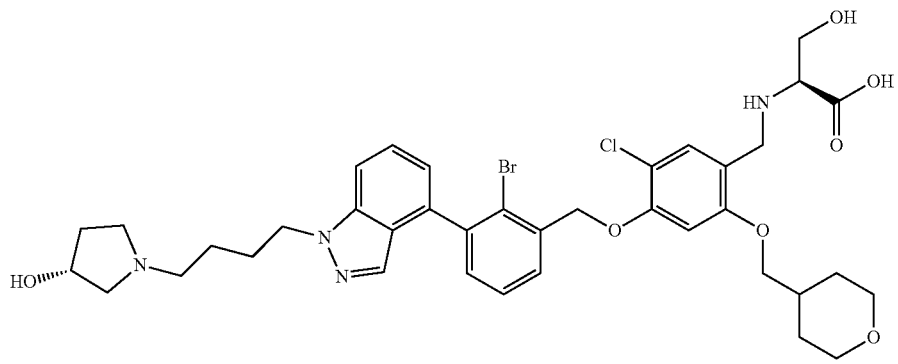 [SMILES: O=C(O)[C@H](CO)NCc1cc(Cl)c(OCc2cccc(-c3cccc4c3cnn4CCCCN3CC[C@@H](O)C3)c2Br)cc1OCC1CCOCC1] |
| 46 | 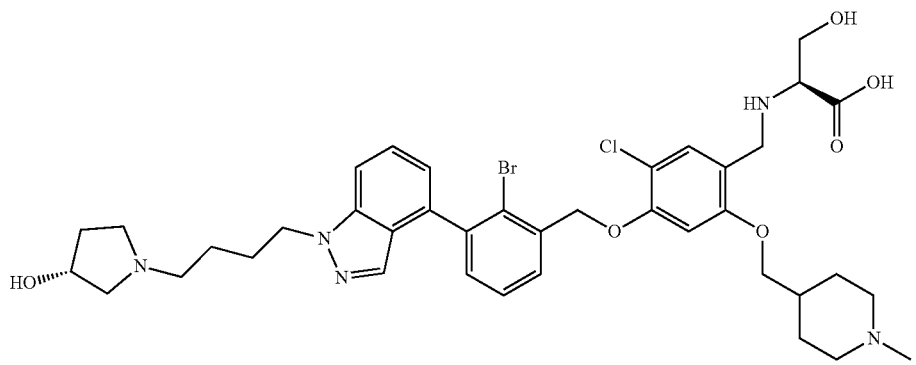 [SMILES: CN1CCC(COc2cc(OCc3cccc(-c4cccc5c4cnn5CCCCN4CC[C@@H](O)C4)c3Br)c(Cl)cc2CN[C@@H](CO)C(=O)O)CC1] |
| 47 | 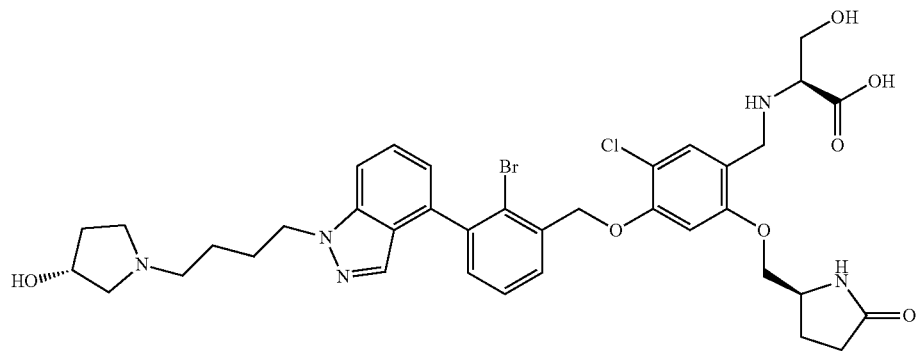 [SMILES: O=C1CC[C@@H](COc2cc(OCc3cccc(-c4cccc5c4cnn5CCCCN4CC[C@@H](O)C4)c3Br)c(Cl)cc2CN[C@@H](CO)C(=O)O)N1] |
| 48 | 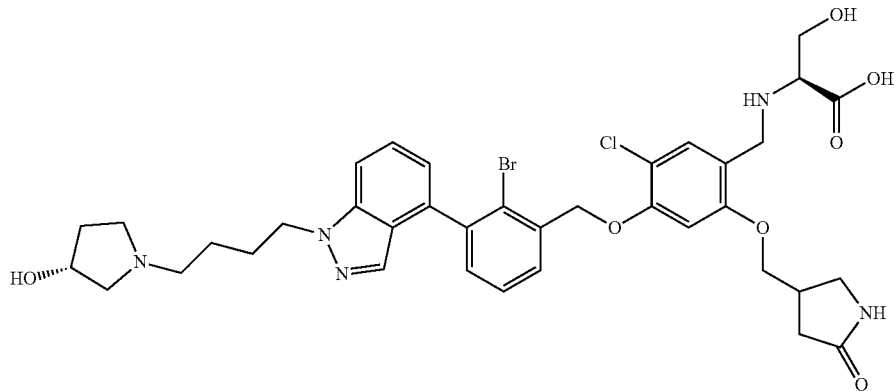 [SMILES: O=C1CC(COc2cc(OCc3cccc(-c4cccc5c4cnn5CCCCN4CC[C@@H](O)C4)c3Br)c(Cl)cc2CN[C@@H](CO)C(=O)O)CN1] |

| No. | Structure |
|---|---|
| 49 | 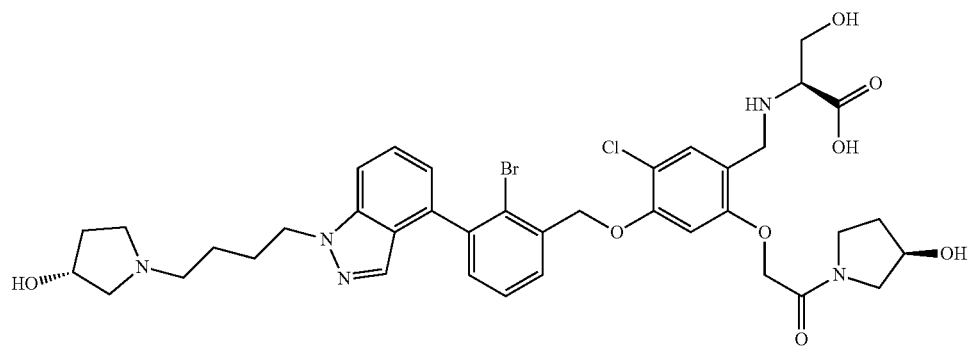 [SMILES: O=C(O)[C@H](CO)NCc1cc(Cl)c(OCc2cccc(-c3cccc4c3cnn4CCCCN3CC[C@@H](O)C3)c2Br)cc1OCC(=O)N1CC[C@@H](O)C1] |
| 50 | 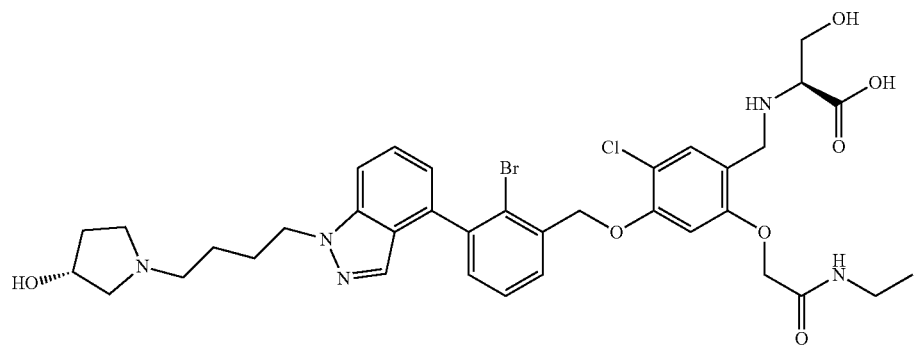 [SMILES: CCNC(=O)COc1cc(OCc2cccc(-c3cccc4c3cnn4CCCCN3CC[C@@H](O)C3)c2Br)c(Cl)cc1CN[C@@H](CO)C(=O)O] |
| 51 | 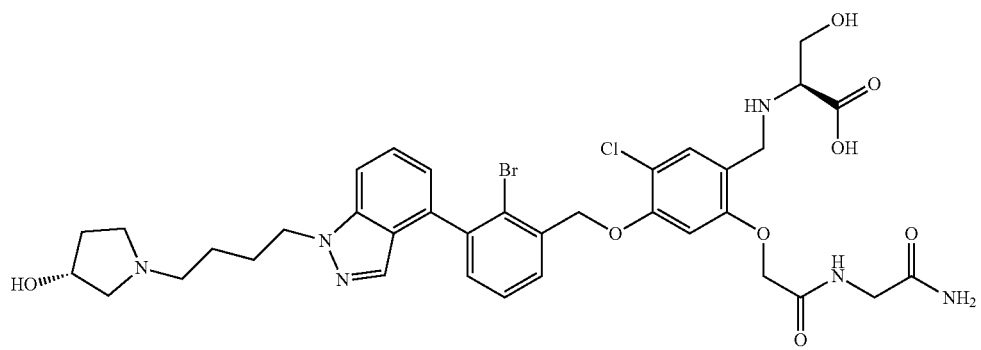 [SMILES: NC(=O)CNC(=O)COc1cc(OCc2cccc(-c3cccc4c3cnn4CCCCN3CC[C@@H](O)C3)c2Br)c(Cl)cc1CN[C@@H](CO)C(=O)O] |
| 52 | 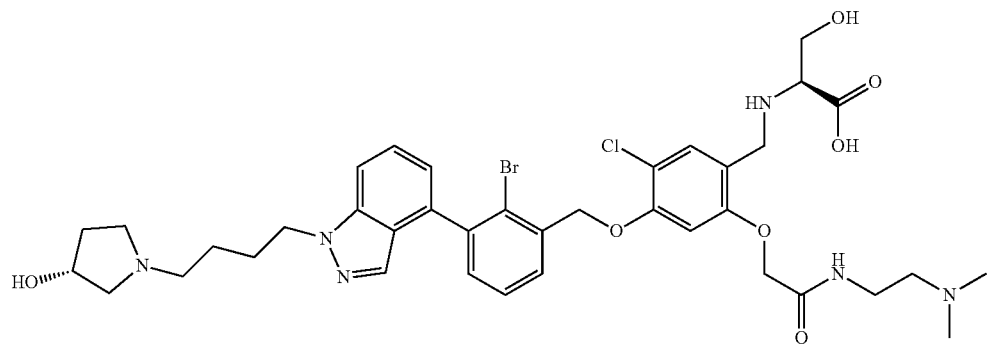 [SMILES: CN(C)CCNC(=O)COc1cc(OCc2cccc(-c3cccc4c3cnn4CCCCN3CC[C@@H](O)C3)c2Br)c(Cl)cc1CN[C@@H](CO)C(=O)O] |

-continued
| No. | Structure |
|---|---|
| 53 | 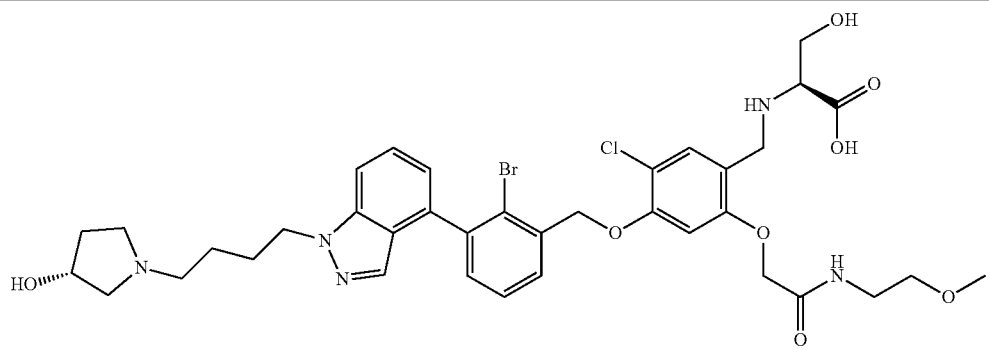 [SMILES: COCCNC(=O)COc1cc(OCc2cccc(-c3cccc4c3cnn4CCCCN3CC[C@@H](O)C3)c2Br)c(Cl)cc1CN[C@@H](CO)C(=O)O] |
| 54 | 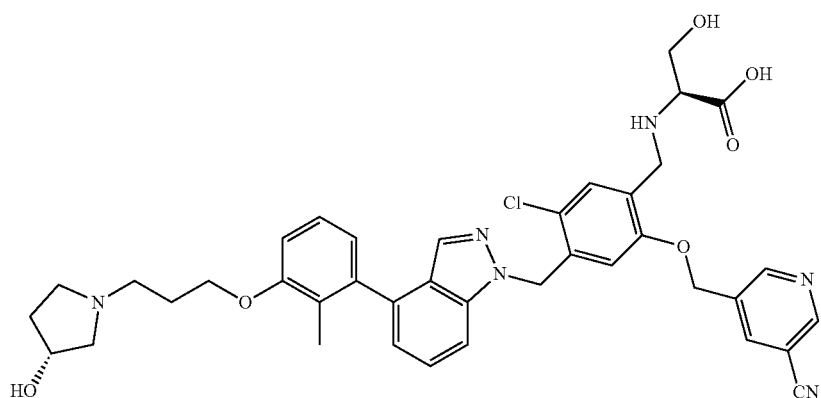 [SMILES: Cc1c(OCCCN2CC[C@@H](O)C2)cccc1-c1cccc2c1cnn2Cc1cc(OCc2cncc(C#N)c2)c(CN[C@@H](CO)C(=O)O)cc1Cl] |
| 55 | 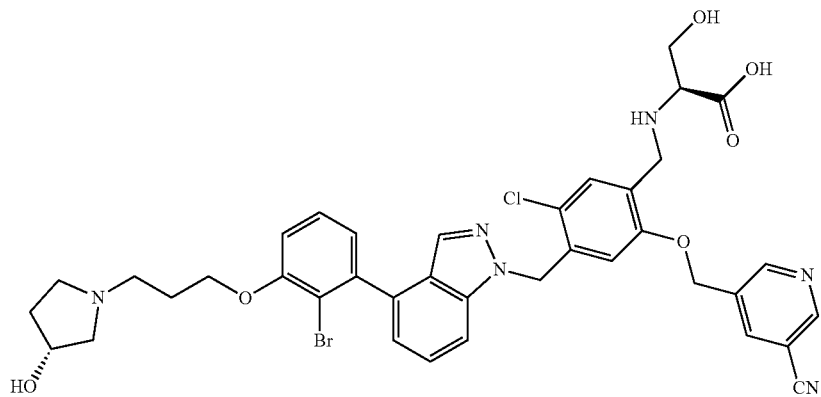 [SMILES: N#Cc1cncc(COc2cc(Cn3ncc4c(-c5cccc(OCCCN6CC[C@@H](O)C6)c5Br)cccc43)c(Cl)cc2CN[C@@H](CO)C(=O)O)c1] |
| 56 | 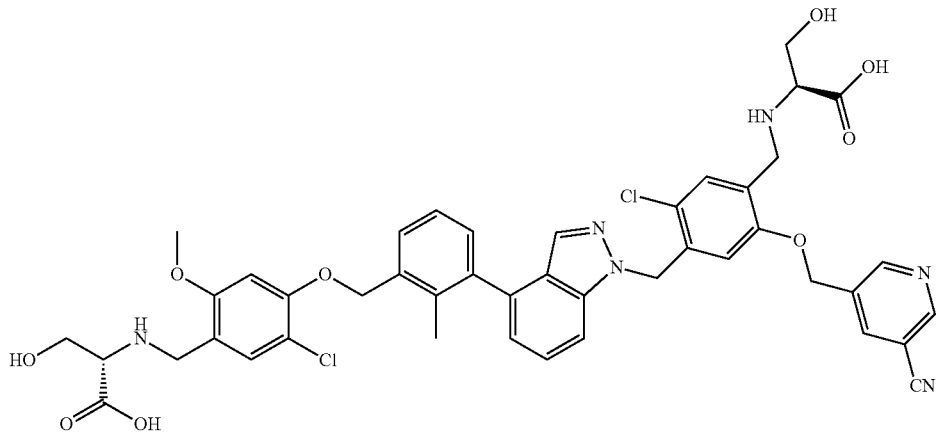 [SMILES: COc1cc(OCc2cccc(-c3cccc4c3cnn4Cc3cc(OCc4cncc(C#N)c4)c(CN[C@@H](CO)C(=O)O)cc3Cl)c2C)c(Cl)cc1CN[C@@H](CO)C(=O)O] |

| No. | Structure |
|---|---|
| 57 | 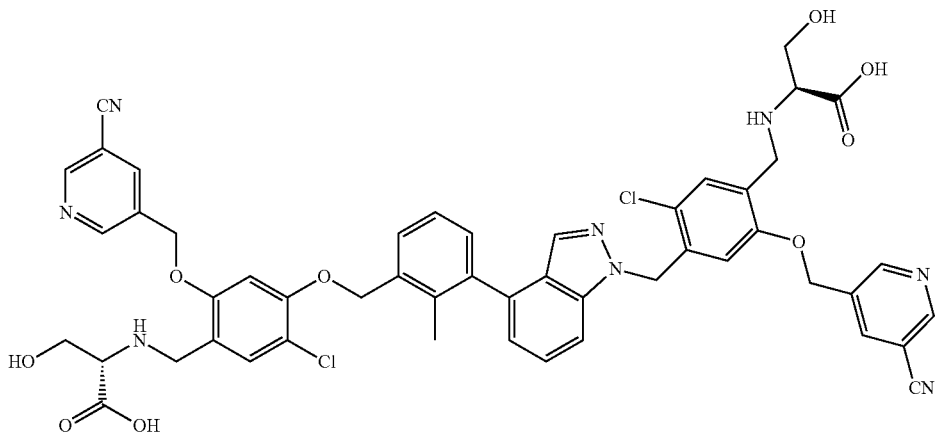 [SMILES: Cc1c(COc2cc(OCc3cncc(C#N)c3)c(CN[C@@H](CO)C(=O)O)cc2Cl)cccc1-c1cccc2c1cnn2Cc1cc(OCc2cncc(C#N)c2)c(CN[C@@H](CO)C(=O)O)cc1Cl] |
| 58 | 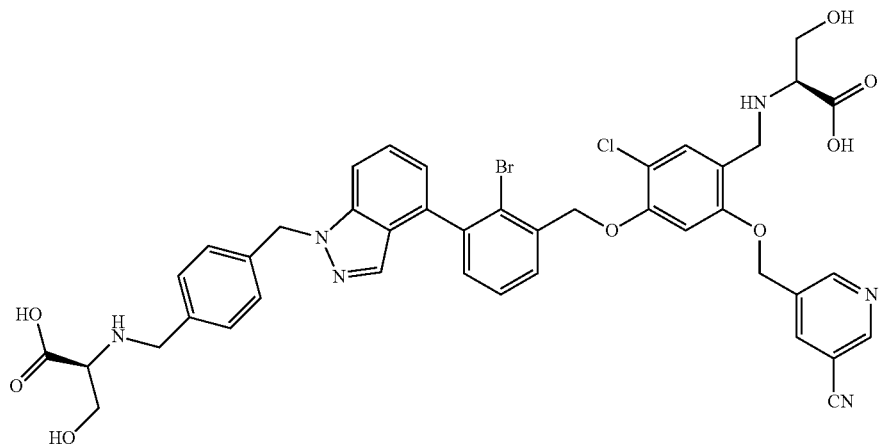 [SMILES: N#Cc1cncc(COc2cc(OCc3cccc(-c4cccc5c4cnn5Cc4ccc(CN[C@@H](CO)C(=O)O)cc4)c3Br)c(Cl)cc2CN[C@@H](CO)C(=O)O)c1] |
| 59 | 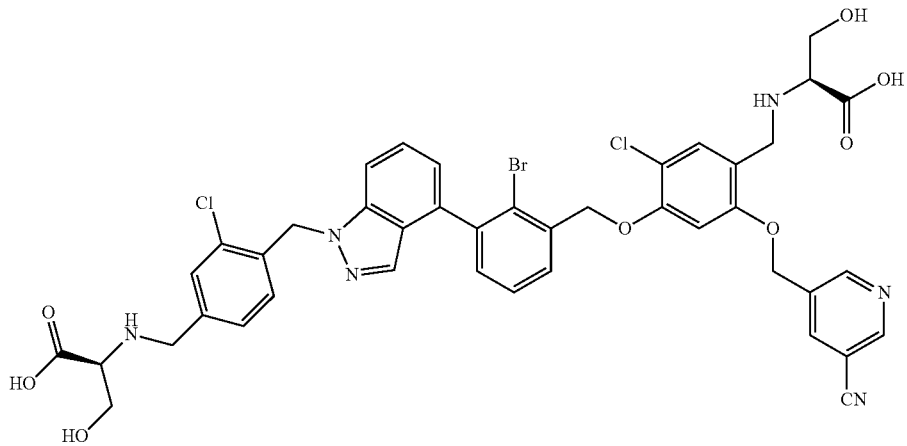 [SMILES: N#Cc1cncc(COc2cc(OCc3cccc(-c4cccc5c4cnn5Cc4ccc(CN[C@@H](CO)C(=O)O)cc4Cl)c3Br)c(Cl)cc2CN[C@@H](CO)C(=O)O)c1] |

| No. | Structure |
|---|---|
| 60 | 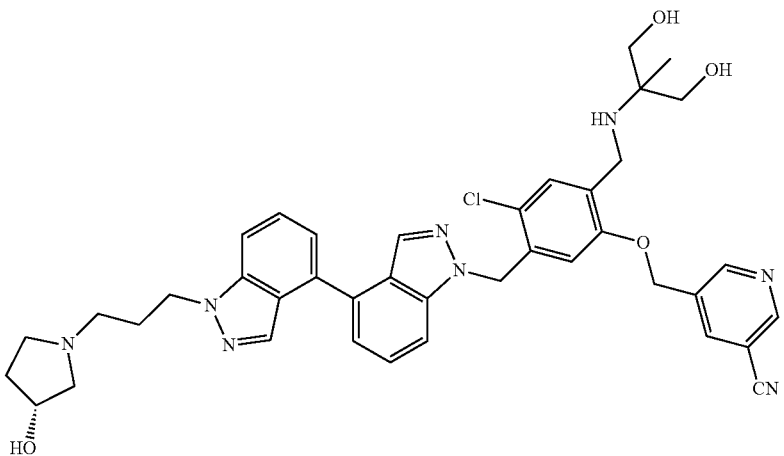 [SMILES: CC(CO)(CO)NCc1cc(Cl)c(Cn2ncc3c(-c4cccc5c4cnn5CCCN4CC[C@@H](O)C4)cccc32)cc1OCc1cncc(C#N)c1] |
| 61 | 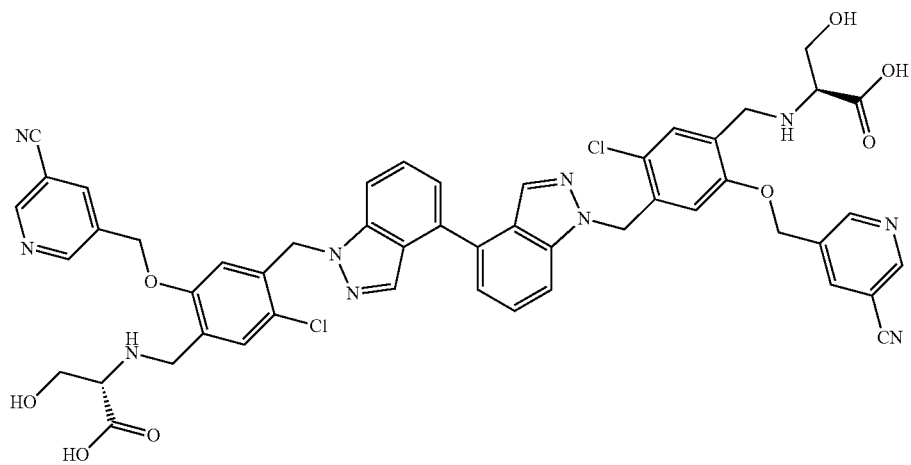 [SMILES: N#Cc1cncc(COc2cc(Cn3ncc4c(-c5cccc6c5cnn6Cc5cc(OCc6cncc(C#N)c6)c(CN[C@@H](CO)C(=O)O)cc5Cl)cccc43)c(Cl)cc2CN[C@@H](CO)C(=O)O)c1] |
| 62 | 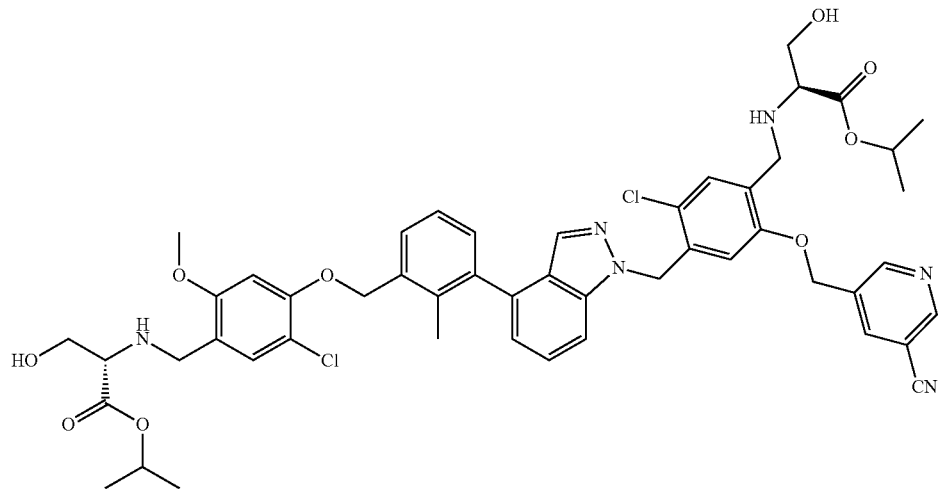 [SMILES: COc1cc(OCc2cccc(-c3cccc4c3cnn4Cc3cc(OCc4cncc(C#N)c4)c(CN[C@@H](CO)C(=O)OC(C)C)cc3Cl)c2C)c(Cl)cc1CN[C@@H](CO)C(=O)OC(C)C] |

| No. | Structure |
|---|---|
| 63 | 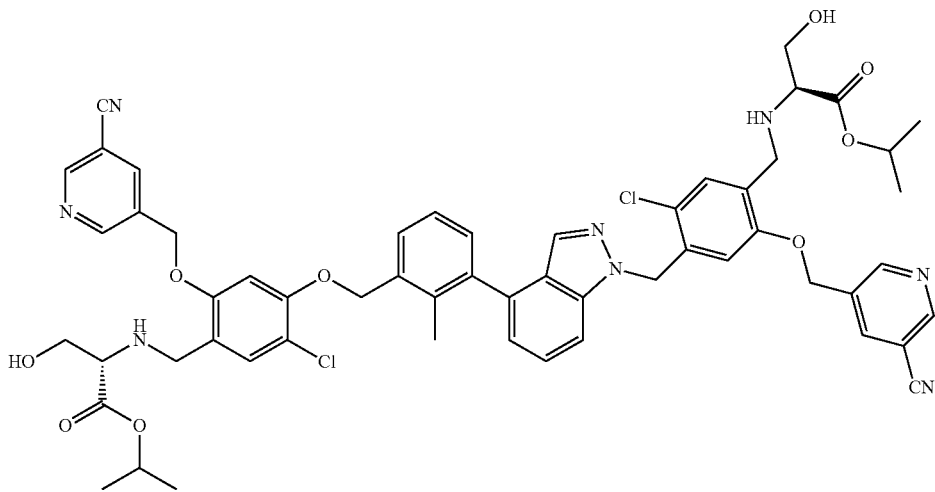 [SMILES: Cc1c(COc2cc(OCc3cncc(C#N)c3)c(CN[C@@H](CO)C(=O)OC(C)C)cc2Cl)cccc1-c1cccc2c1cnn2Cc1cc(OCc2cncc(C#N)c2)c(CN[C@@H](CO)C(=O)OC(C)C)cc1Cl] |
| 64 | 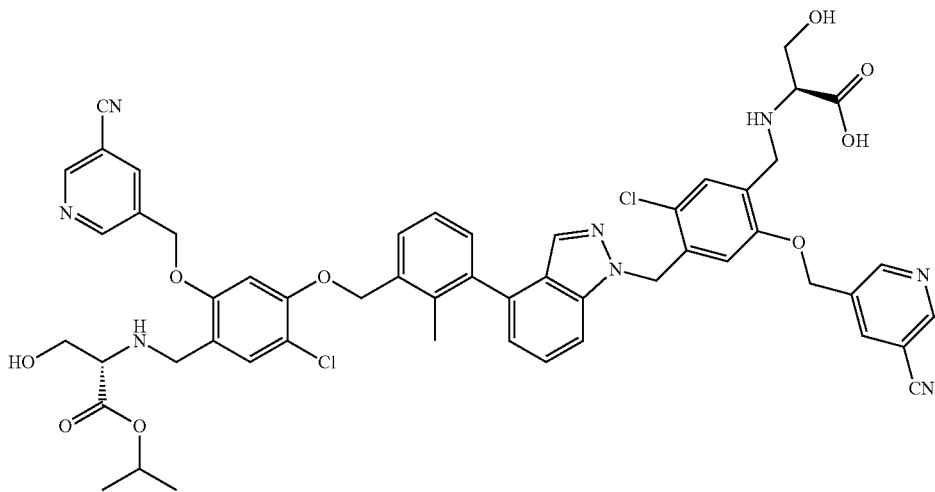 [SMILES: Cc1c(COc2cc(OCc3cncc(C#N)c3)c(CN[C@@H](CO)C(=O)OC(C)C)cc2Cl)cccc1-c1cccc2c1cnn2Cc1cc(OCc2cncc(C#N)c2)c(CN[C@@H](CO)C(=O)O)cc1Cl] |
| 65 | 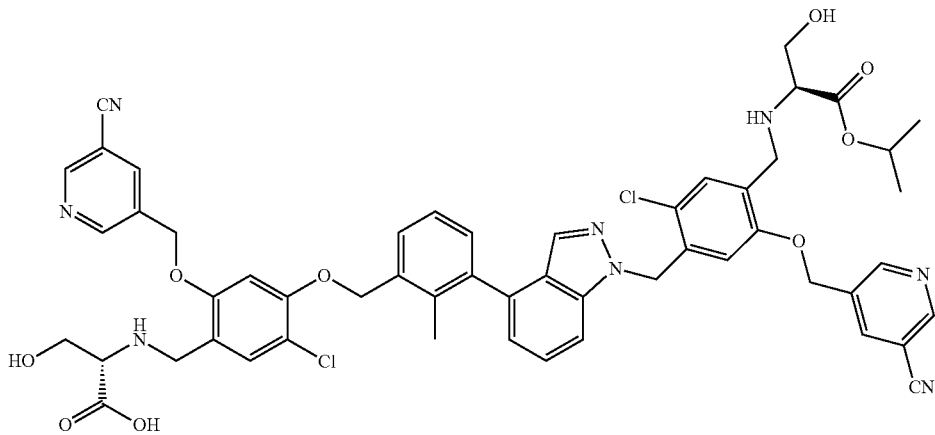 [SMILES: Cc1c(COc2cc(OCc3cncc(C#N)c3)c(CN[C@@H](CO)C(=O)O)cc2Cl)cccc1-c1cccc2c1cnn2Cc1cc(OCc2cncc(C#N)c2)c(CN[C@@H](CO)C(=O)OC(C)C)cc1Cl] |

-continued

| No. | Structure |
|-----|-----------|
| 66 | 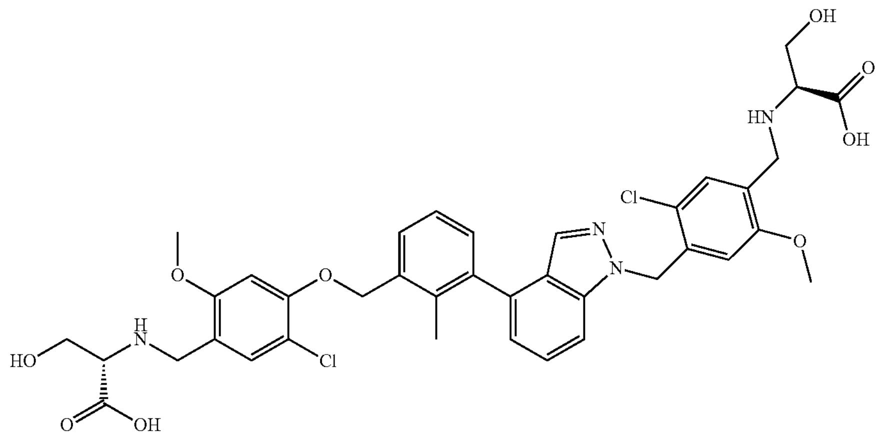 [SMILES: COc1cc(Cn2ncc3c(-c4cccc(COc5cc(OC)c(CN[C@@H](CO)C(=O)O)cc5Cl)c4C)cccc32)c(Cl)cc1CN[C@@H](CO)C(=O)O] |
| 67 | 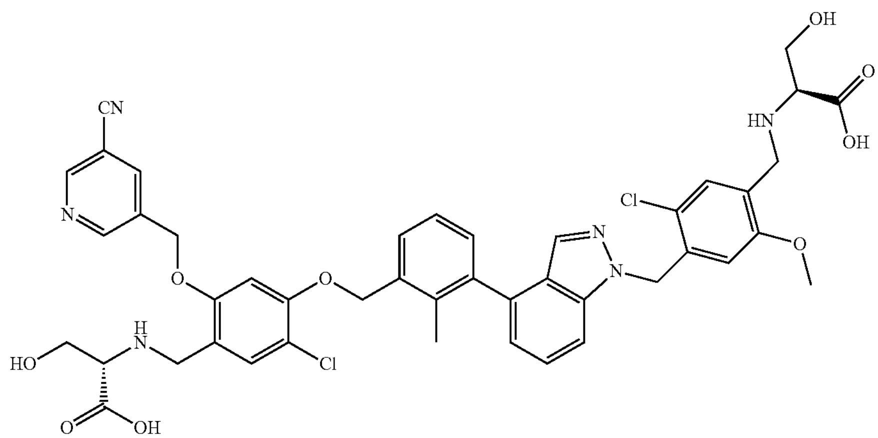 [SMILES: COc1cc(Cn2ncc3c(-c4cccc(COc5cc(OCc6cncc(C#N)c6)c(CN[C@@H](CO)C(=O)O)cc5Cl)c4C)cccc32)c(Cl)cc1CN[C@@H](CO)C(=O)O] |
| 68 | 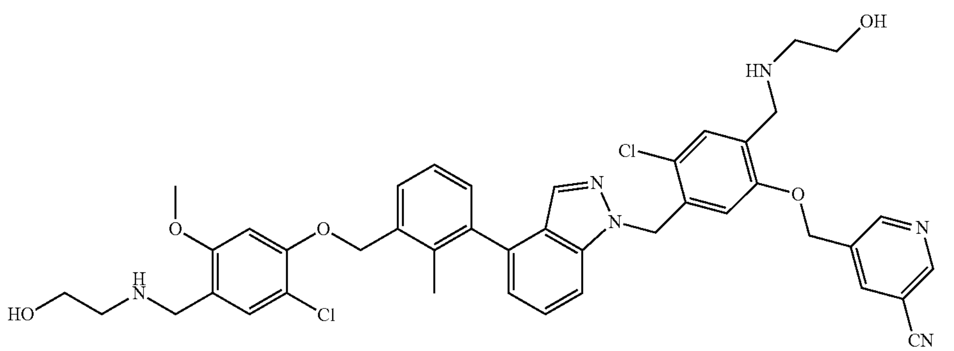 [SMILES: COc1cc(OCc2cccc(-c3cccc4c3cnn4Cc3cc(OCc4cncc(C#N)c4)c(CNCCO)cc3Cl)c2C)c(Cl)cc1CNCCO] |
| 69 | 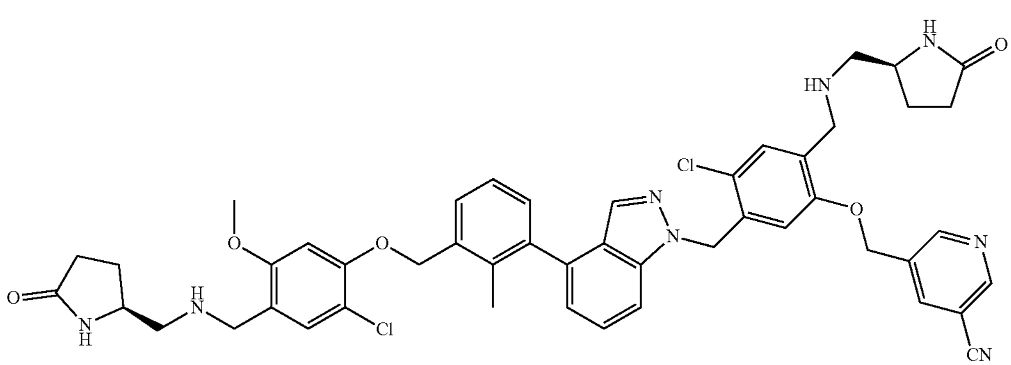 [SMILES: COc1cc(OCc2cccc(-c3cccc4c3cnn4Cc3cc(OCc4cncc(C#N)c4)c(CNC[C@@H]4CCC(=O)N4)cc3Cl)c2C)c(Cl)cc1CNC[C@@H]1CCC(=O)N1] |

| No. | Structure |
|---|---|
| 70 | 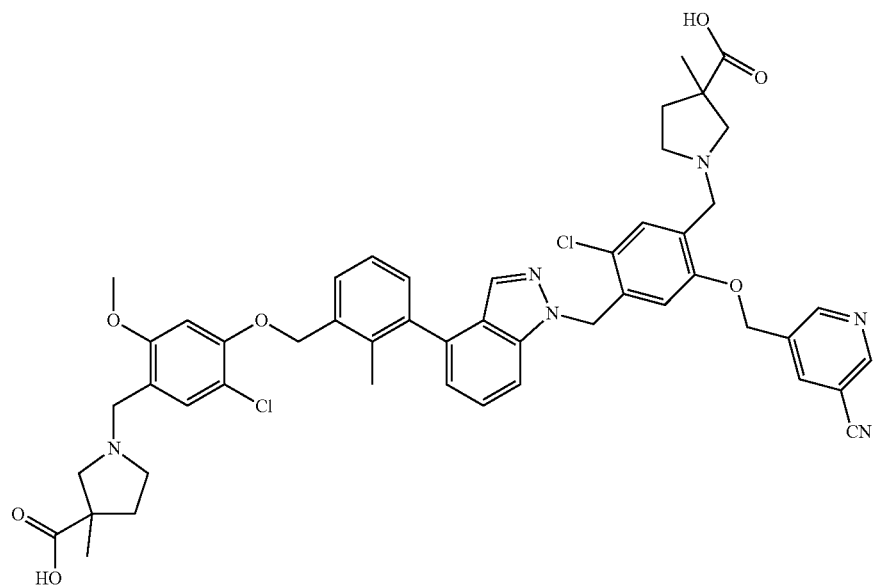 [SMILES: COc1cc(OCc2cccc(-c3cccc4c3cnn4Cc3cc(OCc4cncc(C#N)c4)c(CN4CCC(C)(C(=O)O)C4)cc3Cl)c2C)c(Cl)cc1CN1CCC(C)(C(=O)O)C1] |
| 71 | 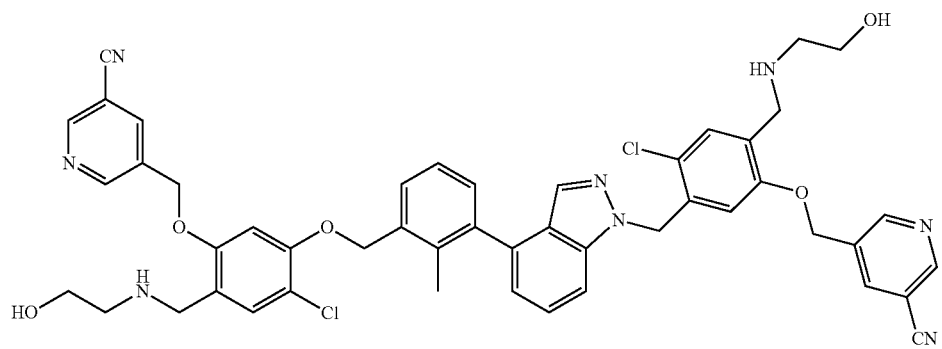 [SMILES: Cc1c(COc2cc(OCc3cncc(C#N)c3)c(CNCCO)cc2Cl)cccc1-c1cccc2c1cnn2Cc1cc(OCc2cncc(C#N)c2)c(CNCCO)cc1Cl] |
| 72 | 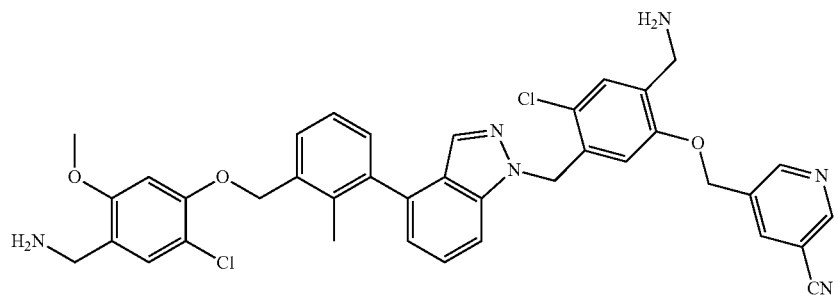 [SMILES: COc1cc(OCc2cccc(-c3cccc4c3cnn4Cc3cc(OCc4cncc(C#N)c4)c(CN)cc3Cl)c2C)c(Cl)cc1CN] |
| 73 | 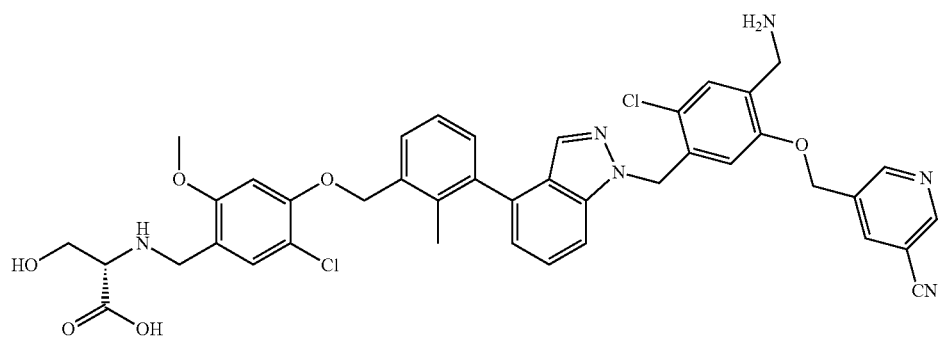 [SMILES: COc1cc(OCc2cccc(-c3cccc4c3cnn4Cc3cc(OCc4cncc(C#N)c4)c(CN)cc3Cl)c2C)c(Cl)cc1CN[C@@H](CO)C(=O)O] |

| No. | Structure |
|---|---|
| 74 | 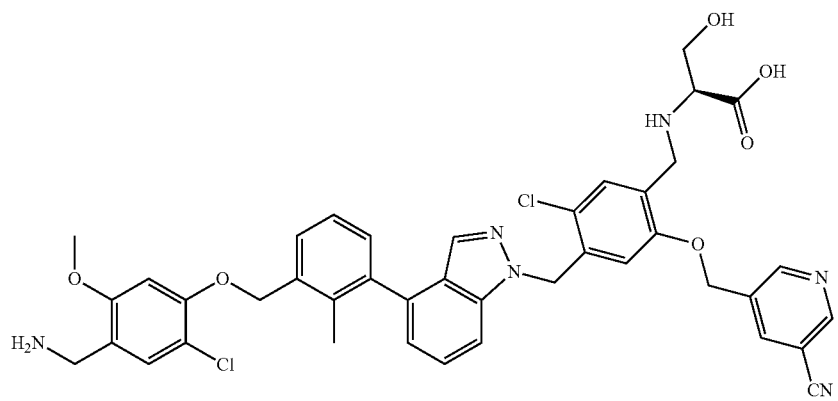 [SMILES: COc1cc(OCc2cccc(-c3cccc4c3cnn4Cc3cc(OCc4cncc(C#N)c4)c(CN[C@@H](CO)C(=O)O)cc3Cl)c2C)c(Cl)cc1CN] |
| 75 | 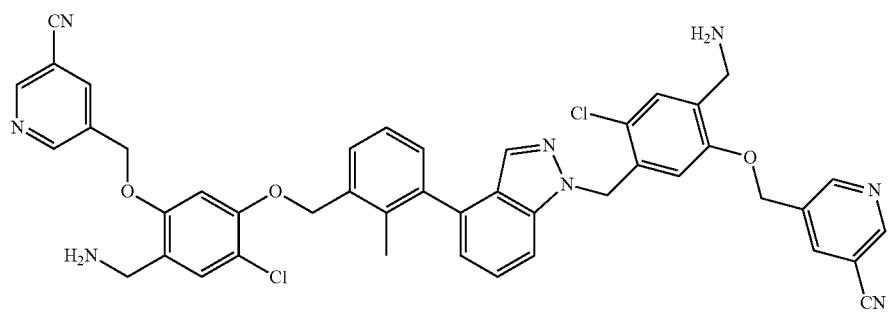 [SMILES: Cc1c(COc2cc(OCc3cncc(C#N)c3)c(CN)cc2Cl)cccc1-c1cccc2c1cnn2Cc1cc(OCc2cncc(C#N)c2)c(CN)cc1Cl] |
| 76 | 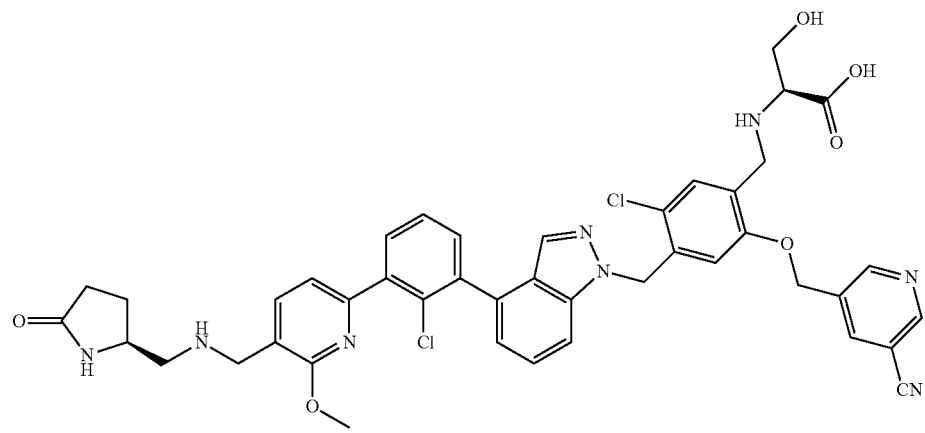 [SMILES: COc1nc(-c2cccc(-c3cccc4c3cnn4Cc3cc(OCc4cncc(C#N)c4)c(CN[C@@H](CO)C(=O)O)cc3Cl)c2Cl)ccc1CNC[C@@H]1CCC(=O)N1] |
| 77 | 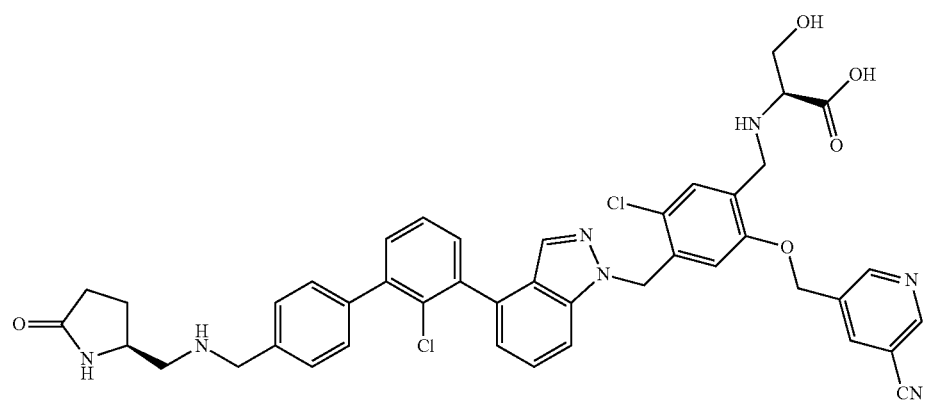 [SMILES: N#Cc1cncc(COc2cc(Cn3ncc4c(-c5cccc(-c6ccc(CNC[C@@H]7CCC(=O)N7)cc6)c5Cl)cccc43)c(Cl)cc2CN[C@@H](CO)C(=O)O)c1] |

| No. | Structure |
|---|---|
| 78 | 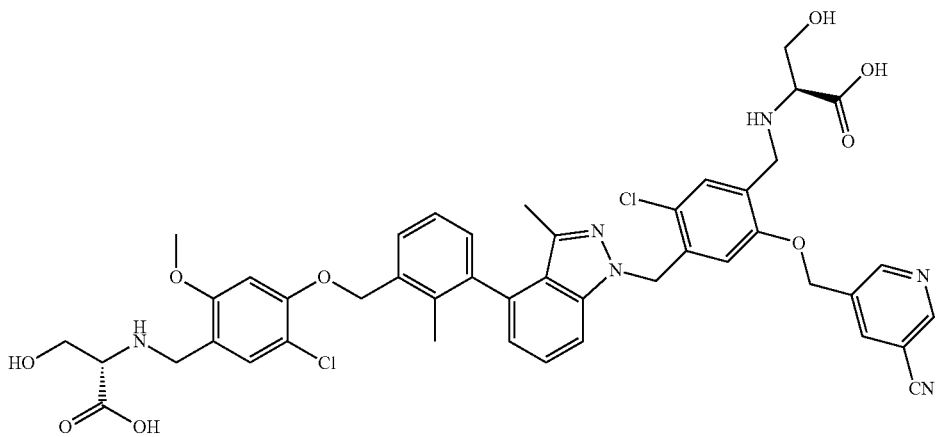 [SMILES: COc1cc(OCc2cccc(-c3cccc4c3c(C)nn4Cc3cc(OCc4cncc(C#N)c4)c(CN[C@@H](CO)C(=O)O)cc3Cl)c2C)c(Cl)cc1CN[C@@H](CO)C(=O)O] |
| 79 | 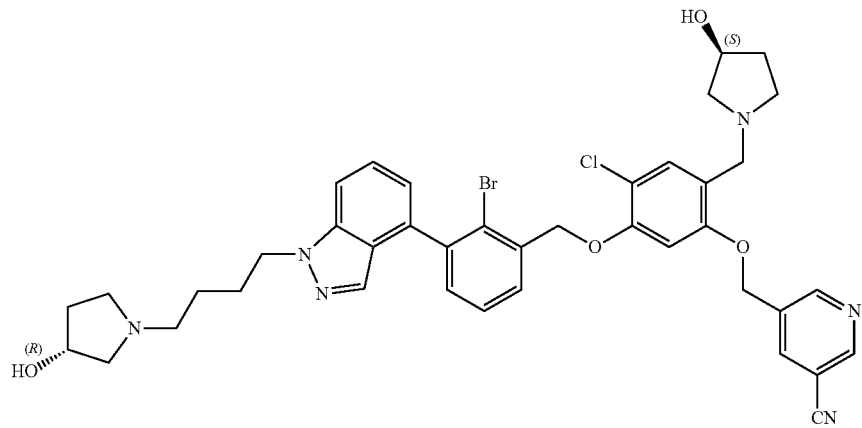 |
| 80 | 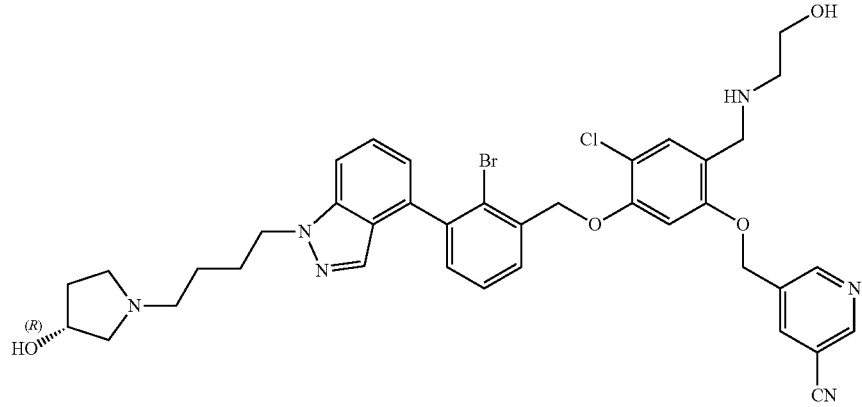 |

-continued
| No. | Structure |
|---|---|
| 81 | 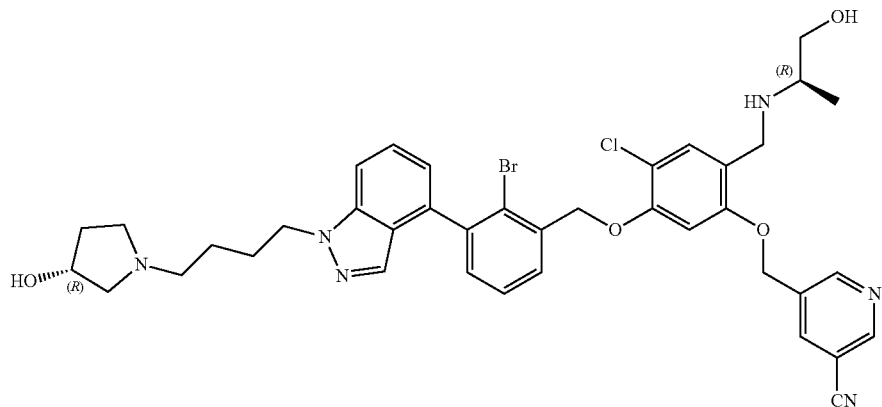 |
| 82 | 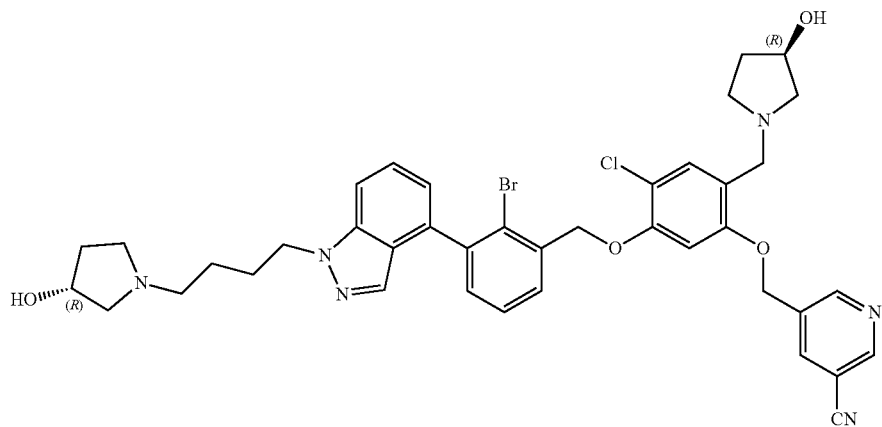 |
| 83 | 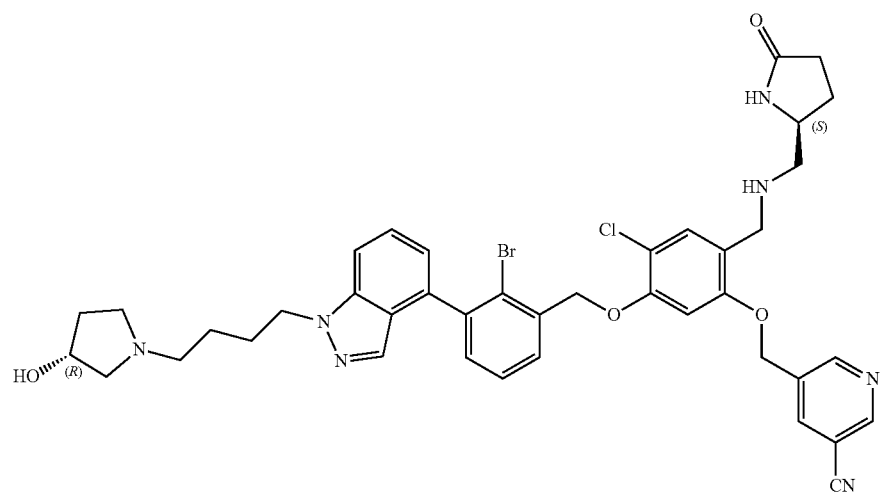 |

| No. | Structure |
|---|---|
| 84 | 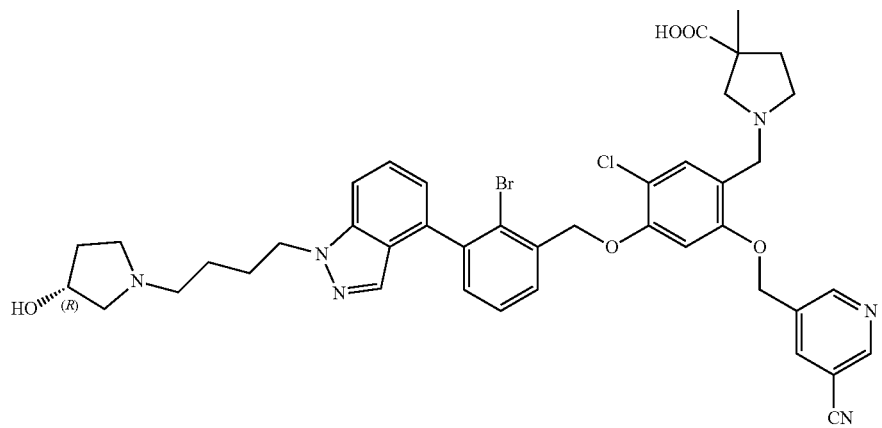 |
| 85 | 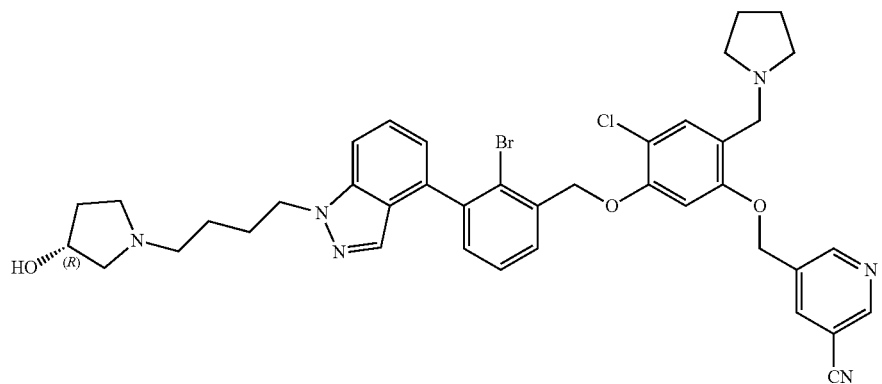 |
| 86 | 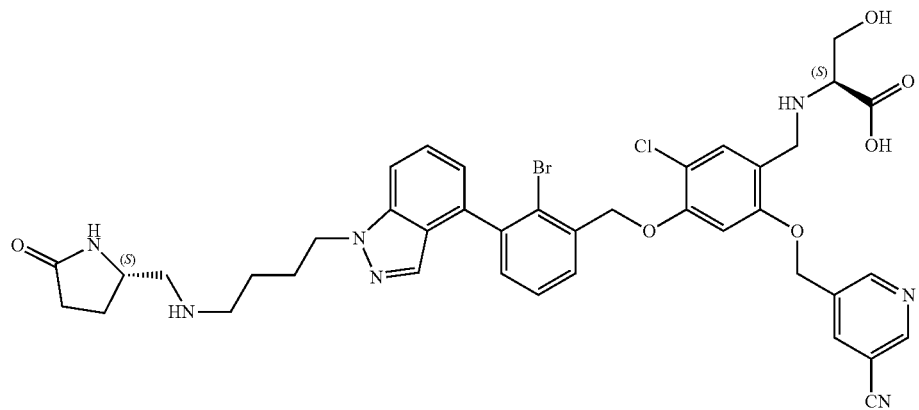 |

-continued
| No. | Structure |
|---|---|
| 87 | 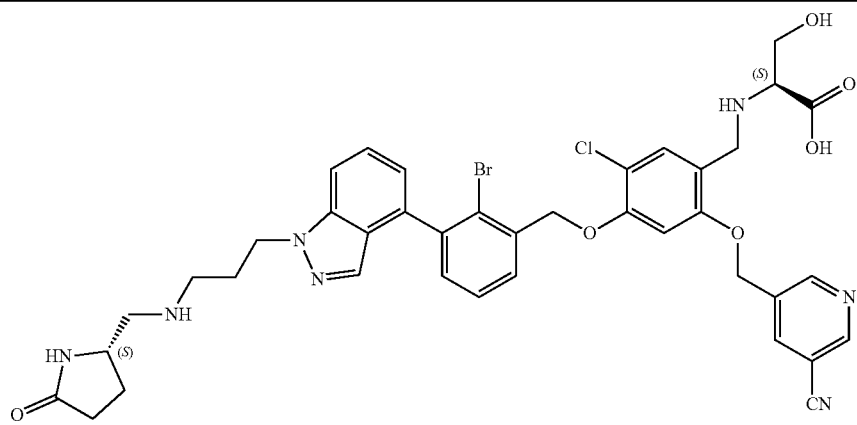 |
| 88 | 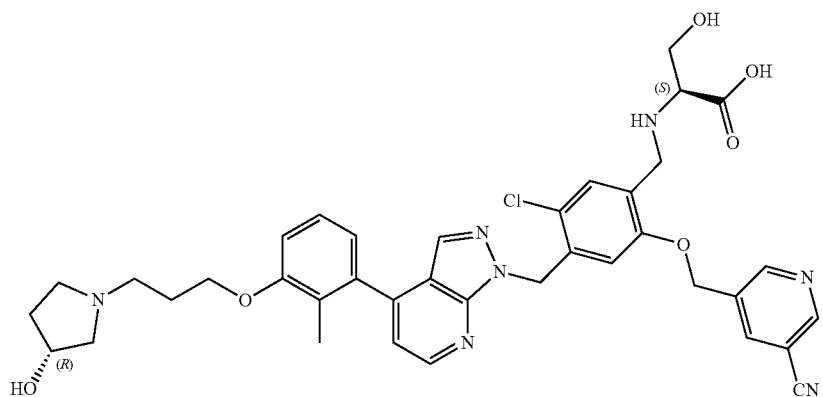 |
| 89 | 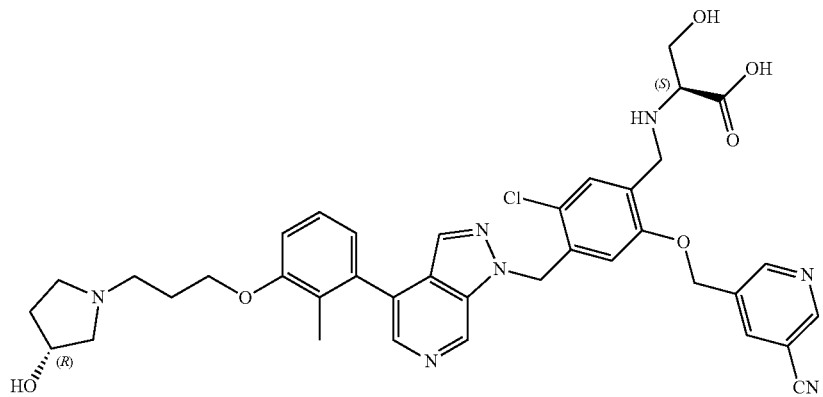 |
| 90 | 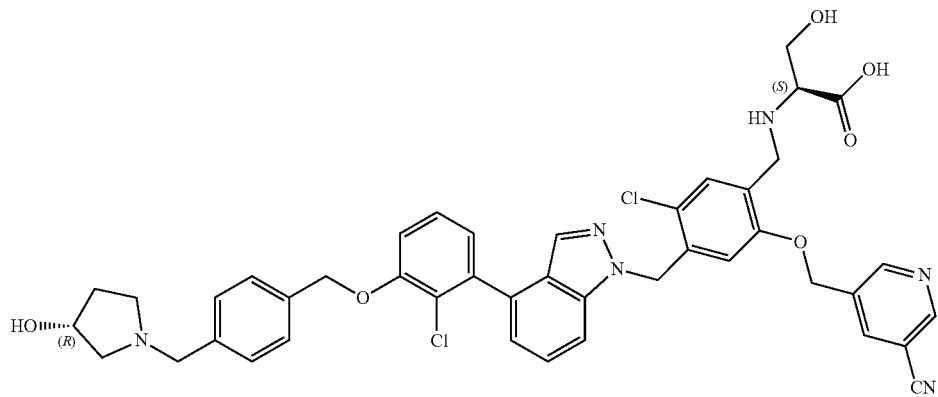 |

-continued
| No. | Structure |
|---|---|
| 91 | 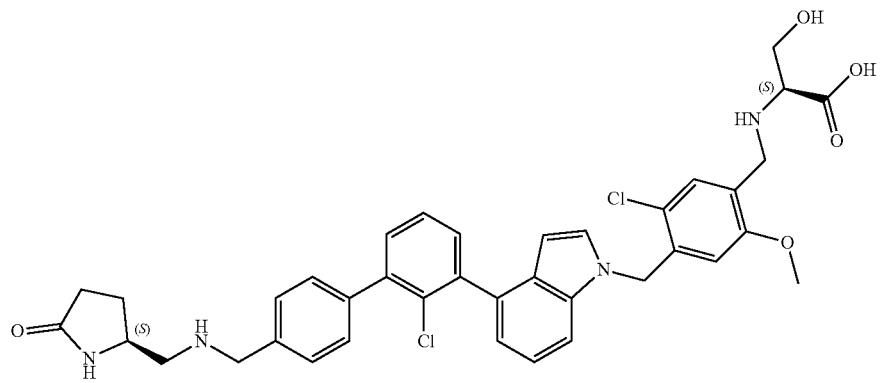 |
| 92 | 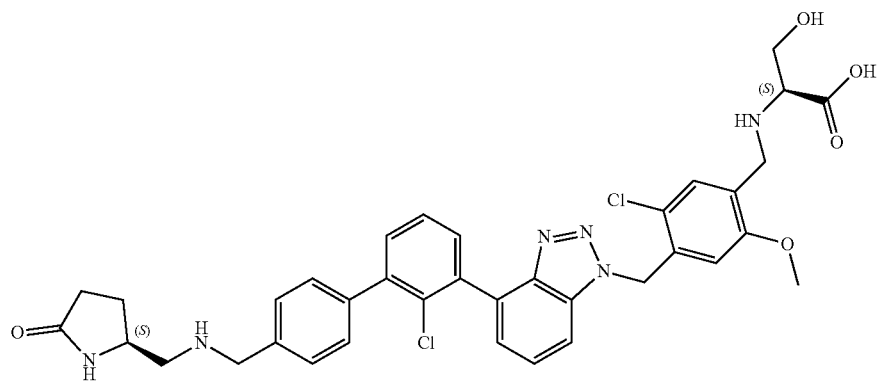 |
| 93 | 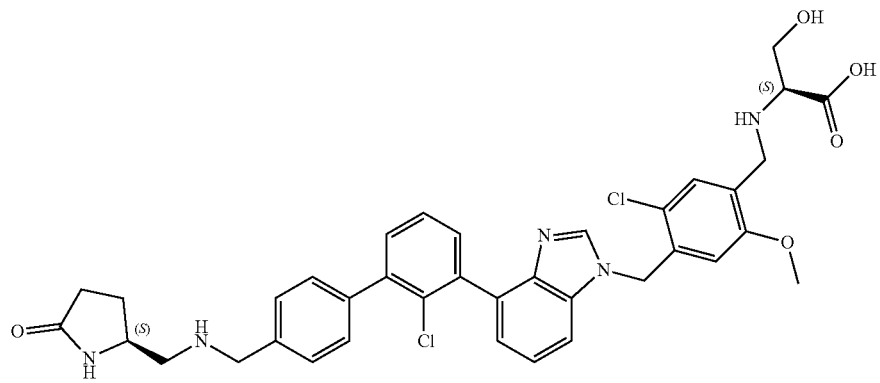 |
| 94 | 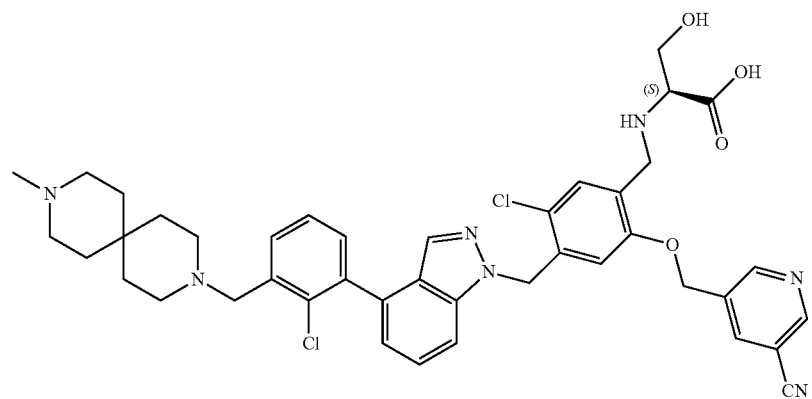 |

| No. | Structure |
|---|---|
| 95 | 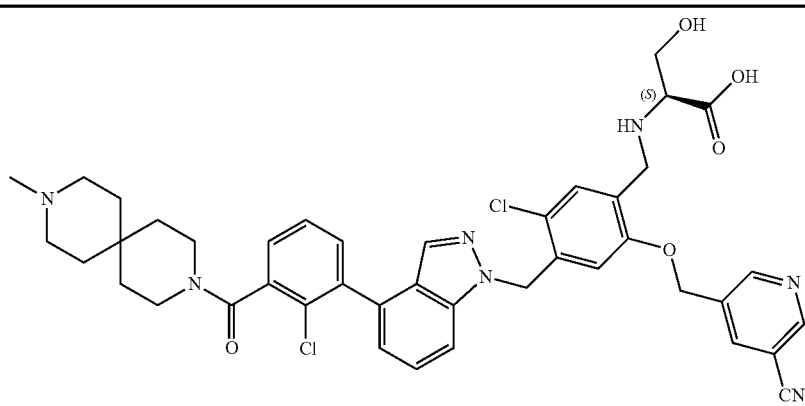 |
| 96 | 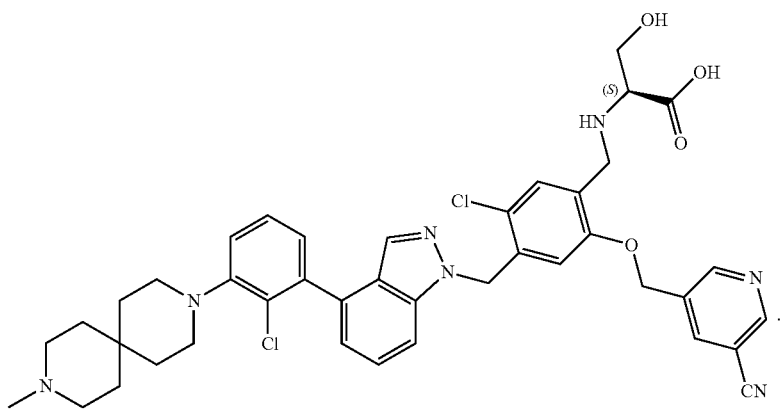 |

18. A method for the treatment of a disease or condition responsive to the inhibition of PD-L1 binding to PD-1, comprising administering to a mammal in need thereof the compound according to claim 1.

19. A method for the inhibition of PD-L1 binding to PD-1, comprising exposing the compound of claim 1 to the PD-L1 and/or PD-1.

20. The method according to claim 18, wherein the disease or condition is selected from the group consisting of tumors, cancers, viral infections, inflammation-related diseases and autoimmune diseases.

21. The compound according to claim 5, wherein Y is selected from the group consisting of 22. The compound according to claim 6, wherein Y is selected from the group consisting of -continued

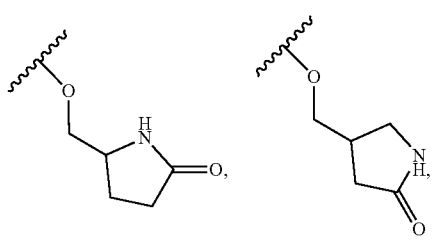

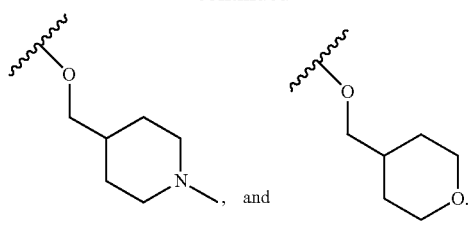

23. The compound according to claim 7, wherein Y is selected from the group consisting of

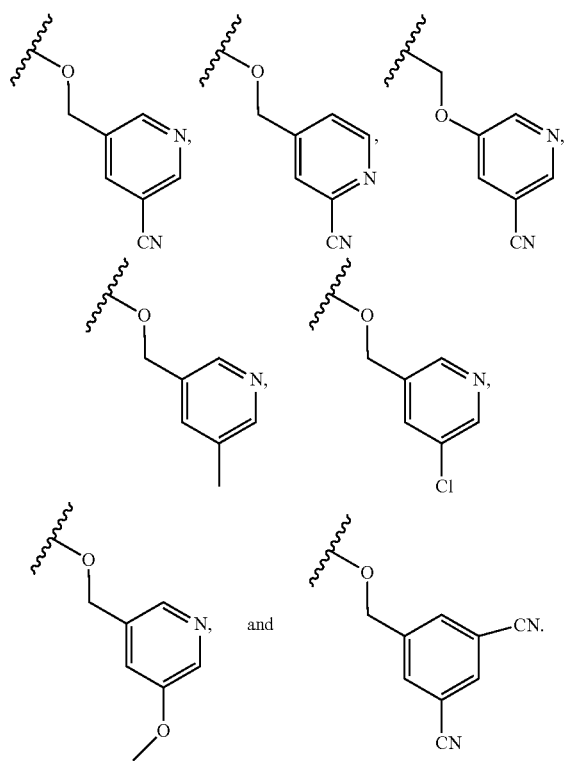

24. The compound according to claim 8, wherein Y is selected from the group consisting of

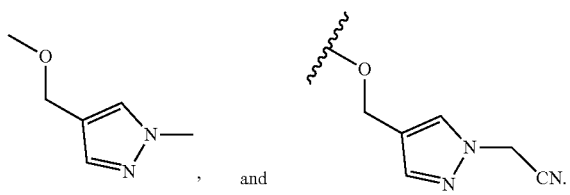

25. The compound according to claim 9, wherein Y is selected from the group consisting of

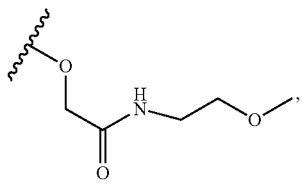

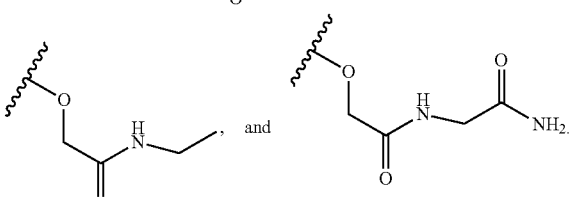

26. The compound according to claim 10, wherein Y is selected from

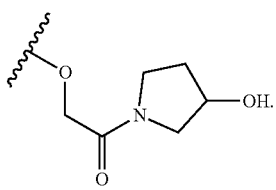 [SMILES: *OCC(=O)N1CCC(O)C1]

27. The compound according to claim 12, wherein A is selected from the group consisting

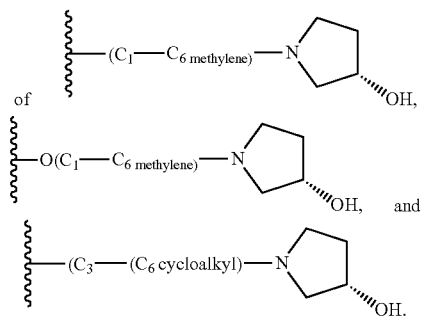

28. The compound according to claim 14, wherein $R^2$ is selected from the group consisting of

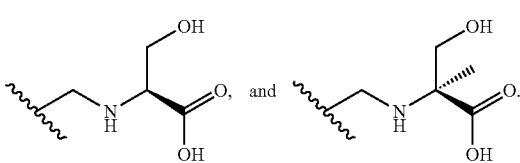

29. The compound according to claim 16, wherein the halogen is chlorine or bromine.

* * * * *